United States Patent
Ruohola-Baker et al.

(10) Patent No.: US 9,416,369 B2
(45) Date of Patent: Aug. 16, 2016

(54) METHODS AND COMPOSITIONS TO MODULATE RNA PROCESSING

(71) Applicant: University of Washington Through Its Center for Commercialization, Seattle, WA (US)

(72) Inventors: Hannele Ruohola-Baker, Seattle, WA (US); Pratyusha Banik, Bothell, WA (US); Alan Beem, Seattle, WA (US); Sandra Shannon, Sammamish, WA (US); Henrik Sperber, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 0 days.

(21) Appl. No.: 14/652,756

(22) PCT Filed: Dec. 18, 2013

(86) PCT No.: PCT/US2013/076256
§ 371 (c)(1),
(2) Date: Jun. 16, 2015

(87) PCT Pub. No.: WO2014/100252
PCT Pub. Date: Jun. 26, 2014

(65) Prior Publication Data
US 2015/0337332 A1 Nov. 26, 2015

Related U.S. Application Data

(60) Provisional application No. 61/738,821, filed on Dec. 18, 2012.

(51) Int. Cl.
| | |
|---|---|
| *C07H 21/02* | (2006.01) |
| *C07H 21/04* | (2006.01) |
| *A61K 48/00* | (2006.01) |
| *C12N 15/63* | (2006.01) |
| *C12N 15/85* | (2006.01) |
| *C12N 15/113* | (2010.01) |
| *C12N 9/22* | (2006.01) |

(52) U.S. Cl.
CPC *C12N 15/85* (2013.01); *C12N 9/22* (2013.01); *C12N 15/113* (2013.01); *C12Y 301/26003* (2013.01); *C12N 15/63* (2013.01); *C12N 2310/14* (2013.01); *C12N 2310/141* (2013.01); *C12N 2310/351* (2013.01); *C12N 2310/533* (2013.01)

(58) Field of Classification Search
CPC ........... C12N 2310/533; C12N 15/113; C12N 2310/11
See application file for complete search history.

(56) References Cited

U.S. PATENT DOCUMENTS 7,232,806 B2    6/2007 Tuschl et al.

OTHER PUBLICATIONS

Abdelmohsen K, Srikantan S, Kang MJ, Gorospe M. 2012. Regulation of senescence by microRNA biogenesis factors. Ageing Res Rev 11(4): 491-500.
Anokye-Danso F, Trivedi CM, Juhr D, Gupta M, Cui Z, Tian Y, Zhang Y, Yang W, Gruber PJ, Epstein JA et al. 2011. Highly efficient miRNA-mediated reprogramming of mouse and human somatic cells to pluripotency. Cell Stem Cell 8(4): 376-388.
Bar M, Wyman SK, Fritz BR, Qi J, Garg KS, Parkin RK, Kroh EM, Bendoraite A, Mitchell PS, Nelson AM et al. 2008. MicroRNA discovery and profiling in human embryonic stem cells by deep sequencing of small RNA libraries. Stem Cells 26(10): 2496-2505.
Bartel DP. 2004. MicroRNAs: genomics, biogenesis, mechanism, and function. Cell 116(2): 281-297.
Basyuk E, Suavet F, Doglio A, Bordonne R, Bertrand E. 2003. Human let-7 stem-loop precursors harbor features of RNase III cleavage products. Nucleic Acids Res 31(22): 6593-6597.
Berezikov E, Chung WJ, Willis J, Cuppen E, Lai EC. 2007. Mammalian mirtron genes. Mol Cell 28(2): 328-336.
Bernstein E, Allis CD. 2005. RNA meets chromatin. Genes Dev 19(14): 1635-1655.
Borchert GM, Lanier W, Davidson BL. 2006. RNA polymerase III transcribes human microRNAs. Nat Struct Mol Biol 13(12): 1097-1101.
Brueckner B, Stresemann C, Kuner R, Mund C, Musch T, Meister M, Sultmann H, Lyko F. 2007. The human let-7a-3 locus contains an epigenetically regulated microRNA gene with oncogenic function. Cancer Res 67(4): 1419-1423.
Chambers SM, Fasano CA, Papapetrou EP, Tomishima M, Sadelain M, Studer L. 2009. Highly efficient neural conversion of human ES and iPS cells by dual inhibition of SMAD signaling. Nat Biotechnol 27(3): 275-280.
Cheloufi S, Dos Santos CO, Chong MM, Hannon GJ. 2010. A dicer-independent miRNA biogenesis pathway that requires Ago catalysis. Nature 465(7298): 584-589.
Chendrimada TP, Gregory RI, Kumaraswamy E, Norman J, Cooch N, Nishikura K, Shiekhattar R. 2005. TRBP recruits the Dicer complex to Agog for microRNA processing and gene silencing. Nature 436(7051): 740-744.
Chong MM, Zhang G, Cheloufi S, Neubert TA, Hannon GJ, Littman DR. 2010. Canonical and alternate functions of the microRNA biogenesis machinery. Genes Dev 24(17): 1951-1960.
Cullen BR. 2006. Viruses and microRNAs. Nat Genet 38 Suppl: S25-30.
Davis BN, Hata A. 2009. Regulation of MicroRNA Biogenesis: A miRiad of mechanisms. Cell Commun Signal 7: 18.

(Continued)

*Primary Examiner* — Amy Bowman
(74) *Attorney, Agent, or Firm* — K&L Gates LLP; Louis C. Cullman; Michelle Glasky Bergman

(57) ABSTRACT

The present disclosure provides methods and compositions to selectively modulate RNA processing. The methods and compositions selectively enhance or repress RNA processing by up- or down-regulating Drosha expression and/or by providing RNA sequences with mis-matches introduced or removed 5 and/or 9-12 nucleotide positions from the Drosha cutting site. Therapeutic uses of the methods and compositions are also described.

13 Claims, 22 Drawing Sheets

(56) References Cited

OTHER PUBLICATIONS

Diederichs S, Haber DA. 2006. Sequence variations of microRNAs in human cancer: alterations in predicted secondary structure do not affect processing. Cancer Res 66(12): 6097-6104.
Du T, Zamore PD. 2005. microPrimer: the biogenesis and function of microRNA. Development 132(21): 4645-4652.
Duan R, Pak C, Jin P. 2007. Single nucleotide polymorphism associated with mature miR-125a alters the processing of pri-miRNA. Hum Mol Genet 16(9): 1124-1131.
Feng Y, Zhang X, Graves P, Zeng Y. 2012. A comprehensive analysis of precursor microRNA cleavage by human Dicer. RNA 18(11): 2083-2092.
Feng Y, Zhang X, Song Q, Li T, Zeng Y. 2011. Drosha processing controls the specificity and efficiency of global . microRNA expression. Biochim Biophys Acta 1809(11-12): 700-707.
Fukuda T, Yamagata K, Fujiyama S, Matsumoto T, Koshida I, Yoshimura K, Mihara M, Naitou M, Endoh H, Nakamura T et al. 2007. Dead-box RNA helicase subunits of the Drosha complex are required for processing of rRNA and a subset of microRNAs. Nat Cell Biol 9(5): 604-611.
Gregory RI, Yan KP, Amuthan G, Chendrimada T, Doratotaj B, Cooch N, Shiekhattar R. 2004. The Microprocessor complex mediates the genesis of microRNAs. Nature 432(7014): 235-240.
Griffiths-Jones S, Grocock RJ, van Dongen S, Bateman A, Enright AJ. 2006. miRBase: microRNA sequences, targets and gene nomenclature. Nucleic Acids Res 34(Database issue): D140-144.
Han J, Pedersen JS, Kwon SC, Belair CD, Kim YK, Yeom KK, Yang WY, Haussler D, Blelloch R, Kim VN. 2009. Posttranscriptional crossregulation between Drosha and DGCR8. Cell 136(1): 75-84.
Hatfield SD, Shcherbata HR, Fischer KA, Nakahara K, Carthew RW, Ruohola-Baker H. 2005. Stem cell division is regulated by the microRNA pathway. Nature 435(7044): 974-978.
Hofacker IL, Fontana W, Stadler PF, Bonhoeffer LS, Tacker M, Schuster P. 1994. Fast folding and comparison of RNA secondary structures. Monatsh Chem 125: 167-188.
Hutvagner G, McLachlan J, Pasquinelli AE, Balint E, Tuschl T, Zamore PD. 2001. A cellular function for the RNA-interference enzyme Dicer in the maturation of the let-7 small temporal RNA. Science 293(5531): 834-838.
Kim VN, Nam JW. 2006. Genomics of microRNA. Trends Genet 22(3): 165-173.
Kuehbacher A, Urbich C, Zeiher AM, Dimmeler S. 2007. Role of Dicer and Drosha for endothelial microRNA expression and angiogenesis. Circ Res 101(1): 59-68.
Kuppusamy KT, Sperber H, Ruohola-Baker H. 2013. MicroRNA Regulation and role in stem cell maintenance, cardiac differentiation and hypertrophy. Curr Mol Med Submitted.
Lagos-Quintana M, Rauhut R, Lendeckel W, Tuschl T. 2001. Identification of novel genes coding for small expressed RNAs. Science 294(5543): 853-858.
Lee Y, Ahn C, Han J, Choi H, Kim J, Yim J, Lee J, Provost P, Radmark O, Kim S et al. 2003. The nuclear RNase III Drosha initiates microRNA processing. Nature 425(6956): 415-419.
Mattick JS, Makunin IV. 2006. Non-coding RNA. Hum Mol Genet 15 Spec No. 1: R17-29.
Nam Y, Chen C, Gregory RI, Chou JJ, Sliz P. 2011. Molecular basis for interaction of let-7 microRNAs with Lin28. Cell 147(5): 1080-1091.
Noland CL, Ma E, Doudna JA. 2011. siRNA repositioning for guide strand selection by human Dicer complexes. Mol Cell 43(1): 110-121.
O'Donnell KA, Wentzel EA, Zeller KI, Dang CV, Mendell JT. 2005. c-Myc-regulated microRNAs modulate E2F1 expression. Nature 435(7043): 839-843.
Qi J, Yu JY, Shcherbata HR, Mathieu J, Wang AJ, Seal S, Zhou W, Stadler BM, Bourgin D, Wang L et al. 2009. microRNAs regulate human embryonic stem cell division. Cell Cycle 8(22): 3729-3741.
Ritchie W, Legendre M, Gautheret D. 2007. RNA stem-loops: to be or not to be cleaved by RNAse III. RNA 13(4): 457-462.
Ruby JG, Jan CH, Bartel DP. 2007. Intronic microRNA precursors that bypass Drosha processing. Nature 448(7149): 83-86.
Shcherbata HR, Hatfield S, Ward EJ, Reynolds S, Fischer KA, Ruohola-Baker H. 2006. The MicroRNA pathway plays a regulatory role in stem cell division. Cell Cycle 5(2): 172-175.
Stadler B, Ivanovska I, Mehta K, Song S, Nelson A, Tan Y, Mathieu J, Darby C, Blau CA, Ware C et al. 2010. Characterization of microRNAs involved in embryonic stem cell states. Stem Cells Dev 19(7): 935-950.
Stadler BM, Ruohola-Baker H. 2008. Small RNAs: keeping stem cells in line. Cell 132(4): 563-566.
Starega-Roslan J, Krol J, Koscianska E, Kozlowski P, Szlachcic WJ, Sobczak K, Krzyzosiak WJ. 2010. Structural basis of microRNA length variety. Nucleic Acids Res 39(1): 257-268.
Stark A, Brennecke J, Bushati N, Russell RB, Cohen SM. 2005. Animal MicroRNAs confer robustness to gene expression and have a significant impact on 3'UTR evolution. Cell 123(6): 1133-1146.
Sun G, Yan J, Noltner K, Feng J, Li H, Sarkis DA, Sommer SS, Rossi JJ. 2009. SNPs in human miRNA genes affect biogenesis and function. RNA 15(9): 1640-1651.
Takada S, Berezikov E, Yamashita Y, Lagos-Quintana M, Kloosterman WP, Enomoto M, Hatanaka H, Fujiwara S, Watanabe H, Soda M et al. 2006. Mouse microRNA profiles determined with a new and sensitive cloning method. Nucleic Acids Res 34(17): e115.
Wu M, Jolicoeur N, Li Z, Zhang L, Fortin Y, L'Abbe D, Yu Z, Shen SH. 2008. Genetic variations of microRNAs in human cancer and their effects on the expression of miRNAs. Carcinogenesis 29(9): 1710-1716.
Zeng Y, Cullen BR. 2003. Sequence requirements for micro RNA processing and function in human cells. RNA 9(1): 112-123.
Zisoulis DG, Kai ZS, Chang RK, Pasquinelli AE. 2012. Autoregulation of microRNA biogenesis by let-7 and Argonaute. Nature 486(7404): 541-544.
Mora et al. 'Enzymatic microRNA detection in microtiter plates with DNA dendrimers. Bio Techniques'. 41(4). pp 420-424. Oct. 2006.
Sperber et al. 'miRNA sensitivity to Drosha levels correlates with pre-miRNA secondly structure'. RNA. 20. pp. 621-631. Mar. 27, 2014.
Karathanasis et al. 'A bioinformatics. approach for investigating the determinants of Drosha processing'. In proceedings of the 13th IEEE International Conference on Bioinformatics and Bioengineering (IEEE BIBE 2013) Nov. 10-13, Chania, Greece. pp. 1-4. Article retrieved from the internet. URL: https://www.mensxmachina.org/files/publications/KarathanasisBIBE13.pdf.
Xing et al. 'cis-Acting Effects on RNA Processing and Drosha Cleavage Prevent Epstein-Barr Virus Latency III BHRF1 Expression'. Journal of Virology. vol. 85, No. 17. pp. 8929-8939. Sep. 2011.
Han et al. 'Molecular Basis for the Recognition of Primary microRNAs by the Drosha-DGCR8 Complex'. Cell. vol. 125. pp. 887-901. Jun. 2, 2006.
Zeng et al. 'Recognition and cleavage of primary microRNA precursors by the nuclear processing enzyme Drosha'. The EMBO Journal. vol. 24, Issue 1. pp. 138-148. Jan. 2005.
PCT/US2013/076256. International Search Report and Written Opinion. May 12, 2014.
Han, J., et al. "The Drosha-DGCR8 complex in primary microRNA processing", Genes Dev 18(24): 3016-27; 2004.
Shcherbata, H.R.. et al., "Stage-Specific Differences in the Requirements for Germline Stem Cell Maintenance in the Drosophila Ovary", Cell Stem Cell 1(6): 698-709, 2007.
Sohn, S.Y., et al., "Crystal Structure of Human DGCR8 Core", Nat Struct Mol Biol 14(9): 847-53, 2007.
Uhlen, M.P., et al., "Towards a Knowledge-Based Human Protein Atlas", Nat Biotechnol. 28(12): 1248-50, 2010.
Westholm, J.O., et al., "Mirtrons:microRNA biogenesis via splicing", Biochimie 93, 1897-1904, 2011.
Winter, J.S., et al., "Many roads to maturity: microRNA biogenesis pathways and their regulation", Nat Cell Biol., 11 (3): 228-34, 2009.

A
Drosha expression in HeLa cells, measured by qPCR, 7 biological replicates

B
Drosha protein expression in HeLa cells hsa-let-7a-1 MI0000060

UGGGAUGAGGUAGUAGGUUGUAUAGUUUUAGGGUCACACCCACCACUGG
GAGAUAACUAUACAAUCUACUGUCUUUCCUA

```
        u    gu                    uuagggucacac
   uggga gag    aguagguuguauaguu               c
   ||||| |||    ||||||||||||||||               c
   auccu uuc    ucaucuaacauaucaa               a
        ug                        uagagggucacc
```

Mismatched positions: 1, 5, 6

Fig 17A hsa-let-7a-2 MI0000061

AGGUUGAGGUAGUAGGUUGUAUAGUUUAGAAUUACAUCAAGGGAGAUAA
CUGUACAGCCUCCUAGCUUUCCU

```
     uu   g   u             uagaa  ua a
   agg  gag uag  agguuguauaguu      u c u
   |||  ||| |||  ||||||||||||||     | | c
   ucc  uuc auc  uccgacaugucaa      a g a
    -u   g   c              --uag  gg a
```

Mismatched positions: 1, 5, 9

Fig 17B hsa-let-7a-3 MI0000062
GGGUGAGGUAGUAGGUUGUAUAGUUUGGGGCUCUGCCCUGCUAUGGGA
UAACUAUACAAUCUACUGUCUUUCCU

```
         u    gu                              ‐ ‐ ‐ ‐ ‐ ‐
  ggg   gag   aguagguuguauaguu               uggggcu
  |||   |||   ||||||||||||||||                |||||| c
  ucc   uuc   ucaucuaacauaucaa               gucccgu
         u    ug                              uaggguauc
```

Mismatched positions: 1, 5, 6

Fig 17C hsa-let-7b MI0000063
CGGGGUGAGGUAGUAGGUUGUGUGGUUUCAGGGCAGUGAUGUUGCCCC
UCGGAAGAUAACUAUACAACCUACUGCCUUCCCUG

```
      u                            ucagggcagugaug
  cgggg   gagguaguagguugugugguu                    u
  |||||   |||||||||||||||||||||||
  guccc   uuccgucaucaacauaucaa                    u
      ‐                            uagaaggcucccg
```

Mismatched position: 1

Fig 17D hsa-let-7c MI0000064

GCAUCCGGGUUGAGGUAGUAGGUUGUAUGGUUUAGAGUUACACCCUGG
GAGUUAACUGUACAACCUUCUAGCUUUCCUUGGAGC

```
         a     uu    g    u                    ua   g  ua a
      gc uccggg   gag  uag  agguuguaugguu    ga  u   c  c
      || ||||||   |||  |||  ||||||||||||    ||  |   |  c
      cg agguuc   uuc  auc  uccaacaugucaa    uu  a   g  c
       -         cu    g    u                --   g  gg u
```

Mismatched positions: 1, 5, 9

Fig 17E hsa-let-7d MI0000065

CCUAGGAAGAGGUAGUAGGUUGCAUAGUUUUAGGGCAGGGAUUUUGCCCACAAGGAGG
UAACUAUACGACCUGCUGCCUUUCUUAGG

```
     a               c         uuagggcagggauu
ccuagga gagguaguagguug auaguu                   u
|||||||  ||||||||||||| ||||||
ggauucu uuccgucguccagc uaucaa                   u
   -              a         uggaggaacacccg
```

Mismatched positions: 1, 16

Fig 17F hsa-let-7e MI0000066

CCCGGGCUGAGGUAGGAGGUUGUAUAGUUGAGGAGGACACCCAAGGAG
AUCACUAUACGGCCUCCUAGCUUUCCCAGG

```
        c    cu   g                        u   ----gga    a
   cc ggg   gag  uaggagguuguauagu ga               gg   c
   || |||   |||  |||||||||||||||| ||                ||   |
   gg ccc   uuc  aucguccggcauauca cu               cc   a
        a    cu   g                   -    agaggaa    c
```

Mismatched positions: 1, 5, 22

Fig 17G hsa-let-7f-1 MI0000067

UCAGAGUGAGGUAGUAGAUUGUAUAGUUGUGGGGUAGUGAUUUUACCC
UGUUCAGGAGAUAACUAUACAAUCUAUUGCCUUCCCUGA

```
      a  ug                              ---------        u
   ucag  g   agguaguagauuguauaguugu           gggguag   g
   ||||  |   ||||||||||||||||||||||           |||||||    a
   aguc  c   ucgguaucuaacauaucaaua           ucccauu   u
      -  cu                       gaggacuug         u
```

Mismatched positions: 1, 2

Fig 17H hsa-let-7f-2 MI0000068

UGUGGGAUGAGGUAGUAGAUUGUAUAGUUUUAGGGUCAUACCCCAUCUU
GGAGAUAACUAUACAGUCUACUGUCUUUCCCACG

```
u       u    gu                  uuagggucauac
guggga  gag  aguagauuguauaguu                 c
||||||  |||  |||||||||||||||
cacccu  uuc  ucaucugacauaucaa                 c
g       -    ug                  uagagguucuac
```

Mismatched positions: 1, 5, 6

Fig 17 I hsa-let-7g MI0000433

AGGCUGAGGUAGUAGUUUGUACAGUUUGAGGGUCUAUGAUACCACCCGG
UACAGGAGAUAACUGUACAGGCCACUGCCUUGCCA

```
a    u        a                ugagg  -a   a     a
ggc  gagguagu quuuguacaguu            gucu  ug  uacc  c
|||  ||||||||  ||||||||||||           ||||   |  ||||
ccg  uuccguca  cggacaugucaa           uaga  ac  augg  c
a    -        c                -----  gg   -    c
```

Mismatched positions: 1, 10

Fig 17J hsa-let-7i MI0000434

CUGGCUGAGGUAGUAGUUUGUGCUGUUGGUCGGGUUGUGACAUUGCCC
GCUGUGGAGAUAACUGCGCAAGCUACUGCCUUGCUA

```
     c    u                         u    --------  u       ugu
  uggc gagguaguaguuugugc guu            gg  cgggu      g
  ||||  |||||||||||||||| |||            ||  |||||      a
  aucg uucggucaucgaacgcg caa            uc  gcccg      c
     -    -                         u    uagaggug  -    uua
```

Mismatched positions: 1, 19

Fig 17K

METHODS AND COMPOSITIONS TO MODULATE RNA PROCESSING

CROSS REFERENCE TO RELATED APPLICATION

This application is a national phase of PCT/US2013/076256 filed on 18 Dec. 2013 which claims priority to U.S. 61/738,821 filed on 18 Dec. 2012, the entire disclosures of both of which are incorporated by reference herein.

STATEMENT OF GOVERNMENT INTEREST

This invention was made with government support under grant no. R01 GM083867, awarded by the National Institutes of Health (NIH). The government has certain rights in the invention.

FIELD OF THE DISCLOSURE

The present disclosure provides methods and compositions to selectively modulate RNA processing. The methods and compositions selectively enhance or repress RNA processing by up- or down-regulating Drosha expression and/or by providing RNA sequences with mis-matches introduced or removed 5 and/or 9-12 nucleotide positions from the Drosha cutting site. Therapeutic uses of the methods and compositions are also described.

BACKGROUND OF THE DISCLOSURE

Generally, for a protein to exert an effect, the cell that will use or secrete the protein must create it. To create a protein the cell first makes a copy of the protein's gene sequence in the nucleus of the cell. This copy of the gene sequence that encodes for the protein (called messenger RNA ("mRNA")) leaves the nucleus and is trafficked to a region of the cell containing ribosomes. Ribosomes read the sequence of the mRNA and create the protein for which it encodes. This process of new protein synthesis is known as translation. A variety of factors affect the rate and efficiency of protein translation. Among the most significant of these factors is the intrinsic stability of the mRNA itself. If the mRNA is degraded quickly within the cell (such as before it reaches a ribosome), it is unable to serve as a template for new protein translation, thus reducing the cell's ability to create the protein for which it encoded.

MicroRNAs (miRNA which also include isomiRs) are a group of short, non-coding RNAs that bind target mRNAs to either inhibit their translation or reduce their stability. miRNAs are transcribed in the nucleus as part of a primary microRNA (pri-miRNA). The length of pri-miRNAs is highly variable, ranging from ~200 up to several thousand nucleotides (nt). pri-miRNAs are cleaved by the cellular Microprocessor complex, which consists of several components, principally Drosha and DGCR8. Drosha and DGCR8 cooperatively bind pri-miRNA, and Drosha cleaves the primary pri-miRNA transcript at ~11 base pairs from the base of the stem-loop, liberating a structure known as the precursor microRNA (pre-miRNA).

pre-miRNA is ~60-70 nt in length and forms a frequently mismatched hairpin structure with a 2 nt 3' overhang. The pre-miRNA is transported from the nucleus to the cytoplasm and is subsequently cleaved by the enzyme Dicer with its cofactor trans-activator RNA (tar)-binding protein (TRBP). Dicer binds the 3'-overhang and cleaves the pre-miRNA ~22 nt from the Drosha-cutting site to remove the terminal loop resulting in an imperfect ~22 nt miRNA/miRNA* duplex. The miRNA enters the RNA-induced silencing complex (RISC), whereas the miRNA* strand is degraded. While the Drosha and Dicer processing mechanisms are described in relation to miRNA, the same mechanisms can process various other RNA types as well including mRNA.

RNAs, including miRNAs, are involved with the onset of various diseases, immunoregulation, neural growth and stem cell renewal and maintenance. RNA levels can be regulated in several ways. For example, pri-miRNA transcription is regulated by common DNA transcription factors, e.g. c-Myc. The Microprocessor complex contains several components besides Drosha and DGCR8, such as the DEAD-box helicases p68 and p72, which have been proposed to stabilize the Microprocessor complex. Other components of the Microprocessor include SMAD proteins which have been found to selectively upregulate certain RNAs, e.g. mir-21. The DGCR8 mRNA has stem loop structures that can be cleaved by the Microprocessor, accordingly giving DGCR8 a self regulating mechanism.

SUMMARY OF THE DISCLOSURE

The current disclosure provides methods and compositions to selectively enhance or repress RNA processing by up- or down-regulating Drosha expression and/or by providing RNA sequences with mis-matches introduced or removed 5 and/or 9-12 nucleotide (nt) positions from the Drosha cutting site. Particularly, the disclosure shows that altered Drosha expression levels can selectively regulate RNAs with particular secondary structures. More particularly, the current disclosure shows that RNA with fewer mismatches located 5 nt and/or 9-12 nt from the Drosha cutting site show greater resilience to reduced Drosha expression (i.e., their cleavage is less affected by reduced Drosha expression). On the other hand, RNA with more mismatches 5 nt and/or 9-12 nt from the Drosha cutting site show reduced cleavage (decreased levels) when Drosha levels are reduced and are thus less resilient to reduced Drosha expression. The current disclosure also shows that Drosha expression fluctuates during development and across different cell types. Understanding this novel mechanism of RNA regulation as well as the fluctuating levels of Drosha expression during development and across cell types allows one to up- or down-regulate Drosha expression to affect RNAs that are expressed within a cell. Conversely or in addition, one can predict changed RNA expression during development and/or in particular cell types and can selectively up- or down-regulate RNA during times of low or high natural expression. The current disclosure also provides for the strategic design of RNAs that can be more or less resilient to changing Drosha expression. Each of these mechanisms provide avenues for intelligent therapeutic design.

BRIEF DESCRIPTION OF THE FIGURES

FIG. 17. Drosha cutting sites and mis-match positions for: A (hsa-let-7a-1; MI0000060); B (hsa-let-7a-2; MI0000061); C (hsa-let-7a-3; MI0000062); D (hsa-let-7b; MI0000063); E (hsa-let-7c; MI0000064); F (hsa-let-7d; MI0000065); G (hsa-let-7e; MI0000066); H (hsa-let-7f-1; MI0000067); I (hsa-let-7f-2; MI0000068); J (hsa-let-7g; MI0000433) and K (hsa-let-7i; MI0000434).

DETAILED DESCRIPTION

Figure 1:
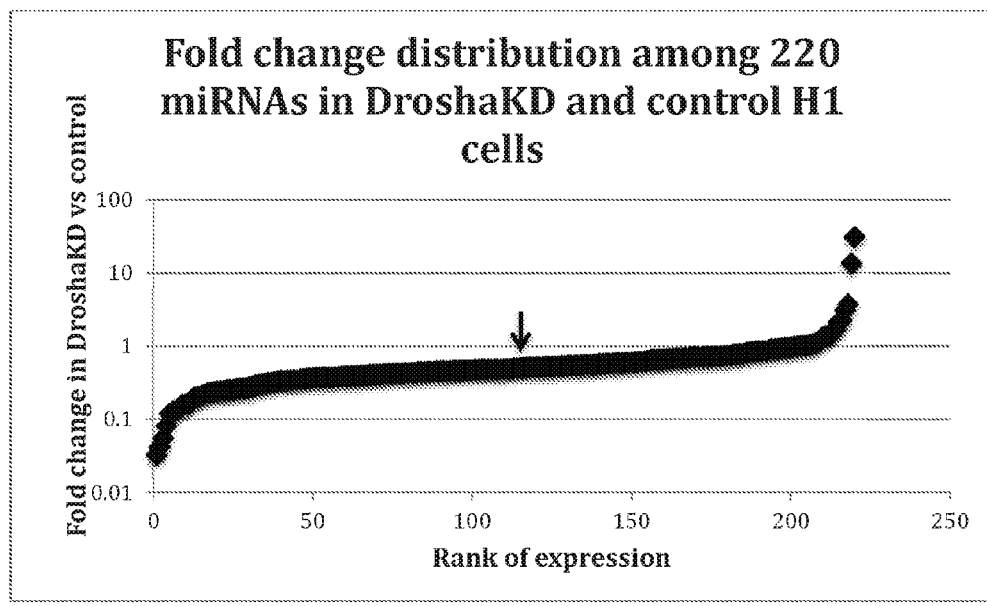
FIG. 1. Fold change of miRNA expression between Drosha knockdown and control H1 hESC for 220 miRNAs assayed by qPCR. Arrow marks median (0.495).

Ribonucleic acid (RNA) is a ubiquitous family of large biological molecules that perform multiple vital roles in the coding, decoding, regulation, and expression of genes. Common types of RNA include double-stranded (dsRNA), double-stranded with a single-stranded overhang, heterogeneous nuclear RNA, messenger RNA (mRNA), micro RNA (miRNA), small nucleolar RNA (snoRNA), ribosomal RNA (rRNA), short interfering RNA (sRNA), small nuclear RNA (snRNA), single-stranded RNA (ssRNA), small hairpin RNA (shRNA), Piwi-interacting RNA (piRNA), transfer RNA (tRNA), long non-coding RNA (lncRNA), long non-coding intergenic RNA (lincRNA) and viral RNA. Particular RNA molecules can fall into more than one RNA type. As used herein, the term "RNA" includes all types of RNA including those listed as the preceding examples and all forms of RNA known to those of ordinary skill in the art. "RNA" can also include any type of nucleic acid polymer that is processed by Drosha or Dicer.

MicroRNAs (miRNA) are a group of short, non-coding RNAs that bind target mRNAs by incomplete complementarity to either inhibit the translation, or reduce the stability of the target mRNA. miRNAs are involved with the onset of various diseases, immunoregulation, neural growth and stem cell renewal and maintenance. Currently 1,872 microRNAs are known to exist in human and many of these are evolutionarily conserved.

miRNAs are transcribed in the nucleus by RNA polymerase II or III as part of a primary microRNA (pri-miRNA).

The length of the pri-miRNA is highly variable, ranging from ~200 up to several thousand nucleotides. The pri-miRNA is cleaved by the Microprocessor, which consists of several components principally Drosha and DGCR8. Drosha and DGCR8 cooperatively bind pri-miRNA, and Drosha cleaves primary transcripts at ~11 base pairs from the base of the stem-loop and liberates a structure known as the precursor microRNA (pre-miRNA), which is ~60-70 nucleotides in length and forms a frequently mismatched hairpin structure with a ~2 nucleotide 3' overhang. A "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. The actual primary sequence of nucleotides within the stem-loop structure is not critical as long as the secondary structure is present (See FIG. 3A). As is known in the art, the secondary structure does not require exact base-pairing. Thus, the stem may include one or more base mismatches. Alternatively, the base-pairing may be exact, i.e. not include any mismatches.

pre-miRNA is transported from the nucleus to the cytoplasm by Exportin-5 and is subsequently cleaved by the enzyme Dicer with its cofactor trans-activator RNA (tar)-binding protein (TRBP). Dicer binds the 3'-overhang and cleaves the pri-miRNA ~22 nt from the Drosha-cutting site to remove the terminal loop resulting in an imperfect ~22 nt miRNA/miRNA* duplex. The miRNA enters the RNA-induced silencing complex (RISC), whereas the miRNA* strand is degraded. While this processing mechanism is described in relation to miRNA, it may also apply to all other forms of RNA and nucleic acid polymers processed by Drosha and Dicer.

RNA levels can be regulated in several ways. For example, pri-miRNA transcription is regulated by common transcription factors such as c-Myc. The Microprocessor complex contains several components besides Drosha and DGCR8, such as the DEAD-box helicases p68 and p72, which have been proposed to stabilize the Microprocessor complex. Other components of the Microprocessor include SMAD proteins which have been found to selectively upregulate certain RNAs such as mir-21. The DGCR8 mRNA has stem loop structures that can be cleaved by the Microprocessor, accordingly giving DGCR8 a self regulating mechanism.

The present disclosure shows that decreasing Drosha expression leads to heterogeneous changes in the expression of RNA. The global but non-uniform impact of Drosha knockdown on RNA expression shows that RNAs are not processed by Drosha at equal rates. Non-uniform processing effects indicate that there is some structural relationship between the Microprocessor and the RNAs it cleaves, and any other associated proteins, which could explain the effects of Drosha-knockdown on expression of specific RNAs.

Figure 2:
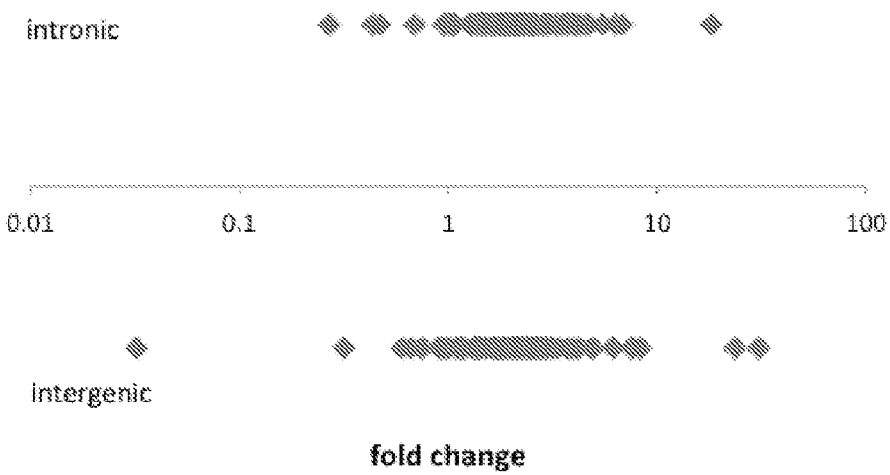
FIG. 2. Fold change of expression for miRNAs between Drosha knockdown and Control H1 hESC for 220 miRNAs assayed by qPCR and grouped by genomic origin (intergenic/intronic).

Particular proteins interact with the Microprocessor and/or RNAs to promote or inhibit processing of RNAs. Without being bound by a particular theory, it is possible that protein-based effects explain much of the variation seen in the Drosha knockdown datasets. However, such specific interactions could be considered as part of a complex feed-back mechanism triggered by Drosha-knockdown. In an effort to quantify broad, global mechanisms, which control RNA biogenesis, the genomic origin of 220 miRNAs was first investigated (some miRNAs skip Drosha-processing). Intronic miRNAs were not expressed differently from intergenic miRNAs (FIG. 2). Given that differences in expression were not explained by genomic origin, the secondary structure of RNAs was examined.

Examination of the secondary structure of RNAs was achieved by a counting mechanism and showed that the group of RNAs unaffected or upregulated by Drosha KD had less mismatched bases 5 nt and 9-12 nt from the Drosha cutting site. Additionally, the method of counting resulted in a very consistent measurement of 21 nt, which is consistent with previous reports indicating that Dicer processing of pre-miRNAs with asymmetric mismatches seems to explain the heterogeneity of length observed amongst mature miRNAs, and is also consistent with the idea that Dicer processing utilizes 'molecular rulers' which are size invariant. A general mechanism which modulates the Drosha processing step in RNA biogenesis based on differences in secondary structure has not been previously described. However, the structure of DGCR8 suggests that the RNA is bound in a bent position. Mismatches would affect the strain of a bent RNA. Without being bound by a particular theory, the present disclosure suggests that when Drosha levels are limiting, RNAs with fewer mis-matches in positions 5 and 9-12 from the Drosha cutting site are processed more efficiently than RNAs with more mis-matches in positions 5 and 9-12 from the Drosha cutting site.

Drosha cutting sites can be identified by those of ordinary skill in the art. In one embodiment, Drosha cutting sites are derived by comparison of hairpin sequences versus mature 5' miRNA sequences. The following table provides hairpin sequences associated with mature 5' miRNA sequences for Drosha cutting site calculation. The beginning of the mature 5' miRNAs corresponds to the Drosha cutting site.

TABLE 1

Exemplary full hairpin and mature 5' miRNA sequences, with positions 5 and 9-12, as determined by the counting methods described herein, shown in bold.

| miRNA name | Full Hairpin Sequence | Mature 5' Sequence |
|---|---|---|
| let-7a-1 | UGGGAUGAGGUAGUAGGUUGUAUAGUU UUAGGGUCACACCCACCACUGGGAGAU AACUAUACAAUCUACUGUCUUUCCUA (SEQ ID NO: 1) | UGAGGUAGUAGGU UGUAUAGUU (SEQ ID NO: 1873) |
| let-7b | CGGGGUGAGGUAGUAGGUUGUGUGGUU UCAGGGCAGUGAUGUUGCCCCUCGGAA GAUAACUAUACAACCUACUGCCUUCCC UG (SEQ ID NO: 4) | UGAGGUAGUAGGU UGUGUGGUU (SEQ ID NO: 1874) |
| let-7c | GCAUCCGGGUUGAGGUAGUAGGUUGUA UGGUUUAGAGUUACACCCUGGGAGUUA ACUGUACAACCUUCUAGCUUUCCUUGG AGC (SEQ ID NO: 5) | UGAGGUAGUAGGU UGUAUAGUU (SEQ ID NO: 1875) |
| let-7d | CCUAGGAAGAGGUAGUAGGUUGCAUAG UUUUAGGGCAGGGAUUUUGCCCACAAG GAGGUAACUAUACGACCUGCUGCCUUU CUUAGG (SEQ ID NO: 6) | AGAGGUAGUAGGU UGCAUAGUU (SEQ ID NO: 1876) |
| let-7e | CCCGGGCUGAGGUAGGAGGUUGUAUAG UUGAGGAGGACACCCAAGGAGAUCACU AUACGGCCUCCUAGCUUUCCCCAGG (SEQ ID NO: 7) | UGAGGUAGGAGGU UGUAUAGUU (SEQ ID NO: 1877) |
| let-7f-1 | UCAGAGUGAGGUAGUAGAUUGUAUAGU UGUGGGGUAGUGAUUUUACCCUGUUCA GGAGAUAACUAUACAAUCUAUUGCCUU CCCUGA (SEQ ID NO: 8) | UGAGGUAGUAGAU UGUAUAGUU (SEQ ID NO: 1878) |

TABLE 1-continued

Exemplary full hairpin and mature 5' miRNA sequences, with positions 5 and 9-12, as determined by the counting methods described herein, shown in bold.

| miRNA name | Full Hairpin Sequence | Mature 5' Sequence |
|---|---|---|
| let-7g | AGGCUGAGGUAGUAGUUUGUACAGUUU GAGGGUCUAUGAUACCACCCGGUACAG GAGAUAACUGUACAGGCCACUGCCUUG CCA (SEQ ID NO: 10) | UGAGGUAGUAGUU UGUACAGUU (SEQ ID NO: 1879) |
| let-7i | CUGGCUGAGGUAGUAGUUUGUGCUGUU GGUCGGGUUGUGACAUUGCCCGCUGUG GAGAUAACUGCGCAAGCUACUGCCUUG CUA (SEQ ID NO: 11) | UGAGGUAGUAGUU UGUGCUGUU (SEQ ID NO: 1880) |
| miR-21 | UGUCGGGUAGCUUAUCAGACUGAUGUU GACUGUUGAAUCUCAUGGCAACACCAG UCGAUGGGCUGUCUGACA (SEQ ID NO: 130) | UAGCUUAUCAGAC UGAUGUUGA (SEQ ID NO: 2021) |
| miR-126 | CGCUGGCGACGGGACAUUAUUACUUUU GGUACGCGCUGUGACACUUCAAACUCG UACCGUGAGUAAUAAUGCGCCGUCCAC GGCA (SEQ ID NO: 35) | CAUUAUUACUUUU GGUACGCG (SEQ ID NO: 1914) |
| miR-152 | UGUCCCCCCCGGCCCAGGUUCUGUGAU ACACUCCGACUCGGGCUCUGGAGCAGU CAGUGCAUGACAGAACUUGGGCCCGGA AGGACC (SEQ ID NO: 72) | AGGUUCUGUGAUA CACUCCGACU (SEQ ID NO: 1960) |

The calculation as described in the preceding table can be performed based on the hairpin and mature 5' sequences of the sequences provided in this disclosure's sequence listing. The following combinations of sequences provide related hairpin and mature 5' sequences.

| Name | Hairpin | Mature 5' | Name | Hairpin | Mature 5' |
|---|---|---|---|---|---|
| let-7a-1 | SEQ ID NO: 1 | SEQ ID NO: 1873 | mir-16-2 | SEQ ID NO: 80 | SEQ ID NO: 1967 |
| let-7a-2 | SEQ ID NO: 2 | SEQ ID NO: 1873 | mir-17 | SEQ ID NO: 81 | SEQ ID NO: 1968 |
| let-7a-3 | SEQ ID NO: 3 | SEQ ID NO: 1873 | mir-18a | SEQ ID NO: 95 | SEQ ID NO: 1979 |
| let-7b | SEQ ID NO: 4 | SEQ ID NO: 1874 | mir-18b | SEQ ID NO: 96 | SEQ ID NO: 1980 |
| let-7c | SEQ ID NO: 5 | SEQ ID NO: 1875 | mir-19a | SEQ ID NO: 114 | SEQ ID NO: 1999 |
| let-7d | SEQ ID NO: 6 | SEQ ID NO: 1876 | mir-19b-1 | SEQ ID NO: 115 | SEQ ID NO: 2000 |
| let-7e | SEQ ID NO: 7 | SEQ ID NO: 1877 | mir-19b-2 | SEQ ID NO: 116 | SEQ ID NO: 2001 |
| let-7f-1 | SEQ ID NO: 8 | SEQ ID NO: 1878 | mir-20a | SEQ ID NO: 128 | SEQ ID NO: 2011 |
| let-7f-2 | SEQ ID NO: 9 | SEQ ID NO: 1878 | mir-20b | SEQ ID NO: 129 | SEQ ID NO: 2012 |
| let-7g | SEQ ID NO: 10 | SEQ ID NO: 1879 | mir-21 | SEQ ID NO: 130 | SEQ ID NO: 2021 |
| let-7i | SEQ ID NO: 11 | SEQ ID NO: 1880 | mir-22 | SEQ ID NO: 144 | SEQ ID NO: 2031 |
| mir-7-3 | SEQ ID NO: 279 | SEQ ID NO: 2708 | mir-23a | SEQ ID NO: 149 | SEQ ID NO: 2035 |
| mir-7-2 | SEQ ID NO: 278 | SEQ ID NO: 2708 | mir-23b | SEQ ID NO: 150 | SEQ ID NO: 2036 |
| mir-7-1 | SEQ ID NO: 277 | SEQ ID NO: 2708 | mir-24-2 | SEQ ID NO: 153 | SEQ ID NO: 2038 |
| mir-9-3 | SEQ ID NO: 286 | SEQ ID NO: 2739 | mir-24-1 | SEQ ID NO: 152 | SEQ ID NO: 2037 |
| mir-9-2 | SEQ ID NO: 281 | SEQ ID NO: 2739 | mir-25 | SEQ ID NO: 154 | SEQ ID NO: 2040 |
| mir-9-1 | SEQ ID NO: 280 | SEQ ID NO: 2739 | mir-26a-1 | SEQ ID NO: 155 | SEQ ID NO: 2043 |
| mir-10a | SEQ ID NO: 24 | SEQ ID NO: 1887 | mir-26a-2 | SEQ ID NO: 156 | SEQ ID NO: 2043 |
| mir-10b | SEQ ID NO: 25 | SEQ ID NO: 1888 | mir-26b | SEQ ID NO: 157 | SEQ ID NO: 2044 |
| mir-15a | SEQ ID NO: 77 | SEQ ID NO: 1965 | mir-27a | SEQ ID NO: 158 | SEQ ID NO: 2045 |
| mir-15b | SEQ ID NO: 78 | SEQ ID NO: 1966 | mir-27b | SEQ ID NO: 159 | SEQ ID NO: 2046 |
| mir-16-1 | SEQ ID NO: 79 | SEQ ID NO: 1967 | mir-28 | SEQ ID NO: 160 | SEQ ID NO: 2047 |
| mir-29a | SEQ ID NO: 165 | SEQ ID NO: 2050 | mir-96 | SEQ ID NO: 288 | SEQ ID NO: 2740 |
| mir-29b-1 | SEQ ID NO: 166 | SEQ ID NO: 2051 | mir-98 | SEQ ID NO: 289 | SEQ ID NO: 2741 |
| mir-29b-2 | SEQ ID NO: 167 | SEQ ID NO: 2052 | mir-99a | SEQ ID NO: 290 | SEQ ID NO: 2742 |
| mir-29c | SEQ ID NO: 168 | SEQ ID NO: 2053 | mir-99b | SEQ ID NO: 291 | SEQ ID NO: 2743 |
| mir-30a | SEQ ID NO: 178 | SEQ ID NO: 2062 | mir-100 | SEQ ID NO: 12 | SEQ ID NO: 1881 |
| mir-30b | SEQ ID NO: 179 | SEQ ID NO: 2063 | mir-101-2 | SEQ ID NO: 14 | SEQ ID NO: 1882 |
| mir-30c-1 | SEQ ID NO: 180 | SEQ ID NO: 2064 | mir-101-1 | SEQ ID NO: 13 | SEQ ID NO: 1882 |
| mir-30c-2 | SEQ ID NO: 181 | SEQ ID NO: 2064 | mir-103a-2 | SEQ ID NO: 16 | SEQ ID NO: 1883 |
| mir-30d | SEQ ID NO: 182 | SEQ ID NO: 2065 | mir-105-2 | SEQ ID NO: 20 | SEQ ID NO: 1884 |
| mir-30e | SEQ ID NO: 183 | SEQ ID NO: 2066 | mir-105-1 | SEQ ID NO: 19 | SEQ ID NO: 1884 |
| mir-31 | SEQ ID NO: 184 | SEQ ID NO: 2086 | mir-106a | SEQ ID NO: 21 | SEQ ID NO: 1885 |
| mir-32 | SEQ ID NO: 185 | SEQ ID NO: 2104 | mir-106b | SEQ ID NO: 22 | SEQ ID NO: 1886 |
| mir-33a | SEQ ID NO: 208 | SEQ ID NO: 2113 | mir-122 | SEQ ID NO: 28 | SEQ ID NO: 1896 |
| mir-33b | SEQ ID NO: 209 | SEQ ID NO: 2114 | mir-124-3 | SEQ ID NO: 31 | SEQ ID NO: 1906 |
| mir-34a | SEQ ID NO: 214 | SEQ ID NO: 2118 | mir-124-2 | SEQ ID NO: 30 | SEQ ID NO: 1906 |
| mir-34b | SEQ ID NO: 215 | SEQ ID NO: 2119 | mir-124-1 | SEQ ID NO: 29 | SEQ ID NO: 1906 |
| mir-34c | SEQ ID NO: 216 | SEQ ID NO: 2120 | mir-125a | SEQ ID NO: 32 | SEQ ID NO: 1912 |
| mir-92a-1 | SEQ ID NO: 282 | SEQ ID NO: 2731 | mir-125b-1 | SEQ ID NO: 33 | SEQ ID NO: 1913 |
| mir-92a-2 | SEQ ID NO: 283 | SEQ ID NO: 2732 | mir-125b-2 | SEQ ID NO: 34 | SEQ ID NO: 1913 |
| mir-92b | SEQ ID NO: 284 | SEQ ID NO: 2733 | mir-126 | SEQ ID NO: 35 | SEQ ID NO: 1914 |
| mir-93 | SEQ ID NO: 285 | SEQ ID NO: 2734 | mir-127 | SEQ ID NO: 36 | SEQ ID NO: 1919 |
| mir-95 | SEQ ID NO: 287 | SEQ ID NO: 2738 | mir-128-1 | SEQ ID NO: 37 | SEQ ID NO: 1921 |
| mir-128-2 | SEQ ID NO: 38 | SEQ ID NO: 1922 | mir-146a | SEQ ID NO: 62 | SEQ ID NO: 1953 |
| mir-129-2 | SEQ ID NO: 40 | SEQ ID NO: 1928 | mir-146b | SEQ ID NO: 63 | SEQ ID NO: 1954 |
| mir-129-1 | SEQ ID NO: 39 | SEQ ID NO: 1928 | mir-148a | SEQ ID NO: 66 | SEQ ID NO: 1955 |
| mir-130a | SEQ ID NO: 41 | SEQ ID NO: 1935 | mir-148b | SEQ ID NO: 67 | SEQ ID NO: 1956 |
| mir-130b | SEQ ID NO: 42 | SEQ ID NO: 1936 | mir-149 | SEQ ID NO: 68 | SEQ ID NO: 1957 |
| mir-132 | SEQ ID NO: 43 | SEQ ID NO: 1937 | mir-150 | SEQ ID NO: 69 | SEQ ID NO: 1958 |
| mir-133a-1 | SEQ ID NO: 44 | SEQ ID NO: 1938 | mir-151a | SEQ ID NO: 70 | SEQ ID NO: 1959 |
| mir-133a-2 | SEQ ID NO: 45 | SEQ ID NO: 1938 | mir-152 | SEQ ID NO: 72 | SEQ ID NO: 1960 |
| mir-134 | SEQ ID NO: 47 | SEQ ID NO: 1940 | mir-153-2 | SEQ ID NO: 74 | SEQ ID NO: 1961 |
| mir-135a-1 | SEQ ID NO: 48 | SEQ ID NO: 1941 | mir-153-1 | SEQ ID NO: 73 | SEQ ID NO: 1961 |
| mir-135a-2 | SEQ ID NO: 49 | SEQ ID NO: 1941 | mir-154 | SEQ ID NO: 75 | SEQ ID NO: 1963 |

| Name | Hairpin | Mature 5' | Name | Hairpin | Mature 5' | Name | Hairpin | Mature 5' | Name | Hairpin | Mature 5' |
|---|---|---|---|---|---|---|---|---|---|---|---|
| mir-135b | SEQ ID NO: 50 | SEQ ID NO: 1942 | mir-155 | SEQ ID NO: 76 | SEQ ID NO: 1964 | mir-323a | SEQ ID NO: 194 | SEQ ID NO: 2101 | mir-370 | SEQ ID NO: 224 | SEQ ID NO: 2156 |
| mir-136 | SEQ ID NO: 51 | SEQ ID NO: 1943 | mir-181a-1 | SEQ ID NO: 82 | SEQ ID NO: 1969 | mir-323b | SEQ ID NO: 195 | SEQ ID NO: 2102 | mir-371a | SEQ ID NO: 225 | SEQ ID NO: 2157 |
| mir-138-2 | SEQ ID NO: 54 | SEQ ID NO: 1944 | mir-181a-2 | SEQ ID NO: 83 | SEQ ID NO: 1969 | mir-324 | SEQ ID NO: 196 | SEQ ID NO: 2103 | mir-371b | SEQ ID NO: 226 | SEQ ID NO: 2158 |
| mir-138-1 | SEQ ID NO: 53 | SEQ ID NO: 1944 | mir-181b-1 | SEQ ID NO: 84 | SEQ ID NO: 1970 | mir-328 | SEQ ID NO: 199 | SEQ ID NO: 2105 | mir-372 | SEQ ID NO: 227 | SEQ ID NO: 2159 |
| mir-139 | SEQ ID NO: 55 | SEQ ID NO: 1945 | mir-181b-2 | SEQ ID NO: 85 | SEQ ID NO: 1970 | mir-329-2 | SEQ ID NO: 201 | SEQ ID NO: 2106 | mir-373 | SEQ ID NO: 228 | SEQ ID NO: 2160 |
| mir-140 | SEQ ID NO: 56 | SEQ ID NO: 1946 | mir-181c | SEQ ID NO: 86 | SEQ ID NO: 1971 | mir-329-1 | SEQ ID NO: 200 | SEQ ID NO: 2106 | mir-374a | SEQ ID NO: 229 | SEQ ID NO: 2161 |
| mir-141 | SEQ ID NO: 57 | SEQ ID NO: 1947 | mir-181d | SEQ ID NO: 87 | SEQ ID NO: 1972 | mir-330 | SEQ ID NO: 202 | SEQ ID NO: 2107 | mir-374b | SEQ ID NO: 230 | SEQ ID NO: 2162 |
| mir-142 | SEQ ID NO: 58 | SEQ ID NO: 1948 | mir-182 | SEQ ID NO: 88 | SEQ ID NO: 1973 | mir-331 | SEQ ID NO: 203 | SEQ ID NO: 2108 | mir-374c | SEQ ID NO: 231 | SEQ ID NO: 2163 |
| mir-143 | SEQ ID NO: 59 | SEQ ID NO: 1949 | mir-183 | SEQ ID NO: 89 | SEQ ID NO: 1974 | mir-335 | SEQ ID NO: 204 | SEQ ID NO: 2109 | mir-376a-1 | SEQ ID NO: 233 | SEQ ID NO: 2165 |
| mir-144 | SEQ ID NO: 60 | SEQ ID NO: 1950 | mir-185 | SEQ ID NO: 91 | SEQ ID NO: 1975 | mir-337 | SEQ ID NO: 205 | SEQ ID NO: 2110 | mir-376a-2 | SEQ ID NO: 234 | SEQ ID NO: 2164 |
| mir-145 | SEQ ID NO: 61 | SEQ ID NO: 1951 | mir-186 | SEQ ID NO: 92 | SEQ ID NO: 1976 | mir-338 | SEQ ID NO: 206 | SEQ ID NO: 2111 | mir-376b | SEQ ID NO: 235 | SEQ ID NO: 2166 |
| mir-187 | SEQ ID NO: 93 | SEQ ID NO: 1977 | mir-204 | SEQ ID NO: 123 | SEQ ID NO: 2007 | mir-339 | SEQ ID NO: 207 | SEQ ID NO: 2112 | mir-376c | SEQ ID NO: 236 | SEQ ID NO: 2167 |
| mir-188 | SEQ ID NO: 94 | SEQ ID NO: 1978 | mir-205 | SEQ ID NO: 124 | SEQ ID NO: 2008 | mir-340 | SEQ ID NO: 210 | SEQ ID NO: 2115 | mir-377 | SEQ ID NO: 237 | SEQ ID NO: 2168 |
| mir-190a | SEQ ID NO: 97 | SEQ ID NO: 1983 | mir-208a | SEQ ID NO: 126 | SEQ ID NO: 2009 | mir-342 | SEQ ID NO: 211 | SEQ ID NO: 2116 | mir-378a | SEQ ID NO: 238 | SEQ ID NO: 2169 |
| mir-191 | SEQ ID NO: 99 | SEQ ID NO: 1988 | mir-208b | SEQ ID NO: 127 | SEQ ID NO: 2010 | mir-345 | SEQ ID NO: 212 | SEQ ID NO: 2117 | mir-379 | SEQ ID NO: 249 | SEQ ID NO: 2170 |
| mir-192 | SEQ ID NO: 100 | SEQ ID NO: 1989 | mir-210 | SEQ ID NO: 131 | SEQ ID NO: 2013 | mir-361 | SEQ ID NO: 217 | SEQ ID NO: 2128 | mir-380 | SEQ ID NO: 250 | SEQ ID NO: 2171 |
| mir-193a | SEQ ID NO: 101 | SEQ ID NO: 1990 | mir-211 | SEQ ID NO: 132 | SEQ ID NO: 2016 | mir-362 | SEQ ID NO: 218 | SEQ ID NO: 2135 | mir-381 | SEQ ID NO: 251 | SEQ ID NO: 2172 |
| mir-193b | SEQ ID NO: 102 | SEQ ID NO: 1991 | mir-212 | SEQ ID NO: 133 | SEQ ID NO: 2018 | mir-382 | SEQ ID NO: 252 | SEQ ID NO: 2173 | mir-486-2 | SEQ ID NO: 300 | SEQ ID NO: 2323 |
| mir-194-2 | SEQ ID NO: 104 | SEQ ID NO: 1992 | mir-214 | SEQ ID NO: 134 | SEQ ID NO: 2019 | mir-383 | SEQ ID NO: 253 | SEQ ID NO: 2174 | mir-486 | SEQ ID NO: 299 | SEQ ID NO: 2323 |
| mir-194-1 | SEQ ID NO: 103 | SEQ ID NO: 1992 | mir-215 | SEQ ID NO: 135 | SEQ ID NO: 2020 | mir-409 | SEQ ID NO: 255 | SEQ ID NO: 2185 | mir-487a | SEQ ID NO: 301 | SEQ ID NO: 2324 |
| mir-195 | SEQ ID NO: 105 | SEQ ID NO: 1993 | mir-216a | SEQ ID NO: 136 | SEQ ID NO: 2022 | mir-410 | SEQ ID NO: 256 | SEQ ID NO: 2186 | mir-487b | SEQ ID NO: 302 | SEQ ID NO: 2325 |
| mir-196a-1 | SEQ ID NO: 106 | SEQ ID NO: 1994 | mir-216b | SEQ ID NO: 137 | SEQ ID NO: 2023 | mir-411 | SEQ ID NO: 257 | SEQ ID NO: 2187 | mir-488 | SEQ ID NO: 303 | SEQ ID NO: 2326 |
| mir-196a-2 | SEQ ID NO: 107 | SEQ ID NO: 1994 | mir-218-2 | SEQ ID NO: 140 | SEQ ID NO: 2024 | mir-412 | SEQ ID NO: 258 | SEQ ID NO: 2188 | mir-489 | SEQ ID NO: 304 | SEQ ID NO: 2327 |
| mir-196b | SEQ ID NO: 108 | SEQ ID NO: 1995 | mir-218-1 | SEQ ID NO: 139 | SEQ ID NO: 2024 | mir-423 | SEQ ID NO: 261 | SEQ ID NO: 2189 | mir-490 | SEQ ID NO: 305 | SEQ ID NO: 2328 |
| mir-197 | SEQ ID NO: 109 | SEQ ID NO: 1996 | mir-219a-1 | SEQ ID NO: 141 | SEQ ID NO: 2025 | mir-424 | SEQ ID NO: 262 | SEQ ID NO: 2190 | mir-491 | SEQ ID NO: 306 | SEQ ID NO: 2329 |
| mir-199a-1 | SEQ ID NO: 111 | SEQ ID NO: 1997 | mir-219a-2 | SEQ ID NO: 142 | SEQ ID NO: 2025 | mir-425 | SEQ ID NO: 263 | SEQ ID NO: 2191 | mir-493 | SEQ ID NO: 308 | SEQ ID NO: 2330 |
| mir-199a-2 | SEQ ID NO: 112 | SEQ ID NO: 1997 | mir-219b | SEQ ID NO: 143 | SEQ ID NO: 2026 | mir-431 | SEQ ID NO: 265 | SEQ ID NO: 2192 | mir-494 | SEQ ID NO: 309 | SEQ ID NO: 2331 |
| mir-199b | SEQ ID NO: 113 | SEQ ID NO: 1998 | mir-221 | SEQ ID NO: 145 | SEQ ID NO: 2027 | mir-432 | SEQ ID NO: 266 | SEQ ID NO: 2193 | mir-495 | SEQ ID NO: 310 | SEQ ID NO: 2332 |
| mir-200a | SEQ ID NO: 117 | SEQ ID NO: 2002 | mir-222 | SEQ ID NO: 146 | SEQ ID NO: 2028 | mir-433 | SEQ ID NO: 267 | SEQ ID NO: 2194 | mir-497 | SEQ ID NO: 312 | SEQ ID NO: 2333 |
| mir-200b | SEQ ID NO: 118 | SEQ ID NO: 2003 | mir-223 | SEQ ID NO: 147 | SEQ ID NO: 2029 | mir-449b | SEQ ID NO: 270 | SEQ ID NO: 2203 | mir-499a | SEQ ID NO: 314 | SEQ ID NO: 2335 |
| mir-200c | SEQ ID NO: 119 | SEQ ID NO: 2004 | mir-224 | SEQ ID NO: 148 | SEQ ID NO: 2030 | mir-449c | SEQ ID NO: 271 | SEQ ID NO: 2204 | mir-499b | SEQ ID NO: 315 | SEQ ID NO: 2336 |
| mir-202 | SEQ ID NO: 120 | SEQ ID NO: 2005 | mir-296 | SEQ ID NO: 161 | SEQ ID NO: 2048 | mir-450a-1 | SEQ ID NO: 272 | SEQ ID NO: 2205 | mir-500a | SEQ ID NO: 316 | SEQ ID NO: 2346 |
| mir-203b | SEQ ID NO: 122 | SEQ ID NO: 2006 | mir-299 | SEQ ID NO: 164 | SEQ ID NO: 2049 | mir-450a-2 | SEQ ID NO: 273 | SEQ ID NO: 2205 | mir-500b | SEQ ID NO: 317 | SEQ ID NO: 2347 |
| mir-301a | SEQ ID NO: 170 | SEQ ID NO: 2054 | mir-363 | SEQ ID NO: 219 | SEQ ID NO: 2136 | mir-450b | SEQ ID NO: 274 | SEQ ID NO: 2206 | mir-501 | SEQ ID NO: 318 | SEQ ID NO: 2350 |
| mir-302a | SEQ ID NO: 172 | SEQ ID NO: 2055 | mir-365a | SEQ ID NO: 220 | SEQ ID NO: 2137 | mir-452 | SEQ ID NO: 292 | SEQ ID NO: 2211 | mir-502 | SEQ ID NO: 319 | SEQ ID NO: 2351 |
| mir-302b | SEQ ID NO: 173 | SEQ ID NO: 2056 | mir-365b | SEQ ID NO: 221 | SEQ ID NO: 2138 | mir-454 | SEQ ID NO: 293 | SEQ ID NO: 2214 | mir-503 | SEQ ID NO: 320 | SEQ ID NO: 2352 |
| mir-302c | SEQ ID NO: 174 | SEQ ID NO: 2057 | mir-367 | SEQ ID NO: 222 | SEQ ID NO: 2143 | mir-455 | SEQ ID NO: 294 | SEQ ID NO: 2215 | mir-504 | SEQ ID NO: 321 | SEQ ID NO: 2353 |
| mir-302d | SEQ ID NO: 175 | SEQ ID NO: 2058 | mir-369 | SEQ ID NO: 223 | SEQ ID NO: 2155 | mir-483 | SEQ ID NO: 296 | SEQ ID NO: 2321 | mir-505 | SEQ ID NO: 322 | SEQ ID NO: 2354 |

| Name | Hairpin | Mature 5' | Name | Hairpin | Mature 5' | Name | Hairpin | Mature 5' | Name | Hairpin | Mature 5' |
|---|---|---|---|---|---|---|---|---|---|---|---|
| mir-485 | SEQ ID NO: 298 | SEQ ID NO: 2322 | mir-506 | SEQ ID NO: 323 | SEQ ID NO: 2355 | mir-548ao | SEQ ID NO: 409 | SEQ ID NO: 2407 | mir-548h-1 | SEQ ID NO: 433 | SEQ ID NO: 2423 |
| mir-508 | SEQ ID NO: 325 | SEQ ID NO: 2356 | mir-517a | SEQ ID NO: 347 | SEQ ID NO: 2372 | mir-548ap | SEQ ID NO: 410 | SEQ ID NO: 2408 | mir-548h-2 | SEQ ID NO: 434 | SEQ ID NO: 2423 |
| mir-509-3 | SEQ ID NO: 328 | SEQ ID NO: 2359 | mir-517b | SEQ ID NO: 348 | SEQ ID NO: 2372 | mir-548aq | SEQ ID NO: 411 | SEQ ID NO: 2409 | mir-548h-3 | SEQ ID NO: 435 | SEQ ID NO: 2423 |
| mir-509-2 | SEQ ID NO: 327 | SEQ ID NO: 2360 | mir-517c | SEQ ID NO: 349 | SEQ ID NO: 2372 | mir-548ar | SEQ ID NO: 412 | SEQ ID NO: 2410 | mir-548h-4 | SEQ ID NO: 436 | SEQ ID NO: 2423 |
| mir-509-1 | SEQ ID NO: 326 | SEQ ID NO: 2360 | mir-518a-1 | SEQ ID NO: 350 | SEQ ID NO: 2375 | mir-548as | SEQ ID NO: 413 | SEQ ID NO: 2411 | mir-548h-5 | SEQ ID NO: 437 | SEQ ID NO: 2423 |
| mir-510 | SEQ ID NO: 329 | SEQ ID NO: 2361 | mir-518a-2 | SEQ ID NO: 351 | SEQ ID NO: 2375 | mir-548at | SEQ ID NO: 414 | SEQ ID NO: 2412 | mir-548j | SEQ ID NO: 442 | SEQ ID NO: 2424 |
| mir-511 | SEQ ID NO: 330 | SEQ ID NO: 2362 | mir-518c | SEQ ID NO: 353 | SEQ ID NO: 2376 | mir-548au | SEQ ID NO: 415 | SEQ ID NO: 2413 | mir-548o | SEQ ID NO: 447 | SEQ ID NO: 2425 |
| mir-512-2 | SEQ ID NO: 332 | SEQ ID NO: 2363 | mir-518d | SEQ ID NO: 354 | SEQ ID NO: 2377 | mir-548o-2 | SEQ ID NO: 448 | SEQ ID NO: 2425 | mir-593 | SEQ ID NO: 507 | SEQ ID NO: 2460 |
| mir-512-1 | SEQ ID NO: 331 | SEQ ID NO: 2363 | mir-518e | SEQ ID NO: 355 | SEQ ID NO: 2378 | mir-548t | SEQ ID NO: 452 | SEQ ID NO: 2426 | mir-597 | SEQ ID NO: 510 | SEQ ID NO: 2461 |
| mir-513a-1 | SEQ ID NO: 333 | SEQ ID NO: 2364 | mir-518f | SEQ ID NO: 356 | SEQ ID NO: 2379 | mir-548x | SEQ ID NO: 456 | SEQ ID NO: 2427 | mir-598 | SEQ ID NO: 511 | SEQ ID NO: 2462 |
| mir-513a-2 | SEQ ID NO: 334 | SEQ ID NO: 2364 | mir-519a-1 | SEQ ID NO: 357 | SEQ ID NO: 2383 | mir-548x-2 | SEQ ID NO: 457 | SEQ ID NO: 2427 | mir-605 | SEQ ID NO: 518 | SEQ ID NO: 2463 |
| mir-513b | SEQ ID NO: 335 | SEQ ID NO: 2365 | mir-519a-2 | SEQ ID NO: 358 | SEQ ID NO: 2383 | mir-550a-1 | SEQ ID NO: 461 | SEQ ID NO: 2429 | mir-615 | SEQ ID NO: 528 | SEQ ID NO: 2464 |
| mir-513c | SEQ ID NO: 336 | SEQ ID NO: 2366 | mir-519b | SEQ ID NO: 359 | SEQ ID NO: 2384 | mir-550a-2 | SEQ ID NO: 462 | SEQ ID NO: 2429 | mir-616 | SEQ ID NO: 529 | SEQ ID NO: 2465 |
| mir-514a-1 | SEQ ID NO: 337 | SEQ ID NO: 2367 | mir-519c | SEQ ID NO: 360 | SEQ ID NO: 2385 | mir-550a-3 | SEQ ID NO: 463 | SEQ ID NO: 2428 | mir-619 | SEQ ID NO: 532 | SEQ ID NO: 2466 |
| mir-514a-2 | SEQ ID NO: 338 | SEQ ID NO: 2367 | mir-519d | SEQ ID NO: 361 | SEQ ID NO: 2386 | mir-550b-2 | SEQ ID NO: 465 | SEQ ID NO: 2430 | mir-624 | SEQ ID NO: 537 | SEQ ID NO: 2467 |
| mir-514a-3 | SEQ ID NO: 339 | SEQ ID NO: 2367 | mir-519e | SEQ ID NO: 362 | SEQ ID NO: 2387 | mir-551b | SEQ ID NO: 467 | SEQ ID NO: 2431 | mir-625 | SEQ ID NO: 538 | SEQ ID NO: 2468 |
| mir-514b | SEQ ID NO: 340 | SEQ ID NO: 2368 | mir-520a | SEQ ID NO: 363 | SEQ ID NO: 2388 | mir-552 | SEQ ID NO: 468 | SEQ ID NO: 2432 | mir-627 | SEQ ID NO: 540 | SEQ ID NO: 2469 |
| mir-515-2 | SEQ ID NO: 342 | SEQ ID NO: 2369 | mir-520c | SEQ ID NO: 365 | SEQ ID NO: 2389 | mir-556 | SEQ ID NO: 472 | SEQ ID NO: 2433 | mir-628 | SEQ ID NO: 541 | SEQ ID NO: 2470 |
| mir-515-1 | SEQ ID NO: 341 | SEQ ID NO: 2369 | mir-520d | SEQ ID NO: 366 | SEQ ID NO: 2390 | mir-561 | SEQ ID NO: 476 | SEQ ID NO: 2448 | mir-629 | SEQ ID NO: 542 | SEQ ID NO: 2471 |
| mir-516a-1 | SEQ ID NO: 343 | SEQ ID NO: 2370 | mir-520f | SEQ ID NO: 368 | SEQ ID NO: 2391 | mir-570 | SEQ ID NO: 484 | SEQ ID NO: 2450 | mir-642a | SEQ ID NO: 555 | SEQ ID NO: 2472 |
| mir-516a-2 | SEQ ID NO: 344 | SEQ ID NO: 2370 | mir-520g | SEQ ID NO: 369 | SEQ ID NO: 2392 | mir-574 | SEQ ID NO: 488 | SEQ ID NO: 2451 | mir-642b | SEQ ID NO: 556 | SEQ ID NO: 2473 |
| mir-516b-1 | SEQ ID NO: 345 | SEQ ID NO: 2371 | mir-522 | SEQ ID NO: 373 | SEQ ID NO: 2393 | mir-576 | SEQ ID NO: 490 | SEQ ID NO: 2452 | mir-651 | SEQ ID NO: 565 | SEQ ID NO: 2492 |
| mir-516b-2 | SEQ ID NO: 346 | SEQ ID NO: 2371 | mir-523 | SEQ ID NO: 374 | SEQ ID NO: 2394 | mir-579 | SEQ ID NO: 493 | SEQ ID NO: 2453 | mir-652 | SEQ ID NO: 566 | SEQ ID NO: 2494 |
| mir-524 | SEQ ID NO: 375 | SEQ ID NO: 2395 | mir-548av | SEQ ID NO: 416 | SEQ ID NO: 2414 | mir-580 | SEQ ID NO: 494 | SEQ ID NO: 2454 | mir-653 | SEQ ID NO: 567 | SEQ ID NO: 2495 |
| mir-525 | SEQ ID NO: 376 | SEQ ID NO: 2396 | mir-548ay | SEQ ID NO: 419 | SEQ ID NO: 2415 | mir-582 | SEQ ID NO: 496 | SEQ ID NO: 2455 | mir-654 | SEQ ID NO: 568 | SEQ ID NO: 2496 |
| mir-526b | SEQ ID NO: 379 | SEQ ID NO: 2397 | mir-548az | SEQ ID NO: 420 | SEQ ID NO: 2416 | mir-584 | SEQ ID NO: 498 | SEQ ID NO: 2456 | mir-655 | SEQ ID NO: 569 | SEQ ID NO: 2497 |
| mir-532 | SEQ ID NO: 381 | SEQ ID NO: 2398 | mir-548b | SEQ ID NO: 421 | SEQ ID NO: 2417 | mir-585 | SEQ ID NO: 499 | SEQ ID NO: 2457 | mir-656 | SEQ ID NO: 570 | SEQ ID NO: 2498 |
| mir-539 | SEQ ID NO: 382 | SEQ ID NO: 2399 | mir-548ba | SEQ ID NO: 422 | SEQ ID NO: 2417 | mir-589 | SEQ ID NO: 503 | SEQ ID NO: 2458 | mir-659 | SEQ ID NO: 573 | SEQ ID NO: 2499 |
| mir-541 | SEQ ID NO: 383 | SEQ ID NO: 2400 | mir-548c | SEQ ID NO: 423 | SEQ ID NO: 2418 | mir-590 | SEQ ID NO: 504 | SEQ ID NO: 2459 | mir-660 | SEQ ID NO: 574 | SEQ ID NO: 2500 |
| mir-542 | SEQ ID NO: 384 | SEQ ID NO: 2401 | mir-548d-1 | SEQ ID NO: 424 | SEQ ID NO: 2419 | mir-664a | SEQ ID NO: 579 | SEQ ID NO: 2501 | mir-889 | SEQ ID NO: 611 | SEQ ID NO: 2728 |
| mir-545 | SEQ ID NO: 388 | SEQ ID NO: 2402 | mir-548d-2 | SEQ ID NO: 425 | SEQ ID NO: 2419 | mir-664b | SEQ ID NO: 580 | SEQ ID NO: 2502 | mir-891a | SEQ ID NO: 613 | SEQ ID NO: 2729 |
| mir-548a-1 | SEQ ID NO: 389 | SEQ ID NO: 2403 | mir-548e | SEQ ID NO: 426 | SEQ ID NO: 2420 | mir-668 | SEQ ID NO: 582 | SEQ ID NO: 2503 | mir-892c | SEQ ID NO: 617 | SEQ ID NO: 2730 |
| mir-548a-2 | SEQ ID NO: 390 | SEQ ID NO: 2403 | mir-548f-1 | SEQ ID NO: 427 | SEQ ID NO: 2421 | mir-670 | SEQ ID NO: 583 | SEQ ID NO: 2504 | mir-937 | SEQ ID NO: 626 | SEQ ID NO: 2735 |
| mir-548a-3 | SEQ ID NO: 391 | SEQ ID NO: 2403 | mir-548f-2 | SEQ ID NO: 428 | SEQ ID NO: 2421 | mir-671 | SEQ ID NO: 584 | SEQ ID NO: 2506 | mir-939 | SEQ ID NO: 628 | SEQ ID NO: 2736 |
| mir-548ah | SEQ ID NO: 401 | SEQ ID NO: 2404 | mir-548f-3 | SEQ ID NO: 429 | SEQ ID NO: 2421 | mir-675 | SEQ ID NO: 585 | SEQ ID NO: 2544 | mir-942 | SEQ ID NO: 634 | SEQ ID NO: 2737 |
| mir-548aj-1 | SEQ ID NO: 403 | SEQ ID NO: 2405 | mir-548f-4 | SEQ ID NO: 430 | SEQ ID NO: 2421 | mir-676 | SEQ ID NO: 586 | SEQ ID NO: 2555 | mir-1178 | SEQ ID NO: 637 | SEQ ID NO: 1889 |
| mir-548aj-2 | SEQ ID NO: 404 | SEQ ID NO: 2405 | mir-548f-5 | SEQ ID NO: 431 | SEQ ID NO: 2421 | mir-708 | SEQ ID NO: 587 | SEQ ID NO: 2684 | mir-1180 | SEQ ID NO: 639 | SEQ ID NO: 1890 |
| mir-548am | SEQ ID NO: 407 | SEQ ID NO: 2406 | mir-548g | SEQ ID NO: 432 | SEQ ID NO: 2422 | mir-744 | SEQ ID NO: 590 | SEQ ID NO: 2706 | mir-1185-2 | SEQ ID NO: 647 | SEQ ID NO: 1891 |

| Name | Hairpin | Mature 5' | Name | Hairpin | Mature 5' | Name | Hairpin | Mature 5' | Name | Hairpin | Mature 5' |
|---|---|---|---|---|---|---|---|---|---|---|---|
| mir-758 | SEQ ID NO: 591 | SEQ ID NO: 2707 | mir-1185-1 | SEQ ID NO: 646 | SEQ ID NO: 1891 | mir-3120 | SEQ ID NO: 824 | SEQ ID NO: 2068 | mir-3160-2 | SEQ ID NO: 872 | SEQ ID NO: 2087 |
| mir-766 | SEQ ID NO: 598 | SEQ ID NO: 2709 | mir-1199 | SEQ ID NO: 650 | SEQ ID NO: 1892 | mir-3121 | SEQ ID NO: 825 | SEQ ID NO: 2069 | mir-3160-1 | SEQ ID NO: 871 | SEQ ID NO: 2087 |
| mir-767 | SEQ ID NO: 599 | SEQ ID NO: 2710 | mir-1207 | SEQ ID NO: 657 | SEQ ID NO: 1893 | mir-3124 | SEQ ID NO: 828 | SEQ ID NO: 2070 | mir-3162 | SEQ ID NO: 874 | SEQ ID NO: 2088 |
| mir-769 | SEQ ID NO: 600 | SEQ ID NO: 2711 | mir-1224 | SEQ ID NO: 659 | SEQ ID NO: 1894 | mir-3126 | SEQ ID NO: 830 | SEQ ID NO: 2071 | mir-3173 | SEQ ID NO: 884 | SEQ ID NO: 2089 |
| mir-770 | SEQ ID NO: 601 | SEQ ID NO: 2712 | mir-1225 | SEQ ID NO: 660 | SEQ ID NO: 1895 | mir-3127 | SEQ ID NO: 831 | SEQ ID NO: 2072 | mir-3177 | SEQ ID NO: 888 | SEQ ID NO: 2090 |
| mir-873 | SEQ ID NO: 603 | SEQ ID NO: 2720 | mir-1226 | SEQ ID NO: 661 | SEQ ID NO: 1897 | mir-3129 | SEQ ID NO: 833 | SEQ ID NO: 2073 | mir-3180-5 | SEQ ID NO: 897 | SEQ ID NO: 2091 |
| mir-874 | SEQ ID NO: 604 | SEQ ID NO: 2721 | mir-1227 | SEQ ID NO: 662 | SEQ ID NO: 1898 | mir-3130-2 | SEQ ID NO: 835 | SEQ ID NO: 2074 | mir-3180-4 | SEQ ID NO: 896 | SEQ ID NO: 2091 |
| mir-875 | SEQ ID NO: 605 | SEQ ID NO: 2722 | mir-1228 | SEQ ID NO: 663 | SEQ ID NO: 1899 | mir-3130-1 | SEQ ID NO: 834 | SEQ ID NO: 2074 | mir-3180-3 | SEQ ID NO: 895 | SEQ ID NO: 2091 |
| mir-876 | SEQ ID NO: 606 | SEQ ID NO: 2723 | mir-1229 | SEQ ID NO: 664 | SEQ ID NO: 1900 | mir-3136 | SEQ ID NO: 842 | SEQ ID NO: 2075 | mir-3180-2 | SEQ ID NO: 894 | SEQ ID NO: 2091 |
| mir-877 | SEQ ID NO: 607 | SEQ ID NO: 2724 | mir-1233-2 | SEQ ID NO: 667 | SEQ ID NO: 1901 | mir-3140 | SEQ ID NO: 846 | SEQ ID NO: 2076 | mir-3180-1 | SEQ ID NO: 893 | SEQ ID NO: 2091 |
| mir-885 | SEQ ID NO: 608 | SEQ ID NO: 2725 | mir-1233-1 | SEQ ID NO: 666 | SEQ ID NO: 1901 | mir-3144 | SEQ ID NO: 850 | SEQ ID NO: 2077 | mir-3184 | SEQ ID NO: 901 | SEQ ID NO: 2092 |
| mir-887 | SEQ ID NO: 609 | SEQ ID NO: 2726 | mir-1236 | SEQ ID NO: 669 | SEQ ID NO: 1902 | mir-3145 | SEQ ID NO: 851 | SEQ ID NO: 2078 | mir-3186 | SEQ ID NO: 903 | SEQ ID NO: 2093 |
| mir-888 | SEQ ID NO: 610 | SEQ ID NO: 2727 | mir-1237 | SEQ ID NO: 670 | SEQ ID NO: 1903 | mir-3150a | SEQ ID NO: 856 | SEQ ID NO: 2079 | mir-3187 | SEQ ID NO: 904 | SEQ ID NO: 2094 |
| mir-1238 | SEQ ID NO: 671 | SEQ ID NO: 1904 | mir-1304 | SEQ ID NO: 759 | SEQ ID NO: 1932 | mir-3150b | SEQ ID NO: 857 | SEQ ID NO: 2080 | mir-3189 | SEQ ID NO: 906 | SEQ ID NO: 2095 |
| mir-1245b | SEQ ID NO: 677 | SEQ ID NO: 1905 | mir-1306 | SEQ ID NO: 761 | SEQ ID NO: 1933 | mir-3151 | SEQ ID NO: 858 | SEQ ID NO: 2081 | mir-3190 | SEQ ID NO: 907 | SEQ ID NO: 2096 |
| mir-1247 | SEQ ID NO: 679 | SEQ ID NO: 1907 | mir-1307 | SEQ ID NO: 762 | SEQ ID NO: 1934 | mir-3152 | SEQ ID NO: 859 | SEQ ID NO: 2082 | mir-3191 | SEQ ID NO: 908 | SEQ ID NO: 2097 |
| mir-1250 | SEQ ID NO: 682 | SEQ ID NO: 1908 | mir-1343 | SEQ ID NO: 767 | SEQ ID NO: 1939 | mir-3156-3 | SEQ ID NO: 866 | SEQ ID NO: 2083 | mir-3192 | SEQ ID NO: 909 | SEQ ID NO: 2098 |
| mir-1251 | SEQ ID NO: 683 | SEQ ID NO: 1909 | mir-1468 | SEQ ID NO: 768 | SEQ ID NO: 1952 | mir-3156-2 | SEQ ID NO: 865 | SEQ ID NO: 2083 | mir-3194 | SEQ ID NO: 911 | SEQ ID NO: 2099 |
| mir-1252 | SEQ ID NO: 684 | SEQ ID NO: 1910 | mir-1537 | SEQ ID NO: 772 | SEQ ID NO: 1962 | mir-3156-1 | SEQ ID NO: 864 | SEQ ID NO: 2083 | mir-3200 | SEQ ID NO: 919 | SEQ ID NO: 2100 |
| mir-1255b-1 | SEQ ID NO: 689 | SEQ ID NO: 1911 | mir-1908 | SEQ ID NO: 778 | SEQ ID NO: 1981 | mir-3529 | SEQ ID NO: 923 | SEQ ID NO: 2121 | mir-3681 | SEQ ID NO: 978 | SEQ ID NO: 2148 |
| mir-1255b-2 | SEQ ID NO: 690 | SEQ ID NO: 1911 | mir-1909 | SEQ ID NO: 779 | SEQ ID NO: 1982 | mir-3591 | SEQ ID NO: 924 | SEQ ID NO: 2122 | mir-3682 | SEQ ID NO: 979 | SEQ ID NO: 2149 |
| mir-1266 | SEQ ID NO: 701 | SEQ ID NO: 1915 | mir-1910 | SEQ ID NO: 780 | SEQ ID NO: 1984 | mir-3605 | SEQ ID NO: 925 | SEQ ID NO: 2123 | mir-3688-2 | SEQ ID NO: 986 | SEQ ID NO: 2150 |
| mir-1271 | SEQ ID NO: 709 | SEQ ID NO: 1916 | mir-1911 | SEQ ID NO: 781 | SEQ ID NO: 1985 | mir-3606 | SEQ ID NO: 926 | SEQ ID NO: 2124 | mir-3688-1 | SEQ ID NO: 985 | SEQ ID NO: 2150 |
| mir-1273g | SEQ ID NO: 716 | SEQ ID NO: 1917 | mir-1914 | SEQ ID NO: 784 | SEQ ID NO: 1986 | mir-3607 | SEQ ID NO: 927 | SEQ ID NO: 2125 | mir-3689a | SEQ ID NO: 987 | SEQ ID NO: 2151 |
| mir-1273h | SEQ ID NO: 717 | SEQ ID NO: 1918 | mir-1915 | SEQ ID NO: 785 | SEQ ID NO: 1987 | mir-3613 | SEQ ID NO: 932 | SEQ ID NO: 2126 | mir-3689b | SEQ ID NO: 988 | SEQ ID NO: 2152 |
| mir-1277 | SEQ ID NO: 720 | SEQ ID NO: 1920 | mir-2114 | SEQ ID NO: 795 | SEQ ID NO: 2014 | mir-3614 | SEQ ID NO: 933 | SEQ ID NO: 2127 | mir-3691 | SEQ ID NO: 996 | SEQ ID NO: 2153 |
| mir-1285-2 | SEQ ID NO: 729 | SEQ ID NO: 1923 | mir-2115 | SEQ ID NO: 796 | SEQ ID NO: 2015 | mir-3616 | SEQ ID NO: 935 | SEQ ID NO: 2129 | mir-3692 | SEQ ID NO: 997 | SEQ ID NO: 2154 |
| mir-1285-1 | SEQ ID NO: 728 | SEQ ID NO: 1923 | mir-2116 | SEQ ID NO: 797 | SEQ ID NO: 2017 | mir-3617 | SEQ ID NO: 936 | SEQ ID NO: 2130 | mir-3912 | SEQ ID NO: 1006 | SEQ ID NO: 2175 |
| mir-1287 | SEQ ID NO: 731 | SEQ ID NO: 1924 | mir-2276 | SEQ ID NO: 799 | SEQ ID NO: 2032 | mir-3619 | SEQ ID NO: 938 | SEQ ID NO: 2131 | mir-3913-2 | SEQ ID NO: 1008 | SEQ ID NO: 2176 |
| mir-1288 | SEQ ID NO: 732 | SEQ ID NO: 1925 | mir-2277 | SEQ ID NO: 800 | SEQ ID NO: 2033 | mir-3620 | SEQ ID NO: 939 | SEQ ID NO: 2132 | mir-3913-1 | SEQ ID NO: 1007 | SEQ ID NO: 2176 |
| mir-1292 | SEQ ID NO: 737 | SEQ ID NO: 1926 | mir-2355 | SEQ ID NO: 802 | SEQ ID NO: 2034 | mir-3622a | SEQ ID NO: 941 | SEQ ID NO: 2133 | mir-3922 | SEQ ID NO: 1018 | SEQ ID NO: 2177 |
| mir-1295b | SEQ ID NO: 741 | SEQ ID NO: 1927 | mir-2467 | SEQ ID NO: 804 | SEQ ID NO: 2039 | mir-3622b | SEQ ID NO: 942 | SEQ ID NO: 2134 | mir-3925 | SEQ ID NO: 1021 | SEQ ID NO: 2178 |
| mir-1296 | SEQ ID NO: 742 | SEQ ID NO: 1929 | mir-2681 | SEQ ID NO: 805 | SEQ ID NO: 2041 | mir-3663 | SEQ ID NO: 959 | SEQ ID NO: 2139 | mir-3927 | SEQ ID NO: 1024 | SEQ ID NO: 2179 |
| mir-1298 | SEQ ID NO: 744 | SEQ ID NO: 1930 | mir-2682 | SEQ ID NO: 806 | SEQ ID NO: 2042 | mir-3664 | SEQ ID NO: 960 | SEQ ID NO: 2140 | mir-3928 | SEQ ID NO: 1025 | SEQ ID NO: 2180 |
| mir-1301 | SEQ ID NO: 746 | SEQ ID NO: 1931 | mir-3064 | SEQ ID NO: 809 | SEQ ID NO: 2059 | mir-3667 | SEQ ID NO: 963 | SEQ ID NO: 2141 | mir-3934 | SEQ ID NO: 1027 | SEQ ID NO: 2181 |
| mir-3065 | SEQ ID NO: 810 | SEQ ID NO: 2060 | mir-3157 | SEQ ID NO: 867 | SEQ ID NO: 2084 | mir-3675 | SEQ ID NO: 972 | SEQ ID NO: 2142 | mir-3940 | SEQ ID NO: 1033 | SEQ ID NO: 2182 |
| mir-3074 | SEQ ID NO: 811 | SEQ ID NO: 2061 | mir-3158-2 | SEQ ID NO: 869 | SEQ ID NO: 2085 | mir-3677 | SEQ ID NO: 973 | SEQ ID NO: 2144 | mir-3942 | SEQ ID NO: 1035 | SEQ ID NO: 2183 |
| mir-3117 | SEQ ID NO: 815 | SEQ ID NO: 2067 | mir-3158-1 | SEQ ID NO: 868 | SEQ ID NO: 2085 | mir-3678 | SEQ ID NO: 974 | SEQ ID NO: 2145 | mir-3944 | SEQ ID NO: 1037 | SEQ ID NO: 2184 |

-continued

| Name | Hairpin | Mature 5' | Name | Hairpin | Mature 5' |
|---|---|---|---|---|---|
| mir-3679 | SEQ ID NO: 975 | SEQ ID NO: 2146 | mir-4423 | SEQ ID NO: 1136 | SEQ ID NO: 2195 |
| mir-3680-2 | SEQ ID NO: 977 | SEQ ID NO: 2147 | mir-4433b | SEQ ID NO: 1147 | SEQ ID NO: 2197 |
| mir-3680-1 | SEQ ID NO: 976 | SEQ ID NO: 2147 | mir-4433 | SEQ ID NO: 1146 | SEQ ID NO: 2196 |
| mir-4436b-1 | SEQ ID NO: 1152 | SEQ ID NO: 2198 | mir-4650-1 | SEQ ID NO: 1284 | SEQ ID NO: 2224 |
| mir-4436b-2 | SEQ ID NO: 1153 | SEQ ID NO: 2198 | mir-4652 | SEQ ID NO: 1287 | SEQ ID NO: 2225 |
| mir-4445 | SEQ ID NO: 1163 | SEQ ID NO: 2199 | mir-4653 | SEQ ID NO: 1288 | SEQ ID NO: 2226 |
| mir-4446 | SEQ ID NO: 1164 | SEQ ID NO: 2200 | mir-4655 | SEQ ID NO: 1290 | SEQ ID NO: 2227 |
| mir-4474 | SEQ ID NO: 1193 | SEQ ID NO: 2201 | mir-4659a | SEQ ID NO: 1294 | SEQ ID NO: 2228 |
| mir-4482 | SEQ ID NO: 1202 | SEQ ID NO: 2202 | mir-4659b | SEQ ID NO: 1295 | SEQ ID NO: 2229 |
| mir-4520a | SEQ ID NO: 1242 | SEQ ID NO: 2207 | mir-4661 | SEQ ID NO: 1297 | SEQ ID NO: 2230 |
| mir-4520b | SEQ ID NO: 1243 | SEQ ID NO: 2208 | mir-4662a | SEQ ID NO: 1298 | SEQ ID NO: 2231 |
| mir-4524a | SEQ ID NO: 1247 | SEQ ID NO: 2209 | mir-4664 | SEQ ID NO: 1301 | SEQ ID NO: 2232 |
| mir-4524b | SEQ ID NO: 1248 | SEQ ID NO: 2210 | mir-4665 | SEQ ID NO: 1302 | SEQ ID NO: 2233 |
| mir-4529 | SEQ ID NO: 1253 | SEQ ID NO: 2212 | mir-4666a | SEQ ID NO: 1303 | SEQ ID NO: 2234 |
| mir-4536-2 | SEQ ID NO: 1261 | SEQ ID NO: 2213 | mir-4667 | SEQ ID NO: 1305 | SEQ ID NO: 2235 |
| mir-4536-1 | SEQ ID NO: 1260 | SEQ ID NO: 2213 | mir-4668 | SEQ ID NO: 1306 | SEQ ID NO: 2236 |
| mir-4632 | SEQ ID NO: 1266 | SEQ ID NO: 2216 | mir-4670 | SEQ ID NO: 1308 | SEQ ID NO: 2237 |
| mir-4633 | SEQ ID NO: 1267 | SEQ ID NO: 2217 | mir-4671 | SEQ ID NO: 1309 | SEQ ID NO: 2238 |
| mir-4638 | SEQ ID NO: 1272 | SEQ ID NO: 2218 | mir-4676 | SEQ ID NO: 1314 | SEQ ID NO: 2239 |
| mir-4639 | SEQ ID NO: 1273 | SEQ ID NO: 2219 | mir-4677 | SEQ ID NO: 1315 | SEQ ID NO: 2240 |
| mir-4640 | SEQ ID NO: 1274 | SEQ ID NO: 2220 | mir-4680 | SEQ ID NO: 1319 | SEQ ID NO: 2241 |
| mir-4645 | SEQ ID NO: 1279 | SEQ ID NO: 2221 | mir-4684 | SEQ ID NO: 1323 | SEQ ID NO: 2242 |
| mir-4646 | SEQ ID NO: 1280 | SEQ ID NO: 2222 | mir-4685 | SEQ ID NO: 1324 | SEQ ID NO: 2243 |
| mir-4649 | SEQ ID NO: 1283 | SEQ ID NO: 2223 | mir-4687 | SEQ ID NO: 1326 | SEQ ID NO: 2244 |
| mir-4650-2 | SEQ ID NO: 1285 | SEQ ID NO: 2224 | mir-4690 | SEQ ID NO: 1329 | SEQ ID NO: 2245 |
| mir-4691 | SEQ ID NO: 1330 | SEQ ID NO: 2246 | mir-4723 | SEQ ID NO: 1361 | SEQ ID NO: 2268 |
| mir-4693 | SEQ ID NO: 1332 | SEQ ID NO: 2247 | mir-4724 | SEQ ID NO: 1362 | SEQ ID NO: 2269 |
| mir-4694 | SEQ ID NO: 1333 | SEQ ID NO: 2248 | mir-4725 | SEQ ID NO: 1363 | SEQ ID NO: 2270 |
| mir-4695 | SEQ ID NO: 1334 | SEQ ID NO: 2249 | mir-4726 | SEQ ID NO: 1364 | SEQ ID NO: 2271 |
| mir-4697 | SEQ ID NO: 1336 | SEQ ID NO: 2250 | mir-4727 | SEQ ID NO: 1365 | SEQ ID NO: 2272 |
| mir-4699 | SEQ ID NO: 1338 | SEQ ID NO: 2251 | mir-4728 | SEQ ID NO: 1366 | SEQ ID NO: 2273 |
| mir-4700 | SEQ ID NO: 1339 | SEQ ID NO: 2252 | mir-4731 | SEQ ID NO: 1369 | SEQ ID NO: 2274 |
| mir-4701 | SEQ ID NO: 1340 | SEQ ID NO: 2253 | mir-4732 | SEQ ID NO: 1370 | SEQ ID NO: 2275 |
| mir-4703 | SEQ ID NO: 1341 | SEQ ID NO: 2254 | mir-4733 | SEQ ID NO: 1371 | SEQ ID NO: 2276 |
| mir-4704 | SEQ ID NO: 1342 | SEQ ID NO: 2255 | mir-4735 | SEQ ID NO: 1373 | SEQ ID NO: 2277 |
| mir-4707 | SEQ ID NO: 1345 | SEQ ID NO: 2256 | mir-4738 | SEQ ID NO: 1376 | SEQ ID NO: 2278 |
| mir-4708 | SEQ ID NO: 1346 | SEQ ID NO: 2257 | mir-4740 | SEQ ID NO: 1378 | SEQ ID NO: 2279 |
| mir-4709 | SEQ ID NO: 1347 | SEQ ID NO: 2258 | mir-4742 | SEQ ID NO: 1380 | SEQ ID NO: 2280 |

-continued

| Name | Hairpin | Mature 5' | Name | Hairpin | Mature 5' |
|---|---|---|---|---|---|
| mir-4711 | SEQ ID NO: 1349 | SEQ ID NO: 2259 | mir-4743 | SEQ ID NO: 1381 | SEQ ID NO: 2281 |
| mir-4712 | SEQ ID NO: 1350 | SEQ ID NO: 2260 | mir-4745 | SEQ ID NO: 1383 | SEQ ID NO: 2282 |
| mir-4713 | SEQ ID NO: 1351 | SEQ ID NO: 2261 | mir-4746 | SEQ ID NO: 1384 | SEQ ID NO: 2283 |
| mir-4714 | SEQ ID NO: 1352 | SEQ ID NO: 2262 | mir-4747 | SEQ ID NO: 1385 | SEQ ID NO: 2284 |
| mir-4715 | SEQ ID NO: 1353 | SEQ ID NO: 2263 | mir-4749 | SEQ ID NO: 1387 | SEQ ID NO: 2285 |
| mir-4716 | SEQ ID NO: 1354 | SEQ ID NO: 2264 | mir-4750 | SEQ ID NO: 1388 | SEQ ID NO: 2286 |
| mir-4717 | SEQ ID NO: 1355 | SEQ ID NO: 2265 | mir-4753 | SEQ ID NO: 1391 | SEQ ID NO: 2287 |
| mir-4720 | SEQ ID NO: 1358 | SEQ ID NO: 2266 | mir-4755 | SEQ ID NO: 1393 | SEQ ID NO: 2288 |
| mir-4722 | SEQ ID NO: 1360 | SEQ ID NO: 2267 | mir-4756 | SEQ ID NO: 1394 | SEQ ID NO: 2289 |
| mir-4757 | SEQ ID NO: 1395 | SEQ ID NO: 2290 | mir-4790 | SEQ ID NO: 1431 | SEQ ID NO: 2311 |
| mir-4758 | SEQ ID NO: 1396 | SEQ ID NO: 2291 | mir-4793 | SEQ ID NO: 1434 | SEQ ID NO: 2312 |
| mir-4760 | SEQ ID NO: 1398 | SEQ ID NO: 2292 | mir-4795 | SEQ ID NO: 1436 | SEQ ID NO: 2313 |
| mir-4761 | SEQ ID NO: 1399 | SEQ ID NO: 2293 | mir-4796 | SEQ ID NO: 1437 | SEQ ID NO: 2314 |
| mir-4762 | SEQ ID NO: 1400 | SEQ ID NO: 2294 | mir-4797 | SEQ ID NO: 1438 | SEQ ID NO: 2315 |
| mir-4763 | SEQ ID NO: 1401 | SEQ ID NO: 2295 | mir-4798 | SEQ ID NO: 1439 | SEQ ID NO: 2316 |
| mir-4764 | SEQ ID NO: 1402 | SEQ ID NO: 2296 | mir-4799 | SEQ ID NO: 1440 | SEQ ID NO: 2317 |
| mir-4766 | SEQ ID NO: 1404 | SEQ ID NO: 2297 | mir-4800 | SEQ ID NO: 1441 | SEQ ID NO: 2318 |
| mir-4768 | SEQ ID NO: 1406 | SEQ ID NO: 2298 | mir-4802 | SEQ ID NO: 1443 | SEQ ID NO: 2319 |
| mir-4769 | SEQ ID NO: 1407 | SEQ ID NO: 2299 | mir-4804 | SEQ ID NO: 1445 | SEQ ID NO: 2320 |
| mir-4772 | SEQ ID NO: 1411 | SEQ ID NO: 2300 | mir-4999 | SEQ ID NO: 1446 | SEQ ID NO: 2334 |
| mir-4774 | SEQ ID NO: 1414 | SEQ ID NO: 2301 | mir-5000 | SEQ ID NO: 1447 | SEQ ID NO: 2337 |
| mir-4776-2 | SEQ ID NO: 1417 | SEQ ID NO: 2302 | mir-5001 | SEQ ID NO: 1448 | SEQ ID NO: 2338 |
| mir-4776-1 | SEQ ID NO: 1416 | SEQ ID NO: 2302 | mir-5002 | SEQ ID NO: 1449 | SEQ ID NO: 2339 |
| mir-4777 | SEQ ID NO: 1418 | SEQ ID NO: 2303 | mir-5003 | SEQ ID NO: 1450 | SEQ ID NO: 2340 |
| mir-4778 | SEQ ID NO: 1419 | SEQ ID NO: 2304 | mir-5004 | SEQ ID NO: 1451 | SEQ ID NO: 2341 |
| mir-4781 | SEQ ID NO: 1422 | SEQ ID NO: 2305 | mir-5006 | SEQ ID NO: 1452 | SEQ ID NO: 2342 |
| mir-4782 | SEQ ID NO: 1423 | SEQ ID NO: 2306 | mir-5007 | SEQ ID NO: 1453 | SEQ ID NO: 2343 |
| mir-4783 | SEQ ID NO: 1424 | SEQ ID NO: 2307 | mir-5008 | SEQ ID NO: 1454 | SEQ ID NO: 2344 |
| mir-4786 | SEQ ID NO: 1427 | SEQ ID NO: 2308 | mir-5009 | SEQ ID NO: 1455 | SEQ ID NO: 2345 |
| mir-4787 | SEQ ID NO: 1428 | SEQ ID NO: 2309 | mir-5010 | SEQ ID NO: 1456 | SEQ ID NO: 2348 |
| mir-4789 | SEQ ID NO: 1430 | SEQ ID NO: 2310 | mir-5011 | SEQ ID NO: 1457 | SEQ ID NO: 2349 |
| mir-5088 | SEQ ID NO: 1460 | SEQ ID NO: 2357 | mir-5699 | SEQ ID NO: 1521 | SEQ ID NO: 2449 |
| mir-5089 | SEQ ID NO: 1461 | SEQ ID NO: 2358 | mir-6499 | SEQ ID NO: 1571 | SEQ ID NO: 2474 |
| mir-5187 | SEQ ID NO: 1471 | SEQ ID NO: 2373 | mir-6500 | SEQ ID NO: 1572 | SEQ ID NO: 2475 |
| mir-5189 | SEQ ID NO: 1473 | SEQ ID NO: 2374 | mir-6501 | SEQ ID NO: 1573 | SEQ ID NO: 2476 |
| mir-5195 | SEQ ID NO: 1479 | SEQ ID NO: 2380 | mir-6502 | SEQ ID NO: 1574 | SEQ ID NO: 2477 |
| mir-5196 | SEQ ID NO: 1480 | SEQ ID NO: 2381 | mir-6503 | SEQ ID NO: 1575 | SEQ ID NO: 2478 |
| mir-5197 | SEQ ID NO: 1481 | SEQ ID NO: 2382 | mir-6504 | SEQ ID NO: 1576 | SEQ ID NO: 2479 |

| Name | Hairpin | Mature 5' | Name | Hairpin | Mature 5' | Name | Hairpin | Mature 5' | Name | Hairpin | Mature 5' |
|---|---|---|---|---|---|---|---|---|---|---|---|
| mir-5571 | SEQ ID NO: 1482 | SEQ ID NO: 2434 | mir-6505 | SEQ ID NO: 1577 | SEQ ID NO: 2480 | mir-6761 | SEQ ID NO: 1640 | SEQ ID NO: 2550 | mir-6780a | SEQ ID NO: 1662 | SEQ ID NO: 2571 |
| mir-5579 | SEQ ID NO: 1484 | SEQ ID NO: 2435 | mir-6506 | SEQ ID NO: 1578 | SEQ ID NO: 2481 | mir-6762 | SEQ ID NO: 1641 | SEQ ID NO: 2551 | mir-6780b | SEQ ID NO: 1663 | SEQ ID NO: 2572 |
| mir-5580 | SEQ ID NO: 1485 | SEQ ID NO: 2436 | mir-6507 | SEQ ID NO: 1579 | SEQ ID NO: 2482 | mir-6763 | SEQ ID NO: 1642 | SEQ ID NO: 2552 | mir-6781 | SEQ ID NO: 1664 | SEQ ID NO: 2573 |
| mir-5581 | SEQ ID NO: 1486 | SEQ ID NO: 2437 | mir-6508 | SEQ ID NO: 1580 | SEQ ID NO: 2483 | mir-6764 | SEQ ID NO: 1643 | SEQ ID NO: 2553 | mir-6782 | SEQ ID NO: 1665 | SEQ ID NO: 2574 |
| mir-5582 | SEQ ID NO: 1487 | SEQ ID NO: 2438 | mir-6509 | SEQ ID NO: 1581 | SEQ ID NO: 2484 | mir-6765 | SEQ ID NO: 1644 | SEQ ID NO: 2554 | mir-6783 | SEQ ID NO: 1666 | SEQ ID NO: 2575 |
| mir-5583-2 | SEQ ID NO: 1489 | SEQ ID NO: 2439 | mir-6510 | SEQ ID NO: 1582 | SEQ ID NO: 2485 | mir-6766 | SEQ ID NO: 1645 | SEQ ID NO: 2556 | mir-6784 | SEQ ID NO: 1667 | SEQ ID NO: 2576 |
| mir-5583-1 | SEQ ID NO: 1488 | SEQ ID NO: 2439 | mir-6511a-1 | SEQ ID NO: 1583 | SEQ ID NO: 2486 | mir-6767 | SEQ ID NO: 1646 | SEQ ID NO: 2557 | mir-6785 | SEQ ID NO: 1668 | SEQ ID NO: 2577 |
| mir-5584 | SEQ ID NO: 1490 | SEQ ID NO: 2440 | mir-6511a-2 | SEQ ID NO: 1584 | SEQ ID NO: 2486 | mir-6768 | SEQ ID NO: 1647 | SEQ ID NO: 2558 | mir-6786 | SEQ ID NO: 1669 | SEQ ID NO: 2578 |
| mir-5585 | SEQ ID NO: 1491 | SEQ ID NO: 2441 | mir-6511a-3 | SEQ ID NO: 1585 | SEQ ID NO: 2486 | mir-6769a | SEQ ID NO: 1648 | SEQ ID NO: 2559 | mir-6787 | SEQ ID NO: 1670 | SEQ ID NO: 2579 |
| mir-5586 | SEQ ID NO: 1492 | SEQ ID NO: 2442 | mir-6511a-4 | SEQ ID NO: 1586 | SEQ ID NO: 2486 | mir-6769b | SEQ ID NO: 1649 | SEQ ID NO: 2560 | mir-6788 | SEQ ID NO: 1671 | SEQ ID NO: 2580 |
| mir-5587 | SEQ ID NO: 1493 | SEQ ID NO: 2443 | mir-6511b-1 | SEQ ID NO: 1587 | SEQ ID NO: 2487 | mir-6770-3 | SEQ ID NO: 1652 | SEQ ID NO: 2561 | mir-6789 | SEQ ID NO: 1672 | SEQ ID NO: 2581 |
| mir-5588 | SEQ ID NO: 1494 | SEQ ID NO: 2444 | mir-6511b-2 | SEQ ID NO: 1588 | SEQ ID NO: 2487 | mir-6770-2 | SEQ ID NO: 1651 | SEQ ID NO: 2561 | mir-6790 | SEQ ID NO: 1673 | SEQ ID NO: 2582 |
| mir-5589 | SEQ ID NO: 1495 | SEQ ID NO: 2445 | mir-6512 | SEQ ID NO: 1589 | SEQ ID NO: 2488 | mir-6770-1 | SEQ ID NO: 1650 | SEQ ID NO: 2561 | mir-6791 | SEQ ID NO: 1674 | SEQ ID NO: 2583 |
| mir-5590 | SEQ ID NO: 1496 | SEQ ID NO: 2446 | mir-6513 | SEQ ID NO: 1590 | SEQ ID NO: 2489 | mir-6771 | SEQ ID NO: 1653 | SEQ ID NO: 2562 | mir-6792 | SEQ ID NO: 1675 | SEQ ID NO: 2584 |
| mir-5591 | SEQ ID NO: 1497 | SEQ ID NO: 2447 | mir-6514 | SEQ ID NO: 1591 | SEQ ID NO: 2490 | mir-6772 | SEQ ID NO: 1654 | SEQ ID NO: 2563 | mir-6793 | SEQ ID NO: 1676 | SEQ ID NO: 2585 |
| mir-6515 | SEQ ID NO: 1592 | SEQ ID NO: 2491 | mir-6737 | SEQ ID NO: 1616 | SEQ ID NO: 2526 | mir-6773 | SEQ ID NO: 1655 | SEQ ID NO: 2564 | mir-6794 | SEQ ID NO: 1677 | SEQ ID NO: 2586 |
| mir-6516 | SEQ ID NO: 1593 | SEQ ID NO: 2493 | mir-6738 | SEQ ID NO: 1617 | SEQ ID NO: 2527 | mir-6774 | SEQ ID NO: 1656 | SEQ ID NO: 2565 | mir-6795 | SEQ ID NO: 1678 | SEQ ID NO: 2587 |
| mir-6715b | SEQ ID NO: 1595 | SEQ ID NO: 2505 | mir-6739 | SEQ ID NO: 1618 | SEQ ID NO: 2528 | mir-6775 | SEQ ID NO: 1657 | SEQ ID NO: 2566 | mir-6796 | SEQ ID NO: 1679 | SEQ ID NO: 2588 |
| mir-6716 | SEQ ID NO: 1596 | SEQ ID NO: 2507 | mir-6740 | SEQ ID NO: 1619 | SEQ ID NO: 2529 | mir-6776 | SEQ ID NO: 1658 | SEQ ID NO: 2567 | mir-6797 | SEQ ID NO: 1680 | SEQ ID NO: 2589 |
| mir-6717 | SEQ ID NO: 1597 | SEQ ID NO: 2508 | mir-6741 | SEQ ID NO: 1620 | SEQ ID NO: 2530 | mir-6777 | SEQ ID NO: 1659 | SEQ ID NO: 2568 | mir-6798 | SEQ ID NO: 1681 | SEQ ID NO: 2590 |
| mir-6718 | SEQ ID NO: 1598 | SEQ ID NO: 2509 | mir-6742 | SEQ ID NO: 1621 | SEQ ID NO: 2531 | mir-6778 | SEQ ID NO: 1660 | SEQ ID NO: 2569 | mir-6799 | SEQ ID NO: 1682 | SEQ ID NO: 2591 |
| mir-6720 | SEQ ID NO: 1600 | SEQ ID NO: 2510 | mir-6743 | SEQ ID NO: 1622 | SEQ ID NO: 2532 | mir-6800 | SEQ ID NO: 1683 | SEQ ID NO: 2592 | mir-6822 | SEQ ID NO: 1705 | SEQ ID NO: 2614 |
| mir-6721 | SEQ ID NO: 1601 | SEQ ID NO: 2511 | mir-6744 | SEQ ID NO: 1623 | SEQ ID NO: 2533 | mir-6801 | SEQ ID NO: 1684 | SEQ ID NO: 2593 | mir-6823 | SEQ ID NO: 1706 | SEQ ID NO: 2615 |
| mir-6722 | SEQ ID NO: 1602 | SEQ ID NO: 2512 | mir-6746 | SEQ ID NO: 1625 | SEQ ID NO: 2534 | mir-6802 | SEQ ID NO: 1685 | SEQ ID NO: 2594 | mir-6824 | SEQ ID NO: 1707 | SEQ ID NO: 2616 |
| mir-6723 | SEQ ID NO: 1603 | SEQ ID NO: 2513 | mir-6747 | SEQ ID NO: 1626 | SEQ ID NO: 2535 | mir-6803 | SEQ ID NO: 1686 | SEQ ID NO: 2595 | mir-6825 | SEQ ID NO: 1708 | SEQ ID NO: 2617 |
| mir-6724 | SEQ ID NO: 1604 | SEQ ID NO: 2514 | mir-6748 | SEQ ID NO: 1627 | SEQ ID NO: 2536 | mir-6804 | SEQ ID NO: 1687 | SEQ ID NO: 2596 | mir-6826 | SEQ ID NO: 1709 | SEQ ID NO: 2618 |
| mir-6726 | SEQ ID NO: 1605 | SEQ ID NO: 2515 | mir-6749 | SEQ ID NO: 1628 | SEQ ID NO: 2537 | mir-6805 | SEQ ID NO: 1688 | SEQ ID NO: 2597 | mir-6827 | SEQ ID NO: 1710 | SEQ ID NO: 2619 |
| mir-6727 | SEQ ID NO: 1606 | SEQ ID NO: 2516 | mir-6750 | SEQ ID NO: 1629 | SEQ ID NO: 2538 | mir-6806 | SEQ ID NO: 1689 | SEQ ID NO: 2598 | mir-6828 | SEQ ID NO: 1711 | SEQ ID NO: 2620 |
| mir-6728 | SEQ ID NO: 1607 | SEQ ID NO: 2517 | mir-6751 | SEQ ID NO: 1630 | SEQ ID NO: 2539 | mir-6807 | SEQ ID NO: 1690 | SEQ ID NO: 2599 | mir-6829 | SEQ ID NO: 1712 | SEQ ID NO: 2621 |
| mir-6729 | SEQ ID NO: 1608 | SEQ ID NO: 2518 | mir-6752 | SEQ ID NO: 1631 | SEQ ID NO: 2540 | mir-6808 | SEQ ID NO: 1691 | SEQ ID NO: 2600 | mir-6830 | SEQ ID NO: 1713 | SEQ ID NO: 2622 |
| mir-6730 | SEQ ID NO: 1609 | SEQ ID NO: 2519 | mir-6753 | SEQ ID NO: 1632 | SEQ ID NO: 2541 | mir-6809 | SEQ ID NO: 1692 | SEQ ID NO: 2601 | mir-6831 | SEQ ID NO: 1714 | SEQ ID NO: 2623 |
| mir-6731 | SEQ ID NO: 1610 | SEQ ID NO: 2520 | mir-6754 | SEQ ID NO: 1633 | SEQ ID NO: 2542 | mir-6810 | SEQ ID NO: 1693 | SEQ ID NO: 2602 | mir-6832 | SEQ ID NO: 1715 | SEQ ID NO: 2624 |
| mir-6732 | SEQ ID NO: 1611 | SEQ ID NO: 2521 | mir-6755 | SEQ ID NO: 1634 | SEQ ID NO: 2543 | mir-6811 | SEQ ID NO: 1694 | SEQ ID NO: 2603 | mir-6833 | SEQ ID NO: 1716 | SEQ ID NO: 2625 |
| mir-6733 | SEQ ID NO: 1612 | SEQ ID NO: 2522 | mir-6756 | SEQ ID NO: 1635 | SEQ ID NO: 2545 | mir-6812 | SEQ ID NO: 1695 | SEQ ID NO: 2604 | mir-6834 | SEQ ID NO: 1717 | SEQ ID NO: 2626 |
| mir-6734 | SEQ ID NO: 1613 | SEQ ID NO: 2523 | mir-6757 | SEQ ID NO: 1636 | SEQ ID NO: 2546 | mir-6813 | SEQ ID NO: 1696 | SEQ ID NO: 2605 | mir-6835 | SEQ ID NO: 1718 | SEQ ID NO: 2627 |
| mir-6735 | SEQ ID NO: 1614 | SEQ ID NO: 2524 | mir-6758 | SEQ ID NO: 1637 | SEQ ID NO: 2547 | mir-6814 | SEQ ID NO: 1697 | SEQ ID NO: 2606 | mir-6836 | SEQ ID NO: 1719 | SEQ ID NO: 2628 |
| mir-6736 | SEQ ID NO: 1615 | SEQ ID NO: 2525 | mir-6759 | SEQ ID NO: 1638 | SEQ ID NO: 2548 | mir-6815 | SEQ ID NO: 1698 | SEQ ID NO: 2607 | mir-6837 | SEQ ID NO: 1720 | SEQ ID NO: 2629 |
| mir-6760 | SEQ ID NO: 1639 | SEQ ID NO: 2549 | mir-6779 | SEQ ID NO: 1661 | SEQ ID NO: 2570 | mir-6816 | SEQ ID NO: 1699 | SEQ ID NO: 2608 | mir-6838 | SEQ ID NO: 1721 | SEQ ID NO: 2630 |

| Name | Hairpin | Mature 5' | Name | Hairpin | Mature 5' |
|---|---|---|---|---|---|
| mir-6817 | SEQ ID NO: 1700 | SEQ ID NO: 2609 | mir-6839 | SEQ ID NO: 1722 | SEQ ID NO: 2631 |
| mir-6818 | SEQ ID NO: 1701 | SEQ ID NO: 2610 | mir-6840 | SEQ ID NO: 1723 | SEQ ID NO: 2632 |
| mir-6819 | SEQ ID NO: 1702 | SEQ ID NO: 2611 | mir-6841 | SEQ ID NO: 1724 | SEQ ID NO: 2633 |
| mir-6820 | SEQ ID NO: 1703 | SEQ ID NO: 2612 | mir-6842 | SEQ ID NO: 1725 | SEQ ID NO: 2634 |
| mir-6821 | SEQ ID NO: 1704 | SEQ ID NO: 2613 | mir-6845 | SEQ ID NO: 1728 | SEQ ID NO: 2635 |
| mir-6846 | SEQ ID NO: 1729 | SEQ ID NO: 2636 | mir-6867 | SEQ ID NO: 1753 | SEQ ID NO: 2655 |
| mir-6847 | SEQ ID NO: 1730 | SEQ ID NO: 2637 | mir-6868 | SEQ ID NO: 1754 | SEQ ID NO: 2656 |
| mir-6848 | SEQ ID NO: 1731 | SEQ ID NO: 2638 | mir-6869 | SEQ ID NO: 1755 | SEQ ID NO: 2657 |
| mir-6849 | SEQ ID NO: 1732 | SEQ ID NO: 2639 | mir-6870 | SEQ ID NO: 1756 | SEQ ID NO: 2658 |
| mir-6850 | SEQ ID NO: 1733 | SEQ ID NO: 2640 | mir-6871 | SEQ ID NO: 1757 | SEQ ID NO: 2659 |
| mir-6851 | SEQ ID NO: 1734 | SEQ ID NO: 2641 | mir-6872 | SEQ ID NO: 1758 | SEQ ID NO: 2660 |
| mir-6852 | SEQ ID NO: 1735 | SEQ ID NO: 2642 | mir-6873 | SEQ ID NO: 1759 | SEQ ID NO: 2661 |
| mir-6853 | SEQ ID NO: 1736 | SEQ ID NO: 2643 | mir-6874 | SEQ ID NO: 1760 | SEQ ID NO: 2662 |
| mir-6854 | SEQ ID NO: 1737 | SEQ ID NO: 2644 | mir-6875 | SEQ ID NO: 1761 | SEQ ID NO: 2663 |
| mir-6855 | SEQ ID NO: 1738 | SEQ ID NO: 2645 | mir-6876 | SEQ ID NO: 1762 | SEQ ID NO: 2664 |
| mir-6856 | SEQ ID NO: 1739 | SEQ ID NO: 2646 | mir-6877 | SEQ ID NO: 1763 | SEQ ID NO: 2665 |
| mir-6857 | SEQ ID NO: 1740 | SEQ ID NO: 2647 | mir-6878 | SEQ ID NO: 1764 | SEQ ID NO: 2666 |
| mir-6858 | SEQ ID NO: 1741 | SEQ ID NO: 2648 | mir-6879 | SEQ ID NO: 1765 | SEQ ID NO: 2667 |
| mir-6859-3 | SEQ ID NO: 1744 | SEQ ID NO: 2649 | mir-6880 | SEQ ID NO: 1766 | SEQ ID NO: 2668 |
| mir-6859-2 | SEQ ID NO: 1743 | SEQ ID NO: 2649 | mir-6881 | SEQ ID NO: 1767 | SEQ ID NO: 2669 |
| mir-6859-1 | SEQ ID NO: 1742 | SEQ ID NO: 2649 | mir-6882 | SEQ ID NO: 1768 | SEQ ID NO: 2670 |
| mir-6861 | SEQ ID NO: 1746 | SEQ ID NO: 2650 | mir-6883 | SEQ ID NO: 1769 | SEQ ID NO: 2671 |
| mir-6862-2 | SEQ ID NO: 1748 | SEQ ID NO: 2651 | mir-6884 | SEQ ID NO: 1770 | SEQ ID NO: 2672 |
| mir-6862-1 | SEQ ID NO: 1747 | SEQ ID NO: 2651 | mir-6885 | SEQ ID NO: 1771 | SEQ ID NO: 2673 |
| mir-6864 | SEQ ID NO: 1750 | SEQ ID NO: 2652 | mir-6886 | SEQ ID NO: 1772 | SEQ ID NO: 2674 |
| mir-6865 | SEQ ID NO: 1751 | SEQ ID NO: 2653 | mir-6887 | SEQ ID NO: 1773 | SEQ ID NO: 2675 |
| mir-6866 | SEQ ID NO: 1752 | SEQ ID NO: 2654 | mir-6888 | SEQ ID NO: 1774 | SEQ ID NO: 2676 |
| mir-6889 | SEQ ID NO: 1775 | SEQ ID NO: 2677 | mir-7152 | SEQ ID NO: 1794 | SEQ ID NO: 2695 |
| mir-6890 | SEQ ID NO: 1776 | SEQ ID NO: 2678 | mir-7153 | SEQ ID NO: 1795 | SEQ ID NO: 2696 |
| mir-6891 | SEQ ID NO: 1777 | SEQ ID NO: 2679 | mir-7154 | SEQ ID NO: 1796 | SEQ ID NO: 2697 |
| mir-6892 | SEQ ID NO: 1778 | SEQ ID NO: 2680 | mir-7155 | SEQ ID NO: 1797 | SEQ ID NO: 2698 |
| mir-6893 | SEQ ID NO: 1779 | SEQ ID NO: 2681 | mir-7156 | SEQ ID NO: 1798 | SEQ ID NO: 2699 |
| mir-6894 | SEQ ID NO: 1780 | SEQ ID NO: 2682 | mir-7157 | SEQ ID NO: 1799 | SEQ ID NO: 2700 |
| mir-6895 | SEQ ID NO: 1781 | SEQ ID NO: 2683 | mir-7158 | SEQ ID NO: 1800 | SEQ ID NO: 2701 |
| mir-7106 | SEQ ID NO: 1782 | SEQ ID NO: 2685 | mir-7159 | SEQ ID NO: 1801 | SEQ ID NO: 2702 |
| mir-7107 | SEQ ID NO: 1783 | SEQ ID NO: 2686 | mir-7160 | SEQ ID NO: 1802 | SEQ ID NO: 2703 |
| mir-7108 | SEQ ID NO: 1784 | SEQ ID NO: 2687 | mir-7161 | SEQ ID NO: 1803 | SEQ ID NO: 2704 |
| mir-7109 | SEQ ID NO: 1785 | SEQ ID NO: 2688 | mir-7162 | SEQ ID NO: 1804 | SEQ ID NO: 2705 |
| mir-7110 | SEQ ID NO: 1786 | SEQ ID NO: 2689 | mir-7843 | SEQ ID NO: 1813 | SEQ ID NO: 2713 |
| mir-7111 | SEQ ID NO: 1787 | SEQ ID NO: 2690 | mir-7844 | SEQ ID NO: 1814 | SEQ ID NO: 2714 |
| mir-7112-2 | SEQ ID NO: 1789 | SEQ ID NO: 2691 | mir-7845 | SEQ ID NO: 1815 | SEQ ID NO: 2715 |
| mir-7112-1 | SEQ ID NO: 1788 | SEQ ID NO: 2691 | mir-7850 | SEQ ID NO: 1820 | SEQ ID NO: 2716 |
| mir-7113 | SEQ ID NO: 1790 | SEQ ID NO: 2692 | mir-7853 | SEQ ID NO: 1823 | SEQ ID NO: 2717 |
| mir-7114 | SEQ ID NO: 1791 | SEQ ID NO: 2693 | mir-7855 | SEQ ID NO: 1825 | SEQ ID NO: 2718 |
| mir-7151 | SEQ ID NO: 1793 | SEQ ID NO: 2694 | mir-7856 | SEQ ID NO: 1826 | SEQ ID NO: 2719 |

As noted, the preceding table is based on the 5' sequence of the particular RNA. If the '3 prime sequence is used to calculate the Drosha cutting site, overhang positions should be accounted for. For example, if the 3' sequence has one nucleotide overhang, positions 5 and 9-12 would correspond to positions 6 and 10-13. If the 3' sequence has two nucleotide overhangs, positions 5 and 9-12 would correspond to positions 7 and 11-14. If the 3' sequence has three nucleotide overhangs, positions 5 and 9-12 would correspond to 8 and 12-15.

Counting to define the Drosha cutting site can also be based on an in silico folding of the miRNA stem loop sequence, such as minimum free energy folding. In these examples, counting can be started by assigning position 1 to the first nucleotide on the 5' strand by the Drosha cutting site in the pre-miRNA portion of the pri-miRNA. Then position numbers can be further assigned along the hairpin moving towards the terminal loop and taking note if the nucleotides are mismatched or matched. In cases where there is an asymmetric mismatch, i.e. one strand contains more nucleotides than the other in a mismatch position, position can be assigned based on the shorter strand. If the asymmetric mismatch has a conformation where one strand contains no mismatched nucleotides, but the other strand does, then the mismatch can be assigned to the higher position. In cases where an assymetric mismatch is located at position 1, the positions can be assigned according to the 5' strand until a matched position is encountered.

FIG. 17 provides examples of counting based on the description in the preceding paragraph. In these examples, the upper sequences contain part of the pri-miRNA sequence, consisting of the pre-miRNA portion and part of the flanking sequence. Below the sequence the folded hairpin is depicted where the upper left part of each figure marks the 5' end of the sequence, and the lower left part of each figure marks the 3' end of the RNA sequence. Mature sequence and its complementary sequence (i.e. the RNA that remains after Drosha and Dicer cleavage) is marked in bold. Positions where mismatches can be removed or inserted to alter sensitivity to changing Drosha levels are underline.

Positions 5 and/or 9-12 can also be determined based on distance from the Drosha cutting site. For example, 65 angstroms is equal to 25 base pairs (bp) of RNA in a helical (paired) form, or ~2.6 angstrom per by RNA. If physical distance in angstroms from a Drosha cutting site is measured along a line following the center of the RNA helix, along the minimum linear path of the shorter strand, the predicted cutting site (Dcp)=0, and the Drosha cutting site (Dc)=0+e, where e is a continuous random variable between +/−7.8a, nucleotide positions would be: (pos. 5 nt)=Dc+(2.6)*5a+r(5)

angstroms, (pos. 9 nt)=Dc+(2.6)*9+r(9) angstroms, . . . (pos. 12 nt)=Dc+(2.6)*12a+r(12) angstroms, where r(x) is the iterative sum of x instances of a continuous random variable between +/−2.6 angstroms divided by the quantity x. If predictions of RNA secondary structure differ from measured structures, position in nucleotide and physical notation should be related as defined. Where multiple subspecies of stable secondary and tertiary structures result from a single sequence of RNA, the relation of position (nt) and physical distance should be calculated for each predicted (or measured) conformation, and modifications applied to either consensus structures, individual structures, or both.

The effects of Drosha expression on RNA based on the number of mis-matches described herein are relative. For example, an RNA with no mis-matches in positions 5 and 9-12 from the Drosha cutting site is least affected by reduced Drosha expression when compared to mRNA with 1, 2, 3, 4 or 5 mis-matches in these positions. RNA with no mis-matches in positions 5 and 9-12 are referred to as "rigid RNAs" herein. Similarly, an RNA with 1 mis-match in positions 5 and 9-12 from the Drosha cutting site is less affected by reduced Drosha expression when compared to mRNA with 2, 3, 4 or 5 mis-matches in these positions. RNA with 1 mis-match in positions 5 and 9-12 are referred to as "semi-rigid RNAs" herein. An RNA with 2 mis-matches in positions 5 and 9-12 from the Drosha cutting site is less affected by reduced Drosha expression when compared to mRNA with 3, 4 or 5 mis-matches in these positions. RNA with 2 mis-match in positions 5 and 9-12 are referred to as "quasi-rigid RNAs" herein. An RNA with 3 mis-matches in positions 5 and 9-12 from the Drosha cutting site is less affected by reduced Drosha expression when compared to mRNA with 4 or 5 mis-matches in these positions. RNA with 3 mis-match in positions 5 and 9-12 are referred to as "mis-matched RNAs" herein. An RNA with 4 mis-matches in positions 5 and 9-12 from the Drosha cutting site is less affected by reduced Drosha expression when compared to mRNA with 5 mis-matches in these positions. RNA with 4 mis-matches in positions 5 and 9-12 are referred to as "highly mis-matched RNAs" herein. An RNA with 5 mis-matches in positions 5 and 9-12 from the Drosha cutting site is most affected by reduced Drosha expression when compared to mRNA with fewer than 5 mis-matches in these positions. RNA with 5 mis-matches in positions 5 and 9-12 are referred to as "fully mis-matched RNAs" herein. Based on the foregoing, low Drosha expression leads to a higher relative percentage of rigid RNAs, followed by semi-rigid RNAs, followed by quasi-rigid RNAs, followed by mis-matched RNAs, followed by highly mis-matched RNAs with the lowest relative percentage of fully-mismatched RNAs. High Drosha expression leads to more equal expression of all RNA types. As used herein, and for convenience only based on the relative nature of the described effects, "unaffected RNAs" can generally include rigid, semi-rigid and quasi-rigid RNAs whereas "affected RNAs" can generally include mis-matched, highly mis-matched and fully-mismatched RNAs.

One of ordinary skill in the art can readily determine whether an RNA is rigid, semi-rigid, quasi-rigid, mis-matched, highly mis-matched or fully mis-matched by referencing available texts and databases.

Exemplary rigid miRNAs include: let7b; let7d; let7f; let7i; miR-1; miR-101; miR-103; miR-105; miR-106a; miR-10a; miR-10b; miR-126*; miR-127; miR-137; miR-138; miR-140; miR-141; miR-142-5p; miR-144; miR-146; miR-153; miR-154; miR-154*; miR-155; miR-17-5p; miR-182*; miR-183; miR-188; miR-189; miR-190; miR-191; miR-192; miR-197; miR-199a*; miR-19a; miR-19b; miR-20; miR-200a; miR-205; miR-206; miR-21; miR-213; miR-22; miR-220; miR-222; miR-224; miR-23b; miR-24; miR-27b; miR-28; miR-299; miR-301; miR-302a; miR-302a*; miR-302b*; miR-302c; miR-302c*; miR-30a-3p; miR-30a-5p; miR-30b; miR-30e-3p; miR-30e-5p; miR-324-5p; miR-326; miR-330; miR-335; miR-337; miR-338; miR-34a; miR-365; miR-368; miR-369; miR-373*; miR-376a; miR-376b; miR-378; miR-380-3p; miR-380-5p; miR-381; miR-382; miR-412; miR-422a; miR-422b; miR-425; miR-429; miR-433; miR-448; miR-449; miR-451; miR-7; miR-9; miR-9*; miR-93; miR-96; and miR-98. Rigid miRNAs can be down-regulated in areas of low Drosha expression by introducing mis-matches in one or more of positions 5 and/or 9-12.

Exemplary semi-rigid miRNAs include: let7a; let7e; let7g; miR-106b; miR-107; miR-122a; miR-124a; miR-126; miR-129; miR-130a; miR-133b; miR-134; miR-135a; miR-139; miR-141; miR-142-3p; miR-143; miR-144; miR-145; miR-147; miR-148a; miR-148b; miR-150; miR-151; miR-152; miR-155; miR-16; miR-17-3p; miR-181a; miR-181b; miR-181c; miR-184; miR-185; miR-186; miR-187; miR-191; miR-192; miR-194; miR-195; miR-196a; miR-198; miR-199a; miR-199b; miR-200a; miR-200c; miR-202; miR-203; miR-204; miR-21; miR-210; miR-215; miR-216; miR-217; miR-218; miR-219; miR-22; miR-224; miR-23a; miR-26a; miR-296; miR-29b; miR-29c; miR-302b; miR-302d; miR-30a-3p; miR-30b; miR-30c; miR-30d; miR-30e-3p; miR-31; miR-32; miR-323; miR-325; miR-328; miR-330; miR-331; miR-338; miR-345; miR-34a; miR-367; miR-371; miR-372; miR-373; miR-374; miR-377; miR-379; miR-380-3p; miR-383; miR-384; miR-410; miR-424; miR-425; miR-431; miR-449; miR-450; miR-452; miR-7; miR-92; miR-93; and miR-96. Semi-rigid miRNAs can be down-regulated in areas of low Drosha expression by introducing mis-matches in one or more of positions 5 and/or 9-12. Semi-rigid miRNAs can be up-regulated in areas of low Drosha expression by removing its mis-match at position 5 and/or 9-12.

Exemplary quasi-rigid miRNAs include: let7c; miR-100; miR-125a; miR-125b; miR-130b; miR-133a; miR-133a; miR-135b; miR-136; miR-148a; miR-149; miR-151; miR-15a; miR-15b; miR-16; miR-18; miR-181a; miR-181c; miR-182; miR-183; miR-196b; miR-19b; miR-200b; miR-200c; miR-202; miR-208; miR-210; miR-211; miR-212; miR-215; miR-216; miR-219; miR-221; miR-23a; miR-26b; miR-27a; miR-301; miR-30d; miR-32; miR-320; miR-324-3p; miR-33; miR-339; miR-342; miR-346; miR-34c; miR-363; miR-370; miR-372; miR-373; miR-423; miR-95; miR-99a; and miR-99b. Quasi-rigid miRNAs can be down-regulated in areas of low Drosha expression by introducing mis-matches in one or more of positions 5 and/or 9-12. Quasi-rigid miRNAs can be up-regulated in areas of low Drosha expression by removing one or more of its mis-matches at position 5 and/or 9-12.

Exemplary mis-matched miRNAs include: miR-128a; miR-128b; miR-132; miR-136; miR-193; miR-200b; miR-214; miR-25; miR-29a; miR-329; miR-340; miR-346; miR-34b; miR-375; and miR-423. Mis-matched miRNAs can be up-regulated in areas of low Drosha expression by removing mis-matches in one or more of positions 5 and/or 9-12. Mis-matched miRNAs can be down-regulated in areas of low Drosha expression by introducing one or more mis-matches at position 5 and/or 9-12.

Exemplary highly-mismatched miRNAs include: miR-340; and miR-342. Highly mis-matched miRNAs can be up-regulated in areas of low Drosha expression by removing mis-matches in one or more of positions 5 and/or 9-12.

Highly mis-matched miRNAs can be down-regulated in areas of low Drosha expression by introducing a mis-match at position 5 and/or 9-12.

Fully mis-matched miRNAs can be up-regulated in areas of low Drosha expression by removing one or more mis-matches at positions 5 and/or 9-12.

As used herein in all instances, nucleotide positions, "5 and/or 9-12" means positions 5 and/or 9 and/or 10 and/or 11 and/or 12. Potential combinations for the introduction or removal of mismatches yield the combinations of matched positions versus mis-matched positions as shown in the following Table 3.

TABLE 3

Matched vs. Mis-Matche Position Combinations in Positions 5 and/or 9-12.

| Position 5 | Position 9 | Position 10 | Position 11 | Position 12 |
|---|---|---|---|---|
| Mis-match | Mis-match | Mis-match | Mis-match | Mis-match |
| Match | Mis-match | Mis-match | Mis-match | Mis-match |
| Mis-match | Match | Mis-match | Mis-match | Mis-match |
| Mis-match | Mis-match | Match | Mis-match | Mis-match |
| Mis-match | Mis-match | Mis-match | Match | Mis-match |
| Mis-match | Mis-match | Mis-match | Mis-match | Match |
| Match | Match | Mis-match | Mis-match | Mis-match |
| Match | Mis-match | Match | Mis-match | Mis-match |
| Match | Mis-match | Mis-match | Match | Mis-match |
| Match | Mis-match | Mis-match | Mis-match | Match |
| Mis-match | Match | Match | Mis-match | Mis-match |
| Mis-match | Match | Mis-match | Match | Mis-match |
| Mis-match | Match | Mis-match | Mis-match | Match |
| Mis-match | Mis-match | Match | Match | Mis-match |
| Mis-match | Mis-match | Match | Mis-match | Match |
| Mis-match | Mis-match | Mis-match | Match | Match |
| Match | Match | Match | Mis-match | Mis-match |
| Match | Match | Mis-match | Match | Mis-match |
| Match | Match | Mis-match | Mis-match | Match |
| Match | Mis-match | Match | Match | Mis-match |
| Match | Mis-match | Match | Mis-match | Match |
| Match | Mis-match | Mis-match | Match | Match |
| Mis-match | Match | Match | Match | Mis-match |
| Mis-match | Match | Match | Mis-match | Match |
| Mis-match | Match | Mis-match | Match | Match |
| Mis-match | Mis-match | Match | Match | Match |
| Match | Match | Match | Match | Mis-match |
| Match | Match | Match | Mis-match | Match |
| Match | Match | Mis-match | Match | Match |
| Match | Mis-match | Match | Match | Match |
| Mis-match | Match | Match | Match | Match |
| Match | Match | Match | Match | Match |

Further, as used herein, "miR" refers to both hairpin structures and/or mature miRNA.

Drosha levels vary between tissues and throughout cell development. For example, the brain expresses higher levels of Drosha than the liver. Further, Drosha levels decrease over the course of T-cell development and as stem cells differentiate into neurons. These differences support the hypothesis that cells could selectively regulate RNA expression by altering Drosha expression level. This is a novel mechanism which may be utilized while designing artificial RNAs either for general stability, or to control expression levels throughout differentiation when Drosha levels change, as well as fine tuning differential expression in different tissue types.

High versus low Drosha expression can be determined or quantified by various methods. For example, in one embodiment, high versus low Drosha expression is a relative determination from samples taken from the same subject. When determined using an intra-subject comparison, high versus low can be compared from the same tissue at different time points or can be compared at the same time using a reference tissue, such as T-cells, liver or brain. Additionally, population reference standards can be created by averaging levels of Drosha expression across a group of subjects at a given time during development and for a particular tissue type. A particular subject's Drosha expression could then be appropriately compared to the population reference to determine if the particular subject's level of Drosha expression is high or low. Another option is to define Drosha expression levels according to fragments per kilobase of exon per million fragments mapped (FPKM). See, for example, the human protein atlas: http://www.proteinatlas.org/ENSG00000113360/tissue. In this method, Drosha levels of FPKM are considered high and Drosha levels <16 FPKM are considered low. Averages can be generated depending on the protein quantification method used. Within this context, the liver exhibits low Drosha expression (9 FPKM) and the brain (cerebral cortex) exhibits high Drosha expression (22 FPKM).

I. Drosha Regulation to Alter Cellular RNA Profiles

The current disclosure provides a mechanism to alter cellular RNA profiles by up- or down-regulating Drosha expression. Down-regulating Drosha expression results in a cellular RNA profile with a higher percentage of unaffected RNAs than if Drosha expression had not been down-regulated. If Drosha expression is naturally low in a cell type or period during development, up-regulating Drosha expression results in a cellular miRNA profiled with a higher percentage of affected RNA than if Drosha expression had not been up-regulated.

As used herein, "down-regulation" of Drosha means a reduction in the presence or activity of the Drosha protein. The reduction in the presence or activity lessens the physiological impact of Drosha within a cell. The down-regulation can occur due to translation of an incomplete Drosha protein sequence; incorrect folding of Drosha; or enhanced degradation of Drosha once formed. Down-regulation of Drosha can also occur due to elimination of the Drosha gene's expression (i.e. gene knockout); insertion of a nucleotide or polynucleotide molecule into the native Drosha gene sequence whereby the expression of the mutated gene is down-regulated (either partially or completely); insertion of a foreign set of base pairs in a Drosha coding region; deletion of any portion of the Drosha gene; reduced transcription of the Drosha gene; incomplete transcription of the Drosha gene; and/or interference with transcription or translation of the Drosha gene or Drosha mRNA.

An up-regulation of Drosha's activity may occur through one or more of increased presence of Drosha or increased potency of Drosha. An increased presence of Drosha can occur through its administration as a protein therapeutic, through genetic modifications that increase its expression and/or by its reduced degradation following administration or formation. Increased expression of Drosha can occur by increasing the copy number of the Drosha gene. Alternatively, a strong and/or inducible promoter may be used to direct the expression of the Drosha gene, the gene being expressed either as a transient expression vehicle or homologously or heterologously incorporated into the genome. In another embodiment, the promoter, regulatory region and/or the ribosome binding site upstream of the Drosha gene can be altered to achieve the over-expression. The expression may also be enhanced by increasing the relative half-life of Drosha mRNA. Increased potency of Drosha can occur through modifying the naturally occurring Drosha sequence to show enhanced cleavage of pri-miRNA.

As is understood by one of ordinary skill in the art, "down-regulation" and "up-regulation" can be measured against a relevant control condition.

II. miRNA Regulation Based on High or Low Drosha Expression

According to the present disclosure, miRNA can also be up- or down-regulated based on naturally occurring Drosha expression levels. For example, when Drosha expression levels are low, it may be desirable to (i) up-regulate affected RNA as these RNA naturally would be down-regulated in tissues with low Drosha expression and/or (ii) down-regulate unaffected RNA as these RNA naturally would be up-regulated in tissues with low Drosha expression. Alternatively, in areas with high Drosha expression, it may be desirable to (i) down-regulate affected RNA as these RNA naturally would be up-regulated in tissues with high Drosha expression and/or (ii) up-regulate unaffected miRNA as these miRNA naturally would be down-regulated as a percentage when compared to affected miRNA in tissues with high Drosha expression.

As used herein, "down-regulation" of RNA means a reduction in the presence or activity of an RNA. The reduction in the presence or activity lessens the physiological impact of the RNA within a cell. The down-regulation can occur due to reduced or incomplete transcription of an RNA gene sequence; enhanced degradation of RNA once it is formed; elimination of the RNA gene's expression (i.e. gene knockout); insertion of a nucleotide or polynucleotide molecule into the native gene sequence whereby expression of the mutated gene is down-regulated (either partially or completely); insertion of a foreign set of base pairs in a coding region; and/or deletion of any portion of the RNA gene.

An up-regulation of an RNA's activity may occur through one or more of increased presence or increased potency of the RNA. An increased presence of RNA can occur through its administration as a therapeutic, through genetic modifications that increase its expression and/or by its reduced degradation following administration or formation. Increased expression of RNA can occur by increasing the copy number of the RNA gene. Alternatively, a strong and/or inducible promoter may be used to direct the expression of the RNA gene, the gene being expressed either as a transient expression vehicle or homologously or heterologously incorporated into the genome. In another embodiment, the promoter, regulatory region and/or the ribosome binding site upstream of the RNA gene can be altered to achieve the over-expression. The expression may also be enhanced by increasing the relative half-life of RNA. Increased potency of miRNA can occur through modifying the naturally occurring sequence to show enhanced mRNA binding.

III. Artificial RNA Design to Provide Enhanced or Repressed RNA Processing

Based on the teachings of the present disclosure, RNA, including miRNA, can be designed to enhance or repress processing of the endogenous form of the RNA by removing or introducing mis-matches into nt positions 5 and/or 9-12 from the Drosha cutting site. Mis-matches are removed to enhance processing by making the RNA less susceptible to down-regulated Drosha expression. Mis-matches are introduced to repress processing by making RNA more susceptible to down-regulated Drosha expression.

Within the context of the designed artificial miRNAs, the term "miRNA" refers to any non-endogenous microRNA molecule that can be involved in RNA-based gene regulation. Accordingly, "miRNA" refers to any type of RNA capable of modulating the productive utilization of mRNA. The term "mRNA" refers to a nucleic acid transcribed from a gene from which a polypeptide is translated, and may include non-translated regions such as a 5'UTR and/or a 3'UTR. An miRNA can include a nucleotide sequence that is completely or partially complementary to any sequence of an mRNA molecule, including translated regions, the 5'UTR, the 3'UTR, and sequences that include both a translated region and a portion of either 5'UTR or 3'UTR. An miRNA may also comprise a nucleotide sequence that is complementary to a region of an mRNA molecule spanning the start codon or the stop codon.

Artificial miRNA can be designed based on any endogenous or naturally-occurring miRNA. Exemplary miRNA for use in the context of the current disclosure include any human, animal, or plant miRNA for various medicinal, veterinary, research, or agricultural purposes. For example, the following human miRNAs could be used: let-7a-1 (SEQ ID NO:1); let-7a-2 (SEQ ID NO:2); let-7a-3 (SEQ ID NO:3); let-7b (SEQ ID NO:4); let-7c (SEQ ID NO:5); let-7d (SEQ ID NO:6); let-7e (SEQ ID NO:7); let-7f-1 (SEQ ID NO:8); let-7f-2 (SEQ ID NO:9); let-7g (SEQ ID NO:10); let-7i (SEQ ID NO:11); miR-1-2 (SEQ ID NO:27); miR-1-1 (SEQ ID NO:26); miR-7-3 (SEQ ID NO:279); miR-7-2 (SEQ ID NO:278); miR-7-1 (SEQ ID NO:277); miR-9-3 (SEQ ID NO:286); miR-9-2 (SEQ ID NO:281); miR-9-1 (SEQ ID NO:280); miR-10a (SEQ ID NO:24); miR-10b (SEQ ID NO:25); miR-15a (SEQ ID NO:77); miR-15b (SEQ ID NO:78); miR-16-2 (SEQ ID NO:80); miR-16-1 (SEQ ID NO:79); miR-17 (SEQ ID NO:81); miR-18a (SEQ ID NO:95); miR-18b (SEQ ID NO:96); miR-19a (SEQ ID NO:114); miR-19b-1 (SEQ ID NO:115); miR-19b-2 (SEQ ID NO:116); miR-20a (SEQ ID NO:128); miR-20b (SEQ ID NO:129); miR-21 (SEQ ID NO:130); miR-22 (SEQ ID NO:144); miR-23a (SEQ ID NO:149); miR-23b (SEQ ID NO:150); miR-23c (SEQ ID NO:151); miR-24-2 (SEQ ID NO:153); miR-24-1 (SEQ ID NO:152); miR-25 (SEQ ID NO:154); miR-26a-1 (SEQ ID NO:155); miR-26a-2 (SEQ ID NO:156); miR-26b (SEQ ID NO:157); miR-27a (SEQ ID NO:158); miR-27b (SEQ ID NO:159); miR-28 (SEQ ID NO:160); miR-29a (SEQ ID NO:165); miR-29b-1 (SEQ ID NO:166); miR-29b-2 (SEQ ID NO:167); miR-29c (SEQ ID NO:168); miR-30a (SEQ ID NO:178); miR-30b (SEQ ID NO:179); miR-30c-1 (SEQ ID NO:180); miR-30c-2 (SEQ ID NO:181); miR-30d (SEQ ID NO:182); miR-30e (SEQ ID NO:183); miR-31 (SEQ ID NO:184); miR-32 (SEQ ID NO:185); miR-33a (SEQ ID NO:208); miR-33b (SEQ ID NO:209); miR-34a (SEQ ID NO:214); miR-34b (SEQ ID NO:215); miR-34c (SEQ ID NO:216); miR-92a-1 (SEQ ID NO:282); miR-92a-2 (SEQ ID NO:283); miR-92b (SEQ ID NO:284); miR-93 (SEQ ID NO:285); miR-95 (SEQ ID NO:287); miR-96 (SEQ ID NO:288); miR-98 (SEQ ID NO:289); miR-99a (SEQ ID NO:290); miR-99b (SEQ ID NO:291); miR-100 (SEQ ID NO:12); miR-101-2 (SEQ ID NO:14); miR-101-1 (SEQ ID NO:13); miR-103a-1 (SEQ ID NO:15); miR-103a-2 (SEQ ID NO:16); miR-103b-1 (SEQ ID NO:17); miR-103b-2 (SEQ ID NO:18); miR-105-2 (SEQ ID NO:20); miR-105-1 (SEQ ID NO:19); miR-106a (SEQ ID NO:21); miR-106b (SEQ ID NO:22); miR-107 (SEQ ID NO:23); miR-122 (SEQ ID NO:28); miR-124-3 (SEQ ID NO:31); miR-124-2 (SEQ ID NO:30); miR-124-1 (SEQ ID NO:29); miR-125a (SEQ ID NO:32); miR-125b-1 (SEQ ID NO:33); miR-125b-2 (SEQ ID NO:34); miR-126 (SEQ ID NO:35); miR-127 (SEQ ID NO:36); miR-128-2 (SEQ ID NO:38); miR-128-1 (SEQ ID NO:37); miR-129-2 (SEQ ID NO:40); miR-129-1 (SEQ ID NO:39); miR-130a (SEQ ID NO:41); miR-130b (SEQ ID NO:42); miR-132 (SEQ ID NO:43); miR-133a-1 (SEQ ID NO:44); miR-133a-2 (SEQ ID NO:45); miR-133b (SEQ ID NO:46); miR-134 (SEQ ID NO:47); miR-135a-1 (SEQ ID NO:48); miR-135a-2 (SEQ ID NO:49); miR-135b (SEQ ID NO:50); miR-136 (SEQ ID NO:51); miR-137 (SEQ ID NO:52); miR-138-2 (SEQ ID NO:54); miR-138-1 (SEQ ID NO:53); miR-139 (SEQ ID NO:55); miR-140 (SEQ ID NO:56); miR-141 (SEQ ID NO:57); miR-142 (SEQ ID NO:58); miR-143 (SEQ ID NO:59); miR-144 (SEQ ID NO:60); miR-145 (SEQ ID NO:61); miR-146a (SEQ ID NO:62); miR-146b (SEQ ID NO:63); miR-147a (SEQ ID NO:64); miR-147b (SEQ ID NO:65); miR-148a (SEQ ID NO:66); miR-148b (SEQ ID NO:67); miR-149 (SEQ ID NO:68); miR-150 (SEQ ID NO:69); miR-151a (SEQ ID NO:70); miR-151b (SEQ ID NO:71); miR-152 (SEQ ID NO:72); miR-153-2 (SEQ ID NO:74); miR-153-1 (SEQ ID NO:73); miR-154 (SEQ ID NO:75); miR-155 (SEQ ID NO:76); miR-181a-1 (SEQ ID NO:82); miR-181a-2 (SEQ ID NO:83); miR-181b-1 (SEQ ID NO:84); miR-181b-2 (SEQ ID NO:85); miR-181c (SEQ ID NO:86); miR-181d (SEQ ID NO:87); miR-182 (SEQ ID NO:88); miR-183 (SEQ ID NO:89); miR-184 (SEQ ID NO:90); miR-185 (SEQ ID NO:91); miR-186 (SEQ ID NO:92); miR-187 (SEQ ID NO:93); miR-188 (SEQ ID NO:94); miR-190a (SEQ ID NO:97); miR-190b (SEQ ID NO:98); miR-191 (SEQ ID NO:99); miR-192 (SEQ ID NO:100); miR-193a (SEQ ID NO:101); miR-193b (SEQ ID NO:102); miR-194-2 (SEQ ID NO:104); miR-194-1 (SEQ ID NO:103); miR-195 (SEQ ID NO:105); miR-196a-1 (SEQ ID NO:106); miR-196a-2 (SEQ ID NO:107); miR-196b (SEQ ID NO:108); miR-197 (SEQ ID NO:109); miR-198 (SEQ ID NO:110); miR-199a-1 (SEQ ID NO:111); miR-199a-2 (SEQ ID NO:112); miR-199b (SEQ ID NO:113); miR-200a (SEQ ID NO:117); miR-200b (SEQ ID NO:118); miR-200c (SEQ ID NO:119); miR-202 (SEQ ID NO:120); miR-203a (SEQ ID NO:121); miR-203b (SEQ ID NO:122); miR-204 (SEQ ID NO:123); miR-205 (SEQ ID NO:124); miR-206 (SEQ ID NO:125); miR-208a (SEQ ID NO:126); miR-208b (SEQ ID NO:127); miR-210 (SEQ ID NO:131); miR-211 (SEQ ID NO:132); miR-212 (SEQ ID NO:133); miR-214 (SEQ ID NO:134); miR-215 (SEQ ID NO:135); miR-216a (SEQ ID NO:136); miR-216b (SEQ ID NO:137); miR-217 (SEQ ID NO:138); miR-218-2 (SEQ ID NO:140); miR-218-1 (SEQ ID NO:139); miR-219a-1 (SEQ ID NO:141); miR-219a-2 (SEQ ID NO:142); miR-219b (SEQ ID NO:143); miR-221 (SEQ ID NO:145); miR-222 (SEQ ID NO:146); miR-223 (SEQ ID NO:147); miR-224 (SEQ ID NO:148); miR-296 (SEQ ID NO:161); miR-297 (SEQ ID NO:162); miR-298 (SEQ ID NO:163); miR-299 (SEQ ID NO:164); miR-300 (SEQ ID NO:169); miR-301a (SEQ ID NO:170); miR-301a (SEQ ID NO:171); miR-302a (SEQ ID NO:172); miR-302b (SEQ ID NO:173); miR-302c (SEQ ID NO:174); miR-302d (SEQ ID NO:175); miR-302e (SEQ ID NO:176); miR-302f (SEQ ID NO:177); miR-320a (SEQ ID NO:186); miR-320b-1 (SEQ ID NO:187); miR-320b-2 (SEQ ID NO:188); miR-320c-1 (SEQ ID NO:189); miR-320c-2 (SEQ ID NO:190); miR-320d-1 (SEQ ID NO:191); miR-320d-2 (SEQ ID NO:192); miR-320e (SEQ ID NO:193); miR-323a (SEQ ID NO:194); miR-323b (SEQ ID NO:195); miR-324 (SEQ ID NO:196); miR-325 (SEQ ID NO:197); miR-326 (SEQ ID NO:198); miR-328 (SEQ ID NO:199); miR-329-2 (SEQ ID NO:201); miR-329-1 (SEQ ID NO:200); miR-330 (SEQ ID NO:202); miR-331 (SEQ ID NO:203); miR-335 (SEQ ID NO:204); miR-337 (SEQ ID NO:205); miR-338 (SEQ ID NO:206); miR-339 (SEQ ID NO:207); miR-340 (SEQ ID NO:210); miR-342 (SEQ ID NO:211); miR-345 (SEQ ID NO:212); miR-346 (SEQ ID NO:213); miR-361 (SEQ ID NO:217); miR-362 (SEQ ID NO:218); miR-363 (SEQ ID NO:219); miR-365a (SEQ ID NO:220); miR-365b (SEQ ID NO:221); miR-367 (SEQ ID NO:222); miR-369 (SEQ ID NO:223); miR-370 (SEQ ID NO:224); miR-371a (SEQ ID NO:225); miR-371b (SEQ ID NO:226); miR-372 (SEQ ID NO:227); miR-373 (SEQ ID NO:228); miR-374a (SEQ ID NO:229); miR-374b (SEQ ID NO:230); miR-374c (SEQ ID NO:231); miR-375 (SEQ ID NO:232); miR-376a-1 (SEQ ID NO:233); miR-376a-2 (SEQ ID NO:234); miR-376b (SEQ ID NO:235); miR-376c (SEQ ID NO:236); miR-377 (SEQ ID NO:237); miR-378a (SEQ ID NO:238); miR-378b (SEQ ID NO:239); miR-378c (SEQ ID NO:240); miR-378d-1 (SEQ ID NO:241); miR-378d-2 (SEQ ID NO:242); miR-378e (SEQ ID NO:243); miR-378f (SEQ ID NO:244); miR-378g (SEQ ID NO:245); miR-378h (SEQ ID NO:246); miR-378i (SEQ ID NO:247); miR-378j (SEQ ID NO:248); miR-379 (SEQ ID NO:249); miR-380 (SEQ ID NO:250); miR-381 (SEQ ID NO:251); miR-382 (SEQ ID NO:252); miR-383 (SEQ ID NO:253); miR-384 (SEQ ID NO:254); miR-409 (SEQ ID NO:255); miR-410 (SEQ ID NO:256); miR-411 (SEQ ID NO:257); miR-412 (SEQ ID NO:258); miR-421 (SEQ ID NO:259); miR-422a (SEQ ID NO:260); miR-423 (SEQ ID NO:261); miR-424 (SEQ ID NO:262); miR-425 (SEQ ID NO:263); miR-429 (SEQ ID NO:264); miR-431 (SEQ ID NO:265); miR-432 (SEQ ID NO:266); miR-433 (SEQ ID NO:267); miR-448 (SEQ ID NO:268); miR-449a (SEQ ID NO:269); miR-449b (SEQ ID NO:270); miR-449c (SEQ ID NO:271); miR-450a-1 (SEQ ID NO:272); miR-450a-2 (SEQ ID NO:273); miR-450b (SEQ ID NO:274); miR-451a (SEQ ID NO:275); miR-451b (SEQ ID NO:276); miR-452 (SEQ ID NO:292); miR-454 (SEQ ID NO:293); miR-455 (SEQ ID NO:294); miR-466 (SEQ ID NO:295); miR-483 (SEQ ID NO:296); miR-484 (SEQ ID NO:297); miR-485 (SEQ ID NO:298); miR-486-2 (SEQ ID NO:300); miR-486 (SEQ ID NO:299); miR-487a (SEQ ID NO:301); miR-487b (SEQ ID NO:302); miR-488 (SEQ ID NO:303); miR-489 (SEQ ID NO:304); miR-490 (SEQ ID NO:305); miR-491 (SEQ ID NO:306); miR-492 (SEQ ID NO:307); miR-493 (SEQ ID NO:308); miR-494 (SEQ ID NO:309); miR-495 (SEQ ID NO:310); miR-496 (SEQ ID NO:311); miR-497 (SEQ ID NO:312); miR-498 (SEQ ID NO:313); miR-499a (SEQ ID NO:314); miR-499b (SEQ ID NO:315); miR-500a (SEQ ID NO:316); miR-500b (SEQ ID NO:317); miR-501 (SEQ ID NO:318); miR-502 (SEQ ID NO:319); miR-503 (SEQ ID NO:320); miR-504 (SEQ ID NO:321); miR-505 (SEQ ID NO:322); miR-506 (SEQ ID NO:323); miR-507 (SEQ ID NO:324); miR-508 (SEQ ID NO:325); miR-509-3 (SEQ ID NO:328); miR-509-2 (SEQ ID NO:327); miR-509-1 (SEQ ID NO:326); miR-510 (SEQ ID NO:329); miR-511 (SEQ ID NO:330); miR-512-2 (SEQ ID NO:332); miR-512-1 (SEQ ID NO:331); miR-513a-1 (SEQ ID NO:333); miR-513a-2 (SEQ ID NO:334); miR-513b (SEQ ID NO:335); miR-513c (SEQ ID NO:336); miR-514a-1 (SEQ ID NO:337); miR-514a-2 (SEQ ID NO:338); miR-514a-3 (SEQ ID NO:339); miR-514b (SEQ ID NO:340); miR-515-2 (SEQ ID NO:342); miR-515-1 (SEQ ID NO:341); miR-516a-1 (SEQ ID NO:343); miR-516a-2 (SEQ ID NO:344); miR-516b-1 (SEQ ID NO:345); miR-516b-2 (SEQ ID NO:346); miR-517a (SEQ ID NO:347); miR-517b (SEQ ID NO:348); miR-517c (SEQ ID NO:349); miR-518a-1 (SEQ ID NO:350); miR-518a-2 (SEQ ID NO:351); miR-518b (SEQ ID NO:352); miR-518c (SEQ ID NO:353); miR-518d (SEQ ID NO:354); miR-518e (SEQ ID NO:355); miR-518f (SEQ ID NO:356); miR-519a-1 (SEQ ID NO:357); miR-519a-2 (SEQ ID NO:358); miR-519b (SEQ ID NO:359); miR-519c (SEQ ID NO:360); miR-519d (SEQ ID NO:361); miR-519e (SEQ ID NO:362); miR-520a (SEQ ID NO:363); miR-520b (SEQ ID NO:364); miR-520c (SEQ ID NO:365); miR-520d (SEQ ID NO:366); miR-520e (SEQ ID NO:367); miR-520f (SEQ ID NO:368); miR-520g (SEQ ID NO:369); miR-520h (SEQ ID NO:370); miR-521-2 (SEQ ID NO:372); miR-521-1 (SEQ ID NO:371); miR-522 (SEQ ID NO:373); miR-523 (SEQ ID NO:374); miR-524 (SEQ ID NO:375); miR-525 (SEQ ID NO:376); miR-526a-1 (SEQ ID NO:377); miR-526a-2 (SEQ ID NO:378); miR-526b (SEQ ID NO:379); miR-527 (SEQ ID NO:380); miR-532 (SEQ ID NO:381); miR-539 (SEQ ID NO:382); miR-541 (SEQ ID NO:383); miR-542 (SEQ ID NO:384); miR-543 (SEQ ID NO:385); miR-544a (SEQ ID NO:386); miR-544b (SEQ ID NO:387); miR-545 (SEQ ID NO:388); miR-548a-1 (SEQ ID NO:389); miR-548a-2 (SEQ ID NO:390); miR-548a-3 (SEQ ID NO:391); miR-548aa-1 (SEQ ID NO:392); miR-548aa-2 (SEQ ID NO:393); miR-548ab (SEQ ID NO:394); miR-548ac (SEQ ID NO:395); miR-548ad (SEQ ID NO:396); miR-548ae-1 (SEQ ID NO:397); miR-548ae-2 (SEQ ID NO:398); miR-548ag-1 (SEQ ID NO:399); miR-548ag-2 (SEQ ID NO:400); miR-548ah (SEQ ID NO:401); miR-548ai (SEQ ID NO:402); miR-548aj-1 (SEQ ID NO:403); miR-548aj-2 (SEQ ID NO:404); miR-548ak (SEQ ID NO:405); miR-548al (SEQ ID NO:406); miR-548am (SEQ ID NO:407); miR-548an (SEQ ID NO:408); miR-548ao (SEQ ID NO:409); miR-548ap (SEQ ID NO:410); miR-548aq (SEQ ID NO:411); miR-548ar (SEQ ID NO:412); miR-548as (SEQ ID NO:413); miR-548at (SEQ ID NO:414); miR-548au (SEQ ID NO:415); miR-548av (SEQ ID NO:416); miR-548aw (SEQ ID NO:417); miR-548ax (SEQ ID NO:418); miR-548ay (SEQ ID NO:419); miR-548az (SEQ ID NO:420); miR-548b (SEQ ID NO:421); miR-548ba (SEQ ID NO:422); miR-548c (SEQ ID NO:423); miR-548d-1 (SEQ ID NO:424); miR-548d-2 (SEQ ID NO:425); miR-548e (SEQ ID NO:426); miR-548f-1 (SEQ ID NO:427); miR-548f-2 (SEQ ID NO:428); miR-548f-3 (SEQ ID NO:429); miR-548f-4 (SEQ ID NO:430); miR-548f-5 (SEQ ID NO:431); miR-548g (SEQ ID NO:432); miR-548h-1 (SEQ ID NO:433); miR-548h-2 (SEQ ID NO:434); miR-548h-3 (SEQ ID NO:435); miR-548h-4 (SEQ ID NO:436); miR-548h-5 (SEQ ID NO:437); miR-548i-1 (SEQ ID NO:438); miR-548i-2 (SEQ ID NO:439); miR-548i-3 (SEQ ID NO:440); miR-548i-4 (SEQ ID NO:441); miR-548j (SEQ ID NO:442); miR-548k (SEQ ID NO:443); miR-548l (SEQ ID NO:444); miR-548m (SEQ ID NO:445); miR-548n (SEQ ID NO:446); miR-548o (SEQ ID NO:447); miR-548o-2 (SEQ ID NO:448); miR-548p (SEQ ID NO:449); miR-548q (SEQ ID NO:450); miR-548s (SEQ ID NO:451); miR-548t (SEQ ID NO:452); miR-548u (SEQ ID NO:453); miR-548v (SEQ ID NO:454); miR-548w (SEQ ID NO:455); miR-548x (SEQ ID NO:456); miR-548x-2 (SEQ ID NO:457); miR-548y (SEQ ID NO:458); miR-548z (SEQ ID NO:459); miR-549a (SEQ ID NO:460); miR-550a-1 (SEQ ID NO:461); miR-550a-2 (SEQ ID NO:462); miR-550a-3 (SEQ ID NO:463); miR-550b-1 (SEQ ID NO:464); miR-550b-2 (SEQ ID NO:465); miR-551a (SEQ ID NO:466); miR-551b (SEQ ID NO:467); miR-552 (SEQ ID NO:468); miR-553 (SEQ ID NO:469); miR-554 (SEQ ID NO:470); miR-555 (SEQ ID NO:471); miR-556 (SEQ ID NO:472); miR-557 (SEQ ID NO:473); miR-558 (SEQ ID NO:474); miR-559 (SEQ ID NO:475); miR-561 (SEQ ID NO:476); miR-562 (SEQ ID NO:477); miR-563 (SEQ ID NO:478); miR-564 (SEQ ID NO:479); miR-566 (SEQ ID NO:480); miR-567 (SEQ ID NO:481); miR-568 (SEQ ID NO:482); miR-569 (SEQ ID NO:483); miR-570 (SEQ ID NO:484); miR-571 (SEQ ID NO:485); miR-572 (SEQ ID NO:486); miR-573 (SEQ ID NO:487); miR-574 (SEQ ID NO:488); miR-575 (SEQ ID NO:489); miR-576 (SEQ ID NO:490); miR-577 (SEQ ID NO:491); miR-578 (SEQ ID NO:492); miR-579 (SEQ ID NO:493); miR-580 (SEQ ID NO:494); miR-581 (SEQ ID NO:495); miR-582 (SEQ ID NO:496); miR-583 (SEQ ID NO:497); miR-584 (SEQ ID NO:498); miR-585 (SEQ ID NO:499); miR-586 (SEQ ID NO:500); miR-587 (SEQ ID NO:501); miR-588 (SEQ ID NO:502); miR-589 (SEQ ID NO:503); miR-590 (SEQ ID NO:504); miR-591 (SEQ ID NO:505); miR-592 (SEQ ID NO:506); miR-593 (SEQ ID NO:507); miR-595 (SEQ ID NO:508); miR-596 (SEQ ID NO:509); miR-597 (SEQ ID NO:510); miR-598 (SEQ ID NO:511); miR-599 (SEQ ID NO:512); miR-600 (SEQ ID NO:513); miR-601 (SEQ ID NO:514); miR-602 (SEQ ID NO:515); miR-603 (SEQ ID NO:516); miR-604 (SEQ ID NO:517); miR-605 (SEQ ID NO:518); miR-606 (SEQ ID NO:519); miR-607 (SEQ ID NO:520); miR-608 (SEQ ID NO:521); miR-609 (SEQ ID NO:522); miR-610 (SEQ ID NO:523); miR-611 (SEQ ID NO:524); miR-612 (SEQ ID NO:525); miR-613 (SEQ ID NO:526); miR-614 (SEQ ID NO:527); miR-615 (SEQ ID NO:528); miR-616 (SEQ ID NO:529); miR-617 (SEQ ID NO:530); miR-618 (SEQ ID NO:531); miR-619 (SEQ ID NO:532); miR-620 (SEQ ID NO:533); miR-621 (SEQ ID NO:534); miR-622 (SEQ ID NO:535); miR-623 (SEQ ID NO:536); miR-624 (SEQ ID NO:537); miR-625 (SEQ ID NO:538); miR-626 (SEQ ID NO:539); miR-627 (SEQ ID NO:540); miR-628 (SEQ ID NO:541); miR-629 (SEQ ID NO:542); miR-630 (SEQ ID NO:543); miR-631 (SEQ ID NO:544); miR-632 (SEQ ID NO:545); miR-633 (SEQ ID NO:546); miR-634 (SEQ ID NO:547); miR-635 (SEQ ID NO:548); miR-636 (SEQ ID NO:549); miR-637 (SEQ ID NO:550); miR-638 (SEQ ID NO:551); miR-639 (SEQ ID NO:552); miR-640 (SEQ ID NO:553); miR-641 (SEQ ID NO:554); miR-642a (SEQ ID NO:555); miR-642b (SEQ ID NO:556); miR-643 (SEQ ID NO:557); miR-644a (SEQ ID NO:558); miR-645 (SEQ ID NO:559); miR-646 (SEQ ID NO:560); miR-647 (SEQ ID NO:561); miR-648 (SEQ ID NO:562); miR-649 (SEQ ID NO:563); miR-650 (SEQ ID NO:564); miR-651 (SEQ ID NO:565); miR-652 (SEQ ID NO:566); miR-653 (SEQ ID NO:567); miR-654 (SEQ ID NO:568); miR-655 (SEQ ID NO:569); miR-656 (SEQ ID NO:570); miR-657 (SEQ ID NO:571); miR-658 (SEQ ID NO:572); miR-659 (SEQ ID NO:573); miR-660 (SEQ ID NO:574); miR-661 (SEQ ID NO:575); miR-662 (SEQ ID NO:576); miR-663a (SEQ ID NO:577); miR-663b (SEQ ID NO:578); miR-664a (SEQ ID NO:579); miR-664b (SEQ ID NO:580); miR-665 (SEQ ID NO:581); miR-668 (SEQ ID NO:582); miR-670 (SEQ ID NO:583); miR-671 (SEQ ID NO:584); miR-675 (SEQ ID NO:585); miR-676 (SEQ ID NO:586); miR-708 (SEQ ID NO:587); miR-711 (SEQ ID NO:588); miR-718 (SEQ ID NO:589); miR-744 (SEQ ID NO:590); miR-758 (SEQ ID NO:591); miR-759 (SEQ ID NO:592); miR-760 (SEQ ID NO:593); miR-761 (SEQ ID NO:594); miR-762 (SEQ ID NO:595); miR-764 (SEQ ID NO:596); miR-765 (SEQ ID NO:597); miR-766 (SEQ ID NO:598); miR-767 (SEQ ID NO:599); miR-769 (SEQ ID NO:600); miR-770 (SEQ ID NO:601); miR-802 (SEQ ID NO:602); miR-873 (SEQ ID NO:603); miR-874 (SEQ ID NO:604); miR-875 (SEQ ID NO:605); miR-876 (SEQ ID NO:606); miR-877 (SEQ ID NO:607); miR-885 (SEQ ID NO:608); miR-887 (SEQ ID NO:609); miR-888 (SEQ ID NO:610); miR-889 (SEQ ID NO:611); miR-890 (SEQ ID NO:612); miR-891a (SEQ ID NO:613); miR-891b (SEQ ID NO:614); miR-892a (SEQ ID NO:615); miR-892b (SEQ ID NO:616); miR-892c (SEQ ID NO:617); miR-920 (SEQ ID NO:618); miR-921 (SEQ ID NO:619); miR-922 (SEQ ID NO:620); miR-924 (SEQ ID NO:621); miR-933 (SEQ ID NO:622); miR-934 (SEQ ID NO:623); miR-935 (SEQ ID NO:624); miR-936 (SEQ ID NO:625); miR-937 (SEQ ID NO:626); miR-938 (SEQ ID NO:627); miR-939 (SEQ ID NO:628); miR-940 (SEQ ID NO:629); miR-941-4 (SEQ ID NO:633); miR-941-3 (SEQ ID NO:632); miR-941-2 (SEQ ID NO:631); miR-941-1 (SEQ ID NO:630); miR-942 (SEQ ID NO:634); miR-943 (SEQ ID NO:635); miR-944 (SEQ ID NO:636); miR-1178 (SEQ ID NO:637); miR-1179 (SEQ ID NO:638); miR-1180 (SEQ ID NO:639);

miR-1181 (SEQ ID NO:640); miR-1182 (SEQ ID NO:641); miR-1183 (SEQ ID NO:642); miR-1184-3 (SEQ ID NO:645); miR-1184-2 (SEQ ID NO:644); miR-1184-1 (SEQ ID NO:643); miR-1185-2 (SEQ ID NO:647); miR-1185-1 (SEQ ID NO:646); miR-1193 (SEQ ID NO:648); miR-1197 (SEQ ID NO:649); miR-1199 (SEQ ID NO:650); miR-1200 (SEQ ID NO:651); miR-1202 (SEQ ID NO:652); miR-1203 (SEQ ID NO:653); miR-1204 (SEQ ID NO:654); miR-1205 (SEQ ID NO:655); miR-1206 (SEQ ID NO:656); miR-1207 (SEQ ID NO:657); miR-1208 (SEQ ID NO:658); miR-1224 (SEQ ID NO:659); miR-1225 (SEQ ID NO:660); miR-1226 (SEQ ID NO:661); miR-1227 (SEQ ID NO:662); miR-1228 (SEQ ID NO:663); miR-1229 (SEQ ID NO:664); miR-1231 (SEQ ID NO:665); miR-1233-2 (SEQ ID NO:667); miR-1233-1 (SEQ ID NO:666); miR-1234 (SEQ ID NO:668); miR-1236 (SEQ ID NO:669); miR-1237 (SEQ ID NO:670); miR-1238 (SEQ ID NO:671); miR-1243 (SEQ ID NO:672); miR-1244-3 (SEQ ID NO:675); miR-1244-2 (SEQ ID NO:674); miR-1244-1 (SEQ ID NO:673); miR-1245a (SEQ ID NO:676); miR-1245b (SEQ ID NO:677); miR-1246 (SEQ ID NO:678); miR-1247 (SEQ ID NO:679); miR-1248 (SEQ ID NO:680); miR-1249 (SEQ ID NO:681); miR-1250 (SEQ ID NO:682); miR-1251 (SEQ ID NO:683); miR-1252 (SEQ ID NO:684); miR-1253 (SEQ ID NO:685); miR-1254-2 (SEQ ID NO:687); miR-1254-1 (SEQ ID NO:686); miR-1255a (SEQ ID NO:688); miR-1255b-1 (SEQ ID NO:689); miR-1255b-2 (SEQ ID NO:690); miR-1256 (SEQ ID NO:691); miR-1257 (SEQ ID NO:692); miR-1258 (SEQ ID NO:693); miR-1260a (SEQ ID NO:694); miR-1260b (SEQ ID NO:695); miR-1261 (SEQ ID NO:696); miR-1262 (SEQ ID NO:697); miR-1263 (SEQ ID NO:698); miR-1264 (SEQ ID NO:699); miR-1265 (SEQ ID NO:700); miR-1266 (SEQ ID NO:701); miR-1267 (SEQ ID NO:702); miR-1268a (SEQ ID NO:703); miR-1268b (SEQ ID NO:704); miR-1269a (SEQ ID NO:705); miR-1269b (SEQ ID NO:706); miR-1270-2 (SEQ ID NO:708); miR-1270-1 (SEQ ID NO:707); miR-1271 (SEQ ID NO:709); miR-1272 (SEQ ID NO:710); miR-1273a (SEQ ID NO:711); miR-1273c (SEQ ID NO:712); miR-1273d (SEQ ID NO:713); miR-1273e (SEQ ID NO:714); miR-1273f (SEQ ID NO:715); miR-1273g (SEQ ID NO:716); miR-1273h (SEQ ID NO:717); miR-1275 (SEQ ID NO:718); miR-1276 (SEQ ID NO:719); miR-1277 (SEQ ID NO:720); miR-1278 (SEQ ID NO:721); miR-1279 (SEQ ID NO:722); miR-1281 (SEQ ID NO:723); miR-1282 (SEQ ID NO:724); miR-1283-2 (SEQ ID NO:726); miR-1283-1 (SEQ ID NO:725); miR-1284 (SEQ ID NO:727); miR-1285-2 (SEQ ID NO:729); miR-1285-1 (SEQ ID NO:728); miR-1286 (SEQ ID NO:730); miR-1287 (SEQ ID NO:731); miR-1288 (SEQ ID NO:732); miR-1289-2 (SEQ ID NO:734); miR-1289-1 (SEQ ID NO:733); miR-1290 (SEQ ID NO:735); miR-1291 (SEQ ID NO:736); miR-1292 (SEQ ID NO:737); miR-1293 (SEQ ID NO:738); miR-1294 (SEQ ID NO:739); miR-1295a (SEQ ID NO:740); miR-1295b (SEQ ID NO:741); miR-1296 (SEQ ID NO:742); miR-1297 (SEQ ID NO:743); miR-1298 (SEQ ID NO:744); miR-1299 (SEQ ID NO:745); miR-1301 (SEQ ID NO:746); miR-1302-11 (SEQ ID NO:749); miR-1302-10 (SEQ ID NO:748); miR-1302-9 (SEQ ID NO:757); miR-1302-8 (SEQ ID NO:756); miR-1302-7 (SEQ ID NO:755); miR-1302-6 (SEQ ID NO:754); miR-1302-5 (SEQ ID NO:753); miR-1302-4 (SEQ ID NO:752); miR-1302-3 (SEQ ID NO:751); miR-1302-2 (SEQ ID NO:750); miR-1302-1 (SEQ ID NO:747); miR-1303 (SEQ ID NO:758); miR-1304 (SEQ ID NO:759); miR-1305 (SEQ ID NO:760); miR-1306 (SEQ ID NO:761); miR-1307 (SEQ ID NO:762); miR-1321 (SEQ ID NO:763); miR-1322 (SEQ ID NO:764); miR-1323 (SEQ ID NO:765); miR-1324 (SEQ ID NO:766); miR-1343 (SEQ ID NO:767); miR-1468 (SEQ ID NO:768); miR-1469 (SEQ ID NO:769); miR-1470 (SEQ ID NO:770); miR-1471 (SEQ ID NO:771); miR-1537 (SEQ ID NO:772); miR-1538 (SEQ ID NO:773); miR-1539 (SEQ ID NO:774); miR-1587 (SEQ ID NO:775); miR-1825 (SEQ ID NO:776); miR-1827 (SEQ ID NO:777); miR-1908 (SEQ ID NO:778); miR-1909 (SEQ ID NO:779); miR-1910 (SEQ ID NO:780); miR-1911 (SEQ ID NO:781); miR-1912 (SEQ ID NO:782); miR-1913 (SEQ ID NO:783); miR-1914 (SEQ ID NO:784); miR-1915 (SEQ ID NO:785); miR-1972-2 (SEQ ID NO:787); miR-1972-1 (SEQ ID NO:786); miR-1973 (SEQ ID NO:788); miR-1976 (SEQ ID NO:789); miR-2052 (SEQ ID NO:790); miR-2053 (SEQ ID NO:791); miR-2054 (SEQ ID NO:792); miR-2110 (SEQ ID NO:793); miR-2113 (SEQ ID NO:794); miR-2114 (SEQ ID NO:795); miR-2115 (SEQ ID NO:796); miR-2116 (SEQ ID NO:797); miR-2117 (SEQ ID NO:798); miR-2276 (SEQ ID NO:799); miR-2277 (SEQ ID NO:800); miR-2278 (SEQ ID NO:801); miR-2355 (SEQ ID NO:802); miR-2392 (SEQ ID NO:803); miR-2467 (SEQ ID NO:804); miR-2681 (SEQ ID NO:805); miR-2682 (SEQ ID NO:806); miR-2861 (SEQ ID NO:807); miR-2909 (SEQ ID NO:808); miR-3064 (SEQ ID NO:809); miR-3065 (SEQ ID NO:810); miR-3074 (SEQ ID NO:811); miR-3115 (SEQ ID NO:812); miR-3116-2 (SEQ ID NO:814); miR-3116-1 (SEQ ID NO:813); miR-3117 (SEQ ID NO:815); miR-3118-6 (SEQ ID NO:821); miR-3118-5 (SEQ ID NO:820); miR-3118-4 (SEQ ID NO:819); miR-3118-3 (SEQ ID NO:818); miR-3118-2 (SEQ ID NO:817); miR-3118-1 (SEQ ID NO:816); miR-3119-2 (SEQ ID NO:823); miR-3119-1 (SEQ ID NO:822); miR-3120 (SEQ ID NO:824); miR-3121 (SEQ ID NO:825); miR-3122 (SEQ ID NO:826); miR-3123 (SEQ ID NO:827); miR-3124 (SEQ ID NO:828); miR-3125 (SEQ ID NO:829); miR-3126 (SEQ ID NO:830); miR-3127 (SEQ ID NO:831); miR-3128 (SEQ ID NO:832); miR-3129 (SEQ ID NO:833); miR-3130-2 (SEQ ID NO:835); miR-3130-1 (SEQ ID NO:834); miR-3131 (SEQ ID NO:836); miR-3132 (SEQ ID NO:837); miR-3133 (SEQ ID NO:838); miR-3134 (SEQ ID NO:839); miR-3135a (SEQ ID NO:840); miR-3135b (SEQ ID NO:841); miR-3136 (SEQ ID NO:842); miR-3137 (SEQ ID NO:843); miR-3138 (SEQ ID NO:844); miR-3139 (SEQ ID NO:845); miR-3140 (SEQ ID NO:846); miR-3141 (SEQ ID NO:847); miR-3142 (SEQ ID NO:848); miR-3143 (SEQ ID NO:849); miR-3144 (SEQ ID NO:850); miR-3145 (SEQ ID NO:851); miR-3146 (SEQ ID NO:852); miR-3147 (SEQ ID NO:853); miR-3148 (SEQ ID NO:854); miR-3149 (SEQ ID NO:855); miR-3150a (SEQ ID NO:856); miR-3150b (SEQ ID NO:857); miR-3151 (SEQ ID NO:858); miR-3152 (SEQ ID NO:859); miR-3153 (SEQ ID NO:860); miR-3154 (SEQ ID NO:861); miR-3155a (SEQ ID NO:862); miR-3155b (SEQ ID NO:863); miR-3156-3 (SEQ ID NO:866); miR-3156-2 (SEQ ID NO:865); miR-3156-1 (SEQ ID NO:864); miR-3157 (SEQ ID NO:867); miR-3158-2 (SEQ ID NO:869); miR-3158-1 (SEQ ID NO:868); miR-3159 (SEQ ID NO:870); miR-3160-2 (SEQ ID NO:872); miR-3160-1 (SEQ ID NO:871); miR-3161 (SEQ ID NO:873); miR-3162 (SEQ ID NO:874); miR-3163 (SEQ ID NO:875); miR-3164 (SEQ ID NO:876); miR-3165 (SEQ ID NO:877); miR-3166 (SEQ ID NO:878); miR-3167 (SEQ ID NO:879); miR-3168 (SEQ ID NO:880); miR-3169 (SEQ ID NO:881); miR-3170 (SEQ ID NO:882); miR-3171 (SEQ ID NO:883); miR-3173 (SEQ ID NO:884); miR-3174 (SEQ ID NO:885); miR-3175 (SEQ ID NO:886); miR-3176 (SEQ ID NO:887); miR-3177 (SEQ ID NO:888); miR-3178 (SEQ ID NO:889); miR-3179-3 (SEQ ID NO:892); miR-3179-2 (SEQ ID NO:891); miR-3179-1 (SEQ ID NO:890); miR-3180-5 (SEQ ID NO:897); miR-3180-4 (SEQ ID NO:896); miR-3180-3 (SEQ ID NO:895); miR-3180-2 (SEQ ID NO:894); miR-3180-1

(SEQ ID NO:893); miR-3181 (SEQ ID NO:898); miR-3182 (SEQ ID NO:899); miR-3183 (SEQ ID NO:900); miR-3184 (SEQ ID NO:901); miR-3185 (SEQ ID NO:902); miR-3186 (SEQ ID NO:903); miR-3187 (SEQ ID NO:904); miR-3188 (SEQ ID NO:905); miR-3189 (SEQ ID NO:906); miR-3190 (SEQ ID NO:907); miR-3191 (SEQ ID NO:908); miR-3192 (SEQ ID NO:909); miR-3193 (SEQ ID NO:910); miR-3194 (SEQ ID NO:911); miR-3195 (SEQ ID NO:912); miR-3196 (SEQ ID NO:913); miR-3197 (SEQ ID NO:914); miR-3198-2 (SEQ ID NO:916); miR-3198-1 (SEQ ID NO:915); miR-3199-2 (SEQ ID NO:918); miR-3199-1 (SEQ ID NO:917); miR-3200 (SEQ ID NO:919); miR-3201 (SEQ ID NO:920); miR-3202-2 (SEQ ID NO:922); miR-3202-1 (SEQ ID NO:921); miR-3529 (SEQ ID NO:923); miR-3591 (SEQ ID NO:924); miR-3605 (SEQ ID NO:925); miR-3606 (SEQ ID NO:926); miR-3607 (SEQ ID NO:927); miR-3609 (SEQ ID NO:928); miR-3610 (SEQ ID NO:929); miR-3611 (SEQ ID NO:930); miR-3612 (SEQ ID NO:931); miR-3613 (SEQ ID NO:932); miR-3614 (SEQ ID NO:933); miR-3615 (SEQ ID NO:934); miR-3616 (SEQ ID NO:935); miR-3617 (SEQ ID NO:936); miR-3618 (SEQ ID NO:937); miR-3619 (SEQ ID NO:938); miR-3620 (SEQ ID NO:939); miR-3621 (SEQ ID NO:940); miR-3622a (SEQ ID NO:941); miR-3622b (SEQ ID NO:942); miR-3646 (SEQ ID NO:943); miR-3648 (SEQ ID NO:944); miR-3649 (SEQ ID NO:945); miR-3650 (SEQ ID NO:946); miR-3651 (SEQ ID NO:947); miR-3652 (SEQ ID NO:948); miR-3653 (SEQ ID NO:949); miR-3654 (SEQ ID NO:950); miR-3655 (SEQ ID NO:951); miR-3656 (SEQ ID NO:952); miR-3657 (SEQ ID NO:953); miR-3658 (SEQ ID NO:954); miR-3659 (SEQ ID NO:955); miR-3660 (SEQ ID NO:956); miR-3661 (SEQ ID NO:957); miR-3662 (SEQ ID NO:958); miR-3663 (SEQ ID NO:959); miR-3664 (SEQ ID NO:960); miR-3665 (SEQ ID NO:961); miR-3666 (SEQ ID NO:962); miR-3667 (SEQ ID NO:963); miR-3668 (SEQ ID NO:964); miR-3669 (SEQ ID NO:965); miR-3670-2 (SEQ ID NO:967); miR-3670-1 (SEQ ID NO:966); miR-3671 (SEQ ID NO:968); miR-3672 (SEQ ID NO:969); miR-3673 (SEQ ID NO:970); miR-3674 (SEQ ID NO:971); miR-3675 (SEQ ID NO:972); miR-3677 (SEQ ID NO:973); miR-3678 (SEQ ID NO:974); miR-3679 (SEQ ID NO:975); miR-3680-2 (SEQ ID NO:977); miR-3680-1 (SEQ ID NO:976); miR-3681 (SEQ ID NO:978); miR-3682 (SEQ ID NO:979); miR-3683 (SEQ ID NO:980); miR-3684 (SEQ ID NO:981); miR-3685 (SEQ ID NO:982); miR-3686 (SEQ ID NO:983); miR-3687 (SEQ ID NO:984); miR-3688-2 (SEQ ID NO:986); miR-3688-1 (SEQ ID NO:985); miR-3689a (SEQ ID NO:987); miR-3689b (SEQ ID NO:988); miR-3689c (SEQ ID NO:989); miR-3689d-1 (SEQ ID NO:990); miR-3689d-2 (SEQ ID NO:991); miR-3689e (SEQ ID NO:992); miR-3689f (SEQ ID NO:993); miR-3690-2 (SEQ ID NO:995); miR-3690-1 (SEQ ID NO:994); miR-3691 (SEQ ID NO:996); miR-3692 (SEQ ID NO:997); miR-3713 (SEQ ID NO:998); miR-3714 (SEQ ID NO:999); miR-3907 (SEQ ID NO:1000); miR-3908 (SEQ ID NO:1001); miR-3909 (SEQ ID NO:1002); miR-3910-2 (SEQ ID NO:1004); miR-3910-1 (SEQ ID NO:1003); miR-3911 (SEQ ID NO:1005); miR-3912 (SEQ ID NO:1006); miR-3913-2 (SEQ ID NO:1008); miR-3913-1 (SEQ ID NO:1007); miR-3914-2 (SEQ ID NO:1010); miR-3914-1 (SEQ ID NO:1009); miR-3915 (SEQ ID NO:1011); miR-3916 (SEQ ID NO:1012); miR-3917 (SEQ ID NO:1013); miR-3918 (SEQ ID NO:1014); miR-3919 (SEQ ID NO:1015); miR-3920 (SEQ ID NO:1016); miR-3921 (SEQ ID NO:1017); miR-3922 (SEQ ID NO:1018); miR-3923 (SEQ ID NO:1019); miR-3924 (SEQ ID NO:1020); miR-3925 (SEQ ID NO:1021); miR-3926-2 (SEQ ID NO:1023); miR-3926-1 (SEQ ID NO:1022); miR-3927 (SEQ ID NO:1024); miR-3928 (SEQ ID NO:1025); miR-3929 (SEQ ID NO:1026); miR-3934 (SEQ ID NO:1027); miR-3935 (SEQ ID NO:1028); miR-3936 (SEQ ID NO:1029); miR-3937 (SEQ ID NO:1030); miR-3938 (SEQ ID NO:1031); miR-3939 (SEQ ID NO:1032); miR-3940 (SEQ ID NO:1033); miR-3941 (SEQ ID NO:1034); miR-3942 (SEQ ID NO:1035); miR-3943 (SEQ ID NO:1036); miR-3944 (SEQ ID NO:1037); miR-3945 (SEQ ID NO:1038); miR-3960 (SEQ ID NO:1039); miR-3972 (SEQ ID NO:1040); miR-3973 (SEQ ID NO:1041); miR-3974 (SEQ ID NO:1042); miR-3975 (SEQ ID NO:1043); miR-3976 (SEQ ID NO:1044); miR-3977 (SEQ ID NO:1045); miR-3978 (SEQ ID NO:1046); miR-4251 (SEQ ID NO:1047); miR-4252 (SEQ ID NO:1048); miR-4253 (SEQ ID NO:1049); miR-4254 (SEQ ID NO:1050); miR-4255 (SEQ ID NO:1051); miR-4256 (SEQ ID NO:1052); miR-4257 (SEQ ID NO:1053); miR-4258 (SEQ ID NO:1054); miR-4259 (SEQ ID NO:1055); miR-4260 (SEQ ID NO:1056); miR-4261 (SEQ ID NO:1057); miR-4262 (SEQ ID NO:1058); miR-4263 (SEQ ID NO:1059); miR-4264 (SEQ ID NO:1060); miR-4265 (SEQ ID NO:1061); miR-4266 (SEQ ID NO:1062); miR-4267 (SEQ ID NO:1063); miR-4268 (SEQ ID NO:1064); miR-4269 (SEQ ID NO:1065); miR-4270 (SEQ ID NO:1066); miR-4271 (SEQ ID NO:1067); miR-4272 (SEQ ID NO:1068); miR-4273 (SEQ ID NO:1069); miR-4274 (SEQ ID NO:1070); miR-4275 (SEQ ID NO:1071); miR-4276 (SEQ ID NO:1072); miR-4277 (SEQ ID NO:1073); miR-4278 (SEQ ID NO:1074); miR-4279 (SEQ ID NO:1075); miR-4280 (SEQ ID NO:1076); miR-4281 (SEQ ID NO:1077); miR-4282 (SEQ ID NO:1078); miR-4283-2 (SEQ ID NO:1080); miR-4283-1 (SEQ ID NO:1079); miR-4284 (SEQ ID NO:1081); miR-4285 (SEQ ID NO:1082); miR-4286 (SEQ ID NO:1083); miR-4287 (SEQ ID NO:1084); miR-4288 (SEQ ID NO:1085); miR-4289 (SEQ ID NO:1086); miR-4290 (SEQ ID NO:1087); miR-4291 (SEQ ID NO:1088); miR-4292 (SEQ ID NO:1089); miR-4293 (SEQ ID NO:1090); miR-4294 (SEQ ID NO:1091); miR-4295 (SEQ ID NO:1092); miR-4296 (SEQ ID NO:1093); miR-4297 (SEQ ID NO:1094); miR-4298 (SEQ ID NO:1095); miR-4299 (SEQ ID NO:1096); miR-4300 (SEQ ID NO:1097); miR-4301 (SEQ ID NO:1098); miR-4302 (SEQ ID NO:1099); miR-4303 (SEQ ID NO:1100); miR-4304 (SEQ ID NO:1101); miR-4305 (SEQ ID NO:1102); miR-4306 (SEQ ID NO:1103); miR-4307 (SEQ ID NO:1104); miR-4308 (SEQ ID NO:1105); miR-4309 (SEQ ID NO:1106); miR-4310 (SEQ ID NO:1107); miR-4311 (SEQ ID NO:1108); miR-4312 (SEQ ID NO:1109); miR-4313 (SEQ ID NO:1110); miR-4314 (SEQ ID NO:1111); miR-4315-2 (SEQ ID NO:1113); miR-4315-1 (SEQ ID NO:1112); miR-4316 (SEQ ID NO:1114); miR-4317 (SEQ ID NO:1115); miR-4318 (SEQ ID NO:1116); miR-4319 (SEQ ID NO:1117); miR-4320 (SEQ ID NO:1118); miR-4321 (SEQ ID NO:1119); miR-4322 (SEQ ID NO:1120); miR-4323 (SEQ ID NO:1121); miR-4324 (SEQ ID NO:1122); miR-4325 (SEQ ID NO:1123); miR-4326 (SEQ ID NO:1124); miR-4327 (SEQ ID NO:1125); miR-4328 (SEQ ID NO:1126); miR-4329 (SEQ ID NO:1127); miR-4330 (SEQ ID NO:1128); miR-4417 (SEQ ID NO:1129); miR-4418 (SEQ ID NO:1130); miR-4419a (SEQ ID NO:1131); miR-4419b (SEQ ID NO:1132); miR-4420 (SEQ ID NO:1133); miR-4421 (SEQ ID NO:1134); miR-4422 (SEQ ID NO:1135); miR-4423 (SEQ ID NO:1136); miR-4424 (SEQ ID NO:1137); miR-4425 (SEQ ID NO:1138); miR-4426 (SEQ ID NO:1139); miR-4427 (SEQ ID NO:1140); miR-4428 (SEQ ID NO:1141); miR-4429 (SEQ ID NO:1142); miR-4430 (SEQ ID NO:1143); miR-4431 (SEQ ID NO:1144); miR-4432 (SEQ ID

NO:1145); miR-4433b (SEQ ID NO:1147); miR-4433 (SEQ ID NO:1146); miR-4434 (SEQ ID NO:1148); miR-4435-2 (SEQ ID NO:1150); miR-4435-1 (SEQ ID NO:1149); miR-4436a (SEQ ID NO:1151); miR-4436b-1 (SEQ ID NO:1152); miR-4436b-2 (SEQ ID NO:1153); miR-4437 (SEQ ID NO:1154); miR-4438 (SEQ ID NO:1155); miR-4439 (SEQ ID NO:1156); miR-4440 (SEQ ID NO:1157); miR-4441 (SEQ ID NO:1158); miR-4442 (SEQ ID NO:1159); miR-4443 (SEQ ID NO:1160); miR-4444-2 (SEQ ID NO:1162); miR-4444-1 (SEQ ID NO:1161); miR-4445 (SEQ ID NO:1163); miR-4446 (SEQ ID NO:1164); miR-4447 (SEQ ID NO:1165); miR-4448 (SEQ ID NO:1166); miR-4449 (SEQ ID NO:1167); miR-4450 (SEQ ID NO:1168); miR-4451 (SEQ ID NO:1169); miR-4452 (SEQ ID NO:1170); miR-4453 (SEQ ID NO:1171); miR-4454 (SEQ ID NO:1172); miR-4455 (SEQ ID NO:1173); miR-4456 (SEQ ID NO:1174); miR-4457 (SEQ ID NO:1175); miR-4458 (SEQ ID NO:1176); miR-4459 (SEQ ID NO:1177); miR-4460 (SEQ ID NO:1178); miR-4461 (SEQ ID NO:1179); miR-4462 (SEQ ID NO:1180); miR-4463 (SEQ ID NO:1181); miR-4464 (SEQ ID NO:1182); miR-4465 (SEQ ID NO:1183); miR-4466 (SEQ ID NO:1184); miR-4467 (SEQ ID NO:1185); miR-4468 (SEQ ID NO:1186); miR-4469 (SEQ ID NO:1187); miR-4470 (SEQ ID NO:1188); miR-4471 (SEQ ID NO:1189); miR-4472-2 (SEQ ID NO:1191); miR-4472-1 (SEQ ID NO:1190); miR-4473 (SEQ ID NO:1192); miR-4474 (SEQ ID NO:1193); miR-4475 (SEQ ID NO:1194); miR-4476 (SEQ ID NO:1195); miR-4477a (SEQ ID NO:1196); miR-4477b (SEQ ID NO:1197); miR-4478 (SEQ ID NO:1198); miR-4479 (SEQ ID NO:1199); miR-4480 (SEQ ID NO:1200); miR-4481 (SEQ ID NO:1201); miR-4482 (SEQ ID NO:1202); miR-4483 (SEQ ID NO:1203); miR-4484 (SEQ ID NO:1204); miR-4485 (SEQ ID NO:1205); miR-4486 (SEQ ID NO:1206); miR-4487 (SEQ ID NO:1207); miR-4488 (SEQ ID NO:1208); miR-4489 (SEQ ID NO:1209); miR-4490 (SEQ ID NO:1210); miR-4491 (SEQ ID NO:1211); miR-4492 (SEQ ID NO:1212); miR-4493 (SEQ ID NO:1213); miR-4494 (SEQ ID NO:1214); miR-4495 (SEQ ID NO:1215); miR-4496 (SEQ ID NO:1216); miR-4497 (SEQ ID NO:1217); miR-4498 (SEQ ID NO:1218); miR-4499 (SEQ ID NO:1219); miR-4500 (SEQ ID NO:1220); miR-4501 (SEQ ID NO:1221); miR-4502 (SEQ ID NO:1222); miR-4503 (SEQ ID NO:1223); miR-4504 (SEQ ID NO:1224); miR-4505 (SEQ ID NO:1225); miR-4506 (SEQ ID NO:1226); miR-4507 (SEQ ID NO:1227); miR-4508 (SEQ ID NO:1228); miR-4509-3 (SEQ ID NO:1231); miR-4509-2 (SEQ ID NO:1230); miR-4509-1 (SEQ ID NO:1229); miR-4510 (SEQ ID NO:1232); miR-4511 (SEQ ID NO:1233); miR-4512 (SEQ ID NO:1234); miR-4513 (SEQ ID NO:1235); miR-4514 (SEQ ID NO:1236); miR-4515 (SEQ ID NO:1237); miR-4516 (SEQ ID NO:1238); miR-4517 (SEQ ID NO:1239); miR-4518 (SEQ ID NO:1240); miR-4519 (SEQ ID NO:1241); miR-4520a (SEQ ID NO:1242); miR-4520b (SEQ ID NO:1243); miR-4521 (SEQ ID NO:1244); miR-4522 (SEQ ID NO:1245); miR-4523 (SEQ ID NO:1246); miR-4524a (SEQ ID NO:1247); miR-4524b (SEQ ID NO:1248); miR-4525 (SEQ ID NO:1249); miR-4526 (SEQ ID NO:1250); miR-4527 (SEQ ID NO:1251); miR-4528 (SEQ ID NO:1252); miR-4529 (SEQ ID NO:1253); miR-4530 (SEQ ID NO:1254); miR-4531 (SEQ ID NO:1255); miR-4532 (SEQ ID NO:1256); miR-4533 (SEQ ID NO:1257); miR-4534 (SEQ ID NO:1258); miR-4535 (SEQ ID NO:1259); miR-4536-2 (SEQ ID NO:1261); miR-4536-1 (SEQ ID NO:1260); miR-4537 (SEQ ID NO:1262); miR-4538 (SEQ ID NO:1263); miR-4539 (SEQ ID NO:1264); miR-4540 (SEQ ID NO:1265); miR-4632 (SEQ ID NO:1266); miR-4633 (SEQ ID NO:1267); miR-4634 (SEQ ID NO:1268); miR-4635 (SEQ ID NO:1269); miR-4636 (SEQ ID NO:1270); miR-4637 (SEQ ID NO:1271); miR-4638 (SEQ ID NO:1272); miR-4639 (SEQ ID NO:1273); miR-4640 (SEQ ID NO:1274); miR-4641 (SEQ ID NO:1275); miR-4642 (SEQ ID NO:1276); miR-4643 (SEQ ID NO:1277); miR-4644 (SEQ ID NO:1278); miR-4645 (SEQ ID NO:1279); miR-4646 (SEQ ID NO:1280); miR-4647 (SEQ ID NO:1281); miR-4648 (SEQ ID NO:1282); miR-4649 (SEQ ID NO:1283); miR-4650-2 (SEQ ID NO:1285); miR-4650-1 (SEQ ID NO:1284); miR-4651 (SEQ ID NO:1286); miR-4652 (SEQ ID NO:1287); miR-4653 (SEQ ID NO:1288); miR-4654 (SEQ ID NO:1289); miR-4655 (SEQ ID NO:1290); miR-4656 (SEQ ID NO:1291); miR-4657 (SEQ ID NO:1292); miR-4658 (SEQ ID NO:1293); miR-4659a (SEQ ID NO:1294); miR-4659b (SEQ ID NO:1295); miR-4660 (SEQ ID NO:1296); miR-4661 (SEQ ID NO:1297); miR-4662a (SEQ ID NO:1298); miR-4662b (SEQ ID NO:1299); miR-4663 (SEQ ID NO:1300); miR-4664 (SEQ ID NO:1301); miR-4665 (SEQ ID NO:1302); miR-4666a (SEQ ID NO:1303); miR-4666b (SEQ ID NO:1304); miR-4667 (SEQ ID NO:1305); miR-4668 (SEQ ID NO:1306); miR-4669 (SEQ ID NO:1307); miR-4670 (SEQ ID NO:1308); miR-4671 (SEQ ID NO:1309); miR-4672 (SEQ ID NO:1310); miR-4673 (SEQ ID NO:1311); miR-4674 (SEQ ID NO:1312); miR-4675 (SEQ ID NO:1313); miR-4676 (SEQ ID NO:1314); miR-4677 (SEQ ID NO:1315); miR-4678 (SEQ ID NO:1316); miR-4679-2 (SEQ ID NO:1318); miR-4679-1 (SEQ ID NO:1317); miR-4680 (SEQ ID NO:1319); miR-4681 (SEQ ID NO:1320); miR-4682 (SEQ ID NO:1321); miR-4683 (SEQ ID NO:1322); miR-4684 (SEQ ID NO:1323); miR-4685 (SEQ ID NO:1324); miR-4686 (SEQ ID NO:1325); miR-4687 (SEQ ID NO:1326); miR-4688 (SEQ ID NO:1327); miR-4689 (SEQ ID NO:1328); miR-4690 (SEQ ID NO:1329); miR-4691 (SEQ ID NO:1330); miR-4692 (SEQ ID NO:1331); miR-4693 (SEQ ID NO:1332); miR-4694 (SEQ ID NO:1333); miR-4695 (SEQ ID NO:1334); miR-4696 (SEQ ID NO:1335); miR-4697 (SEQ ID NO:1336); miR-4698 (SEQ ID NO:1337); miR-4699 (SEQ ID NO:1338); miR-4700 (SEQ ID NO:1339); miR-4701 (SEQ ID NO:1340); miR-4703 (SEQ ID NO:1341); miR-4704 (SEQ ID NO:1342); miR-4705 (SEQ ID NO:1343); miR-4706 (SEQ ID NO:1344); miR-4707 (SEQ ID NO:1345); miR-4708 (SEQ ID NO:1346); miR-4709 (SEQ ID NO:1347); miR-4710 (SEQ ID NO:1348); miR-4711 (SEQ ID NO:1349); miR-4712 (SEQ ID NO:1350); miR-4713 (SEQ ID NO:1351); miR-4714 (SEQ ID NO:1352); miR-4715 (SEQ ID NO:1353); miR-4716 (SEQ ID NO:1354); miR-4717 (SEQ ID NO:1355); miR-4718 (SEQ ID NO:1356); miR-4719 (SEQ ID NO:1357); miR-4720 (SEQ ID NO:1358); miR-4721 (SEQ ID NO:1359); miR-4722 (SEQ ID NO:1360); miR-4723 (SEQ ID NO:1361); miR-4724 (SEQ ID NO:1362); miR-4725 (SEQ ID NO:1363); miR-4726 (SEQ ID NO:1364); miR-4727 (SEQ ID NO:1365); miR-4728 (SEQ ID NO:1366); miR-4729 (SEQ ID NO:1367); miR-4730 (SEQ ID NO:1368); miR-4731 (SEQ ID NO:1369); miR-4732 (SEQ ID NO:1370); miR-4733 (SEQ ID NO:1371); miR-4734 (SEQ ID NO:1372); miR-4735 (SEQ ID NO:1373); miR-4736 (SEQ ID NO:1374); miR-4737 (SEQ ID NO:1375); miR-4738 (SEQ ID NO:1376); miR-4739 (SEQ ID NO:1377); miR-4740 (SEQ ID NO:1378); miR-4741 (SEQ ID NO:1379); miR-4742 (SEQ ID NO:1380); miR-4743 (SEQ ID NO:1381); miR-4744 (SEQ ID NO:1382); miR-4745 (SEQ ID NO:1383); miR-4746 (SEQ ID NO:1384); miR-4747 (SEQ ID NO:1385);

miR-4748 (SEQ ID NO:1386); miR-4749 (SEQ ID NO:1387); miR-4750 (SEQ ID NO:1388); miR-4751 (SEQ ID NO:1389); miR-4752 (SEQ ID NO:1390); miR-4753 (SEQ ID NO:1391); miR-4754 (SEQ ID NO:1392); miR-4755 (SEQ ID NO:1393); miR-4756 (SEQ ID NO:1394); miR-4757 (SEQ ID NO:1395); miR-4758 (SEQ ID NO:1396); miR-4759 (SEQ ID NO:1397); miR-4760 (SEQ ID NO:1398); miR-4761 (SEQ ID NO:1399); miR-4762 (SEQ ID NO:1400); miR-4763 (SEQ ID NO:1401); miR-4764 (SEQ ID NO:1402); miR-4765 (SEQ ID NO:1403); miR-4766 (SEQ ID NO:1404); miR-4767 (SEQ ID NO:1405); miR-4768 (SEQ ID NO:1406); miR-4769 (SEQ ID NO:1407); miR-4770 (SEQ ID NO:1408); miR-4771-2 (SEQ ID NO:1410); miR-4771-1 (SEQ ID NO:1409); miR-4772 (SEQ ID NO:1411); miR-4773-2 (SEQ ID NO:1413); miR-4773-1 (SEQ ID NO:1412); miR-4774 (SEQ ID NO:1414); miR-4775 (SEQ ID NO:1415); miR-4776-2 (SEQ ID NO:1417); miR-4776-1 (SEQ ID NO:1416); miR-4777 (SEQ ID NO:1418); miR-4778 (SEQ ID NO:1419); miR-4779 (SEQ ID NO:1420); miR-4780 (SEQ ID NO:1421); miR-4781 (SEQ ID NO:1422); miR-4782 (SEQ ID NO:1423); miR-4783 (SEQ ID NO:1424); miR-4784 (SEQ ID NO:1425); miR-4785 (SEQ ID NO:1426); miR-4786 (SEQ ID NO:1427); miR-4787 (SEQ ID NO:1428); miR-4788 (SEQ ID NO:1429); miR-4789 (SEQ ID NO:1430); miR-4790 (SEQ ID NO:1431); miR-4791 (SEQ ID NO:1432); miR-4792 (SEQ ID NO:1433); miR-4793 (SEQ ID NO:1434); miR-4794 (SEQ ID NO:1435); miR-4795 (SEQ ID NO:1436); miR-4796 (SEQ ID NO:1437); miR-4797 (SEQ ID NO:1438); miR-4798 (SEQ ID NO:1439); miR-4799 (SEQ ID NO:1440); miR-4800 (SEQ ID NO:1441); miR-4801 (SEQ ID NO:1442); miR-4802 (SEQ ID NO:1443); miR-4803 (SEQ ID NO:1444); miR-4804 (SEQ ID NO:1445); miR-4999 (SEQ ID NO:1446); miR-5000 (SEQ ID NO:1447); miR-5001 (SEQ ID NO:1448); miR-5002 (SEQ ID NO:1449); miR-5003 (SEQ ID NO:1450); miR-5004 (SEQ ID NO:1451); miR-5006 (SEQ ID NO:1452); miR-5007 (SEQ ID NO:1453); miR-5008 (SEQ ID NO:1454); miR-5009 (SEQ ID NO:1455); miR-5010 (SEQ ID NO:1456); miR-5011 (SEQ ID NO:1457); miR-5047 (SEQ ID NO:1458); miR-5087 (SEQ ID NO:1459); miR-5088 (SEQ ID NO:1460); miR-5089 (SEQ ID NO:1461); miR-5090 (SEQ ID NO:1462); miR-5091 (SEQ ID NO:1463); miR-5092 (SEQ ID NO:1464); miR-5093 (SEQ ID NO:1465); miR-5094 (SEQ ID NO:1466); miR-5095 (SEQ ID NO:1467); miR-5096 (SEQ ID NO:1468); miR-5100 (SEQ ID NO:1469); miR-5186 (SEQ ID NO:1470); miR-5187 (SEQ ID NO:1471); miR-5188 (SEQ ID NO:1472); miR-5189 (SEQ ID NO:1473); miR-5190 (SEQ ID NO:1474); miR-5191 (SEQ ID NO:1475); miR-5192 (SEQ ID NO:1476); miR-5193 (SEQ ID NO:1477); miR-5194 (SEQ ID NO:1478); miR-5195 (SEQ ID NO:1479); miR-5196 (SEQ ID NO:1480); miR-5197 (SEQ ID NO:1481); miR-5571 (SEQ ID NO:1482); miR-5572 (SEQ ID NO:1483); miR-5579 (SEQ ID NO:1484); miR-5580 (SEQ ID NO:1485); miR-5581 (SEQ ID NO:1486); miR-5582 (SEQ ID NO:1487); miR-5583-2 (SEQ ID NO:1489); miR-5583-1 (SEQ ID NO:1488); miR-5584 (SEQ ID NO:1490); miR-5585 (SEQ ID NO:1491); miR-5586 (SEQ ID NO:1492); miR-5587 (SEQ ID NO:1493); miR-5588 (SEQ ID NO:1494); miR-5589 (SEQ ID NO:1495); miR-5590 (SEQ ID NO:1496); miR-5591 (SEQ ID NO:1497); miR-5680 (SEQ ID NO:1498); miR-5681a (SEQ ID NO:1499); miR-5681b (SEQ ID NO:1500); miR-5682 (SEQ ID NO:1501); miR-5683 (SEQ ID NO:1502); miR-5684 (SEQ ID NO:1503); miR-5685 (SEQ ID NO:1504); miR-5687 (SEQ ID NO:1505); miR-5688 (SEQ ID NO:1506); miR-5689 (SEQ ID NO:1507); miR-5690 (SEQ ID NO:1508); miR-5691 (SEQ ID NO:1509); miR-5692a-1 (SEQ ID NO:1510); miR-5692a-2 (SEQ ID NO:1511); miR-5692b (SEQ ID NO:1512); miR-5692c-1 (SEQ ID NO:1513); miR-5692c-2 (SEQ ID NO:1514); miR-5693 (SEQ ID NO:1515); miR-5694 (SEQ ID NO:1516); miR-5695 (SEQ ID NO:1517); miR-5696 (SEQ ID NO:1518); miR-5697 (SEQ ID NO:1519); miR-5698 (SEQ ID NO:1520); miR-5699 (SEQ ID NO:1521); miR-5700 (SEQ ID NO:1522); miR-5701-2 (SEQ ID NO:1524); miR-5701-1 (SEQ ID NO:1523); miR-5702 (SEQ ID NO:1525); miR-5703 (SEQ ID NO:1526); miR-5704 (SEQ ID NO:1527); miR-5705 (SEQ ID NO:1528); miR-5706 (SEQ ID NO:1529); miR-5707 (SEQ ID NO:1530); miR-5708 (SEQ ID NO:1531); miR-5739 (SEQ ID NO:1532); miR-5787 (SEQ ID NO:1533); miR-6068 (SEQ ID NO:1534); miR-6069 (SEQ ID NO:1535); miR-6070 (SEQ ID NO:1536); miR-6071 (SEQ ID NO:1537); miR-6072 (SEQ ID NO:1538); miR-6073 (SEQ ID NO:1539); miR-6074 (SEQ ID NO:1540); miR-6075 (SEQ ID NO:1541); miR-6076 (SEQ ID NO:1542); miR-6077-2 (SEQ ID NO:1544); miR-6077-1 (SEQ ID NO:1543); miR-6078 (SEQ ID NO:1545); miR-6079 (SEQ ID NO:1546); miR-6080 (SEQ ID NO:1547); miR-6081 (SEQ ID NO:1548); miR-6082 (SEQ ID NO:1549); miR-6083 (SEQ ID NO:1550); miR-6084 (SEQ ID NO:1551); miR-6085 (SEQ ID NO:1552); miR-6086 (SEQ ID NO:1553); miR-6087 (SEQ ID NO:1554); miR-6088 (SEQ ID NO:1555); miR-6089-2 (SEQ ID NO:1557); miR-6089-1 (SEQ ID NO:1556); miR-6090 (SEQ ID NO:1558); miR-6124 (SEQ ID NO:1559); miR-6125 (SEQ ID NO:1560); miR-6126 (SEQ ID NO:1561); miR-6127 (SEQ ID NO:1562); miR-6128 (SEQ ID NO:1563); miR-6129 (SEQ ID NO:1564); miR-6130 (SEQ ID NO:1565); miR-6131 (SEQ ID NO:1566); miR-6132 (SEQ ID NO:1567); miR-6133 (SEQ ID NO:1568); miR-6134 (SEQ ID NO:1569); miR-6165 (SEQ ID NO:1570); miR-6499 (SEQ ID NO:1571); miR-6500 (SEQ ID NO:1572); miR-6501 (SEQ ID NO:1573); miR-6502 (SEQ ID NO:1574); miR-6503 (SEQ ID NO:1575); miR-6504 (SEQ ID NO:1576); miR-6505 (SEQ ID NO:1577); miR-6506 (SEQ ID NO:1578); miR-6507 (SEQ ID NO:1579); miR-6508 (SEQ ID NO:1580); miR-6509 (SEQ ID NO:1581); miR-6510 (SEQ ID NO:1582); miR-6511a-1 (SEQ ID NO:1583); miR-6511a-2 (SEQ ID NO:1584); miR-6511a-3 (SEQ ID NO:1585); miR-6511a-4 (SEQ ID NO:1586); miR-6511b-1 (SEQ ID NO:1587); miR-6511b-2 (SEQ ID NO:1588); miR-6512 (SEQ ID NO:1589); miR-6513 (SEQ ID NO:1590); miR-6514 (SEQ ID NO:1591); miR-6515 (SEQ ID NO:1592); miR-6516 (SEQ ID NO:1593); miR-6715a (SEQ ID NO:1594); miR-6715b (SEQ ID NO:1595); miR-6716 (SEQ ID NO:1596); miR-6717 (SEQ ID NO:1597); miR-6718 (SEQ ID NO:1598); miR-6719 (SEQ ID NO:1599); miR-6720 (SEQ ID NO:1600); miR-6721 (SEQ ID NO:1601); miR-6722 (SEQ ID NO:1602); miR-6723 (SEQ ID NO:1603); miR-6724 (SEQ ID NO:1604); miR-6726 (SEQ ID NO:1605); miR-6727 (SEQ ID NO:1606); miR-6728 (SEQ ID NO:1607); miR-6729 (SEQ ID NO:1608); miR-6730 (SEQ ID NO:1609); miR-6731 (SEQ ID NO:1610); miR-6732 (SEQ ID NO:1611); miR-6733 (SEQ ID NO:1612); miR-6734 (SEQ ID NO:1613); miR-6735 (SEQ ID NO:1614); miR-6736 (SEQ ID NO:1615); miR-6737 (SEQ ID NO:1616); miR-6738 (SEQ ID NO:1617); miR-6739 (SEQ ID NO:1618); miR-6740 (SEQ ID NO:1619); miR-6741 (SEQ ID NO:1620); miR-6742 (SEQ ID NO:1621); miR-6743 (SEQ ID NO:1622); miR-6744 (SEQ ID NO:1623); miR-6745 (SEQ ID NO:1624); miR-6746 (SEQ ID NO:1625);

miR-6747 (SEQ ID NO:1626); miR-6748 (SEQ ID NO:1627); miR-6749 (SEQ ID NO:1628); miR-6750 (SEQ ID NO:1629); miR-6751 (SEQ ID NO:1630); miR-6752 (SEQ ID NO:1631); miR-6753 (SEQ ID NO:1632); miR-6754 (SEQ ID NO:1633); miR-6755 (SEQ ID NO:1634); miR-6756 (SEQ ID NO:1635); miR-6757 (SEQ ID NO:1636); miR-6758 (SEQ ID NO:1637); miR-6759 (SEQ ID NO:1638); miR-6760 (SEQ ID NO:1639); miR-6761 (SEQ ID NO:1640); miR-6762 (SEQ ID NO:1641); miR-6763 (SEQ ID NO:1642); miR-6764 (SEQ ID NO:1643); miR-6765 (SEQ ID NO:1644); miR-6766 (SEQ ID NO:1645); miR-6767 (SEQ ID NO:1646); miR-6768 (SEQ ID NO:1647); miR-6769a (SEQ ID NO:1648); miR-6769b (SEQ ID NO:1649); miR-6770-3 (SEQ ID NO:1652); miR-6770-2 (SEQ ID NO:1651); miR-6770-1 (SEQ ID NO:1650); miR-6771 (SEQ ID NO:1653); miR-6772 (SEQ ID NO:1654); miR-6773 (SEQ ID NO:1655); miR-6774 (SEQ ID NO:1656); miR-6775 (SEQ ID NO:1657); miR-6776 (SEQ ID NO:1658); miR-6777 (SEQ ID NO:1659); miR-6778 (SEQ ID NO:1660); miR-6779 (SEQ ID NO:1661); miR-6780a (SEQ ID NO:1662); miR-6780b (SEQ ID NO:1663); miR-6781 (SEQ ID NO:1664); miR-6782 (SEQ ID NO:1665); miR-6783 (SEQ ID NO:1666); miR-6784 (SEQ ID NO:1667); miR-6785 (SEQ ID NO:1668); miR-6786 (SEQ ID NO:1669); miR-6787 (SEQ ID NO:1670); miR-6788 (SEQ ID NO:1671); miR-6789 (SEQ ID NO:1672); miR-6790 (SEQ ID NO:1673); miR-6791 (SEQ ID NO:1674); miR-6792 (SEQ ID NO:1675); miR-6793 (SEQ ID NO:1676); miR-6794 (SEQ ID NO:1677); miR-6795 (SEQ ID NO:1678); miR-6796 (SEQ ID NO:1679); miR-6797 (SEQ ID NO:1680); miR-6798 (SEQ ID NO:1681); miR-6799 (SEQ ID NO:1682); miR-6800 (SEQ ID NO:1683); miR-6801 (SEQ ID NO:1684); miR-6802 (SEQ ID NO:1685); miR-6803 (SEQ ID NO:1686); miR-6804 (SEQ ID NO:1687); miR-6805 (SEQ ID NO:1688); miR-6806 (SEQ ID NO:1689); miR-6807 (SEQ ID NO:1690); miR-6808 (SEQ ID NO:1691); miR-6809 (SEQ ID NO:1692); miR-6810 (SEQ ID NO:1693); miR-6811 (SEQ ID NO:1694); miR-6812 (SEQ ID NO:1695); miR-6813 (SEQ ID NO:1696); miR-6814 (SEQ ID NO:1697); miR-6815 (SEQ ID NO:1698); miR-6816 (SEQ ID NO:1699); miR-6817 (SEQ ID NO:1700); miR-6818 (SEQ ID NO:1701); miR-6819 (SEQ ID NO:1702); miR-6820 (SEQ ID NO:1703); miR-6821 (SEQ ID NO:1704); miR-6822 (SEQ ID NO:1705); miR-6823 (SEQ ID NO:1706); miR-6824 (SEQ ID NO:1707); miR-6825 (SEQ ID NO:1708); miR-6826 (SEQ ID NO:1709); miR-6827 (SEQ ID NO:1710); miR-6828 (SEQ ID NO:1711); miR-6829 (SEQ ID NO:1712); miR-6830 (SEQ ID NO:1713); miR-6831 (SEQ ID NO:1714); miR-6832 (SEQ ID NO:1715); miR-6833 (SEQ ID NO:1716); miR-6834 (SEQ ID NO:1717); miR-6835 (SEQ ID NO:1718); miR-6836 (SEQ ID NO:1719); miR-6837 (SEQ ID NO:1720); miR-6838 (SEQ ID NO:1721); miR-6839 (SEQ ID NO:1722); miR-6840 (SEQ ID NO:1723); miR-6841 (SEQ ID NO:1724); miR-6842 (SEQ ID NO:1725); miR-6843 (SEQ ID NO:1726); miR-6844 (SEQ ID NO:1727); miR-6845 (SEQ ID NO:1728); miR-6846 (SEQ ID NO:1729); miR-6847 (SEQ ID NO:1730); miR-6848 (SEQ ID NO:1731); miR-6849 (SEQ ID NO:1732); miR-6850 (SEQ ID NO:1733); miR-6851 (SEQ ID NO:1734); miR-6852 (SEQ ID NO:1735); miR-6853 (SEQ ID NO:1736); miR-6854 (SEQ ID NO:1737); miR-6855 (SEQ ID NO:1738); miR-6856 (SEQ ID NO:1739); miR-6857 (SEQ ID NO:1740); miR-6858 (SEQ ID NO:1741); miR-6859-3 (SEQ ID NO:1744); miR-6859-2 (SEQ ID NO:1743); miR-6859-1 (SEQ ID NO:1742); miR-6860 (SEQ ID NO:1745); miR-6861 (SEQ ID NO:1746); miR-6862-2 (SEQ ID NO:1748); miR-6862-1 (SEQ ID NO:1747); miR-6863 (SEQ ID NO:1749); miR-6864 (SEQ ID NO:1750); miR-6865 (SEQ ID NO:1751); miR-6866 (SEQ ID NO:1752); miR-6867 (SEQ ID NO:1753); miR-6868 (SEQ ID NO:1754); miR-6869 (SEQ ID NO:1755); miR-6870 (SEQ ID NO:1756); miR-6871 (SEQ ID NO:1757); miR-6872 (SEQ ID NO:1758); miR-6873 (SEQ ID NO:1759); miR-6874 (SEQ ID NO:1760); miR-6875 (SEQ ID NO:1761); miR-6876 (SEQ ID NO:1762); miR-6877 (SEQ ID NO:1763); miR-6878 (SEQ ID NO:1764); miR-6879 (SEQ ID NO:1765); miR-6880 (SEQ ID NO:1766); miR-6881 (SEQ ID NO:1767); miR-6882 (SEQ ID NO:1768); miR-6883 (SEQ ID NO:1769); miR-6884 (SEQ ID NO:1770); miR-6885 (SEQ ID NO:1771); miR-6886 (SEQ ID NO:1772); miR-6887 (SEQ ID NO:1773); miR-6888 (SEQ ID NO:1774); miR-6889 (SEQ ID NO:1775); miR-6890 (SEQ ID NO:1776); miR-6891 (SEQ ID NO:1777); miR-6892 (SEQ ID NO:1778); miR-6893 (SEQ ID NO:1779); miR-6894 (SEQ ID NO:1780); miR-6895 (SEQ ID NO:1781); miR-7106 (SEQ ID NO:1782); miR-7107 (SEQ ID NO:1783); miR-7108 (SEQ ID NO:1784); miR-7109 (SEQ ID NO:1785); miR-7110 (SEQ ID NO:1786); miR-7111 (SEQ ID NO:1787); miR-7112-2 (SEQ ID NO:1789); miR-7112-1 (SEQ ID NO:1788); miR-7113 (SEQ ID NO:1790); miR-7114 (SEQ ID NO:1791); miR-7150 (SEQ ID NO:1792); miR-7151 (SEQ ID NO:1793); miR-7152 (SEQ ID NO:1794); miR-7153 (SEQ ID NO:1795); miR-7154 (SEQ ID NO:1796); miR-7155 (SEQ ID NO:1797); miR-7156 (SEQ ID NO:1798); miR-7157 (SEQ ID NO:1799); miR-7158 (SEQ ID NO:1800); miR-7159 (SEQ ID NO:1801); miR-7160 (SEQ ID NO:1802); miR-7161 (SEQ ID NO:1803); miR-7162 (SEQ ID NO:1804); miR-7515 (SEQ ID NO:1805); miR-7641-2 (SEQ ID NO:1807); miR-7641-1 (SEQ ID NO:1806); miR-7702 (SEQ ID NO:1808); miR-7703 (SEQ ID NO:1809); miR-7704 (SEQ ID NO:1810); miR-7705 (SEQ ID NO:1811); miR-7706 (SEQ ID NO:1812); miR-7843 (SEQ ID NO:1813); miR-7844 (SEQ ID NO:1814); miR-7845 (SEQ ID NO:1815); miR-7846 (SEQ ID NO:1816); miR-7847 (SEQ ID NO:1817); miR-7848 (SEQ ID NO:1818); miR-7849 (SEQ ID NO:1819); miR-7850 (SEQ ID NO:1820); miR-7851 (SEQ ID NO:1821); miR-7852 (SEQ ID NO:1822); miR-7853 (SEQ ID NO:1823); miR-7854 (SEQ ID NO:1824); miR-7855 (SEQ ID NO:1825); miR-7856 (SEQ ID NO:1826); miR-7973-2 (SEQ ID NO:1828); miR-7973-1 (SEQ ID NO:1827); miR-7974 (SEQ ID NO:1829); miR-7975 (SEQ ID NO:1830); miR-7976 (SEQ ID NO:1831); miR-7977 (SEQ ID NO:1832); miR-7978 (SEQ ID NO:1833); miR-8052 (SEQ ID NO:1834); miR-8053 (SEQ ID NO:1835); miR-8054 (SEQ ID NO:1836); miR-8055 (SEQ ID NO:1837); miR-8056 (SEQ ID NO:1838); miR-8057 (SEQ ID NO:1839); miR-8058 (SEQ ID NO:1840); miR-8059 (SEQ ID NO:1841); miR-8060 (SEQ ID NO:1842); miR-8061 (SEQ ID NO:1843); miR-8062 (SEQ ID NO:1844); miR-8063 (SEQ ID NO:1845); miR-8064 (SEQ ID NO:1846); miR-8065 (SEQ ID NO:1847); miR-8066 (SEQ ID NO:1848); miR-8067 (SEQ ID NO:1849); miR-8068 (SEQ ID NO:1850); miR-8069 (SEQ ID NO:1851); miR-8070 (SEQ ID NO:1852); miR-8071-2 (SEQ ID NO:1854); miR-8071-1 (SEQ ID NO:1853); miR-8072 (SEQ ID NO:1855); miR-8073 (SEQ ID NO:1856); miR-8074 (SEQ ID NO:1857); miR-8075 (SEQ ID NO:1858); miR-8076 (SEQ ID NO:1859); miR-8077 (SEQ ID NO:1860); miR-8078 (SEQ ID NO:1861); miR-8079 (SEQ ID NO:1862); miR-8080 (SEQ ID NO:1863); miR-8081 (SEQ ID NO:1864); miR-8082 (SEQ ID NO:1865); miR-8083 (SEQ ID NO:1866);

miR-8084 (SEQ ID NO:1867); miR-8085 (SEQ ID NO:1868); miR-8086 (SEQ ID NO:1869); miR-8087 (SEQ ID NO:1870); miR-8088 (SEQ ID NO:1871); and miR-8089 (SEQ ID NO:1872).

The following dog miRNA could be used: let-7a-1 (SEQ ID NO:2744); let-7a-2 (SEQ ID NO:2745); let-7b (SEQ ID NO:2746); let-7c (SEQ ID NO:2747); let-7e (SEQ ID NO:2748); let-7f (SEQ ID NO:2749); let-7g (SEQ ID NO:2750); let-7j (SEQ ID NO:2751); miR-1-1 (SEQ ID NO:2752); miR-1-2 (SEQ ID NO:2753); miR-7-1 (SEQ ID NO:2754); miR-7-2 (SEQ ID NO:2755); miR-7-3 (SEQ ID NO:2756); miR-9-1 (SEQ ID NO:2757); miR-9-2 (SEQ ID NO:2758); miR-9-3 (SEQ ID NO:2759); miR-10a (SEQ ID NO:2760); miR-10b (SEQ ID NO:2761); miR-15a (SEQ ID NO:2762); miR-15b (SEQ ID NO:2763); miR-16-1 (SEQ ID NO:2764); miR-16-2 (SEQ ID NO:2765); miR-17 (SEQ ID NO:2766); miR-18a (SEQ ID NO:2767); miR-18b (SEQ ID NO:2768); miR-19a (SEQ ID NO:2769); miR-19b-1 (SEQ ID NO:2770); miR-19b-2 (SEQ ID NO:2771); miR-20a (SEQ ID NO:2772); miR-20b (SEQ ID NO:2773); miR-21 (SEQ ID NO:2774); miR-22 (SEQ ID NO:2775); miR-23a (SEQ ID NO:2776); miR-23b (SEQ ID NO:2777); miR-24-1 (SEQ ID NO:2778); miR-24-2 (SEQ ID NO:2779); miR-25 (SEQ ID NO:2780); miR-26a-1 (SEQ ID NO:2781); miR-26a-2 (SEQ ID NO:2782); miR-26b (SEQ ID NO:2783); miR-27a (SEQ ID NO:2784); miR-27b (SEQ ID NO:2785); miR-28 (SEQ ID NO:2786); miR-29a (SEQ ID NO:2787); miR-29b-1 (SEQ ID NO:2788); miR-29b-2 (SEQ ID NO:2789); miR-29c-1 (SEQ ID NO:2790); miR-29c-2 (SEQ ID NO:2791); miR-30a (SEQ ID NO:2792); miR-30b (SEQ ID NO:2793); miR-30c-1 (SEQ ID NO:2794); miR-30c-2 (SEQ ID NO:2795); miR-30d (SEQ ID NO:2796); miR-30e (SEQ ID NO:2797); miR-31 (SEQ ID NO:2798); miR-32 (SEQ ID NO:2799); miR-33a (SEQ ID NO:2800); miR-33b (SEQ ID NO:2801); miR-34a (SEQ ID NO:2802); miR-34b (SEQ ID NO:2803); miR-34c (SEQ ID NO:2804); miR-92a-1 (SEQ ID NO:2805); miR-92a-2 (SEQ ID NO:2806); miR-92b (SEQ ID NO:2807); miR-93 (SEQ ID NO:2808); miR-95 (SEQ ID NO:2809); miR-96 (SEQ ID NO:2810); miR-98 (SEQ ID NO:2811); miR-99a-1 (SEQ ID NO:2812); miR-99a-2 (SEQ ID NO:2813); miR-99b (SEQ ID NO:2814); miR-101-1 (SEQ ID NO:2815); miR-101-2 (SEQ ID NO:2816); miR-103-1 (SEQ ID NO:2817); miR-103-2 (SEQ ID NO:2818); miR-105a (SEQ ID NO:2819); miR-105b (SEQ ID NO:2820); miR-106a (SEQ ID NO:2821); miR-106b (SEQ ID NO:2822); miR-107 (SEQ ID NO:2823); miR-122 (SEQ ID NO:2824); miR-124-1 (SEQ ID NO:2825); miR-124-2 (SEQ ID NO:2826); miR-124-3 (SEQ ID NO:2827); miR-125a (SEQ ID NO:2828); miR-125b-1 (SEQ ID NO:2829); miR-125b-2 (SEQ ID NO:2830); miR-126 (SEQ ID NO:2831); miR-127 (SEQ ID NO:2832); miR-128-1 (SEQ ID NO:2833); miR-128-2 (SEQ ID NO:2834); miR-129-1 (SEQ ID NO:2835); miR-129-2 (SEQ ID NO:2836); miR-130a (SEQ ID NO:2837); miR-130b (SEQ ID NO:2838); miR-132 (SEQ ID NO:2839); miR-133a (SEQ ID NO:2840); miR-133b (SEQ ID NO:2841); miR-133c (SEQ ID NO:2842); miR-134 (SEQ ID NO:2843); miR-135a-1 (SEQ ID NO:2844); miR-135a-2 (SEQ ID NO:2845); miR-135b (SEQ ID NO:2846); miR-136 (SEQ ID NO:2847); miR-137 (SEQ ID NO:2848); miR-138a (SEQ ID NO:2849); miR-138b (SEQ ID NO:2850); miR-139 (SEQ ID NO:2851); miR-140 (SEQ ID NO:2852); miR-141 (SEQ ID NO:2853); miR-142 (SEQ ID NO:2854); miR-143 (SEQ ID NO:2855); miR-144 (SEQ ID NO:2856); miR-145 (SEQ ID NO:2857); miR-146a (SEQ ID NO:2858); miR-146b (SEQ ID NO:2859); miR-147 (SEQ ID NO:2860); miR-148a (SEQ ID NO:2861); miR-148b (SEQ ID NO:2862); miR-149 (SEQ ID NO:2863); miR-150 (SEQ ID NO:2864); miR-151 (SEQ ID NO:2865); miR-152 (SEQ ID NO:2866); miR-153 (SEQ ID NO:2867); miR-155 (SEQ ID NO:2868); miR-181a-1 (SEQ ID NO:2869); miR-181a-2 (SEQ ID NO:2870); miR-181b-1 (SEQ ID NO:2871); miR-181b-2 (SEQ ID NO:2872); miR-181c (SEQ ID NO:2873); miR-181d (SEQ ID NO:2874); miR-182 (SEQ ID NO:2875); miR-183 (SEQ ID NO:2876); miR-184 (SEQ ID NO:2877); miR-185 (SEQ ID NO:2878); miR-186 (SEQ ID NO:2879); miR-187 (SEQ ID NO:2880); miR-188 (SEQ ID NO:2881); miR-190a (SEQ ID NO:2882); miR-190b (SEQ ID NO:2883); miR-191 (SEQ ID NO:2884); miR-192 (SEQ ID NO:2885); miR-193a (SEQ ID NO:2886); miR-193b (SEQ ID NO:2887); miR-194 (SEQ ID NO:2888); miR-195 (SEQ ID NO:2889); miR-196a-1 (SEQ ID NO:2890); miR-196a-2 (SEQ ID NO:2891); miR-196b (SEQ ID NO:2892); miR-197 (SEQ ID NO:2893); miR-199-1 (SEQ ID NO:2894); miR-199-2 (SEQ ID NO:2895); miR-199-3 (SEQ ID NO:2896); miR-200a (SEQ ID NO:2897); miR-200b (SEQ ID NO:2898); miR-200c (SEQ ID NO:2899); miR-202 (SEQ ID NO:2900); miR-203 (SEQ ID NO:2901); miR-204 (SEQ ID NO:2902); miR-205 (SEQ ID NO:2903); miR-206 (SEQ ID NO:2904); miR-207 (SEQ ID NO:2905); miR-208a (SEQ ID NO:2906); miR-208b (SEQ ID NO:2907); miR-210 (SEQ ID NO:2908); miR-211 (SEQ ID NO:2909); miR-212 (SEQ ID NO:2910); miR-214 (SEQ ID NO:2911); miR-215 (SEQ ID NO:2912); miR-216a (SEQ ID NO:2913); miR-216b (SEQ ID NO:2914); miR-217 (SEQ ID NO:2915); miR-218-1 (SEQ ID NO:2916); miR-218-2 (SEQ ID NO:2917); miR-219-1 (SEQ ID NO:2918); miR-219-2 (SEQ ID NO:2919); miR-221 (SEQ ID NO:2920); miR-222 (SEQ ID NO:2921); miR-223 (SEQ ID NO:2922); miR-224 (SEQ ID NO:2923); miR-299 (SEQ ID NO:2924); miR-300 (SEQ ID NO:2925); miR-301a (SEQ ID NO:2926); miR-301b (SEQ ID NO:2927); miR-302a (SEQ ID NO:2928); miR-302b (SEQ ID NO:2929); miR-302c (SEQ ID NO:2930); miR-302d (SEQ ID NO:2931); miR-320 (SEQ ID NO:2932); miR-323 (SEQ ID NO:2933); miR-324 (SEQ ID NO:2934); miR-325 (SEQ ID NO:2935); miR-326 (SEQ ID NO:2936); miR-328 (SEQ ID NO:2937); miR-329a (SEQ ID NO:2938); miR-329b (SEQ ID NO:2939); miR-330 (SEQ ID NO:2940); miR-331 (SEQ ID NO:2941); miR-335 (SEQ ID NO:2942); miR-338 (SEQ ID NO:2943); miR-340 (SEQ ID NO:2944); miR-342 (SEQ ID NO:2945); miR-345 (SEQ ID NO:2946); miR-346 (SEQ ID NO:2947); miR-350 (SEQ ID NO:2948); miR-361 (SEQ ID NO:2949); miR-362 (SEQ ID NO:2950); miR-363 (SEQ ID NO:2951); miR-365-1 (SEQ ID NO:2952); miR-365-2 (SEQ ID NO:2953); miR-367 (SEQ ID NO:2954); miR-369 (SEQ ID NO:2955); miR-370 (SEQ ID NO:2956); miR-371 (SEQ ID NO:2957); miR-374a (SEQ ID NO:2958); miR-374b (SEQ ID NO:2959); miR-375 (SEQ ID NO:2960); miR-376a-1 (SEQ ID NO:2961); miR-376a-2 (SEQ ID NO:2962); miR-376a-3 (SEQ ID NO:2963); miR-376b (SEQ ID NO:2964); miR-376c (SEQ ID NO:2965); miR-377 (SEQ ID NO:2966); miR-378 (SEQ ID NO:2967); miR-379 (SEQ ID NO:2968); miR-380 (SEQ ID NO:2969); miR-381 (SEQ ID NO:2970); miR-382 (SEQ ID NO:2971); miR-383 (SEQ ID NO:2972); miR-384 (SEQ ID NO:2973); miR-409 (SEQ ID NO:2974); miR-410 (SEQ ID NO:2975); miR-411 (SEQ ID NO:2976); miR-421 (SEQ ID NO:2977); miR-423a (SEQ ID NO:2978); miR-424 (SEQ ID NO:2979); miR-425 (SEQ ID NO:2980); miR-429 (SEQ ID NO:2981); miR-432 (SEQ ID NO:2982); miR-433 (SEQ ID NO:2983); miR-448 (SEQ ID NO:2984); miR-449 (SEQ ID NO:2985); miR-450a (SEQ ID NO:2986); miR-450b (SEQ ID NO:2987); miR-451 (SEQ ID NO:2988); miR-452 (SEQ ID NO:2989); miR-454 (SEQ ID NO:2990); miR-455 (SEQ ID NO:2991); miR-483 (SEQ ID NO:2992);

miR-485 (SEQ ID NO:2993); miR-487a (SEQ ID NO:2994); miR-487b (SEQ ID NO:2995); miR-488 (SEQ ID NO:2996); miR-489 (SEQ ID NO:2997); miR-490 (SEQ ID NO:2998); miR-491 (SEQ ID NO:2999); miR-493 (SEQ ID NO:3000); miR-494 (SEQ ID NO:3001); miR-495 (SEQ ID NO:3002); miR-496 (SEQ ID NO:3003); miR-497 (SEQ ID NO:3004); miR-499 (SEQ ID NO:3005); miR-500 (SEQ ID NO:3006); miR-502 (SEQ ID NO:3007); miR-503 (SEQ ID NO:3008); miR-504 (SEQ ID NO:3009); miR-505 (SEQ ID NO:3010); miR-514 (SEQ ID NO:3011); miR-532 (SEQ ID NO:3012); miR-539 (SEQ ID NO:3013); miR-542 (SEQ ID NO:3014); miR-543 (SEQ ID NO:3015); miR-544 (SEQ ID NO:3016); miR-545 (SEQ ID NO:3017); miR-551a (SEQ ID NO:3018); miR-551b (SEQ ID NO:3019); miR-568 (SEQ ID NO:3020); miR-574 (SEQ ID NO:3021); miR-578 (SEQ ID NO:3022); miR-582 (SEQ ID NO:3023); miR-589 (SEQ ID NO:3024); miR-590 (SEQ ID NO:3025); miR-592 (SEQ ID NO:3026); miR-599 (SEQ ID NO:3027); miR-615 (SEQ ID NO:3028); miR-628 (SEQ ID NO:3029); miR-631 (SEQ ID NO:3030); miR-632 (SEQ ID NO:3031); miR-652 (SEQ ID NO:3032); miR-653 (SEQ ID NO:3033); miR-660 (SEQ ID NO:3034); miR-664 (SEQ ID NO:3035); miR-665 (SEQ ID NO:3036); miR-671 (SEQ ID NO:3037); miR-676 (SEQ ID NO:3038); miR-708 (SEQ ID NO:3039); miR-718 (SEQ ID NO:3040); miR-758 (SEQ ID NO:3041); miR-759 (SEQ ID NO:3042); miR-761 (SEQ ID NO:3043); miR-764 (SEQ ID NO:3044); miR-802 (SEQ ID NO:3045); miR-872 (SEQ ID NO:3046); miR-874 (SEQ ID NO:3047); miR-875 (SEQ ID NO:3048); miR-876 (SEQ ID NO:3049); miR-885 (SEQ ID NO:3050); miR-1199 (SEQ ID NO:3051); miR-1271 (SEQ ID NO:3052); miR-1306 (SEQ ID NO:3053); miR-1307 (SEQ ID NO:3054); miR-1835 (SEQ ID NO:3055); miR-1836 (SEQ ID NO:3056); miR-1837-1 (SEQ ID NO:3057); miR-1837-2 (SEQ ID NO:3058); miR-1837-3 (SEQ ID NO:3059); miR-1837-4 (SEQ ID NO:3060); miR-1838 (SEQ ID NO:3061); miR-1839 (SEQ ID NO:3062); miR-1840 (SEQ ID NO:3063); miR-1841 (SEQ ID NO:3064); miR-1842 (SEQ ID NO:3065); miR-1843 (SEQ ID NO:3066); and miR-1844 (SEQ ID NO:3067).

The following horse miRNAs could be used: let-7a (SEQ ID NO:3068); let-7a-2 (SEQ ID NO:3069); let-7c (SEQ ID NO:3070); let-7d (SEQ ID NO:3071); let-7e (SEQ ID NO:3072); let-7f (SEQ ID NO:3073); let-7g (SEQ ID NO:3074); miR-1-1 (SEQ ID NO:3075); miR-1-2 (SEQ ID NO:3076); miR-7-1 (SEQ ID NO:3077); miR-7-2 (SEQ ID NO:3078); miR-7-3 (SEQ ID NO:3079); miR-9a (SEQ ID NO:3080); miR-9a-2 (SEQ ID NO:3081); miR-10a (SEQ ID NO:3082); miR-10b (SEQ ID NO:3083); miR-15a (SEQ ID NO:3084); miR-15b (SEQ ID NO:3085); miR-16-1 (SEQ ID NO:3086); miR-16-2 (SEQ ID NO:3087); miR-17 (SEQ ID NO:3088); miR-18a (SEQ ID NO:3089); miR-18b (SEQ ID NO:3090); miR-19a (SEQ ID NO:3091); miR-19b (SEQ ID NO:3092); miR-19b-2 (SEQ ID NO:3093); miR-20a (SEQ ID NO:3094); miR-20b (SEQ ID NO:3095); miR-21 (SEQ ID NO:3096); miR-22 (SEQ ID NO:3097); miR-23a (SEQ ID NO:3098); miR-23b (SEQ ID NO:3099); miR-24-1 (SEQ ID NO:3100); miR-24-2 (SEQ ID NO:3101); miR-25 (SEQ ID NO:3102); miR-26a (SEQ ID NO:3103); miR-26a-2 (SEQ ID NO:3104); miR-27a (SEQ ID NO:3105); miR-27b (SEQ ID NO:3106); miR-28 (SEQ ID NO:3107); miR-29a (SEQ ID NO:3108); miR-29b (SEQ ID NO:3109); miR-29b-2 (SEQ ID NO:3110); miR-29c (SEQ ID NO:3111); miR-29c-2 (SEQ ID NO:3112); miR-30b (SEQ ID NO:3113); miR-30c (SEQ ID NO:3114); miR-30c-2 (SEQ ID NO:3115); miR-30d (SEQ ID NO:3116); miR-30e (SEQ ID NO:3117); miR-31 (SEQ ID NO:3118); miR-32 (SEQ ID NO:3119); miR-33a (SEQ ID NO:3120); miR-33b (SEQ ID NO:3121); miR-34a (SEQ ID NO:3122); miR-34b (SEQ ID NO:3123); miR-34c (SEQ ID NO:3124); miR-92a (SEQ ID NO:3125); miR-92a-2 (SEQ ID NO:3126); miR-92b (SEQ ID NO:3127); miR-93 (SEQ ID NO:3128); miR-95 (SEQ ID NO:3129); miR-96 (SEQ ID NO:3130); miR-98 (SEQ ID NO:3131); miR-99a-2 (SEQ ID NO:3132); miR-99b (SEQ ID NO:3133); miR-100 (SEQ ID NO:3134); miR-101-1 (SEQ ID NO:3135); miR-101-2 (SEQ ID NO:3136); miR-103 (SEQ ID NO:3137); miR-105 (SEQ ID NO:3138); miR-106a (SEQ ID NO:3139); miR-106b (SEQ ID NO:3140); miR-107a (SEQ ID NO:3141); miR-107b (SEQ ID NO:3142); miR-122 (SEQ ID NO:3143); miR-124-1 (SEQ ID NO:3144); miR-124-2 (SEQ ID NO:3145); miR-125a (SEQ ID NO:3146); miR-125b (SEQ ID NO:3147); miR-125b-2 (SEQ ID NO:3148); miR-126 (SEQ ID NO:3149); miR-127 (SEQ ID NO:3150); miR-128-1 (SEQ ID NO:3151); miR-128-2 (SEQ ID NO:3152); miR-129a (SEQ ID NO:3153); miR-129b (SEQ ID NO:3154); miR-130a (SEQ ID NO:3155); miR-130b (SEQ ID NO:3156); miR-132 (SEQ ID NO:3157); miR-133a (SEQ ID NO:3158); miR-133a-2 (SEQ ID NO:3159); miR-133b (SEQ ID NO:3160); miR-134 (SEQ ID NO:3161); miR-135a (SEQ ID NO:3162); miR-135a-2 (SEQ ID NO:3163); miR-135b (SEQ ID NO:3164); miR-136 (SEQ ID NO:3165); miR-137 (SEQ ID NO:3166); miR-138-1 (SEQ ID NO:3167); miR-138-2 (SEQ ID NO:3168); miR-139 (SEQ ID NO:3169); miR-140 (SEQ ID NO:3170); miR-141 (SEQ ID NO:3171); miR-142 (SEQ ID NO:3172); miR-143 (SEQ ID NO:3173); miR-144 (SEQ ID NO:3174); miR-145 (SEQ ID NO:3175); miR-146a (SEQ ID NO:3176); miR-146b (SEQ ID NO:3177); miR-147b (SEQ ID NO:3178); miR-148a (SEQ ID NO:3179); miR-148b (SEQ ID NO:3180); miR-149 (SEQ ID NO:3181); miR-150 (SEQ ID NO:3182); miR-151 (SEQ ID NO:3183); miR-153-1 (SEQ ID NO:3184); miR-153-2 (SEQ ID NO:3185); miR-154 (SEQ ID NO:3186); miR-155 (SEQ ID NO:3187); miR-181a (SEQ ID NO:3188); miR-181a-2 (SEQ ID NO:3189); miR-181b (SEQ ID NO:3190); miR-182 (SEQ ID NO:3191); miR-183 (SEQ ID NO:3192); miR-184 (SEQ ID NO:3193); miR-186 (SEQ ID NO:3194); miR-187 (SEQ ID NO:3195); miR-188 (SEQ ID NO:3196); miR-190a (SEQ ID NO:3197); miR-190b (SEQ ID NO:3198); miR-191 (SEQ ID NO:3199); miR-192 (SEQ ID NO:3200); miR-193a (SEQ ID NO:3201); miR-193b (SEQ ID NO:3202); miR-194-1 (SEQ ID NO:3203); miR-194-2 (SEQ ID NO:3204); miR-195 (SEQ ID NO:3205); miR-196a (SEQ ID NO:3206); miR-196b (SEQ ID NO:3207); miR-197 (SEQ ID NO:3208); miR-199a (SEQ ID NO:3209); miR-199b (SEQ ID NO:3210); miR-200a (SEQ ID NO:3211); miR-200b (SEQ ID NO:3212); miR-200c (SEQ ID NO:3213); miR-204b-2 (SEQ ID NO:3214); miR-205 (SEQ ID NO:3215); miR-206-2 (SEQ ID NO:3216); miR-208a (SEQ ID NO:3217); miR-208b (SEQ ID NO:3218); miR-211 (SEQ ID NO:3219); miR-212 (SEQ ID NO:3220); miR-214 (SEQ ID NO:3221); miR-215 (SEQ ID NO:3222); miR-216a (SEQ ID NO:3223); miR-216b (SEQ ID NO:3224); miR-217 (SEQ ID NO:3225); miR-218-1 (SEQ ID NO:3226); miR-218-2 (SEQ ID NO:3227); miR-219-1 (SEQ ID NO:3228); miR-219-2 (SEQ ID NO:3229); miR-221 (SEQ ID NO:3230); miR-222 (SEQ ID NO:3231); miR-223 (SEQ ID NO:3232); miR-224 (SEQ ID NO:3233); miR-296 (SEQ ID NO:3234); miR-299 (SEQ ID NO:3235); miR-301a (SEQ ID NO:3236); miR-301b (SEQ ID NO:3237); miR-302a (SEQ ID NO:3238); miR-302b (SEQ ID NO:3239); miR-302c (SEQ ID NO:3240); miR-302d (SEQ ID NO:3241); miR-323 (SEQ ID NO:3242); miR-324 (SEQ ID NO:3243); miR-326 (SEQ ID NO:3244); miR-328 (SEQ ID NO:3245); miR-329 (SEQ ID NO:3246); miR-330 (SEQ ID NO:3247); miR-331 (SEQ ID NO:3248);

miR-335 (SEQ ID NO:3249); miR-337 (SEQ ID NO:3250); miR-338 (SEQ ID NO:3251); miR-340 (SEQ ID NO:3252); miR-342 (SEQ ID NO:3253); miR-345 (SEQ ID NO:3254); miR-346 (SEQ ID NO:3255); miR-350 (SEQ ID NO:3256); miR-361 (SEQ ID NO:3257); miR-362 (SEQ ID NO:3258); miR-363 (SEQ ID NO:3259); miR-365-1 (SEQ ID NO:3260); miR-365-2 (SEQ ID NO:3261); miR-367 (SEQ ID NO:3262); miR-369 (SEQ ID NO:3263); miR-370 (SEQ ID NO:3264); miR-371 (SEQ ID NO:3265); miR-374a (SEQ ID NO:3266); miR-374b (SEQ ID NO:3267); miR-376a (SEQ ID NO:3268); miR-376b (SEQ ID NO:3269); miR-376c (SEQ ID NO:3270); miR-377 (SEQ ID NO:3271); miR-378 (SEQ ID NO:3272); miR-379 (SEQ ID NO:3273); miR-380 (SEQ ID NO:3274); miR-381 (SEQ ID NO:3275); miR-382 (SEQ ID NO:3276); miR-383 (SEQ ID NO:3277); miR-384 (SEQ ID NO:3278); miR-409 (SEQ ID NO:3279); miR-410 (SEQ ID NO:3280); miR-411 (SEQ ID NO:3281); miR-412 (SEQ ID NO:3282); miR-421 (SEQ ID NO:3283); miR-423 (SEQ ID NO:3284); miR-424 (SEQ ID NO:3285); miR-429 (SEQ ID NO:3286); miR-431 (SEQ ID NO:3287); miR-432 (SEQ ID NO:3288); miR-433 (SEQ ID NO:3289); miR-448 (SEQ ID NO:3290); miR-449a (SEQ ID NO:3291); miR-450a (SEQ ID NO:3292); miR-450b (SEQ ID NO:3293); miR-450c (SEQ ID NO:3294); miR-451 (SEQ ID NO:3295); miR-454 (SEQ ID NO:3296); miR-485 (SEQ ID NO:3297); miR-486 (SEQ ID NO:3298); miR-487a (SEQ ID NO:3299); miR-487b (SEQ ID NO:3300); miR-488 (SEQ ID NO:3301); miR-489 (SEQ ID NO:3302); miR-490 (SEQ ID NO:3303); miR-491 (SEQ ID NO:3304); miR-492-1 (SEQ ID NO:3305); miR-492-2 (SEQ ID NO:3306); miR-493a (SEQ ID NO:3307); miR-493b (SEQ ID NO:3308); miR-494 (SEQ ID NO:3309); miR-495 (SEQ ID NO:3310); miR-496 (SEQ ID NO:3311); miR-497 (SEQ ID NO:3312); miR-499 (SEQ ID NO:3313); miR-500-1 (SEQ ID NO:3314); miR-500-2 (SEQ ID NO:3315); miR-501 (SEQ ID NO:3316); miR-502 (SEQ ID NO:3317); miR-503 (SEQ ID NO:3318); miR-504 (SEQ ID NO:3319); miR-505 (SEQ ID NO:3320); miR-507 (SEQ ID NO:3321); miR-508 (SEQ ID NO:3322); miR-509 (SEQ ID NO:3323); miR-514 (SEQ ID NO:3324); miR-532 (SEQ ID NO:3325); miR-539 (SEQ ID NO:3326); miR-541 (SEQ ID NO:3327); miR-542 (SEQ ID NO:3328); miR-543 (SEQ ID NO:3329); miR-544-2 (SEQ ID NO:3330); miR-544b (SEQ ID NO:3331); miR-545 (SEQ ID NO:3332); miR-551a (SEQ ID NO:3333); miR-551b (SEQ ID NO:3334); miR-568 (SEQ ID NO:3335); miR-582 (SEQ ID NO:3336); miR-590 (SEQ ID NO:3337); miR-592 (SEQ ID NO:3338); miR-598 (SEQ ID NO:3339); miR-615 (SEQ ID NO:3340); miR-628a (SEQ ID NO:3341); miR-632 (SEQ ID NO:3342); miR-652 (SEQ ID NO:3343); miR-653 (SEQ ID NO:3344); miR-655 (SEQ ID NO:3345); miR-656 (SEQ ID NO:3346); miR-660 (SEQ ID NO:3347); miR-664 (SEQ ID NO:3348); miR-670 (SEQ ID NO:3349); miR-671 (SEQ ID NO:3350); miR-672 (SEQ ID NO:3351); miR-675 (SEQ ID NO:3352); miR-684 (SEQ ID NO:3353); miR-703 (SEQ ID NO:3354); miR-708 (SEQ ID NO:3355); miR-711 (SEQ ID NO:3356); miR-758 (SEQ ID NO:3357); miR-761 (SEQ ID NO:3358); miR-763 (SEQ ID NO:3359); miR-764 (SEQ ID NO:3360); miR-767 (SEQ ID NO:3361); miR-769a (SEQ ID NO:3362); miR-769b (SEQ ID NO:3363); miR-770 (SEQ ID NO:3364); miR-802 (SEQ ID NO:3365); miR-872 (SEQ ID NO:3366); miR-873 (SEQ ID NO:3367); miR-874 (SEQ ID NO:3368); miR-876 (SEQ ID NO:3369); miR-885 (SEQ ID NO:3370); miR-889 (SEQ ID NO:3371); miR-1179 (SEQ ID NO:3372); miR-1180 (SEQ ID NO:3373); miR-1185 (SEQ ID NO:3374); miR-1193 (SEQ ID NO:3375); miR-1197 (SEQ ID NO:3376); miR-1204 (SEQ ID NO:3377); miR-1244 (SEQ ID NO:3378); miR-1248 (SEQ ID NO:3379); miR-1255b (SEQ ID NO:3380); miR-1261 (SEQ ID NO:3381); miR-1264 (SEQ ID NO:3382); miR-1271 (SEQ ID NO:3383); miR-1282 (SEQ ID NO:3384); miR-1289 (SEQ ID NO:3385); miR-1291a (SEQ ID NO:3386); miR-1291b (SEQ ID NO:3387); miR-1296 (SEQ ID NO:3388); miR-1298 (SEQ ID NO:3389); miR-1301 (SEQ ID NO:3390); miR-1302-1 (SEQ ID NO:3391); miR-1302b-2 (SEQ ID NO:3392); miR-1302c-5 (SEQ ID NO:3393); miR-1302d-4 (SEQ ID NO:3394); miR-1302e-6 (SEQ ID NO:3395); miR-1302e-7 (SEQ ID NO:3396); miR-1461 (SEQ ID NO:3397); miR-1468 (SEQ ID NO:3398); miR-1597 (SEQ ID NO:3399); miR-1839 (SEQ ID NO:3400); miR-1842 (SEQ ID NO:3401); miR-1892 (SEQ ID NO:3402); miR-1898 (SEQ ID NO:3403); miR-1902 (SEQ ID NO:3404); miR-1905a (SEQ ID NO:3405); miR-1905b (SEQ ID NO:3406); miR-1905c (SEQ ID NO:3407); and miR-1912 (SEQ ID NO:3408).

The following mouse miRNAs could be used: let-7a-1 (SEQ ID NO:3409); let-7a-2 (SEQ ID NO:3410); let-7b (SEQ ID NO:3411); let-7c-1 (SEQ ID NO:3412); let-7c-2 (SEQ ID NO:3413); let-7d (SEQ ID NO:3414); let-7e (SEQ ID NO:3415); let-7f-1 (SEQ ID NO:3416); let-7f-2 (SEQ ID NO:3417); let-7g (SEQ ID NO:3418); let-7i (SEQ ID NO:3419); let-7j (SEQ ID NO:3420); let-7k (SEQ ID NO:3421); miR-1a-1 (SEQ ID NO:3422); miR-1a-2 (SEQ ID NO:3423); miR-1b (SEQ ID NO:3424); miR-7a-1 (SEQ ID NO:3425); miR-7a-2 (SEQ ID NO:3426); miR-7b (SEQ ID NO:3427); miR-9-1 (SEQ ID NO:3428); miR-9-2 (SEQ ID NO:3429); miR-9-3 (SEQ ID NO:3430); miR-10a (SEQ ID NO:3431); miR-10b (SEQ ID NO:3432); miR-15a (SEQ ID NO:3433); miR-15b (SEQ ID NO:3434); miR-16-1 (SEQ ID NO:3435); miR-16-2 (SEQ ID NO:3436); miR-17 (SEQ ID NO:3437); miR-18a (SEQ ID NO:3438); miR-18b (SEQ ID NO:3439); miR-19a (SEQ ID NO:3440); miR-19b-1 (SEQ ID NO:3441); miR-19b-2 (SEQ ID NO:3442); miR-20a (SEQ ID NO:3443); miR-20b (SEQ ID NO:3444); miR-21a (SEQ ID NO:3445); miR-21b (SEQ ID NO:3446); miR-21c (SEQ ID NO:3447); miR-22 (SEQ ID NO:3448); miR-23a (SEQ ID NO:3449); miR-23b (SEQ ID NO:3450); miR-24-1 (SEQ ID NO:3451); miR-24-2 (SEQ ID NO:3452); miR-25 (SEQ ID NO:3453); miR-26a-1 (SEQ ID NO:3454); miR-26a-2 (SEQ ID NO:3455); miR-26b (SEQ ID NO:3456); miR-27a (SEQ ID NO:3457); miR-27b (SEQ ID NO:3458); miR-28a (SEQ ID NO:3459); miR-28b (SEQ ID NO:3460); miR-28c (SEQ ID NO:3461); miR-29a (SEQ ID NO:3462); miR-29b-1 (SEQ ID NO:3463); miR-29b-2 (SEQ ID NO:3464); miR-29c (SEQ ID NO:3465); miR-30a (SEQ ID NO:3466); miR-30b (SEQ ID NO:3467); miR-30c-1 (SEQ ID NO:3468); miR-30c-2 (SEQ ID NO:3469); miR-30d (SEQ ID NO:3470); miR-30e (SEQ ID NO:3471); miR-30f (SEQ ID NO:3472); miR-31 (SEQ ID NO:3473); miR-32 (SEQ ID NO:3474); miR-33 (SEQ ID NO:3475); miR-34a (SEQ ID NO:3476); miR-34b (SEQ ID NO:3477); miR-34c (SEQ ID NO:3478); miR-92a-1 (SEQ ID NO:3479); miR-92a-2 (SEQ ID NO:3480); miR-92b (SEQ ID NO:3481); miR-93 (SEQ ID NO:3482); miR-96 (SEQ ID NO:3483); miR-98 (SEQ ID NO:3484); miR-99a (SEQ ID NO:3485); miR-99b (SEQ ID NO:3486); miR-100 (SEQ ID NO:3487); miR-101a (SEQ ID NO:3488); miR-101b (SEQ ID NO:3489); miR-101c (SEQ ID NO:3490); miR-103-1 (SEQ ID NO:3491); miR-103-2 (SEQ ID NO:3492); miR-105 (SEQ ID NO:3493); miR-106a (SEQ ID NO:3494); miR-106b (SEQ ID NO:3495); miR-107 (SEQ ID NO:3496); miR-122 (SEQ ID NO:3497); miR-124-1 (SEQ ID NO:3498); miR-124-2 (SEQ ID NO:3499); miR-124-3 (SEQ ID NO:3500); miR-125a (SEQ ID NO:3501); miR-125b-1 (SEQ ID NO:3502); miR-125b-2 (SEQ ID NO:3503); miR- 126a (SEQ ID NO:3504); miR-126b (SEQ ID NO:3505); miR-127 (SEQ ID NO:3506); miR-128-1 (SEQ ID NO:3507); miR-128-2 (SEQ ID NO:3508); miR-129-1 (SEQ ID NO:3509); miR-129-2 (SEQ ID NO:3510); miR-129b (SEQ ID NO:3511); miR-130a (SEQ ID NO:3512); miR-130b (SEQ ID NO:3513); miR-130c (SEQ ID NO:3514); miR-132 (SEQ ID NO:3515); miR-133a-1 (SEQ ID NO:3516); miR-133a-2 (SEQ ID NO:3517); miR-133b (SEQ ID NO:3518); miR-133c (SEQ ID NO:3519); miR-134 (SEQ ID NO:3520); miR-135a-1 (SEQ ID NO:3521); miR-135a-2 (SEQ ID NO:3522); miR-135b (SEQ ID NO:3523); miR-136 (SEQ ID NO:3524); miR-137 (SEQ ID NO:3525); miR-138-1 (SEQ ID NO:3526); miR-138-2 (SEQ ID NO:3527); miR-139 (SEQ ID NO:3528); miR-140 (SEQ ID NO:3529); miR-141 (SEQ ID NO:3530); miR-142 (SEQ ID NO:3531); miR-142b (SEQ ID NO:3532); miR-143 (SEQ ID NO:3533); miR-144 (SEQ ID NO:3534); miR-145a (SEQ ID NO:3535); miR-145b (SEQ ID NO:3536); miR-146a (SEQ ID NO:3537); miR-146b (SEQ ID NO:3538); miR-147 (SEQ ID NO:3539); miR-148a (SEQ ID NO:3540); miR-148b (SEQ ID NO:3541); miR-149 (SEQ ID NO:3542); miR-150 (SEQ ID NO:3543); miR-151 (SEQ ID NO:3544); miR-152 (SEQ ID NO:3545); miR-153 (SEQ ID NO:3546); miR-154 (SEQ ID NO:3547); miR-155 (SEQ ID NO:3548); miR-181a-1 (SEQ ID NO:3549); miR-181a-2 (SEQ ID NO:3550); miR-181b-1 (SEQ ID NO:3551); miR-181b-2 (SEQ ID NO:3552); miR-181c (SEQ ID NO:3553); miR-181d (SEQ ID NO:3554); miR-182 (SEQ ID NO:3555); miR-183 (SEQ ID NO:3556); miR-184 (SEQ ID NO:3557); miR-185 (SEQ ID NO:3558); miR-186 (SEQ ID NO:3559); miR-187 (SEQ ID NO:3560); miR-188 (SEQ ID NO:3561); miR-190a (SEQ ID NO:3562); miR-190b (SEQ ID NO:3563); miR-191 (SEQ ID NO:3564); miR-192 (SEQ ID NO:3565); miR-193a (SEQ ID NO:3566); miR-193b (SEQ ID NO:3567); miR-194-1 (SEQ ID NO:3568); miR-194-2 (SEQ ID NO:3569); miR-195a (SEQ ID NO:3570); miR-195b (SEQ ID NO:3571); miR-196a-1 (SEQ ID NO:3572); miR-196a-2 (SEQ ID NO:3573); miR-196b (SEQ ID NO:3574); miR-199a-1 (SEQ ID NO:3575); miR-199a-2 (SEQ ID NO:3576); miR-199b (SEQ ID NO:3577); miR-200a (SEQ ID NO:3578); miR-200b (SEQ ID NO:3579); miR-200c (SEQ ID NO:3580); miR-201 (SEQ ID NO:3581); miR-202 (SEQ ID NO:3582); miR-203 (SEQ ID NO:3583); miR-204 (SEQ ID NO:3584); miR-205 (SEQ ID NO:3585); miR-206 (SEQ ID NO:3586); miR-207 (SEQ ID NO:3587); miR-208a (SEQ ID NO:3588); miR-208b (SEQ ID NO:3589); miR-210 (SEQ ID NO:3590); miR-211 (SEQ ID NO:3591); miR-212 (SEQ ID NO:3592); miR-214 (SEQ ID NO:3593); miR-215 (SEQ ID NO:3594); miR-216a (SEQ ID NO:3595); miR-216b (SEQ ID NO:3596); miR-216c (SEQ ID NO:3597); miR-217 (SEQ ID NO:3598); miR-218-1 (SEQ ID NO:3599); miR-218-2 (SEQ ID NO:3600); miR-219a-1 (SEQ ID NO:3601); miR-219a-2 (SEQ ID NO:3602); miR-219b (SEQ ID NO:3603); miR-219c (SEQ ID NO:3604); miR-221 (SEQ ID NO:3605); miR-222 (SEQ ID NO:3606); miR-223 (SEQ ID NO:3607); miR-224 (SEQ ID NO:3608); miR-290a (SEQ ID NO:3609); miR-290b (SEQ ID NO:3610); miR-291a (SEQ ID NO:3611); miR-291b (SEQ ID NO:3612); miR-292 (SEQ ID NO:3613); miR-292b (SEQ ID NO:3614); miR-293 (SEQ ID NO:3615); miR-294 (SEQ ID NO:3616); miR-295 (SEQ ID NO:3617); miR-296 (SEQ ID NO:3618); miR-297a-1 (SEQ ID NO:3619); miR-297a-2 (SEQ ID NO:3620); miR-297a-3 (SEQ ID NO:3621); miR-297a-4 (SEQ ID NO:3622); miR-297b (SEQ ID NO:3623); miR-297c (SEQ ID NO:3624); miR-298 (SEQ ID NO:3625); miR-299a (SEQ ID NO:3626); miR-299b (SEQ ID NO:3627); miR-300 (SEQ ID NO:3628); miR-301a (SEQ ID NO:3629); miR-301b (SEQ ID NO:3630); miR-302a (SEQ ID NO:3631); miR-302b (SEQ ID NO:3632); miR-302c (SEQ ID NO:3633); miR-302d (SEQ ID NO:3634); miR-320 (SEQ ID NO:3635); miR-322 (SEQ ID NO:3636); miR-323 (SEQ ID NO:3637); miR-324 (SEQ ID NO:3638); miR-325 (SEQ ID NO:3639); miR-326 (SEQ ID NO:3640); miR-327 (SEQ ID NO:3641); miR-328 (SEQ ID NO:3642); miR-329 (SEQ ID NO:3643); miR-330 (SEQ ID NO:3644); miR-331 (SEQ ID NO:3645); miR-335 (SEQ ID NO:3646); miR-337 (SEQ ID NO:3647); miR-338 (SEQ ID NO:3648); miR-339 (SEQ ID NO:3649); miR-340 (SEQ ID NO:3650); miR-341 (SEQ ID NO:3651); miR-342 (SEQ ID NO:3652); miR-343 (SEQ ID NO:3653); miR-344-1 (SEQ ID NO:3654); miR-344-2 (SEQ ID NO:3655); miR-344b (SEQ ID NO:3656); miR-344c (SEQ ID NO:3657); miR-344d-1 (SEQ ID NO:3658); miR-344d-2 (SEQ ID NO:3659); miR-344d-3 (SEQ ID NO:3660); miR-344e (SEQ ID NO:3661); miR-344f (SEQ ID NO:3662); miR-344g (SEQ ID NO:3663); miR-344h-1 (SEQ ID NO:3664); miR-344h-2 (SEQ ID NO:3665); miR-344i (SEQ ID NO:3666); miR-345 (SEQ ID NO:3667); miR-346 (SEQ ID NO:3668); miR-350 (SEQ ID NO:3669); miR-351 (SEQ ID NO:3670); miR-361 (SEQ ID NO:3671); miR-362 (SEQ ID NO:3672); miR-363 (SEQ ID NO:3673); miR-365-1 (SEQ ID NO:3674); miR-365-2 (SEQ ID NO:3675); miR-367 (SEQ ID NO:3676); miR-369 (SEQ ID NO:3677); miR-370 (SEQ ID NO:3678); miR-374b (SEQ ID NO:3679); miR-374c (SEQ ID NO:3680); miR-375 (SEQ ID NO:3681); miR-376a (SEQ ID NO:3682); miR-376b (SEQ ID NO:3683); miR-376c (SEQ ID NO:3684); miR-377 (SEQ ID NO:3685); miR-378a (SEQ ID NO:3686); miR-378b (SEQ ID NO:3687); miR-378c (SEQ ID NO:3688); miR-378d (SEQ ID NO:3689); miR-379 (SEQ ID NO:3690); miR-380 (SEQ ID NO:3691); miR-381 (SEQ ID NO:3692); miR-382 (SEQ ID NO:3693); miR-383 (SEQ ID NO:3694); miR-384 (SEQ ID NO:3695); miR-409 (SEQ ID NO:3696); miR-410 (SEQ ID NO:3697); miR-411 (SEQ ID NO:3698); miR-412 (SEQ ID NO:3699); miR-421 (SEQ ID NO:3700); miR-423 (SEQ ID NO:3701); miR-425 (SEQ ID NO:3702); miR-429 (SEQ ID NO:3703); miR-431 (SEQ ID NO:3704); miR-432 (SEQ ID NO:3705); miR-433 (SEQ ID NO:3706); miR-434 (SEQ ID NO:3707); miR-448 (SEQ ID NO:3708); miR-449a (SEQ ID NO:3709); miR-449b (SEQ ID NO:3710); miR-449c (SEQ ID NO:3711); miR-450a-1 (SEQ ID NO:3712); miR-450a-2 (SEQ ID NO:3713); miR-450b (SEQ ID NO:3714); miR-451a (SEQ ID NO:3715); miR-451b (SEQ ID NO:3716); miR-452 (SEQ ID NO:3717); miR-453 (SEQ ID NO:3718); miR-455 (SEQ ID NO:3719); miR-463 (SEQ ID NO:3720); miR-465a (SEQ ID NO:3721); miR-465b-1 (SEQ ID NO:3722); miR-465b-2 (SEQ ID NO:3723); miR-465c-1 (SEQ ID NO:3724); miR-465c-2 (SEQ ID NO:3725); miR-465d (SEQ ID NO:3726); miR-466a (SEQ ID NO:3727); miR-466b-1 (SEQ ID NO:3728); miR-466b-2 (SEQ ID NO:3729); miR-466b-3 (SEQ ID NO:3730); miR-466b-4 (SEQ ID NO:3731); miR-466b-5 (SEQ ID NO:3732); miR-466b-6 (SEQ ID NO:3733); miR-466b-7 (SEQ ID NO:3734); miR-466b-8 (SEQ ID NO:3735); miR-466c-1 (SEQ ID NO:3736); miR-466c-2 (SEQ ID NO:3737); miR-466d (SEQ ID NO:3738); miR-466e (SEQ ID NO:3739); miR-466f-1 (SEQ ID NO:3740); miR-466f-2 (SEQ ID NO:3741); miR-466f-3 (SEQ ID NO:3742); miR-466f-4 (SEQ ID NO:3743); miR-466g (SEQ ID NO:3744); miR-466h (SEQ ID NO:3745); miR-466i (SEQ ID NO:3746); miR-466j (SEQ ID NO:3747); miR-466k (SEQ ID NO:3748); miR-466l (SEQ ID NO:3749); miR-466m (SEQ ID NO:3750); miR-466n (SEQ ID NO:3751); miR-466o (SEQ ID NO:3752); miR-466p (SEQ ID NO:3753); miR-466q (SEQ ID NO:3754); miR-467a-1 (SEQ ID NO:3755);

miR-467a-10 (SEQ ID NO:3756); miR-467a-2 (SEQ ID NO:3757); miR-467a-3 (SEQ ID NO:3758); miR-467a-4 (SEQ ID NO:3759); miR-467a-5 (SEQ ID NO:3760); miR-467a-6 (SEQ ID NO:3761); miR-467a-7 (SEQ ID NO:3762); miR-467a-8 (SEQ ID NO:3763); miR-467a-9 (SEQ ID NO:3764); miR-467b (SEQ ID NO:3765); miR-467c (SEQ ID NO:3766); miR-467d (SEQ ID NO:3767); miR-467e (SEQ ID NO:3768); miR-467f (SEQ ID NO:3769); miR-467g (SEQ ID NO:3770); miR-467h (SEQ ID NO:3771); miR-468 (SEQ ID NO:3772); miR-470 (SEQ ID NO:3773); miR-471 (SEQ ID NO:3774); miR-483 (SEQ ID NO:3775); miR-484 (SEQ ID NO:3776); miR-485 (SEQ ID NO:3777); miR-486 (SEQ ID NO:3778); miR-487b (SEQ ID NO:3779); miR-488 (SEQ ID NO:3780); miR-489 (SEQ ID NO:3781); miR-490 (SEQ ID NO:3782); miR-491 (SEQ ID NO:3783); miR-493 (SEQ ID NO:3784); miR-494 (SEQ ID NO:3785); miR-495 (SEQ ID NO:3786); miR-496a (SEQ ID NO:3787); miR-496b (SEQ ID NO:3788); miR-497 (SEQ ID NO:3789); miR-497b (SEQ ID NO:3790); miR-499 (SEQ ID NO:3791); miR-500 (SEQ ID NO:3792); miR-501 (SEQ ID NO:3793); miR-503 (SEQ ID NO:3794); miR-504 (SEQ ID NO:3795); miR-505 (SEQ ID NO:3796); miR-509 (SEQ ID NO:3797); miR-511 (SEQ ID NO:3798); miR-532 (SEQ ID NO:3799); miR-539 (SEQ ID NO:3800); miR-540 (SEQ ID NO:3801); miR-541 (SEQ ID NO:3802); miR-542 (SEQ ID NO:3803); miR-543 (SEQ ID NO:3804); miR-544 (SEQ ID NO:3805); miR-546 (SEQ ID NO:3806); miR-547 (SEQ ID NO:3807); miR-551b (SEQ ID NO:3808); miR-568 (SEQ ID NO:3809); miR-574 (SEQ ID NO:3810); miR-582 (SEQ ID NO:3811); miR-590 (SEQ ID NO:3812); miR-592 (SEQ ID NO:3813); miR-598 (SEQ ID NO:3814); miR-599 (SEQ ID NO:3815); miR-615 (SEQ ID NO:3816); miR-652 (SEQ ID NO:3817); miR-653 (SEQ ID NO:3818); miR-654 (SEQ ID NO:3819); miR-664 (SEQ ID NO:3820); miR-665 (SEQ ID NO:3821); miR-666 (SEQ ID NO:3822); miR-667 (SEQ ID NO:3823); miR-668 (SEQ ID NO:3824); miR-669a-1 (SEQ ID NO:3825); miR-669a-10 (SEQ ID NO:3826); miR-669a-11 (SEQ ID NO:3827); miR-669a-12 (SEQ ID NO:3828); miR-669a-2 (SEQ ID NO:3829); miR-669a-3 (SEQ ID NO:3830); miR-669a-4 (SEQ ID NO:3831); miR-669a-5 (SEQ ID NO:3832); miR-669a-6 (SEQ ID NO:3833); miR-669a-7 (SEQ ID NO:3834); miR-669a-8 (SEQ ID NO:3835); miR-669a-9 (SEQ ID NO:3836); miR-669b (SEQ ID NO:3837); miR-669c (SEQ ID NO:3838); miR-669d (SEQ ID NO:3839); miR-669d-2 (SEQ ID NO:3840); miR-669e (SEQ ID NO:3841); miR-669f (SEQ ID NO:3842); miR-669g (SEQ ID NO:3843); miR-669h (SEQ ID NO:3844); miR-669i (SEQ ID NO:3845); miR-669j (SEQ ID NO:3846); miR-669k (SEQ ID NO:3847); miR-669l (SEQ ID NO:3848); miR-669m-1 (SEQ ID NO:3849); miR-669m-2 (SEQ ID NO:3850); miR-669n (SEQ ID NO:3851); miR-669o (SEQ ID NO:3852); miR-669p-1 (SEQ ID NO:3853); miR-669p-2 (SEQ ID NO:3854); miR-670 (SEQ ID NO:3855); miR-671 (SEQ ID NO:3856); miR-672 (SEQ ID NO:3857); miR-673 (SEQ ID NO:3858); miR-674 (SEQ ID NO:3859); miR-675 (SEQ ID NO:3860); miR-676 (SEQ ID NO:3861); miR-677 (SEQ ID NO:3862); miR-678 (SEQ ID NO:3863); miR-679 (SEQ ID NO:3864); miR-680-1 (SEQ ID NO:3865); miR-680-2 (SEQ ID NO:3866); miR-680-3 (SEQ ID NO:3867); miR-681 (SEQ ID NO:3868); miR-682 (SEQ ID NO:3869); miR-683-1 (SEQ ID NO:3870); miR-683-2 (SEQ ID NO:3871); miR-684-1 (SEQ ID NO:3872); miR-684-2 (SEQ ID NO:3873); miR-686 (SEQ ID NO:3874); miR-687 (SEQ ID NO:3875); miR-688 (SEQ ID NO:3876); miR-690 (SEQ ID NO:3877); miR-691 (SEQ ID NO:3878); miR-692-1 (SEQ ID NO:3879); miR-692-2 (SEQ ID NO:3880); miR-692-3 (SEQ ID NO:3881); miR-693 (SEQ ID NO:3882); miR-694 (SEQ ID NO:3883); miR-695 (SEQ ID NO:3884); miR-696 (SEQ ID NO:3885); miR-697 (SEQ ID NO:3886); miR-698 (SEQ ID NO:3887); miR-700 (SEQ ID NO:3888); miR-701 (SEQ ID NO:3889); miR-702 (SEQ ID NO:3890); miR-703 (SEQ ID NO:3891); miR-704 (SEQ ID NO:3892); miR-705 (SEQ ID NO:3893); miR-706 (SEQ ID NO:3894); miR-707 (SEQ ID NO:3895); miR-708 (SEQ ID NO:3896); miR-709 (SEQ ID NO:3897); miR-710 (SEQ ID NO:3898); miR-711 (SEQ ID NO:3899); miR-712 (SEQ ID NO:3900); miR-713 (SEQ ID NO:3901); miR-714 (SEQ ID NO:3902); miR-717 (SEQ ID NO:3903); miR-718 (SEQ ID NO:3904); miR-719 (SEQ ID NO:3905); miR-721 (SEQ ID NO:3906); miR-741 (SEQ ID NO:3907); miR-742 (SEQ ID NO:3908); miR-743a (SEQ ID NO:3909); miR-743b (SEQ ID NO:3910); miR-744 (SEQ ID NO:3911); miR-758 (SEQ ID NO:3912); miR-759 (SEQ ID NO:3913); miR-760 (SEQ ID NO:3914); miR-761 (SEQ ID NO:3915); miR-762 (SEQ ID NO:3916); miR-763 (SEQ ID NO:3917); miR-764 (SEQ ID NO:3918); miR-767 (SEQ ID NO:3919); miR-770 (SEQ ID NO:3920); miR-802 (SEQ ID NO:3921); miR-804 (SEQ ID NO:3922); miR-871 (SEQ ID NO:3923); miR-872 (SEQ ID NO:3924); miR-873a (SEQ ID NO:3925); miR-873b (SEQ ID NO:3926); miR-874 (SEQ ID NO:3927); miR-875 (SEQ ID NO:3928); miR-876 (SEQ ID NO:3929); miR-877 (SEQ ID NO:3930); miR-878 (SEQ ID NO:3931); miR-879 (SEQ ID NO:3932); miR-880 (SEQ ID NO:3933); miR-881 (SEQ ID NO:3934); miR-882 (SEQ ID NO:3935); miR-883a (SEQ ID NO:3936); miR-883b (SEQ ID NO:3937); miR-1187 (SEQ ID NO:3938); miR-1188 (SEQ ID NO:3939); miR-1190 (SEQ ID NO:3940); miR-1191 (SEQ ID NO:3941); miR-1191b (SEQ ID NO:3942); miR-1192 (SEQ ID NO:3943); miR-1193 (SEQ ID NO:3944); miR-1194 (SEQ ID NO:3945); miR-1195 (SEQ ID NO:3946); miR-1197 (SEQ ID NO:3947); miR-1198 (SEQ ID NO:3948); miR-1199 (SEQ ID NO:3949); miR-1224 (SEQ ID NO:3950); miR-1231 (SEQ ID NO:3951); miR-1247 (SEQ ID NO:3952); miR-1249 (SEQ ID NO:3953); miR-1251 (SEQ ID NO:3954); miR-1258 (SEQ ID NO:3955); miR-1264 (SEQ ID NO:3956); miR-1291 (SEQ ID NO:3957); miR-1298 (SEQ ID NO:3958); miR-1306 (SEQ ID NO:3959); miR-1668 (SEQ ID NO:3960); miR-1839 (SEQ ID NO:3961); miR-1843a (SEQ ID NO:3962); miR-1843b (SEQ ID NO:3963); miR-1892 (SEQ ID NO:3964); miR-1893 (SEQ ID NO:3965); miR-1894 (SEQ ID NO:3966); miR-1895 (SEQ ID NO:3967); miR-1896 (SEQ ID NO:3968); miR-1897 (SEQ ID NO:3969); miR-1898 (SEQ ID NO:3970); miR-1899 (SEQ ID NO:3971); miR-1900 (SEQ ID NO:3972); miR-1901 (SEQ ID NO:3973); miR-1902 (SEQ ID NO:3974); miR-1903 (SEQ ID NO:3975); miR-1904 (SEQ ID NO:3976); miR-1905 (SEQ ID NO:3977); miR-1906-1 (SEQ ID NO:3978); miR-1906-2 (SEQ ID NO:3979); miR-1907 (SEQ ID NO:3980); miR-1912 (SEQ ID NO:3981); miR-1927 (SEQ ID NO:3982); miR-1928 (SEQ ID NO:3983); miR-1929 (SEQ ID NO:3984); miR-1930 (SEQ ID NO:3985); miR-1931 (SEQ ID NO:3986); miR-1932 (SEQ ID NO:3987); miR-1933 (SEQ ID NO:3988); miR-1934 (SEQ ID NO:3989); miR-1936 (SEQ ID NO:3990); miR-1938 (SEQ ID NO:3991); miR-1940 (SEQ ID NO:3992); miR-1941 (SEQ ID NO:3993); miR-1942 (SEQ ID NO:3994); miR-1943 (SEQ ID NO:3995); miR-1945 (SEQ ID NO:3996); miR-1946a (SEQ ID NO:3997); miR-1946b (SEQ ID NO:3998); miR-1947 (SEQ ID NO:3999); miR-1948 (SEQ ID NO:4000); miR-1949 (SEQ ID NO:4001); miR-1950 (SEQ ID NO:4002); miR-1951 (SEQ ID NO:4003); miR-1952 (SEQ ID NO:4004); miR-1953 (SEQ ID NO:4005); miR-1954 (SEQ ID NO:4006); miR-1955 (SEQ ID NO:4007);

miR-1956 (SEQ ID NO:4008); miR-1957a (SEQ ID NO:4009); miR-1957b (SEQ ID NO:4010); miR-1958 (SEQ ID NO:4011); miR-1960 (SEQ ID NO:4012); miR-1961 (SEQ ID NO:4013); miR-1962 (SEQ ID NO:4014); miR-1963 (SEQ ID NO:4015); miR-1964 (SEQ ID NO:4016); miR-1966 (SEQ ID NO:4017); miR-1967 (SEQ ID NO:4018); miR-1968 (SEQ ID NO:4019); miR-1969 (SEQ ID NO:4020); miR-1970 (SEQ ID NO:4021); miR-1971 (SEQ ID NO:4022); miR-1981 (SEQ ID NO:4023); miR-1982 (SEQ ID NO:4024); miR-1983 (SEQ ID NO:4025); miR-2136 (SEQ ID NO:4026); miR-2137 (SEQ ID NO:4027); miR-2139 (SEQ ID NO:4028); miR-2183 (SEQ ID NO:4029); miR-2861 (SEQ ID NO:4030); miR-3057 (SEQ ID NO:4031); miR-3058 (SEQ ID NO:4032); miR-3059 (SEQ ID NO:4033); miR-3060 (SEQ ID NO:4034); miR-3061 (SEQ ID NO:4035); miR-3062 (SEQ ID NO:4036); miR-3063 (SEQ ID NO:4037); miR-3064 (SEQ ID NO:4038); miR-3065 (SEQ ID NO:4039); miR-3066 (SEQ ID NO:4040); miR-3067 (SEQ ID NO:4041); miR-3068 (SEQ ID NO:4042); miR-3069 (SEQ ID NO:4043); miR-3070a (SEQ ID NO:4044); miR-3070b (SEQ ID NO:4045); miR-3071 (SEQ ID NO:4046); miR-3072 (SEQ ID NO:4047); miR-3073a (SEQ ID NO:4048); miR-3073b (SEQ ID NO:4049); miR-3074-1 (SEQ ID NO:4050); miR-3074-2 (SEQ ID NO:4051); miR-3075 (SEQ ID NO:4052); miR-3076 (SEQ ID NO:4053); miR-3077 (SEQ ID NO:4054); miR-3078 (SEQ ID NO:4055); miR-3079 (SEQ ID NO:4056); miR-3080 (SEQ ID NO:4057); miR-3081 (SEQ ID NO:4058); miR-3082 (SEQ ID NO:4059); miR-3083 (SEQ ID NO:4060); miR-3084-1 (SEQ ID NO:4061); miR-3084-2 (SEQ ID NO:4062); miR-3085 (SEQ ID NO:4063); miR-3086 (SEQ ID NO:4064); miR-3087 (SEQ ID NO:4065); miR-3088 (SEQ ID NO:4066); miR-3089 (SEQ ID NO:4067); miR-3090 (SEQ ID NO:4068); miR-3091 (SEQ ID NO:4069); miR-3092 (SEQ ID NO:4070); miR-3093 (SEQ ID NO:4071); miR-3094 (SEQ ID NO:4072); miR-3095 (SEQ ID NO:4073); miR-3097 (SEQ ID NO:4074); miR-3098 (SEQ ID NO:4075); miR-3099 (SEQ ID NO:4076); miR-3100 (SEQ ID NO:4077); miR-3101 (SEQ ID NO:4078); miR-3102 (SEQ ID NO:4079); miR-3103 (SEQ ID NO:4080); miR-3104 (SEQ ID NO:4081); miR-3105 (SEQ ID NO:4082); miR-3106 (SEQ ID NO:4083); miR-3107 (SEQ ID NO:4084); miR-3108 (SEQ ID NO:4085); miR-3109 (SEQ ID NO:4086); miR-3110 (SEQ ID NO:4087); miR-3112 (SEQ ID NO:4088); miR-3113 (SEQ ID NO:4089); miR-3470a (SEQ ID NO:4090); miR-3470b (SEQ ID NO:4091); miR-3471-1 (SEQ ID NO:4092); miR-3471-2 (SEQ ID NO:4093); miR-3472 (SEQ ID NO:4094); miR-3473a (SEQ ID NO:4095); miR-3473b (SEQ ID NO:4096); miR-3473c (SEQ ID NO:4097); miR-3473d (SEQ ID NO:4098); miR-3473e (SEQ ID NO:4099); miR-3473f (SEQ ID NO:4100); miR-3473g (SEQ ID NO:4101); miR-3474 (SEQ ID NO:4102); miR-3475 (SEQ ID NO:4103); miR-3535 (SEQ ID NO:4104); miR-3544 (SEQ ID NO:4105); miR-3547 (SEQ ID NO:4106); miR-3569 (SEQ ID NO:4107); miR-3572 (SEQ ID NO:4108); miR-3620 (SEQ ID NO:4109); miR-3960 (SEQ ID NO:4110); miR-3961 (SEQ ID NO:4111); miR-3962 (SEQ ID NO:4112); miR-3963 (SEQ ID NO:4113); miR-3964 (SEQ ID NO:4114); miR-3965 (SEQ ID NO:4115); miR-3966 (SEQ ID NO:4116); miR-3967 (SEQ ID NO:4117); miR-3968 (SEQ ID NO:4118); miR-3969 (SEQ ID NO:4119); miR-3970 (SEQ ID NO:4120); miR-3971 (SEQ ID NO:4121); miR-5046 (SEQ ID NO:4122); miR-5098 (SEQ ID NO:4123); miR-5099 (SEQ ID NO:4124); miR-5100 (SEQ ID NO:4125); miR-5101 (SEQ ID NO:4126); miR-5103 (SEQ ID NO:4127); miR-5104 (SEQ ID NO:4128); miR-5106 (SEQ ID NO:4129); miR-5107 (SEQ ID NO:4130); miR-5108 (SEQ ID NO:4131); miR-5110 (SEQ ID NO:4132); miR-5112 (SEQ ID NO:4133); miR-5113 (SEQ ID NO:4134); miR-5114 (SEQ ID NO:4135); miR-5116 (SEQ ID NO:4136); miR-5118 (SEQ ID NO:4137); miR-5119 (SEQ ID NO:4138); miR-5120 (SEQ ID NO:4139); miR-5121 (SEQ ID NO:4140); miR-5122 (SEQ ID NO:4141); miR-5123 (SEQ ID NO:4142); miR-5124a (SEQ ID NO:4143); miR-5124b (SEQ ID NO:4144); miR-5125 (SEQ ID NO:4145); miR-5126 (SEQ ID NO:4146); miR-5127 (SEQ ID NO:4147); miR-5128 (SEQ ID NO:4148); miR-5129 (SEQ ID NO:4149); miR-5130 (SEQ ID NO:4150); miR-5131 (SEQ ID NO:4151); miR-5132 (SEQ ID NO:4152); miR-5133 (SEQ ID NO:4153); miR-5134 (SEQ ID NO:4154); miR-5135 (SEQ ID NO:4155); miR-5136 (SEQ ID NO:4156); miR-5615-1 (SEQ ID NO:4157); miR-5615-2 (SEQ ID NO:4158); miR-5616 (SEQ ID NO:4159); miR-5617 (SEQ ID NO:4160); miR-5618 (SEQ ID NO:4161); miR-5619 (SEQ ID NO:4162); miR-5620 (SEQ ID NO:4163); miR-5621 (SEQ ID NO:4164); miR-5622 (SEQ ID NO:4165); miR-5623 (SEQ ID NO:4166); miR-5624 (SEQ ID NO:4167); miR-5625 (SEQ ID NO:4168); miR-5626 (SEQ ID NO:4169); miR-5627 (SEQ ID NO:4170); miR-5709 (SEQ ID NO:4171); miR-5710 (SEQ ID NO:4172); miR-6236 (SEQ ID NO:4173); miR-6237 (SEQ ID NO:4174); miR-6238 (SEQ ID NO:4175); miR-6239 (SEQ ID NO:4176); miR-6240 (SEQ ID NO:4177); miR-6241 (SEQ ID NO:4178); miR-6244 (SEQ ID NO:4179); miR-6335 (SEQ ID NO:4180); miR-6336 (SEQ ID NO:4181); miR-6337 (SEQ ID NO:4182); miR-6338 (SEQ ID NO:4183); miR-6339 (SEQ ID NO:4184); miR-6340 (SEQ ID NO:4185); miR-6341 (SEQ ID NO:4186); miR-6342 (SEQ ID NO:4187); miR-6343 (SEQ ID NO:4188); miR-6344 (SEQ ID NO:4189); miR-6345 (SEQ ID NO:4190); miR-6346 (SEQ ID NO:4191); miR-6347 (SEQ ID NO:4192); miR-6348 (SEQ ID NO:4193); miR-6349 (SEQ ID NO:4194); miR-6350 (SEQ ID NO:4195); miR-6351 (SEQ ID NO:4196); miR-6352 (SEQ ID NO:4197); miR-6353 (SEQ ID NO:4198); miR-6354 (SEQ ID NO:4199); miR-6355 (SEQ ID NO:4200); miR-6356 (SEQ ID NO:4201); miR-6357 (SEQ ID NO:4202); miR-6358 (SEQ ID NO:4203); miR-6359 (SEQ ID NO:4204); miR-6360 (SEQ ID NO:4205); miR-6361 (SEQ ID NO:4206); miR-6362 (SEQ ID NO:4207); miR-6363 (SEQ ID NO:4208); miR-6364 (SEQ ID NO:4209); miR-6365 (SEQ ID NO:4210); miR-6366 (SEQ ID NO:4211); miR-6367 (SEQ ID NO:4212); miR-6368 (SEQ ID NO:4213); miR-6369 (SEQ ID NO:4214); miR-6370 (SEQ ID NO:4215); miR-6371 (SEQ ID NO:4216); miR-6372 (SEQ ID NO:4217); miR-6373 (SEQ ID NO:4218); miR-6374 (SEQ ID NO:4219); miR-6375 (SEQ ID NO:4220); miR-6376 (SEQ ID NO:4221); miR-6377 (SEQ ID NO:4222); miR-6378 (SEQ ID NO:4223); miR-6379 (SEQ ID NO:4224); miR-6380 (SEQ ID NO:4225); miR-6381 (SEQ ID NO:4226); miR-6382 (SEQ ID NO:4227); miR-6383 (SEQ ID NO:4228); miR-6384 (SEQ ID NO:4229); miR-6385 (SEQ ID NO:4230); miR-6386 (SEQ ID NO:4231); miR-6387 (SEQ ID NO:4232); miR-6388 (SEQ ID NO:4233); miR-6389 (SEQ ID NO:4234); miR-6390 (SEQ ID NO:4235); miR-6391 (SEQ ID NO:4236); miR-6392 (SEQ ID NO:4237); miR-6393 (SEQ ID NO:4238); miR-6394 (SEQ ID NO:4239); miR-6395 (SEQ ID NO:4240); miR-6396 (SEQ ID NO:4241); miR-6397 (SEQ ID NO:4242); miR-6398 (SEQ ID NO:4243); miR-6399 (SEQ ID NO:4244); miR-6400 (SEQ ID NO:4245); miR-6401 (SEQ ID NO:4246); miR-6402 (SEQ ID NO:4247); miR-6403 (SEQ ID

NO:4248); miR-6404 (SEQ ID NO:4249); miR-6405 (SEQ ID NO:4250); miR-6406 (SEQ ID NO:4251); miR-6407 (SEQ ID NO:4252); miR-6408 (SEQ ID NO:4253); miR-6409 (SEQ ID NO:4254); miR-6410 (SEQ ID NO:4255); miR-6411 (SEQ ID NO:4256); miR-6412 (SEQ ID NO:4257); miR-6413 (SEQ ID NO:4258); miR-6414 (SEQ ID NO:4259); miR-6415 (SEQ ID NO:4260); miR-6416 (SEQ ID NO:4261); miR-6417 (SEQ ID NO:4262); miR-6418 (SEQ ID NO:4263); miR-6419 (SEQ ID NO:4264); miR-6420 (SEQ ID NO:4265); miR-6481 (SEQ ID NO:4266); miR-6516 (SEQ ID NO:4267); miR-6537 (SEQ ID NO:4268); miR-6538 (SEQ ID NO:4269); miR-6539 (SEQ ID NO:4270); miR-6540 (SEQ ID NO:4271); miR-6541 (SEQ ID NO:4272); miR-6546 (SEQ ID NO:4273); miR-6715 (SEQ ID NO:4274); miR-6769b (SEQ ID NO:4275); miR-6896 (SEQ ID NO:4276); miR-6897 (SEQ ID NO:4277); miR-6898 (SEQ ID NO:4278); miR-6899 (SEQ ID NO:4279); miR-6900 (SEQ ID NO:4280); miR-6901 (SEQ ID NO:4281); miR-6902 (SEQ ID NO:4282); miR-6903 (SEQ ID NO:4283); miR-6904 (SEQ ID NO:4284); miR-6905 (SEQ ID NO:4285); miR-6906 (SEQ ID NO:4286); miR-6907 (SEQ ID NO:4287); miR-6908 (SEQ ID NO:4288); miR-6909 (SEQ ID NO:4289); miR-6910 (SEQ ID NO:4290); miR-6911 (SEQ ID NO:4291); miR-6912 (SEQ ID NO:4292); miR-6913 (SEQ ID NO:4293); miR-6914 (SEQ ID NO:4294); miR-6915 (SEQ ID NO:4295); miR-6916 (SEQ ID NO:4296); miR-6917 (SEQ ID NO:4297); miR-6918 (SEQ ID NO:4298); miR-6919 (SEQ ID NO:4299); miR-6920 (SEQ ID NO:4300); miR-6921 (SEQ ID NO:4301); miR-6922 (SEQ ID NO:4302); miR-6923 (SEQ ID NO:4303); miR-6924 (SEQ ID NO:4304); miR-6925 (SEQ ID NO:4305); miR-6926 (SEQ ID NO:4306); miR-6927 (SEQ ID NO:4307); miR-6928 (SEQ ID NO:4308); miR-6929 (SEQ ID NO:4309); miR-6930 (SEQ ID NO:4310); miR-6931 (SEQ ID NO:4311); miR-6932 (SEQ ID NO:4312); miR-6933 (SEQ ID NO:4313); miR-6934 (SEQ ID NO:4314); miR-6935 (SEQ ID NO:4315); miR-6936 (SEQ ID NO:4316); miR-6937 (SEQ ID NO:4317); miR-6938 (SEQ ID NO:4318); miR-6939 (SEQ ID NO:4319); miR-6940 (SEQ ID NO:4320); miR-6941 (SEQ ID NO:4321); miR-6942 (SEQ ID NO:4322); miR-6943 (SEQ ID NO:4323); miR-6944 (SEQ ID NO:4324); miR-6945 (SEQ ID NO:4325); miR-6946 (SEQ ID NO:4326); miR-6947 (SEQ ID NO:4327); miR-6948 (SEQ ID NO:4328); miR-6949 (SEQ ID NO:4329); miR-6950 (SEQ ID NO:4330); miR-6951 (SEQ ID NO:4331); miR-6952 (SEQ ID NO:4332); miR-6953 (SEQ ID NO:4333); miR-6954 (SEQ ID NO:4334); miR-6955 (SEQ ID NO:4335); miR-6956 (SEQ ID NO:4336); miR-6957 (SEQ ID NO:4337); miR-6958 (SEQ ID NO:4338); miR-6959 (SEQ ID NO:4339); miR-6960 (SEQ ID NO:4340); miR-6961 (SEQ ID NO:4341); miR-6962 (SEQ ID NO:4342); miR-6963 (SEQ ID NO:4343); miR-6964 (SEQ ID NO:4344); miR-6965 (SEQ ID NO:4345); miR-6966 (SEQ ID NO:4346); miR-6967 (SEQ ID NO:4347); miR-6968 (SEQ ID NO:4348); miR-6969 (SEQ ID NO:4349); miR-6970 (SEQ ID NO:4350); miR-6971 (SEQ ID NO:4351); miR-6972 (SEQ ID NO:4352); miR-6973a (SEQ ID NO:4353); miR-6973b (SEQ ID NO:4354); miR-6974 (SEQ ID NO:4355); miR-6975 (SEQ ID NO:4356); miR-6976 (SEQ ID NO:4357); miR-6977 (SEQ ID NO:4358); miR-6978 (SEQ ID NO:4359); miR-6979 (SEQ ID NO:4360); miR-6980 (SEQ ID NO:4361); miR-6981 (SEQ ID NO:4362); miR-6982 (SEQ ID NO:4363); miR-6983 (SEQ ID NO:4364); miR-6984 (SEQ ID NO:4365); miR-6985 (SEQ ID NO:4366); miR-6986 (SEQ ID NO:4367); miR-6987 (SEQ ID NO:4368); miR-6988 (SEQ ID NO:4369); miR-6989 (SEQ ID NO:4370); miR-6990 (SEQ ID NO:4371); miR-6991 (SEQ ID NO:4372); miR-6992 (SEQ ID NO:4373); miR-6993 (SEQ ID NO:4374); miR-6994 (SEQ ID NO:4375); miR-6995 (SEQ ID NO:4376); miR-6996 (SEQ ID NO:4377); miR-6997 (SEQ ID NO:4378); miR-6998 (SEQ ID NO:4379); miR-6999 (SEQ ID NO:4380); miR-7000 (SEQ ID NO:4381); miR-7001 (SEQ ID NO:4382); miR-7002 (SEQ ID NO:4383); miR-7003 (SEQ ID NO:4384); miR-7004 (SEQ ID NO:4385); miR-7005 (SEQ ID NO:4386); miR-7006 (SEQ ID NO:4387); miR-7007 (SEQ ID NO:4388); miR-7008 (SEQ ID NO:4389); miR-7009 (SEQ ID NO:4390); miR-7010 (SEQ ID NO:4391); miR-7011 (SEQ ID NO:4392); miR-7012 (SEQ ID NO:4393); miR-7013 (SEQ ID NO:4394); miR-7014 (SEQ ID NO:4395); miR-7015 (SEQ ID NO:4396); miR-7016 (SEQ ID NO:4397); miR-7017 (SEQ ID NO:4398); miR-7018 (SEQ ID NO:4399); miR-7019 (SEQ ID NO:4400); miR-7020 (SEQ ID NO:4401); miR-7021 (SEQ ID NO:4402); miR-7022 (SEQ ID NO:4403); miR-7023 (SEQ ID NO:4404); miR-7024 (SEQ ID NO:4405); miR-7025 (SEQ ID NO:4406); miR-7026 (SEQ ID NO:4407); miR-7027 (SEQ ID NO:4408); miR-7028 (SEQ ID NO:4409); miR-7029 (SEQ ID NO:4410); miR-7030 (SEQ ID NO:4411); miR-7031 (SEQ ID NO:4412); miR-7032 (SEQ ID NO:4413); miR-7033 (SEQ ID NO:4414); miR-7034 (SEQ ID NO:4415); miR-7035 (SEQ ID NO:4416); miR-7036 (SEQ ID NO:4417); miR-7036b (SEQ ID NO:4418); miR-7037 (SEQ ID NO:4419); miR-7038 (SEQ ID NO:4420); miR-7039 (SEQ ID NO:4421); miR-7040 (SEQ ID NO:4422); miR-7041 (SEQ ID NO:4423); miR-7042 (SEQ ID NO:4424); miR-7043 (SEQ ID NO:4425); miR-7044 (SEQ ID NO:4426); miR-7045 (SEQ ID NO:4427); miR-7046 (SEQ ID NO:4428); miR-7047 (SEQ ID NO:4429); miR-7048 (SEQ ID NO:4430); miR-7049 (SEQ ID NO:4431); miR-7050 (SEQ ID NO:4432); miR-7051 (SEQ ID NO:4433); miR-7052 (SEQ ID NO:4434); miR-7053 (SEQ ID NO:4435); miR-7054 (SEQ ID NO:4436); miR-7055 (SEQ ID NO:4437); miR-7056 (SEQ ID NO:4438); miR-7057 (SEQ ID NO:4439); miR-7058 (SEQ ID NO:4440); miR-7059 (SEQ ID NO:4441); miR-7060 (SEQ ID NO:4442); miR-7061 (SEQ ID NO:4443); miR-7062 (SEQ ID NO:4444); miR-7063 (SEQ ID NO:4445); miR-7064 (SEQ ID NO:4446); miR-7065 (SEQ ID NO:4447); miR-7066 (SEQ ID NO:4448); miR-7067 (SEQ ID NO:4449); miR-7068 (SEQ ID NO:4450); miR-7069 (SEQ ID NO:4451); miR-7070 (SEQ ID NO:4452); miR-7071 (SEQ ID NO:4453); miR-7072 (SEQ ID NO:4454); miR-7073 (SEQ ID NO:4455); miR-7074 (SEQ ID NO:4456); miR-7075 (SEQ ID NO:4457); miR-7076 (SEQ ID NO:4458); miR-7077 (SEQ ID NO:4459); miR-7078 (SEQ ID NO:4460); miR-7079 (SEQ ID NO:4461); miR-7080 (SEQ ID NO:4462); miR-7081 (SEQ ID NO:4463); miR-7082 (SEQ ID NO:4464); miR-7083 (SEQ ID NO:4465); miR-7084 (SEQ ID NO:4466); miR-7085 (SEQ ID NO:4467); miR-7086 (SEQ ID NO:4468); miR-7087 (SEQ ID NO:4469); miR-7088 (SEQ ID NO:4470); miR-7089 (SEQ ID NO:4471); miR-7090 (SEQ ID NO:4472); miR-7091 (SEQ ID NO:4473); miR-7092 (SEQ ID NO:4474); miR-7093 (SEQ ID NO:4475); miR-7094-1 (SEQ ID NO:4476); miR-7094-2 (SEQ ID NO:4477); miR-7115 (SEQ ID NO:4478); miR-7116 (SEQ ID NO:4479); miR-7117 (SEQ ID NO:4480); miR-7118 (SEQ ID NO:4481); miR-7119 (SEQ ID NO:4482); miR-7210 (SEQ ID NO:4483); miR-7211 (SEQ ID NO:4484); miR-7212 (SEQ ID NO:4485); miR-7213 (SEQ ID NO:4486); miR-7214 (SEQ ID NO:4487); miR-7215 (SEQ ID NO:4488); miR-7216 (SEQ ID NO:4489);

miR-7217 (SEQ ID NO:4490); miR-7218 (SEQ ID NO:4491); miR-7219 (SEQ ID NO:4492); miR-7220 (SEQ ID NO:4493); miR-7221 (SEQ ID NO:4494); miR-7222 (SEQ ID NO:4495); miR-7223 (SEQ ID NO:4496); miR-7224 (SEQ ID NO:4497); miR-7225 (SEQ ID NO:4498); miR-7226 (SEQ ID NO:4499); miR-7227 (SEQ ID NO:4500); miR-7228 (SEQ ID NO:4501); miR-7229 (SEQ ID NO:4502); miR-7230 (SEQ ID NO:4503); miR-7231 (SEQ ID NO:4504); miR-7232 (SEQ ID NO:4505); miR-7233 (SEQ ID NO:4506); miR-7234 (SEQ ID NO:4507); miR-7235 (SEQ ID NO:4508); miR-7236 (SEQ ID NO:4509); miR-7237 (SEQ ID NO:4510); miR-7238 (SEQ ID NO:4511); miR-7239 (SEQ ID NO:4512); miR-7240 (SEQ ID NO:4513); miR-7241 (SEQ ID NO:4514); miR-7242 (SEQ ID NO:4515); miR-7243 (SEQ ID NO:4516); miR-7578 (SEQ ID NO:4517); miR-7646 (SEQ ID NO:4518); miR-7647 (SEQ ID NO:4519); miR-7648 (SEQ ID NO:4520); miR-7649 (SEQ ID NO:4521); miR-7650 (SEQ ID NO:4522); miR-7651 (SEQ ID NO:4523); miR-7652 (SEQ ID NO:4524); miR-7653 (SEQ ID NO:4525); miR-7654 (SEQ ID NO:4526); miR-7655 (SEQ ID NO:4527); miR-7656 (SEQ ID NO:4528); miR-7657 (SEQ ID NO:4529); miR-7658 (SEQ ID NO:4530); miR-7659 (SEQ ID NO:4531); miR-7660 (SEQ ID NO:4532); miR-7661 (SEQ ID NO:4533); miR-7662 (SEQ ID NO:4534); miR-7663 (SEQ ID NO:4535); miR-7664 (SEQ ID NO:4536); miR-7665 (SEQ ID NO:4537); miR-7666 (SEQ ID NO:4538); miR-7667 (SEQ ID NO:4539); miR-7668 (SEQ ID NO:4540); miR-7669 (SEQ ID NO:4541); miR-7670 (SEQ ID NO:4542); miR-7671 (SEQ ID NO:4543); miR-7672 (SEQ ID NO:4544); miR-7673 (SEQ ID NO:4545); miR-7674 (SEQ ID NO:4546); miR-7675 (SEQ ID NO:4547); miR-7676-1 (SEQ ID NO:4548); miR-7676-2 (SEQ ID NO:4549); miR-7677 (SEQ ID NO:4550); miR-7678 (SEQ ID NO:4551); miR-7679 (SEQ ID NO:4552); miR-7680 (SEQ ID NO:4553); miR-7681 (SEQ ID NO:4554); miR-7682 (SEQ ID NO:4555); miR-7683 (SEQ ID NO:4556); miR-7684 (SEQ ID NO:4557); miR-7685 (SEQ ID NO:4558); miR-7686 (SEQ ID NO:4559); miR-7687 (SEQ ID NO:4560); miR-7688 (SEQ ID NO:4561); miR-7689 (SEQ ID NO:4562); miR-8090 (SEQ ID NO:4563); miR-8091 (SEQ ID NO:4564); miR-8092 (SEQ ID NO:4565); miR-8093 (SEQ ID NO:4566); miR-8094 (SEQ ID NO:4567); miR-8095 (SEQ ID NO:4568); miR-8096 (SEQ ID NO:4569); miR-8097 (SEQ ID NO:4570); miR-8098 (SEQ ID NO:4571); miR-8099-1 (SEQ ID NO:4572); miR-8099-2 (SEQ ID NO:4573); miR-8100 (SEQ ID NO:4574); miR-8101 (SEQ ID NO:4575); miR-8102 (SEQ ID NO:4576); miR-8103 (SEQ ID NO:4577); miR-8104 (SEQ ID NO:4578); miR-8105 (SEQ ID NO:4579); miR-8106 (SEQ ID NO:4580); miR-8107 (SEQ ID NO:4581); miR-8108 (SEQ ID NO:4582); miR-8109 (SEQ ID NO:4583); miR-8110 (SEQ ID NO:4584); miR-8111 (SEQ ID NO:4585); miR-8112 (SEQ ID NO:4586); miR-8113 (SEQ ID NO:4587); miR-8114 (SEQ ID NO:4588); miR-8115 (SEQ ID NO:4589); miR-8116 (SEQ ID NO:4590); miR-8117 (SEQ ID NO:4591); miR-8118 (SEQ ID NO:4592); miR-8119 (SEQ ID NO:4593); and miR-8120 (SEQ ID NO:4594).

The following rat miRNAs could be used: let-7a-1 (SEQ ID NO:4595); let-7a-2 (SEQ ID NO:4596); let-7b (SEQ ID NO:4597); let-7c-1 (SEQ ID NO:4598); let-7c-2 (SEQ ID NO:4599); let-7d (SEQ ID NO:4600); let-7e (SEQ ID NO:4601); let-7f-1 (SEQ ID NO:4602); let-7f-2 (SEQ ID NO:4603); let-7i (SEQ ID NO:4604); miR-1 (SEQ ID NO:4605); miR-7a-1 (SEQ ID NO:4606); miR-7a-2 (SEQ ID NO:4607); miR-7b (SEQ ID NO:4608); miR-9a-1 (SEQ ID NO:4609); miR-9a-2 (SEQ ID NO:4610); miR-9a-3 (SEQ ID NO:4611); miR-9b-1 (SEQ ID NO:4612); miR-9b-2 (SEQ ID NO:4613); miR-9b-3 (SEQ ID NO:4614); miR-10a (SEQ ID NO:4615); miR-10b (SEQ ID NO:4616); miR-15b (SEQ ID NO:4617); miR-16 (SEQ ID NO:4618); miR-17-1 (SEQ ID NO:4619); miR-17-2 (SEQ ID NO:4620); miR-18a (SEQ ID NO:4621); miR-19a (SEQ ID NO:4622); miR-19b-1 (SEQ ID NO:4623); miR-19b-2 (SEQ ID NO:4624); miR-20a (SEQ ID NO:4625); miR-20b (SEQ ID NO:4626); miR-21 (SEQ ID NO:4627); miR-22 (SEQ ID NO:4628); miR-23a (SEQ ID NO:4629); miR-23b (SEQ ID NO:4630); miR-24-1 (SEQ ID NO:4631); miR-24-2 (SEQ ID NO:4632); miR-25 (SEQ ID NO:4633); miR-26a (SEQ ID NO:4634); miR-26b (SEQ ID NO:4635); miR-27a (SEQ ID NO:4636); miR-27b (SEQ ID NO:4637); miR-28 (SEQ ID NO:4638); miR-29a (SEQ ID NO:4639); miR-29b-1 (SEQ ID NO:4640); miR-29b-2 (SEQ ID NO:4641); miR-29c (SEQ ID NO:4642); miR-30a (SEQ ID NO:4643); miR-30b (SEQ ID NO:4644); miR-30c-1 (SEQ ID NO:4645); miR-30c-2 (SEQ ID NO:4646); miR-30d (SEQ ID NO:4647); miR-30e (SEQ ID NO:4648); miR-31a (SEQ ID NO:4649); miR-31b (SEQ ID NO:4650); miR-32 (SEQ ID NO:4651); miR-33 (SEQ ID NO:4652); miR-34a (SEQ ID NO:4653); miR-34b (SEQ ID NO:4654); miR-34c (SEQ ID NO:4655); miR-92a-1 (SEQ ID NO:4656); miR-92a-2 (SEQ ID NO:4657); miR-92b (SEQ ID NO:4658); miR-93 (SEQ ID NO:4659); miR-96 (SEQ ID NO:4660); miR-98 (SEQ ID NO:4661); miR-99a (SEQ ID NO:4662); miR-99b (SEQ ID NO:4663); miR-100 (SEQ ID NO:4664); miR-101a (SEQ ID NO:4665); miR-101b (SEQ ID NO:4666); miR-103-1 (SEQ ID NO:4667); miR-103-2 (SEQ ID NO:4668); miR-105 (SEQ ID NO:4669); miR-106b (SEQ ID NO:4670); miR-107 (SEQ ID NO:4671); miR-122 (SEQ ID NO:4672); miR-124-1 (SEQ ID NO:4673); miR-124-2 (SEQ ID NO:4674); miR-124-3 (SEQ ID NO:4675); miR-125a (SEQ ID NO:4676); miR-125b-1 (SEQ ID NO:4677); miR-125b-2 (SEQ ID NO:4678); miR-126a (SEQ ID NO:4679); miR-126b (SEQ ID NO:4680); miR-127 (SEQ ID NO:4681); miR-128-1 (SEQ ID NO:4682); miR-128-2 (SEQ ID NO:4683); miR-129-1 (SEQ ID NO:4684); miR-129-2 (SEQ ID NO:4685); miR-130a (SEQ ID NO:4686); miR-130b (SEQ ID NO:4687); miR-132 (SEQ ID NO:4688); miR-133a (SEQ ID NO:4689); miR-133b (SEQ ID NO:4690); miR-133c (SEQ ID NO:4691); miR-134 (SEQ ID NO:4692); miR-135a (SEQ ID NO:4693); miR-135b (SEQ ID NO:4694); miR-136 (SEQ ID NO:4695); miR-137 (SEQ ID NO:4696); miR-138-1 (SEQ ID NO:4697); miR-138-2 (SEQ ID NO:4698); miR-139 (SEQ ID NO:4699); miR-140 (SEQ ID NO:4700); miR-141 (SEQ ID NO:4701); miR-142 (SEQ ID NO:4702); miR-143 (SEQ ID NO:4703); miR-144 (SEQ ID NO:4704); miR-145 (SEQ ID NO:4705); miR-146a (SEQ ID NO:4706); miR-146b (SEQ ID NO:4707); miR-147 (SEQ ID NO:4708); miR-148b (SEQ ID NO:4709); miR-150 (SEQ ID NO:4710); miR-151 (SEQ ID NO:4711); miR-152 (SEQ ID NO:4712); miR-153 (SEQ ID NO:4713); miR-154 (SEQ ID NO:4714); miR-155 (SEQ ID NO:4715); miR-181a-1 (SEQ ID NO:4716); miR-181a-2 (SEQ ID NO:4717); miR-181b-1 (SEQ ID NO:4718); miR-181b-2 (SEQ ID NO:4719); miR-181c (SEQ ID NO:4720); miR-181d (SEQ ID NO:4721); miR-182 (SEQ ID NO:4722); miR-183 (SEQ ID NO:4723); miR-184 (SEQ ID NO:4724); miR-185 (SEQ ID NO:4725); miR-186 (SEQ ID NO:4726); miR-187 (SEQ ID NO:4727); miR-188 (SEQ ID NO:4728); miR-190a (SEQ ID NO:4729); miR-190b (SEQ ID NO:4730); miR-191a (SEQ ID NO:4731); miR-191b (SEQ ID NO:4732); miR-192 (SEQ ID NO:4733); miR-193 (SEQ ID NO:4734); miR-194-1 (SEQ ID NO:4735); miR-194-2 (SEQ ID NO:4736); miR-195

(SEQ ID NO:4737); miR-196a (SEQ ID NO:4738); miR-196b (SEQ ID NO:4739); miR-196c (SEQ ID NO:4740); miR-199a (SEQ ID NO:4741); miR-200a (SEQ ID NO:4742); miR-200b (SEQ ID NO:4743); miR-200c (SEQ ID NO:4744); miR-201 (SEQ ID NO:4745); miR-202 (SEQ ID NO:4746); miR-203a (SEQ ID NO:4747); miR-203b (SEQ ID NO:4748); miR-204 (SEQ ID NO:4749); miR-205 (SEQ ID NO:4750); miR-206 (SEQ ID NO:4751); miR-207 (SEQ ID NO:4752); miR-208a (SEQ ID NO:4753); miR-208b (SEQ ID NO:4754); miR-210 (SEQ ID NO:4755); miR-211 (SEQ ID NO:4756); miR-212 (SEQ ID NO:4757); miR-214 (SEQ ID NO:4758); miR-215 (SEQ ID NO:4759); miR-216a (SEQ ID NO:4760); miR-216b (SEQ ID NO:4761); miR-217 (SEQ ID NO:4762); miR-218a-1 (SEQ ID NO:4763); miR-218a-2 (SEQ ID NO:4764); miR-218b (SEQ ID NO:4765); miR-219a-1 (SEQ ID NO:4766); miR-219a-2 (SEQ ID NO:4767); miR-219b (SEQ ID NO:4768); miR-221 (SEQ ID NO:4769); miR-222 (SEQ ID NO:4770); miR-223 (SEQ ID NO:4771); miR-224 (SEQ ID NO:4772); miR-290 (SEQ ID NO:4773); miR-291a (SEQ ID NO:4774); miR-291b (SEQ ID NO:4775); miR-292 (SEQ ID NO:4776); miR-293 (SEQ ID NO:4777); miR-294 (SEQ ID NO:4778); miR-295-1 (SEQ ID NO:4779); miR-295-2 (SEQ ID NO:4780); miR-296 (SEQ ID NO:4781); miR-297 (SEQ ID NO:4782); miR-298 (SEQ ID NO:4783); miR-299a (SEQ ID NO:4784); miR-299b (SEQ ID NO:4785); miR-300 (SEQ ID NO:4786); miR-301a (SEQ ID NO:4787); miR-301b (SEQ ID NO:4788); miR-320 (SEQ ID NO:4789); miR-322 (SEQ ID NO:4790); miR-323 (SEQ ID NO:4791); miR-324 (SEQ ID NO:4792); miR-325 (SEQ ID NO:4793); miR-326 (SEQ ID NO:4794); miR-327 (SEQ ID NO:4795); miR-328a (SEQ ID NO:4796); miR-328b (SEQ ID NO:4797); miR-329 (SEQ ID NO:4798); miR-330 (SEQ ID NO:4799); miR-331 (SEQ ID NO:4800); miR-335 (SEQ ID NO:4801); miR-336 (SEQ ID NO:4802); miR-337 (SEQ ID NO:4803); miR-338 (SEQ ID NO:4804); miR-339 (SEQ ID NO:4805); miR-340 (SEQ ID NO:4806); miR-341 (SEQ ID NO:4807); miR-342 (SEQ ID NO:4808); miR-343 (SEQ ID NO:4809); miR-344a-1 (SEQ ID NO:4810); miR-344a-2 (SEQ ID NO:4811); miR-344b-1 (SEQ ID NO:4812); miR-344b-2 (SEQ ID NO:4813); miR-344g (SEQ ID NO:4814); miR-344i (SEQ ID NO:4815); miR-345 (SEQ ID NO:4816); miR-346 (SEQ ID NO:4817); miR-347 (SEQ ID NO:4818); miR-349 (SEQ ID NO:4819); miR-350 (SEQ ID NO:4820); miR-351 (SEQ ID NO:4821); miR-352 (SEQ ID NO:4822); miR-361 (SEQ ID NO:4823); miR-362 (SEQ ID NO:4824); miR-363 (SEQ ID NO:4825); miR-365 (SEQ ID NO:4826); miR-369 (SEQ ID NO:4827); miR-370 (SEQ ID NO:4828); miR-374 (SEQ ID NO:4829); miR-375 (SEQ ID NO:4830); miR-376a (SEQ ID NO:4831); miR-376b (SEQ ID NO:4832); miR-376c (SEQ ID NO:4833); miR-377 (SEQ ID NO:4834); miR-378a (SEQ ID NO:4835); miR-378b (SEQ ID NO:4836); miR-379 (SEQ ID NO:4837); miR-380 (SEQ ID NO:4838); miR-381 (SEQ ID NO:4839); miR-382 (SEQ ID NO:4840); miR-383 (SEQ ID NO:4841); miR-384 (SEQ ID NO:4842); miR-409a (SEQ ID NO:4843); miR-409b (SEQ ID NO:4844); miR-410 (SEQ ID NO:4845); miR-411 (SEQ ID NO:4846); miR-412 (SEQ ID NO:4847); miR-421 (SEQ ID NO:4848); miR-423 (SEQ ID NO:4849); miR-425 (SEQ ID NO:4850); miR-429 (SEQ ID NO:4851); miR-431 (SEQ ID NO:4852); miR-433 (SEQ ID NO:4853); miR-434 (SEQ ID NO:4854); miR-448 (SEQ ID NO:4855); miR-449a (SEQ ID NO:4856); miR-449c (SEQ ID NO:4857); miR-450a (SEQ ID NO:4858); miR-451 (SEQ ID NO:4859); miR-455 (SEQ ID NO:4860); miR-463 (SEQ ID NO:4861); miR-465 (SEQ ID NO:4862); miR-466-1 (SEQ ID NO:4863); miR-466b-2 (SEQ ID NO:4864); miR-466c (SEQ ID NO:4865); miR-466d (SEQ ID NO:4866); miR-471 (SEQ ID NO:4867); miR-483 (SEQ ID NO:4868); miR-484 (SEQ ID NO:4869); miR-485 (SEQ ID NO:4870); miR-487b (SEQ ID NO:4871); miR-488 (SEQ ID NO:4872); miR-489 (SEQ ID NO:4873); miR-490 (SEQ ID NO:4874); miR-493 (SEQ ID NO:4875); miR-494 (SEQ ID NO:4876); miR-495 (SEQ ID NO:4877); miR-496 (SEQ ID NO:4878); miR-497 (SEQ ID NO:4879); miR-499 (SEQ ID NO:4880); miR-500 (SEQ ID NO:4881); miR-501 (SEQ ID NO:4882); miR-503 (SEQ ID NO:4883); miR-504 (SEQ ID NO:4884); miR-505 (SEQ ID NO:4885); miR-509 (SEQ ID NO:4886); miR-511 (SEQ ID NO:4887); miR-532 (SEQ ID NO:4888); miR-539 (SEQ ID NO:4889); miR-540 (SEQ ID NO:4890); miR-541 (SEQ ID NO:4891); miR-542 (SEQ ID NO:4892); miR-543 (SEQ ID NO:4893); miR-544 (SEQ ID NO:4894); miR-547 (SEQ ID NO:4895); miR-551b (SEQ ID NO:4896); miR-568 (SEQ ID NO:4897); miR-582 (SEQ ID NO:4898); miR-592 (SEQ ID NO:4899); miR-598 (SEQ ID NO:4900); miR-615 (SEQ ID NO:4901); miR-628 (SEQ ID NO:4902); miR-632 (SEQ ID NO:4903); miR-652 (SEQ ID NO:4904); miR-653 (SEQ ID NO:4905); miR-664-1 (SEQ ID NO:4906); miR-664-2 (SEQ ID NO:4907); miR-665 (SEQ ID NO:4908); miR-666 (SEQ ID NO:4909); miR-667 (SEQ ID NO:4910); miR-668 (SEQ ID NO:4911); miR-671 (SEQ ID NO:4912); miR-672 (SEQ ID NO:4913); miR-673 (SEQ ID NO:4914); miR-674 (SEQ ID NO:4915); miR-675 (SEQ ID NO:4916); miR-678 (SEQ ID NO:4917); miR-679 (SEQ ID NO:4918); miR-702 (SEQ ID NO:4919); miR-708 (SEQ ID NO:4920); miR-711 (SEQ ID NO:4921); miR-741 (SEQ ID NO:4922); miR-742 (SEQ ID NO:4923); miR-743a (SEQ ID NO:4924); miR-743b (SEQ ID NO:4925); miR-758 (SEQ ID NO:4926); miR-759 (SEQ ID NO:4927); miR-760 (SEQ ID NO:4928); miR-761 (SEQ ID NO:4929); miR-764 (SEQ ID NO:4930); miR-770 (SEQ ID NO:4931); miR-802 (SEQ ID NO:4932); miR-871 (SEQ ID NO:4933); miR-872 (SEQ ID NO:4934); miR-873 (SEQ ID NO:4935); miR-874 (SEQ ID NO:4936); miR-875 (SEQ ID NO:4937); miR-876 (SEQ ID NO:4938); miR-877 (SEQ ID NO:4939); miR-878 (SEQ ID NO:4940); miR-879 (SEQ ID NO:4941); miR-880 (SEQ ID NO:4942); miR-881 (SEQ ID NO:4943); miR-883 (SEQ ID NO:4944); miR-935 (SEQ ID NO:4945); miR-1188 (SEQ ID NO:4946); miR-1193 (SEQ ID NO:4947); miR-1199 (SEQ ID NO:4948); miR-1224 (SEQ ID NO:4949); miR-1249 (SEQ ID NO:4950); miR-1298 (SEQ ID NO:4951); miR-1306 (SEQ ID NO:4952); miR-1839 (SEQ ID NO:4953); miR-1843 (SEQ ID NO:4954); miR-1912 (SEQ ID NO:4955); miR-1949 (SEQ ID NO:4956); miR-2985 (SEQ ID NO:4957); miR-3065 (SEQ ID NO:4958); miR-3068 (SEQ ID NO:4959); miR-3072 (SEQ ID NO:4960); miR-3074 (SEQ ID NO:4961); miR-3075 (SEQ ID NO:4962); miR-3085 (SEQ ID NO:4963); miR-3099 (SEQ ID NO:4964); miR-3102 (SEQ ID NO:4965); miR-3120 (SEQ ID NO:4966); miR-3473 (SEQ ID NO:4967); miR-3541 (SEQ ID NO:4968); miR-3542 (SEQ ID NO:4969); miR-3543 (SEQ ID NO:4970); miR-3544 (SEQ ID NO:4971); miR-3546 (SEQ ID NO:4972); miR-3547 (SEQ ID NO:4973); miR-3548 (SEQ ID NO:4974); miR-3549 (SEQ ID NO:4975); miR-3550 (SEQ ID NO:4976); miR-3551 (SEQ ID NO:4977); miR-3552 (SEQ ID NO:4978); miR-3553 (SEQ ID NO:4979); miR-3556a (SEQ ID NO:4980); miR-3556b (SEQ ID NO:4981); miR-3557 (SEQ ID NO:4982); miR-3558 (SEQ ID NO:4983); miR-3559 (SEQ ID NO:4984); miR-3560 (SEQ ID NO:4985); miR-3561 (SEQ ID NO:4986); miR-3562 (SEQ ID NO:4987); miR-3564 (SEQ ID NO:4988); miR-3566 (SEQ ID NO:4989); miR-3568 (SEQ ID NO:4990); miR-3569 (SEQ ID NO:4991); miR-3570 (SEQ ID NO:4992); miR-3571 (SEQ ID NO:4993); miR-3572 (SEQ ID NO:4994);

miR-3573 (SEQ ID NO:4995); miR-3574 (SEQ ID NO:4996); miR-3575 (SEQ ID NO:4997); miR-3576 (SEQ ID NO:4998); miR-3577 (SEQ ID NO:4999); miR-3578 (SEQ ID NO:5000); miR-3579 (SEQ ID NO:5001); miR-3580 (SEQ ID NO:5002); miR-3583 (SEQ ID NO:5003); miR-3584 (SEQ ID NO:5004); miR-3585 (SEQ ID NO:5005); miR-3586 (SEQ ID NO:5006); miR-3587 (SEQ ID NO:5007); miR-3588 (SEQ ID NO:5008); miR-3589 (SEQ ID NO:5009); miR-3590 (SEQ ID NO:5010); miR-3591 (SEQ ID NO:5011); miR-3592 (SEQ ID NO:5012); miR-3593 (SEQ ID NO:5013); miR-3594 (SEQ ID NO:5014); miR-3595 (SEQ ID NO:5015); miR-3596a (SEQ ID NO:5016); miR-3596b (SEQ ID NO:5017); miR-3596c (SEQ ID NO:5018); miR-3596d (SEQ ID NO:5019); miR-6215 (SEQ ID NO:5020); miR-6216 (SEQ ID NO:5021); miR-6314 (SEQ ID NO:5022); miR-6315 (SEQ ID NO:5023); miR-6316 (SEQ ID NO:5024); miR-6317 (SEQ ID NO:5025); miR-6318 (SEQ ID NO:5026); miR-6319 (SEQ ID NO:5027); miR-6320 (SEQ ID NO:5028); miR-6321 (SEQ ID NO:5029); miR-6322 (SEQ ID NO:5030); miR-6323 (SEQ ID NO:5031); miR-6324 (SEQ ID NO:5032); miR-6325 (SEQ ID NO:5033); miR-6326 (SEQ ID NO:5034); miR-6327 (SEQ ID NO:5035); miR-6328 (SEQ ID NO:5036); miR-6329 (SEQ ID NO:5037); miR-6330 (SEQ ID NO:5038); miR-6331 (SEQ ID NO:5039); miR-6332 (SEQ ID NO:5040); miR-6333 (SEQ ID NO:5041); miR-6334 (SEQ ID NO:5042); and miR-7578 (SEQ ID NO:5043).

The following fruit fly miRNAs could be used: bantam (SEQ ID NO:5044); let-7 (SEQ ID NO:5045); miR-1 (SEQ ID NO:5046); miR-2a-1 (SEQ ID NO:5047); miR-2a-2 (SEQ ID NO:5048); miR-2b-1 (SEQ ID NO:5049); miR-2b-2 (SEQ ID NO:5050); miR-2c (SEQ ID NO:5051); miR-3 (SEQ ID NO:5052); miR-4 (SEQ ID NO:5053); miR-5 (SEQ ID NO:5054); miR-6-1 (SEQ ID NO:5055); miR-6-2 (SEQ ID NO:5056); miR-6-3 (SEQ ID NO:5057); miR-7 (SEQ ID NO:5058); miR-8 (SEQ ID NO:5059); miR-9a (SEQ ID NO:5060); miR-9b (SEQ ID NO:5061); miR-9c (SEQ ID NO:5062); miR-10 (SEQ ID NO:5063); miR-11 (SEQ ID NO:5064); miR-12 (SEQ ID NO:5065); miR-13a (SEQ ID NO:5066); miR-13b-1 (SEQ ID NO:5067); miR-13b-2 (SEQ ID NO:5068); miR-14 (SEQ ID NO:5069); miR-31a (SEQ ID NO:5070); miR-31b (SEQ ID NO:5071); miR-33 (SEQ ID NO:5072); miR-34 (SEQ ID NO:5073); miR-79 (SEQ ID NO:5074); miR-87 (SEQ ID NO:5075); miR-92a (SEQ ID NO:5076); miR-92b (SEQ ID NO:5077); miR-100 (SEQ ID NO:5078); miR-124 (SEQ ID NO:5079); miR-125 (SEQ ID NO:5080); miR-133 (SEQ ID NO:5081); miR-137 (SEQ ID NO:5082); miR-184 (SEQ ID NO:5083); miR-190 (SEQ ID NO:5084); miR-193 (SEQ ID NO:5085); miR-210 (SEQ ID NO:5086); miR-219 (SEQ ID NO:5087); miR-252 (SEQ ID NO:5088); miR-263a (SEQ ID NO:5089); miR-263b (SEQ ID NO:5090); miR-274 (SEQ ID NO:5091); miR-275 (SEQ ID NO:5092); miR-276a (SEQ ID NO:5093); miR-276b (SEQ ID NO:5094); miR-277 (SEQ ID NO:5095); miR-278 (SEQ ID NO:5096); miR-279 (SEQ ID NO:5097); miR-280 (SEQ ID NO:5098); miR-281-1 (SEQ ID NO:5099); miR-281-2 (SEQ ID NO:5100); miR-282 (SEQ ID NO:5101); miR-283 (SEQ ID NO:5102); miR-284 (SEQ ID NO:5103); miR-285 (SEQ ID NO:5104); miR-286 (SEQ ID NO:5105); miR-287 (SEQ ID NO:5106); miR-288 (SEQ ID NO:5107); miR-289 (SEQ ID NO:5108); miR-303 (SEQ ID NO:5109); miR-304 (SEQ ID NO:5110); miR-305 (SEQ ID NO:5111); miR-306 (SEQ ID NO:5112); miR-307a (SEQ ID NO:5113); miR-307b (SEQ ID NO:5114); miR-308 (SEQ ID NO:5115); miR-309 (SEQ ID NO:5116); miR-310 (SEQ ID NO:5117); miR-311 (SEQ ID NO:5118); miR-312 (SEQ ID NO:5119); miR-313 (SEQ ID NO:5120); miR-314 (SEQ ID NO:5121); miR-315 (SEQ ID NO:5122); miR-316 (SEQ ID NO:5123); miR-317 (SEQ ID NO:5124); miR-318 (SEQ ID NO:5125); miR-375 (SEQ ID NO:5126); miR-927 (SEQ ID NO:5127); miR-929 (SEQ ID NO:5128); miR-932 (SEQ ID NO:5129); miR-954 (SEQ ID NO:5130); miR-955 (SEQ ID NO:5131); miR-956 (SEQ ID NO:5132); miR-957 (SEQ ID NO:5133); miR-958 (SEQ ID NO:5134); miR-959 (SEQ ID NO:5135); miR-960 (SEQ ID NO:5136); miR-961 (SEQ ID NO:5137); miR-962 (SEQ ID NO:5138); miR-963 (SEQ ID NO:5139); miR-964 (SEQ ID NO:5140); miR-965 (SEQ ID NO:5141); miR-966 (SEQ ID NO:5142); miR-967 (SEQ ID NO:5143); miR-968 (SEQ ID NO:5144); miR-969 (SEQ ID NO:5145); miR-970 (SEQ ID NO:5146); miR-971 (SEQ ID NO:5147); miR-972 (SEQ ID NO:5148); miR-973 (SEQ ID NO:5149); miR-974 (SEQ ID NO:5150); miR-975 (SEQ ID NO:5151); miR-976 (SEQ ID NO:5152); miR-977 (SEQ ID NO:5153); miR-978 (SEQ ID NO:5154); miR-979 (SEQ ID NO:5155); miR-980 (SEQ ID NO:5156); miR-981 (SEQ ID NO:5157); miR-982 (SEQ ID NO:5158); miR-983-1 (SEQ ID NO:5159); miR-983-2 (SEQ ID NO:5160); miR-984 (SEQ ID NO:5161); miR-985 (SEQ ID NO:5162); miR-986 (SEQ ID NO:5163); miR-987 (SEQ ID NO:5164); miR-988 (SEQ ID NO:5165); miR-989 (SEQ ID NO:5166); miR-990 (SEQ ID NO:5167); miR-991 (SEQ ID NO:5168); miR-992 (SEQ ID NO:5169); miR-993 (SEQ ID NO:5170); miR-994 (SEQ ID NO:5171); miR-995 (SEQ ID NO:5172); miR-996 (SEQ ID NO:5173); miR-997 (SEQ ID NO:5174); miR-998 (SEQ ID NO:5175); miR-999 (SEQ ID NO:5176); miR-1000 (SEQ ID NO:5177); miR-1001 (SEQ ID NO:5178); miR-1002 (SEQ ID NO:5179); miR-1003 (SEQ ID NO:5180); miR-1004 (SEQ ID NO:5181); miR-1005 (SEQ ID NO:5182); miR-1006 (SEQ ID NO:5183); miR-1007 (SEQ ID NO:5184); miR-1008 (SEQ ID NO:5185); miR-1009 (SEQ ID NO:5186); miR-1010 (SEQ ID NO:5187); miR-1011 (SEQ ID NO:5188); miR-1012 (SEQ ID NO:5189); miR-1013 (SEQ ID NO:5190); miR-1014 (SEQ ID NO:5191); miR-1015 (SEQ ID NO:5192); miR-1016 (SEQ ID NO:5193); miR-1017 (SEQ ID NO:5194); miR-2279 (SEQ ID NO:5195); miR-2280 (SEQ ID NO:5196); miR-2281 (SEQ ID NO:5197); miR-2282 (SEQ ID NO:5198); miR-2283 (SEQ ID NO:5199); miR-2489 (SEQ ID NO:5200); miR-2490 (SEQ ID NO:5201); miR-2491 (SEQ ID NO:5202); miR-2492 (SEQ ID NO:5203); miR-2493 (SEQ ID NO:5204); miR-2494 (SEQ ID NO:5205); miR-2495 (SEQ ID NO:5206); miR-2496 (SEQ ID NO:5207); miR-2497 (SEQ ID NO:5208); miR-2498 (SEQ ID NO:5209); miR-2499 (SEQ ID NO:5210); miR-2500 (SEQ ID NO:5211); miR-2501 (SEQ ID NO:5212); miR-2535b (SEQ ID NO:5213); miR-3641 (SEQ ID NO:5214); miR-3642 (SEQ ID NO:5215); miR-3643 (SEQ ID NO:5216); miR-3644 (SEQ ID NO:5217); miR-3645 (SEQ ID NO:5218); miR-4908 (SEQ ID NO:5219); miR-4909 (SEQ ID NO:5220); miR-4910 (SEQ ID NO:5221); miR-4911 (SEQ ID NO:5222); miR-4912 (SEQ ID NO:5223); miR-4913 (SEQ ID NO:5224); miR-4914 (SEQ ID NO:5225); miR-4915 (SEQ ID NO:5226); miR-4916 (SEQ ID NO:5227); miR-4917 (SEQ ID NO:5228); miR-4918 (SEQ ID NO:5229); miR-4919 (SEQ ID NO:5230); miR-4939 (SEQ ID NO:5231); miR-4940 (SEQ ID NO:5232); miR-4941 (SEQ ID NO:5233); miR-4942 (SEQ ID NO:5234); miR-4943 (SEQ ID NO:5235); miR-4944 (SEQ ID NO:5236); miR-4945 (SEQ ID NO:5237); miR-4946 (SEQ ID NO:5238); miR-4947 (SEQ ID NO:5239); miR-4948 (SEQ ID NO:5240); miR-4949 (SEQ ID NO:5241); miR-4950 (SEQ ID NO:5242); miR-4951 (SEQ ID NO:5243); miR-4952 (SEQ ID NO:5244); miR-4953 (SEQ ID NO:5245);

miR-4954 (SEQ ID NO:5246); miR-4955 (SEQ ID NO:5247); miR-4956 (SEQ ID NO:5248); miR-4957 (SEQ ID NO:5249); miR-4958 (SEQ ID NO:5250); miR-4959 (SEQ ID NO:5251); miR-4960 (SEQ ID NO:5252); miR-4961 (SEQ ID NO:5253); miR-4962 (SEQ ID NO:5254); miR-4963 (SEQ ID NO:5255); miR-4964 (SEQ ID NO:5256); miR-4965 (SEQ ID NO:5257); miR-4966 (SEQ ID NO:5258); miR-4967 (SEQ ID NO:5259); miR-4968 (SEQ ID NO:5260); miR-4969 (SEQ ID NO:5261); miR-4970 (SEQ ID NO:5262); miR-4971 (SEQ ID NO:5263); miR-4972 (SEQ ID NO:5264); miR-4973 (SEQ ID NO:5265); miR-4974 (SEQ ID NO:5266); miR-4975 (SEQ ID NO:5267); miR-4976 (SEQ ID NO:5268); miR-4977 (SEQ ID NO:5269); miR-4978 (SEQ ID NO:5270); miR-4979 (SEQ ID NO:5271); miR-4980 (SEQ ID NO:5272); miR-4981 (SEQ ID NO:5273); miR-4982 (SEQ ID NO:5274); miR-4983 (SEQ ID NO:5275); miR-4984 (SEQ ID NO:5276); miR-4985 (SEQ ID NO:5277); miR-4986 (SEQ ID NO:5278); miR-4987 (SEQ ID NO:5279); miR-iab-4 (SEQ ID NO:5280); and miR-iab-8 (SEQ ID NO:5281).

The following cow miRNA could be used: let-7a-1 (SEQ ID NO:5282); let-7a-2 (SEQ ID NO:5283); let-7a-3 (SEQ ID NO:5284); let-7b (SEQ ID NO:5285); let-7c (SEQ ID NO:5286); let-7d (SEQ ID NO:5287); let-7e (SEQ ID NO:5288); let-7f-1 (SEQ ID NO:5289); let-7f-2 (SEQ ID NO:5290); let-7g (SEQ ID NO:5291); let-7i (SEQ ID NO:5292); miR-1-1 (SEQ ID NO:5293); miR-1-2 (SEQ ID NO:5294); miR-7-1 (SEQ ID NO:5295); miR-7-2 (SEQ ID NO:5296); miR-7-3 (SEQ ID NO:5297); miR-9-1 (SEQ ID NO:5298); miR-9-2 (SEQ ID NO:5299); miR-10a (SEQ ID NO:5300); miR-10b (SEQ ID NO:5301); miR-15a (SEQ ID NO:5302); miR-15b (SEQ ID NO:5303); miR-16a (SEQ ID NO:5304); miR-16b (SEQ ID NO:5305); miR-17 (SEQ ID NO:5306); miR-18a (SEQ ID NO:5307); miR-18b (SEQ ID NO:5308); miR-19a (SEQ ID NO:5309); miR-19b (SEQ ID NO:5310); miR-19b-2 (SEQ ID NO:5311); miR-20a (SEQ ID NO:5312); miR-20b (SEQ ID NO:5313); miR-21 (SEQ ID NO:5314); miR-22 (SEQ ID NO:5315); miR-23a (SEQ ID NO:5316); miR-23b (SEQ ID NO:5317); miR-24-1 (SEQ ID NO:5318); miR-24-2 (SEQ ID NO:5319); miR-25 (SEQ ID NO:5320); miR-26a-1 (SEQ ID NO:5321); miR-26a-2 (SEQ ID NO:5322); miR-26b (SEQ ID NO:5323); miR-26c (SEQ ID NO:5324); miR-27a (SEQ ID NO:5325); miR-27b (SEQ ID NO:5326); miR-28 (SEQ ID NO:5327); miR-29a (SEQ ID NO:5328); miR-29b-1 (SEQ ID NO:5329); miR-29b-2 (SEQ ID NO:5330); miR-29c (SEQ ID NO:5331); miR-29d (SEQ ID NO:5332); miR-29e (SEQ ID NO:5333); miR-30a (SEQ ID NO:5334); miR-30b (SEQ ID NO:5335); miR-30c (SEQ ID NO:5336); miR-30d (SEQ ID NO:5337); miR-30e (SEQ ID NO:5338); miR-30f (SEQ ID NO:5339); miR-31 (SEQ ID NO:5340); miR-32 (SEQ ID NO:5341); miR-33a (SEQ ID NO:5342); miR-33b (SEQ ID NO:5343); miR-34a (SEQ ID NO:5344); miR-34b (SEQ ID NO:5345); miR-34c (SEQ ID NO:5346); miR-92a-1 (SEQ ID NO:5347); miR-92a-2 (SEQ ID NO:5348); miR-92b (SEQ ID NO:5349); miR-93 (SEQ ID NO:5350); miR-95 (SEQ ID NO:5351); miR-96 (SEQ ID NO:5352); miR-98 (SEQ ID NO:5353); miR-99a (SEQ ID NO:5354); miR-99b (SEQ ID NO:5355); miR-100 (SEQ ID NO:5356); miR-101-1 (SEQ ID NO:5357); miR-101-2 (SEQ ID NO:5358); miR-103-1 (SEQ ID NO:5359); miR-103-2 (SEQ ID NO:5360); miR-105a (SEQ ID NO:5361); miR-105b (SEQ ID NO:5362); miR-106a (SEQ ID NO:5363); miR-106b (SEQ ID NO:5364); miR-107 (SEQ ID NO:5365); miR-122 (SEQ ID NO:5366); miR-124a-1 (SEQ ID NO:5367); miR-124a-2 (SEQ ID NO:5368); miR-124b (SEQ ID NO:5369); miR-125a (SEQ ID NO:5370); miR-125b-1 (SEQ ID NO:5371); miR-125b-2 (SEQ ID NO:5372); miR-126 (SEQ ID NO:5373); miR-127 (SEQ ID NO:5374); miR-128-1 (SEQ ID NO:5375); miR-128-2 (SEQ ID NO:5376); miR-129-1 (SEQ ID NO:5377); miR-129-2 (SEQ ID NO:5378); miR-130a (SEQ ID NO:5379); miR-130b (SEQ ID NO:5380); miR-132 (SEQ ID NO:5381); miR-133a-1 (SEQ ID NO:5382); miR-133a-2 (SEQ ID NO:5383); miR-133b (SEQ ID NO:5384); miR-133c (SEQ ID NO:5385); miR-134 (SEQ ID NO:5386); miR-135a-1 (SEQ ID NO:5387); miR-135a-2 (SEQ ID NO:5388); miR-135b (SEQ ID NO:5389); miR-136 (SEQ ID NO:5390); miR-137 (SEQ ID NO:5391); miR-138-1 (SEQ ID NO:5392); miR-138-2 (SEQ ID NO:5393); miR-139 (SEQ ID NO:5394); miR-140 (SEQ ID NO:5395); miR-141 (SEQ ID NO:5396); miR-142 (SEQ ID NO:5397); miR-143 (SEQ ID NO:5398); miR-144 (SEQ ID NO:5399); miR-145 (SEQ ID NO:5400); miR-146a (SEQ ID NO:5401); miR-146b (SEQ ID NO:5402); miR-147 (SEQ ID NO:5403); miR-148a (SEQ ID NO:5404); miR-148b (SEQ ID NO:5405); miR-149 (SEQ ID NO:5406); miR-150 (SEQ ID NO:5407); miR-151 (SEQ ID NO:5408); miR-152 (SEQ ID NO:5409); miR-153-1 (SEQ ID NO:5410); miR-153-2 (SEQ ID NO:5411); miR-154a (SEQ ID NO:5412); miR-154b (SEQ ID NO:5413); miR-154c (SEQ ID NO:5414); miR-155 (SEQ ID NO:5415); miR-181a-1 (SEQ ID NO:5416); miR-181a-2 (SEQ ID NO:5417); miR-181b-1 (SEQ ID NO:5418); miR-181b-2 (SEQ ID NO:5419); miR-181c (SEQ ID NO:5420); miR-181d (SEQ ID NO:5421); miR-182 (SEQ ID NO:5422); miR-183 (SEQ ID NO:5423); miR-184 (SEQ ID NO:5424); miR-185 (SEQ ID NO:5425); miR-186 (SEQ ID NO:5426); miR-187 (SEQ ID NO:5427); miR-188 (SEQ ID NO:5428); miR-190a (SEQ ID NO:5429); miR-190b (SEQ ID NO:5430); miR-191 (SEQ ID NO:5431); miR-192 (SEQ ID NO:5432); miR-193a (SEQ ID NO:5433); miR-193a-2 (SEQ ID NO:5434); miR-193b (SEQ ID NO:5435); miR-194-1 (SEQ ID NO:5436); miR-194-2 (SEQ ID NO:5437); miR-195 (SEQ ID NO:5438); miR-196a-1 (SEQ ID NO:5439); miR-196a-2 (SEQ ID NO:5440); miR-196b (SEQ ID NO:5441); miR-197 (SEQ ID NO:5442); miR-199a-1 (SEQ ID NO:5443); miR-199a-2 (SEQ ID NO:5444); miR-199b (SEQ ID NO:5445); miR-199c (SEQ ID NO:5446); miR-200a (SEQ ID NO:5447); miR-200b (SEQ ID NO:5448); miR-200c (SEQ ID NO:5449); miR-202 (SEQ ID NO:5450); miR-204 (SEQ ID NO:5451); miR-205 (SEQ ID NO:5452); miR-206 (SEQ ID NO:5453); miR-208a (SEQ ID NO:5454); miR-208b (SEQ ID NO:5455); miR-210 (SEQ ID NO:5456); miR-211 (SEQ ID NO:5457); miR-212 (SEQ ID NO:5458); miR-214 (SEQ ID NO:5459); miR-215 (SEQ ID NO:5460); miR-216a (SEQ ID NO:5461); miR-216b (SEQ ID NO:5462); miR-217 (SEQ ID NO:5463); miR-218-1 (SEQ ID NO:5464); miR-218-2 (SEQ ID NO:5465); miR-219 (SEQ ID NO:5466); miR-219-2 (SEQ ID NO:5467); miR-221 (SEQ ID NO:5468); miR-222 (SEQ ID NO:5469); miR-223 (SEQ ID NO:5470); miR-224 (SEQ ID NO:5471); miR-296 (SEQ ID NO:5472); miR-299 (SEQ ID NO:5473); miR-301a (SEQ ID NO:5474); miR-301b (SEQ ID NO:5475); miR-302a (SEQ ID NO:5476); miR-302b (SEQ ID NO:5477); miR-302c (SEQ ID NO:5478); miR-302d (SEQ ID NO:5479); miR-320a-1 (SEQ ID NO:5480); miR-320a-2 (SEQ ID NO:5481); miR-320b (SEQ ID NO:5482); miR-323 (SEQ ID NO:5483); miR-324 (SEQ ID NO:5484); miR-326 (SEQ ID NO:5485); miR-328 (SEQ ID NO:5486); miR-329a (SEQ ID NO:5487); miR-329b (SEQ ID NO:5488); miR-330 (SEQ ID NO:5489); miR-331 (SEQ ID NO:5490); miR-335 (SEQ ID NO:5491); miR-338 (SEQ ID NO:5492); miR-339a (SEQ ID NO:5493); miR-339b (SEQ ID NO:5494); miR-340 (SEQ ID NO:5495); miR-342 (SEQ ID NO:5496); miR-345 (SEQ ID NO:5497); miR-346 (SEQ ID NO:5498); miR-361 (SEQ ID NO:5499); miR-362 (SEQ ID NO:5500); miR-363 (SEQ ID NO:5501); miR-365-1 (SEQ ID NO:5502); miR-365-2 (SEQ ID NO:5503); miR-367 (SEQ ID NO:5504); miR-369 (SEQ ID NO:5505); miR-370 (SEQ ID NO:5506); miR-371 (SEQ ID NO:5507); miR-374a (SEQ ID NO:5508); miR-374b (SEQ ID NO:5509); miR-375 (SEQ ID NO:5510); miR-376a (SEQ ID NO:5511); miR-376b (SEQ ID NO:5512); miR-376c (SEQ ID NO:5513); miR-376d (SEQ ID NO:5514); miR-376e (SEQ ID NO:5515); miR-377 (SEQ ID NO:5516); miR-378-1 (SEQ ID NO:5517); miR-378-2 (SEQ ID NO:5518); miR-378b (SEQ ID NO:5519); miR-378c (SEQ ID NO:5520); miR-379 (SEQ ID NO:5521); miR-380 (SEQ ID NO:5522); miR-381 (SEQ ID NO:5523); miR-382 (SEQ ID NO:5524); miR-383 (SEQ ID NO:5525); miR-409a (SEQ ID NO:5526); miR-409b (SEQ ID NO:5527); miR-410 (SEQ ID NO:5528); miR-411a (SEQ ID NO:5529); miR-411b (SEQ ID NO:5530); miR-411c (SEQ ID NO:5531); miR-412 (SEQ ID NO:5532); miR-421 (SEQ ID NO:5533); miR-423 (SEQ ID NO:5534); miR-424 (SEQ ID NO:5535); miR-425 (SEQ ID NO:5536); miR-429 (SEQ ID NO:5537); miR-431 (SEQ ID NO:5538); miR-432 (SEQ ID NO:5539); miR-433 (SEQ ID NO:5540); miR-448 (SEQ ID NO:5541); miR-449a (SEQ ID NO:5542); miR-449b (SEQ ID NO:5543); miR-449c (SEQ ID NO:5544); miR-449d (SEQ ID NO:5545); miR-450a-1 (SEQ ID NO:5546); miR-450a-2 (SEQ ID NO:5547); miR-450b (SEQ ID NO:5548); miR-451 (SEQ ID NO:5549); miR-452 (SEQ ID NO:5550); miR-453 (SEQ ID NO:5551); miR-454 (SEQ ID NO:5552); miR-455 (SEQ ID NO:5553); miR-483 (SEQ ID NO:5554); miR-484 (SEQ ID NO:5555); miR-485 (SEQ ID NO:5556); miR-486 (SEQ ID NO:5557); miR-487a (SEQ ID NO:5558); miR-487b (SEQ ID NO:5559); miR-488 (SEQ ID NO:5560); miR-489 (SEQ ID NO:5561); miR-490 (SEQ ID NO:5562); miR-491 (SEQ ID NO:5563); miR-493 (SEQ ID NO:5564); miR-494 (SEQ ID NO:5565); miR-495 (SEQ ID NO:5566); miR-496 (SEQ ID NO:5567); miR-497 (SEQ ID NO:5568); miR-499 (SEQ ID NO:5569); miR-500 (SEQ ID NO:5570); miR-502a-1 (SEQ ID NO:5571); miR-502a-2 (SEQ ID NO:5572); miR-502b (SEQ ID NO:5573); miR-503 (SEQ ID NO:5574); miR-504 (SEQ ID NO:5575); miR-505 (SEQ ID NO:5576); miR-532 (SEQ ID NO:5577); miR-539 (SEQ ID NO:5578); miR-541 (SEQ ID NO:5579); miR-542 (SEQ ID NO:5580); miR-543 (SEQ ID NO:5581); miR-544a (SEQ ID NO:5582); miR-544b-1 (SEQ ID NO:5583); miR-544b-2 (SEQ ID NO:5584); miR-545 (SEQ ID NO:5585); miR-551a (SEQ ID NO:5586); miR-551b (SEQ ID NO:5587); miR-562 (SEQ ID NO:5588); miR-568 (SEQ ID NO:5589); miR-574 (SEQ ID NO:5590); miR-582 (SEQ ID NO:5591); miR-584-1 (SEQ ID NO:5592); miR-584-2 (SEQ ID NO:5593); miR-584-3 (SEQ ID NO:5594); miR-584-4 (SEQ ID NO:5595); miR-584-5 (SEQ ID NO:5596); miR-584-6 (SEQ ID NO:5597); miR-584-7 (SEQ ID NO:5598); miR-584-8 (SEQ ID NO:5599); miR-592 (SEQ ID NO:5600); miR-599 (SEQ ID NO:5601); miR-615 (SEQ ID NO:5602); miR-628 (SEQ ID NO:5603); miR-631 (SEQ ID NO:5604); miR-652 (SEQ ID NO:5605); miR-653 (SEQ ID NO:5606); miR-654 (SEQ ID NO:5607); miR-655 (SEQ ID NO:5608); miR-656 (SEQ ID NO:5609); miR-658 (SEQ ID NO:5610); miR-660 (SEQ ID NO:5611); miR-664 (SEQ ID NO:5612); miR-664b (SEQ ID NO:5613); miR-665 (SEQ ID NO:5614); miR-669 (SEQ ID NO:5615); miR-670 (SEQ ID NO:5616); miR-671 (SEQ ID NO:5617); miR-677 (SEQ ID NO:5618); miR-708 (SEQ ID NO:5619); miR-744 (SEQ ID NO:5620); miR-758 (SEQ ID NO:5621); miR-759 (SEQ ID NO:5622); miR-760 (SEQ ID NO:5623); miR-761 (SEQ ID NO:5624); miR-763 (SEQ ID NO:5625); miR-764 (SEQ ID NO:5626); miR-767 (SEQ ID NO:5627); miR-769 (SEQ ID NO:5628); miR-873 (SEQ ID NO:5629); miR-874 (SEQ ID NO:5630); miR-875 (SEQ ID NO:5631); miR-876 (SEQ ID NO:5632); miR-877 (SEQ ID NO:5633); miR-885 (SEQ ID NO:5634); miR-935 (SEQ ID NO:5635); miR-940 (SEQ ID NO:5636); miR-1179 (SEQ ID NO:5637); miR-1185 (SEQ ID NO:5638); miR-1193 (SEQ ID NO:5639); miR-1197 (SEQ ID NO:5640); miR-1224 (SEQ ID NO:5641); miR-1225 (SEQ ID NO:5642); miR-1246 (SEQ ID NO:5643); miR-1247 (SEQ ID NO:5644); miR-1248-1 (SEQ ID NO:5645); miR-1248-2 (SEQ ID NO:5646); miR-1249 (SEQ ID NO:5647); miR-1251 (SEQ ID NO:5648); miR-1256 (SEQ ID NO:5649); miR-1260b (SEQ ID NO:5650); miR-1271 (SEQ ID NO:5651); miR-1277 (SEQ ID NO:5652); miR-1281 (SEQ ID NO:5653); miR-1282 (SEQ ID NO:5654); miR-1284 (SEQ ID NO:5655); miR-1287 (SEQ ID NO:5656); miR-1291 (SEQ ID NO:5657); miR-1296 (SEQ ID NO:5658); miR-1298 (SEQ ID NO:5659); miR-1301 (SEQ ID NO:5660); miR-1306 (SEQ ID NO:5661); miR-1307 (SEQ ID NO:5662); miR-1343 (SEQ ID NO:5663); miR-1388 (SEQ ID NO:5664); miR-1434 (SEQ ID NO:5665); miR-1468 (SEQ ID NO:5666); miR-1584 (SEQ ID NO:5667); miR-1603 (SEQ ID NO:5668); miR-1721 (SEQ ID NO:5669); miR-1777a (SEQ ID NO:5670); miR-1777b (SEQ ID NO:5671); miR-1814a (SEQ ID NO:5672); miR-1814b (SEQ ID NO:5673); miR-1814c (SEQ ID NO:5674); miR-1835 (SEQ ID NO:5675); miR-1839 (SEQ ID NO:5676); miR-1843 (SEQ ID NO:5677); miR-1940 (SEQ ID NO:5678); miR-2284a (SEQ ID NO:5679); miR-2284aa-1 (SEQ ID NO:5680); miR-2284aa-2 (SEQ ID NO:5681); miR-2284aa-3 (SEQ ID NO:5682); miR-2284aa-4 (SEQ ID NO:5683); miR-2284ab (SEQ ID NO:5684); miR-2284ac (SEQ ID NO:5685); miR-2284b (SEQ ID NO:5686); miR-2284c (SEQ ID NO:5687); miR-2284d (SEQ ID NO:5688); miR-2284e (SEQ ID NO:5689); miR-2284f (SEQ ID NO:5690); miR-2284g (SEQ ID NO:5691); miR-2284h (SEQ ID NO:5692); miR-2284i (SEQ ID NO:5693); miR-2284j (SEQ ID NO:5694); miR-2284k (SEQ ID NO:5695); miR-2284l (SEQ ID NO:5696); miR-2284m (SEQ ID NO:5697); miR-2284n (SEQ ID NO:5698); miR-2284o (SEQ ID NO:5699); miR-2284p (SEQ ID NO:5700); miR-2284q (SEQ ID NO:5701); miR-2284r (SEQ ID NO:5702); miR-2284s (SEQ ID NO:5703); miR-2284t (SEQ ID NO:5704); miR-2284u (SEQ ID NO:5705); miR-2284v (SEQ ID NO:5706); miR-2284w (SEQ ID NO:5707); miR-2284x (SEQ ID NO:5708); miR-2284y-1 (SEQ ID NO:5709); miR-2284y-2 (SEQ ID NO:5710); miR-2284y-3 (SEQ ID NO:5711); miR-2284y-4 (SEQ ID NO:5712); miR-2284y-5 (SEQ ID NO:5713); miR-2284y-6 (SEQ ID NO:5714); miR-2284y-7 (SEQ ID NO:5715); miR-2284z-1 (SEQ ID NO:5716); miR-2284z-2 (SEQ ID NO:5717); miR-2284z-3 (SEQ ID NO:5718); miR-2284z-4 (SEQ ID NO:5719); miR-2284z-5 (SEQ ID NO:5720); miR-2284z-6 (SEQ ID NO:5721); miR-2284z-7 (SEQ ID NO:5722); miR-2285a (SEQ ID NO:5723); miR-2285aa (SEQ ID NO:5724); miR-2285ab (SEQ ID NO:5725); miR-2285ac (SEQ ID NO:5726); miR-2285ad (SEQ ID NO:5727); miR-2285ae (SEQ ID NO:5728); miR-2285af-1 (SEQ ID NO:5729); miR-2285af-2 (SEQ ID NO:5730); miR-2285b-1 (SEQ ID NO:5731); miR-2285b-2 (SEQ ID NO:5732); miR-2285c (SEQ ID NO:5733); miR-2285d (SEQ ID NO:5734); miR-2285e-1 (SEQ ID NO:5735); miR-2285e-2 (SEQ ID NO:5736); miR-2285f-1 (SEQ ID NO:5737); miR-2285f-2 (SEQ ID NO:5738); miR-2285g-1 (SEQ ID NO:5739); miR-2285g-2 (SEQ ID NO:5740); miR-2285g-3 (SEQ ID NO:5741); miR-2285h (SEQ ID NO:5742); miR-2285i (SEQ ID NO:5743); miR-2285j-1 (SEQ ID NO:5744); miR-2285j-2 (SEQ ID NO:5745); miR-2285k-1 (SEQ ID NO:5746); miR-2285k-2 (SEQ ID NO:5747); miR-2285k-3 (SEQ ID NO:5748); miR-2285k-4 (SEQ ID NO:5749); miR-2285k-5 (SEQ ID NO:5750); miR-2285l (SEQ ID NO:5751); miR-2285m-1 (SEQ ID NO:5752); miR-2285m-2 (SEQ ID NO:5753); miR-2285m-3 (SEQ ID NO:5754); miR-2285m-4 (SEQ ID NO:5755); miR-2285m-5 (SEQ ID NO:5756); miR-2285n-1 (SEQ ID NO:5757); miR-2285n-2 (SEQ ID NO:5758); miR-2285n-3 (SEQ ID NO:5759); miR-2285n-4 (SEQ ID NO:5760); miR-2285n-5 (SEQ ID NO:5761); miR-2285n-6 (SEQ ID NO:5762); miR-2285n-7 (SEQ ID NO:5763); miR-2285o-1 (SEQ ID NO:5764); miR-2285o-2 (SEQ ID NO:5765); miR-2285o-3 (SEQ ID NO:5766); miR-2285o-4 (SEQ ID NO:5767); miR-2285o-5 (SEQ ID NO:5768); miR-2285p (SEQ ID NO:5769); miR-2285q (SEQ ID NO:5770); miR-2285r (SEQ ID NO:5771); miR-2285s (SEQ ID NO:5772); miR-2285t (SEQ ID NO:5773); miR-2285u (SEQ ID NO:5774); miR-2285v (SEQ ID NO:5775); miR-2285w (SEQ ID NO:5776); miR-2285x (SEQ ID NO:5777); miR-2285y (SEQ ID NO:5778); miR-2285z (SEQ ID NO:5779); miR-2286 (SEQ ID NO:5780); miR-2287 (SEQ ID NO:5781); miR-2288 (SEQ ID NO:5782); miR-2289 (SEQ ID NO:5783); miR-2290 (SEQ ID NO:5784); miR-2291 (SEQ ID NO:5785); miR-2292 (SEQ ID NO:5786); miR-2293 (SEQ ID NO:5787); miR-2294 (SEQ ID NO:5788); miR-2295 (SEQ ID NO:5789); miR-2296 (SEQ ID NO:5790); miR-2297 (SEQ ID NO:5791); miR-2298 (SEQ ID NO:5792); miR-2299 (SEQ ID NO:5793); miR-2300a (SEQ ID NO:5794); miR-2300b (SEQ ID NO:5795); miR-2301 (SEQ ID NO:5796); miR-2302 (SEQ ID NO:5797); miR-2303 (SEQ ID NO:5798); miR-2304 (SEQ ID NO:5799); miR-2305 (SEQ ID NO:5800); miR-2306 (SEQ ID NO:5801); miR-2307 (SEQ ID NO:5802); miR-2308 (SEQ ID NO:5803); miR-2309 (SEQ ID NO:5804); miR-2310 (SEQ ID NO:5805); miR-2311 (SEQ ID NO:5806); miR-2312 (SEQ ID NO:5807); miR-2313 (SEQ ID NO:5808); miR-2314 (SEQ ID NO:5809); miR-2315 (SEQ ID NO:5810); miR-2316 (SEQ ID NO:5811); miR-2317 (SEQ ID NO:5812); miR-2318 (SEQ ID NO:5813); miR-2319a (SEQ ID NO:5814); miR-2319b (SEQ ID NO:5815); miR-2320 (SEQ ID NO:5816); miR-2321 (SEQ ID NO:5817); miR-2322 (SEQ ID NO:5818); miR-2323 (SEQ ID NO:5819); miR-2324 (SEQ ID NO:5820); miR-2325a (SEQ ID NO:5821); miR-2325b (SEQ ID NO:5822); miR-2325c (SEQ ID NO:5823); miR-2326 (SEQ ID NO:5824); miR-2327 (SEQ ID NO:5825); miR-2328 (SEQ ID NO:5826); miR-2329-1 (SEQ ID NO:5827); miR-2329-2 (SEQ ID NO:5828); miR-2330 (SEQ ID NO:5829); miR-2331 (SEQ ID NO:5830); miR-2332 (SEQ ID NO:5831); miR-2333 (SEQ ID NO:5832); miR-2334 (SEQ ID NO:5833); miR-2335 (SEQ ID NO:5834); miR-2336 (SEQ ID NO:5835); miR-2337 (SEQ ID NO:5836); miR-2338 (SEQ ID NO:5837); miR-2339 (SEQ ID NO:5838); miR-2340 (SEQ ID NO:5839); miR-2341 (SEQ ID NO:5840); miR-2342 (SEQ ID NO:5841); miR-2343 (SEQ ID NO:5842); miR-2344 (SEQ ID NO:5843); miR-2345 (SEQ ID NO:5844); miR-2346 (SEQ ID NO:5845); miR-2347 (SEQ ID NO:5846); miR-2348 (SEQ ID NO:5847); miR-2349 (SEQ ID NO:5848); miR-2350 (SEQ ID NO:5849); miR-2351 (SEQ ID NO:5850); miR-2352 (SEQ ID NO:5851); miR-2353 (SEQ ID NO:5852); miR-2354 (SEQ ID NO:5853); miR-2355 (SEQ ID NO:5854); miR-2356 (SEQ ID NO:5855); miR-2357 (SEQ ID NO:5856); miR-2358 (SEQ ID NO:5857); miR-2359 (SEQ ID NO:5858); miR-2360 (SEQ ID NO:5859); miR-2361 (SEQ ID NO:5860); miR-2362 (SEQ ID NO:5861); miR-2363-1 (SEQ ID NO:5862); miR-2363-2 (SEQ ID NO:5863); miR-2364 (SEQ ID NO:5864); miR-2365 (SEQ ID NO:5865); miR-2366 (SEQ ID NO:5866); miR-2367 (SEQ ID NO:5867); miR-2368 (SEQ ID NO:5868); miR-2369 (SEQ ID NO:5869); miR-2370 (SEQ ID NO:5870); miR-2371 (SEQ ID NO:5871); miR-2372 (SEQ ID NO:5872); miR-2373 (SEQ ID NO:5873); miR-2374 (SEQ ID NO:5874); miR-2375 (SEQ ID NO:5875); miR-2376 (SEQ ID NO:5876); miR-2377 (SEQ ID NO:5877); miR-2378 (SEQ ID NO:5878); miR-2379 (SEQ ID NO:5879); miR-2380 (SEQ ID NO:5880); miR-2381 (SEQ ID NO:5881); miR-2382 (SEQ ID NO:5882); miR-2383 (SEQ ID NO:5883); miR-2384 (SEQ ID NO:5884); miR-2385 (SEQ ID NO:5885); miR-2386 (SEQ ID NO:5886); miR-2387 (SEQ ID NO:5887); miR-2388 (SEQ ID NO:5888); miR-2389 (SEQ ID NO:5889); miR-2390 (SEQ ID NO:5890); miR-2392 (SEQ ID NO:5891); miR-2393 (SEQ ID NO:5892); miR-2394 (SEQ ID NO:5893); miR-2395 (SEQ ID NO:5894); miR-2396 (SEQ ID NO:5895); miR-2397 (SEQ ID NO:5896); miR-2398 (SEQ ID NO:5897); miR-2399 (SEQ ID NO:5898); miR-2400 (SEQ ID NO:5899); miR-2401 (SEQ ID NO:5900); miR-2402 (SEQ ID NO:5901); miR-2403 (SEQ ID NO:5902); miR-2404-1 (SEQ ID NO:5903); miR-2404-2 (SEQ ID NO:5904); miR-2405 (SEQ ID NO:5905); miR-2406 (SEQ ID NO:5906); miR-2407 (SEQ ID NO:5907); miR-2408 (SEQ ID NO:5908); miR-2409 (SEQ ID NO:5909); miR-2410 (SEQ ID NO:5910); miR-2411 (SEQ ID NO:5911); miR-2412 (SEQ ID NO:5912); miR-2413 (SEQ ID NO:5913); miR-2414 (SEQ ID NO:5914); miR-2415 (SEQ ID NO:5915); miR-2416 (SEQ ID NO:5916); miR-2417 (SEQ ID NO:5917); miR-2418 (SEQ ID NO:5918); miR-2419 (SEQ ID NO:5919); miR-2420 (SEQ ID NO:5920); miR-2421 (SEQ ID NO:5921); miR-2422 (SEQ ID NO:5922); miR-2423 (SEQ ID NO:5923); miR-2424 (SEQ ID NO:5924); miR-2425 (SEQ ID NO:5925); miR-2426 (SEQ ID NO:5926); miR-2427 (SEQ ID NO:5927); miR-2428 (SEQ ID NO:5928); miR-2429 (SEQ ID NO:5929); miR-2430 (SEQ ID NO:5930); miR-2431 (SEQ ID NO:5931); miR-2432 (SEQ ID NO:5932); miR-2433 (SEQ ID NO:5933); miR-2434 (SEQ ID NO:5934); miR-2435 (SEQ ID NO:5935); miR-2436 (SEQ ID NO:5936); miR-2437 (SEQ ID NO:5937); miR-2438 (SEQ ID NO:5938); miR-2439 (SEQ ID NO:5939); miR-2440 (SEQ ID NO:5940); miR-2441 (SEQ ID NO:5941); miR-2442 (SEQ ID NO:5942); miR-2443 (SEQ ID NO:5943); miR-2444 (SEQ ID NO:5944); miR-2446 (SEQ ID NO:5945); miR-2447 (SEQ ID NO:5946); miR-2448 (SEQ ID NO:5947); miR-2449 (SEQ ID NO:5948); miR-2450a (SEQ ID NO:5949); miR-2450b (SEQ ID NO:5950); miR-2450c (SEQ ID NO:5951); miR-2451 (SEQ ID NO:5952); miR-2452 (SEQ ID NO:5953); miR-2453 (SEQ ID NO:5954); miR-2454 (SEQ ID NO:5955); miR-2455 (SEQ ID NO:5956); miR-2456 (SEQ ID NO:5957); miR-2457 (SEQ ID NO:5958); miR-2458 (SEQ ID NO:5959); miR-2459 (SEQ ID NO:5960); miR-2460 (SEQ ID NO:5961); miR-2461 (SEQ ID NO:5962); miR-2462 (SEQ ID NO:5963); miR-2463 (SEQ ID NO:5964); miR-2464 (SEQ ID NO:5965); miR-2465 (SEQ ID NO:5966); miR-2466 (SEQ ID NO:5967); miR-2467 (SEQ ID NO:5968); miR-2468 (SEQ ID NO:5969); miR-2469 (SEQ ID NO:5970); miR-2470 (SEQ ID NO:5971); miR-2471 (SEQ ID NO:5972); miR-2472 (SEQ ID NO:5973); miR-2473 (SEQ ID NO:5974); miR-2474 (SEQ ID NO:5975); miR-2475 (SEQ ID NO:5976); miR-2477 (SEQ ID NO:5977); miR-2478 (SEQ ID NO:5978); miR-2479 (SEQ ID NO:5979); miR-2480 (SEQ ID NO:5980); miR-2481 (SEQ ID NO:5981); miR-2482 (SEQ ID NO:5982); miR-2483 (SEQ ID NO:5983); miR-2484 (SEQ ID NO:5984); miR-2485 (SEQ ID NO:5985); miR-2486 (SEQ ID NO:5986); miR-2487 (SEQ ID NO:5987); miR-2488 (SEQ ID NO:5988); miR-2489 (SEQ ID NO:5989); miR-2881 (SEQ ID NO:5990); miR-2882 (SEQ ID NO:5991); miR-2883 (SEQ ID NO:5992); miR-2885 (SEQ ID NO:5993); miR-2886 (SEQ ID NO:5994); miR-2887-1 (SEQ ID NO:5995); miR-2887-2 (SEQ ID NO:5996); miR-2888-1 (SEQ ID NO:5997); miR-2888-2 (SEQ ID NO:5998); miR-2889 (SEQ ID NO:5999); miR-2890 (SEQ ID NO:6000); miR-2891 (SEQ ID NO:6001); miR-2892 (SEQ ID NO:6002); miR-2893 (SEQ ID NO:6003); miR-2894 (SEQ ID NO:6004); miR-2895 (SEQ ID NO:6005); miR-2896 (SEQ ID NO:6006); miR-2897 (SEQ ID NO:6007); miR-2898 (SEQ ID NO:6008); miR-2899 (SEQ ID NO:6009); miR-2900 (SEQ ID NO:6010); miR-2901 (SEQ ID NO:6011); miR-2902 (SEQ ID NO:6012); miR-2903 (SEQ ID NO:6013); miR-2904-1 (SEQ ID NO:6014); miR-2904-2 (SEQ ID NO:6015); miR-2904-3 (SEQ ID NO:6016); miR-2917 (SEQ ID NO:6017); miR-2957 (SEQ ID NO:6018); miR-3120 (SEQ ID NO:6019); miR-3141 (SEQ ID NO:6020); miR-3154 (SEQ ID NO:6021); miR-3431 (SEQ ID NO:6022); miR-3432-1 (SEQ ID NO:6023); miR-3432-2 (SEQ ID NO:6024); miR-3578 (SEQ ID NO:6025); miR-3596 (SEQ ID NO:6026); miR-3600 (SEQ ID NO:6027); miR-3601 (SEQ ID NO:6028); miR-3602 (SEQ ID NO:6029); miR-3604-1 (SEQ ID NO:6030); miR-3604-2 (SEQ ID NO:6031); miR-3613 (SEQ ID NO:6032); miR-3613b (SEQ ID NO:6033); miR-3660 (SEQ ID NO:6034); miR-3956 (SEQ ID NO:6035); miR-3957 (SEQ ID NO:6036); miR-4286-1 (SEQ ID NO:6037); miR-4286-2 (SEQ ID NO:6038); miR-6119 (SEQ ID NO:6039); miR-6120 (SEQ ID NO:6040); miR-6121 (SEQ ID NO:6041); miR-6122 (SEQ ID NO:6042); miR-6123 (SEQ ID NO:6043); miR-6516 (SEQ ID NO:6044); miR-6517 (SEQ ID NO:6045); miR-6518 (SEQ ID NO:6046); miR-6519 (SEQ ID NO:6047); miR-6520 (SEQ ID NO:6048); miR-6521 (SEQ ID NO:6049); miR-6522 (SEQ ID NO:6050); miR-6523 (SEQ ID NO:6051); miR-6523b (SEQ ID NO:6052); miR-6524 (SEQ ID NO:6053); miR-6525 (SEQ ID NO:6054); miR-6526-1 (SEQ ID NO:6055); miR-6526-2 (SEQ ID NO:6056); miR-6526-3 (SEQ ID NO:6057); miR-6527 (SEQ ID NO:6058); miR-6528 (SEQ ID NO:6059); miR-6529 (SEQ ID NO:6060); miR-6529b (SEQ ID NO:6061); miR-6530 (SEQ ID NO:6062); miR-6531 (SEQ ID NO:6063); miR-6532 (SEQ ID NO:6064); miR-6533 (SEQ ID NO:6065); miR-6534 (SEQ ID NO:6066); miR-6535 (SEQ ID NO:6067); miR-6536-1 (SEQ ID NO:6068); miR-6536-2 (SEQ ID NO:6069); miR-7691 (SEQ ID NO:6070); miR-7857 (SEQ ID NO:6071); miR-7858 (SEQ ID NO:6072); miR-7859 (SEQ ID NO:6073); miR-7860 (SEQ ID NO:6074); miR-7861 (SEQ ID NO:6075); miR-7862 (SEQ ID NO:6076); miR-7863 (SEQ ID NO:6077); miR-7864 (SEQ ID NO:6078); and miR-7865 (SEQ ID NO:6079).

The following sheep miRNAs could be used: let-7a (SEQ ID NO:6080); let-7b (SEQ ID NO:6081); let-7c (SEQ ID NO:6082); let-7d (SEQ ID NO:6083); let-7f (SEQ ID NO:6084); let-7g (SEQ ID NO:6085); let-7i (SEQ ID NO:6086); miR-10a (SEQ ID NO:6087); miR-10b (SEQ ID NO:6088); miR-16b (SEQ ID NO:6089); miR-17 (SEQ ID NO:6090); miR-19b (SEQ ID NO:6091); miR-21 (SEQ ID NO:6092); miR-22 (SEQ ID NO:6093); miR-23a (SEQ ID NO:6094); miR-23b (SEQ ID NO:6095); miR-25 (SEQ ID NO:6096); miR-26a (SEQ ID NO:6097); miR-26b (SEQ ID NO:6098); miR-27a (SEQ ID NO:6099); miR-29a (SEQ ID NO:6100); miR-29b (SEQ ID NO:6101); miR-30a (SEQ ID NO:6102); miR-30b (SEQ ID NO:6103); miR-30c (SEQ ID NO:6104); miR-30d (SEQ ID NO:6105); miR-99a (SEQ ID NO:6106); miR-103 (SEQ ID NO:6107); miR-106a (SEQ ID NO:6108); miR-106b (SEQ ID NO:6109); miR-107 (SEQ ID NO:6110); miR-125b (SEQ ID NO:6111); miR-127 (SEQ ID NO:6112); miR-133 (SEQ ID NO:6113); miR-134 (SEQ ID NO:6114); miR-136 (SEQ ID NO:6115); miR-143 (SEQ ID NO:6116); miR-148a (SEQ ID NO:6117); miR-150 (SEQ ID NO:6118); miR-152 (SEQ ID NO:6119); miR-154a (SEQ ID NO:6120); miR-154b (SEQ ID NO:6121); miR-181a-1 (SEQ ID NO:6122); miR-181a-2 (SEQ ID NO:6123); miR-191 (SEQ ID NO:6124); miR-194 (SEQ ID NO:6125); miR-199a (SEQ ID NO:6126); miR-200a (SEQ ID NO:6127); miR-200b (SEQ ID NO:6128); miR-200c (SEQ ID NO:6129); miR-218a (SEQ ID NO:6130); miR-221 (SEQ ID NO:6131); miR-299 (SEQ ID NO:6132); miR-323a (SEQ ID NO:6133); miR-323b (SEQ ID NO:6134); miR-323c (SEQ ID NO:6135); miR-329a (SEQ ID NO:6136); miR-329b (SEQ ID NO:6137); miR-362 (SEQ ID NO:6138); miR-369 (SEQ ID NO:6139); miR-370 (SEQ ID NO:6140); miR-374a (SEQ ID NO:6141); miR-374b (SEQ ID NO:6142); miR-376a (SEQ ID NO:6143); miR-376b (SEQ ID NO:6144); miR-376c (SEQ ID NO:6145); miR-376d (SEQ ID NO:6146); miR-376e (SEQ ID NO:6147); miR-377 (SEQ ID NO:6148); miR-379 (SEQ ID NO:6149); miR-380 (SEQ ID NO:6150); miR-381 (SEQ ID NO:6151); miR-382 (SEQ ID NO:6152); miR-409 (SEQ ID NO:6153); miR-410 (SEQ ID NO:6154); miR-411a (SEQ ID NO:6155); miR-411b (SEQ ID NO:6156); miR-412 (SEQ ID NO:6157); miR-431 (SEQ ID NO:6158); miR-432 (SEQ ID NO:6159); miR-433 (SEQ ID NO:6160); miR-485 (SEQ ID NO:6161); miR-487a (SEQ ID NO:6162); miR-487b (SEQ ID NO:6163); miR-493 (SEQ ID NO:6164); miR-494 (SEQ ID NO:6165); miR-495 (SEQ ID NO:6166); miR-496 (SEQ ID NO:6167); miR-539 (SEQ ID NO:6168); miR-541 (SEQ ID NO:6169); miR-543 (SEQ ID NO:6170); miR-544 (SEQ ID NO:6171); miR-654 (SEQ ID NO:6172); miR-655 (SEQ ID NO:6173); miR-665 (SEQ ID NO:6174); miR-668 (SEQ ID NO:6175); miR-758 (SEQ ID NO:6176); miR-1185 (SEQ ID NO:6177); miR-1193 (SEQ ID NO:6178); miR-1197 (SEQ ID NO:6179); miR-3955 (SEQ ID NO:6180); miR-3956 (SEQ ID NO:6181); miR-3957 (SEQ ID NO:6182); miR-3958 (SEQ ID NO:6183); and miR-3959 (SEQ ID NO:6184).

The following pig miRNAs could be used: let-7a-1 (SEQ ID NO:6185); let-7a-2 (SEQ ID NO:6186); let-7c (SEQ ID NO:6187); let-7d (SEQ ID NO:6188); let-7e (SEQ ID NO:6189); let-7f-1 (SEQ ID NO:6190); let-7f-2 (SEQ ID NO:6191); let-7g (SEQ ID NO:6192); let-7i (SEQ ID NO:6193); miR-1 (SEQ ID NO:6194); miR-7-1 (SEQ ID NO:6195); miR-7-2 (SEQ ID NO:6196); miR-9-1 (SEQ ID NO:6197); miR-9-2 (SEQ ID NO:6198); miR-9-3 (SEQ ID NO:6199); miR-10a (SEQ ID NO:6200); miR-10b (SEQ ID NO:6201); miR-15a (SEQ ID NO:6202); miR-15b (SEQ ID NO:6203); miR-16-1 (SEQ ID NO:6204); miR-16-2 (SEQ ID NO:6205); miR-17 (SEQ ID NO:6206); miR-18a (SEQ ID NO:6207); miR-18b (SEQ ID NO:6208); miR-19a (SEQ ID NO:6209); miR-19b-1 (SEQ ID NO:6210); miR-19b-2 (SEQ ID NO:6211); miR-20a (SEQ ID NO:6212); miR-20b-1 (SEQ ID NO:6213); miR-20b-2 (SEQ ID NO:6214); miR-21 (SEQ ID NO:6215); miR-22 (SEQ ID NO:6216); miR-23a (SEQ ID NO:6217); miR-23b (SEQ ID NO:6218); miR-24-1 (SEQ ID NO:6219); miR-24-2 (SEQ ID NO:6220); miR-26a (SEQ ID NO:6221); miR-27a (SEQ ID NO:6222); miR-27b (SEQ ID NO:6223); miR-28 (SEQ ID NO:6224); miR-29a (SEQ ID NO:6225); miR-29b-1 (SEQ ID NO:6226); miR-29b-2 (SEQ ID NO:6227); miR-29c (SEQ ID NO:6228); miR-30a (SEQ ID NO:6229); miR-30b (SEQ ID NO:6230); miR-30c-1 (SEQ ID NO:6231); miR- 30c-2 (SEQ ID NO:6232); miR-30d (SEQ ID NO:6233); miR-30e (SEQ ID NO:6234); miR-31 (SEQ ID NO:6235); miR-32 (SEQ ID NO:6236); miR-34a (SEQ ID NO:6237); miR-34c-1 (SEQ ID NO:6238); miR-34c-2 (SEQ ID NO:6239); miR-92a-1 (SEQ ID NO:6240); miR-92a-2 (SEQ ID NO:6241); miR-92b (SEQ ID NO:6242); miR-95 (SEQ ID NO:6243); miR-98 (SEQ ID NO:6244); miR-99a (SEQ ID NO:6245); miR-99b (SEQ ID NO:6246); miR-100 (SEQ ID NO:6247); miR-101-1 (SEQ ID NO:6248); miR-101-2 (SEQ ID NO:6249); miR-103-1 (SEQ ID NO:6250); miR-103-2 (SEQ ID NO:6251); miR-105-1 (SEQ ID NO:6252); miR-105-2 (SEQ ID NO:6253); miR-106a (SEQ ID NO:6254); miR-107 (SEQ ID NO:6255); miR-122 (SEQ ID NO:6256); miR-124a-1 (SEQ ID NO:6257); miR-124a-2 (SEQ ID NO:6258); miR-125a (SEQ ID NO:6259); miR-125b-1 (SEQ ID NO:6260); miR-125b-2 (SEQ ID NO:6261); miR-126 (SEQ ID NO:6262); miR-127 (SEQ ID NO:6263); miR-128-1 (SEQ ID NO:6264); miR-128-2 (SEQ ID NO:6265); miR-129a (SEQ ID NO:6266); miR-129b (SEQ ID NO:6267); miR-130a (SEQ ID NO:6268); miR-130b (SEQ ID NO:6269); miR-132 (SEQ ID NO:6270); miR-133a-1 (SEQ ID NO:6271); miR-133a-2 (SEQ ID NO:6272); miR-133b (SEQ ID NO:6273); miR-135-1 (SEQ ID NO:6274); miR-135-2 (SEQ ID NO:6275); miR-136 (SEQ ID NO:6276); miR-137 (SEQ ID NO:6277); miR-138 (SEQ ID NO:6278); miR-139 (SEQ ID NO:6279); miR-140 (SEQ ID NO:6280); miR-142 (SEQ ID NO:6281); miR-143 (SEQ ID NO:6282); miR-144 (SEQ ID NO:6283); miR-145 (SEQ ID NO:6284); miR-146a (SEQ ID NO:6285); miR-146b (SEQ ID NO:6286); miR-148a (SEQ ID NO:6287); miR-148b (SEQ ID NO:6288); miR-149 (SEQ ID NO:6289); miR-150-1 (SEQ ID NO:6290); miR-150-2 (SEQ ID NO:6291); miR-151 (SEQ ID NO:6292); miR-152 (SEQ ID NO:6293); miR-153 (SEQ ID NO:6294); miR-155 (SEQ ID NO:6295); miR-181a-1 (SEQ ID NO:6296); miR-181a-2 (SEQ ID NO:6297); miR-181b-1 (SEQ ID NO:6298); miR-181b-2 (SEQ ID NO:6299); miR-181c (SEQ ID NO:6300); miR-181d (SEQ ID NO:6301); miR-182 (SEQ ID NO:6302); miR-183 (SEQ ID NO:6303); miR-184 (SEQ ID NO:6304); miR-185 (SEQ ID NO:6305); miR-186 (SEQ ID NO:6306); miR-187 (SEQ ID NO:6307); miR-190a (SEQ ID NO:6308); miR-190b (SEQ ID NO:6309); miR-191 (SEQ ID NO:6310); miR-192 (SEQ ID NO:6311); miR-193a (SEQ ID NO:6312); miR-194a (SEQ ID NO:6313); miR-194b (SEQ ID NO:6314); miR-195 (SEQ ID NO:6315); miR-196a-1 (SEQ ID NO:6316); miR-196a-2 (SEQ ID NO:6317); miR-196b-1 (SEQ ID NO:6318); miR-196b-2 (SEQ ID NO:6319); miR-199a-1 (SEQ ID NO:6320); miR-199a-2 (SEQ ID NO:6321); miR-199b (SEQ ID NO:6322); miR-202 (SEQ ID NO:6323); miR-204 (SEQ ID NO:6324); miR-205 (SEQ ID NO:6325); miR-206 (SEQ ID NO:6326); miR-208b (SEQ ID NO:6327); miR-210 (SEQ ID NO:6328); miR-212 (SEQ ID NO:6329); miR-214 (SEQ ID NO:6330); miR-215 (SEQ ID NO:6331); miR-216-1 (SEQ ID NO:6332); miR-216-2 (SEQ ID NO:6333); miR-217-1 (SEQ ID NO:6334); miR-217-2 (SEQ ID NO:6335); miR-218-1 (SEQ ID NO:6336); miR-218-2 (SEQ ID NO:6337); miR-218b (SEQ ID NO:6338); miR-219 (SEQ ID NO:6339); miR-221 (SEQ ID NO:6340); miR-222 (SEQ ID NO:6341); miR-224 (SEQ ID NO:6342); miR-296 (SEQ ID NO:6343); miR-299 (SEQ ID NO:6344); miR-301 (SEQ ID NO:6345); miR-320 (SEQ ID NO:6346); miR-323 (SEQ ID NO:6347); miR-324 (SEQ ID NO:6348); miR-325 (SEQ ID NO:6349); miR-326 (SEQ ID NO:6350); miR-328 (SEQ ID NO:6351); miR-331 (SEQ ID NO:6352); miR-335 (SEQ ID NO:6353); miR-338 (SEQ ID NO:6354); miR-339-1 (SEQ ID NO:6355); miR-339-2 (SEQ ID NO:6356); miR-340-1 (SEQ ID NO:6357); miR-340-2 (SEQ ID NO:6358); miR-342 (SEQ ID NO:6359); miR-345-1 (SEQ ID NO:6360); miR-345-2 (SEQ ID NO:6361); miR-361 (SEQ ID NO:6362); miR-362 (SEQ ID NO:6363); miR-363-1 (SEQ ID NO:6364); miR-363-2 (SEQ ID NO:6365); miR-365-1 (SEQ ID NO:6366); miR-365-2 (SEQ ID NO:6367); miR-369 (SEQ ID NO:6368); miR-370 (SEQ ID NO:6369); miR-374a (SEQ ID NO:6370); miR-374b (SEQ ID NO:6371); miR-376a (SEQ ID NO:6372); miR-376b (SEQ ID NO:6373); miR-376c (SEQ ID NO:6374); miR-378-1 (SEQ ID NO:6375); miR-378-2 (SEQ ID NO:6376); miR-381 (SEQ ID NO:6377); miR-382 (SEQ ID NO:6378); miR-383 (SEQ ID NO:6379); miR-411 (SEQ ID NO:6380); miR-421 (SEQ ID NO:6381); miR-423 (SEQ ID NO:6382); miR-424 (SEQ ID NO:6383); miR-425 (SEQ ID NO:6384); miR-429 (SEQ ID NO:6385); miR-432 (SEQ ID NO:6386); miR-450a (SEQ ID NO:6387); miR-450b (SEQ ID NO:6388); miR-450c (SEQ ID NO:6389); miR-451 (SEQ ID NO:6390); miR-452 (SEQ ID NO:6391); miR-455 (SEQ ID NO:6392); miR-484 (SEQ ID NO:6393); miR-486-1 (SEQ ID NO:6394); miR-486-2 (SEQ ID NO:6395); miR-487b (SEQ ID NO:6396); miR-489 (SEQ ID NO:6397); miR-490-1 (SEQ ID NO:6398); miR-490-2 (SEQ ID NO:6399); miR-491 (SEQ ID NO:6400); miR-493 (SEQ ID NO:6401); miR-494 (SEQ ID NO:6402); miR-497 (SEQ ID NO:6403); miR-499 (SEQ ID NO:6404); miR-500 (SEQ ID NO:6405); miR-503 (SEQ ID NO:6406); miR-504 (SEQ ID NO:6407); miR-505 (SEQ ID NO:6408); miR-532 (SEQ ID NO:6409); miR-542 (SEQ ID NO:6410); miR-545 (SEQ ID NO:6411); miR-551a (SEQ ID NO:6412); miR-574 (SEQ ID NO:6413); miR-582 (SEQ ID NO:6414); miR-615 (SEQ ID NO:6415); miR-628 (SEQ ID NO:6416); miR-652 (SEQ ID NO:6417); miR-664 (SEQ ID NO:6418); miR-671 (SEQ ID NO:6419); miR-676-1 (SEQ ID NO:6420); miR-676-2 (SEQ ID NO:6421); miR-708 (SEQ ID NO:6422); miR-744 (SEQ ID NO:6423); miR-758 (SEQ ID NO:6424); miR-769 (SEQ ID NO:6425); miR-874 (SEQ ID NO:6426); miR-885 (SEQ ID NO:6427); miR-935 (SEQ ID NO:6428); miR-1224 (SEQ ID NO:6429); miR-1249-1 (SEQ ID NO:6430); miR-1249-2 (SEQ ID NO:6431); miR-1271 (SEQ ID NO:6432); miR-1277 (SEQ ID NO:6433); miR-1285 (SEQ ID NO:6434); miR-1296 (SEQ ID NO:6435); miR-1306 (SEQ ID NO:6436); miR-1307 (SEQ ID NO:6437); miR-1343 (SEQ ID NO:6438); miR-1468 (SEQ ID NO:6439); miR-1839 (SEQ ID NO:6440); miR-2320 (SEQ ID NO:6441); miR-2366-1 (SEQ ID NO:6442); miR-2366-2 (SEQ ID NO:6443); miR-2411 (SEQ ID NO:6444); miR-2483 (SEQ ID NO:6445); miR-3613 (SEQ ID NO:6446); miR-4331 (SEQ ID NO:6447); miR-4332 (SEQ ID NO:6448); miR-4334 (SEQ ID NO:6449); miR-4335 (SEQ ID NO:6450); miR-4337 (SEQ ID NO:6451); miR-4338 (SEQ ID NO:6452); miR-4339 (SEQ ID NO:6453); miR-7134 (SEQ ID NO:6454); miR-7135 (SEQ ID NO:6455); miR-7136 (SEQ ID NO:6456); miR-7137 (SEQ ID NO:6457); miR-7138 (SEQ ID NO:6458); miR-7139 (SEQ ID NO:6459); miR-7140 (SEQ ID NO:6460); miR-7141 (SEQ ID NO:6461); miR-7142 (SEQ ID NO:6462); miR-7143 (SEQ ID NO:6463); and miR-7144 (SEQ ID NO:6464).

The following rice miRNAs can be used: MIR156a (SEQ ID NO:6465); MIR156b (SEQ ID NO:6466); MIR156c (SEQ ID NO:6467); MIR156d (SEQ ID NO:6468); MIR156e (SEQ ID NO:6469); MIR156f (SEQ ID NO:6470); MIR156g (SEQ ID NO:6471); MIR156h (SEQ ID NO:6472); MIR156i (SEQ ID NO:6473); MIR156j (SEQ ID NO:6474); MIR156k (SEQ ID NO:6475); MIR156l (SEQ ID NO:6476); MIR159a (SEQ ID NO:6477); MIR159b (SEQ ID NO:6478); MIR159c (SEQ ID NO:6479); MIR159d (SEQ ID NO:6480); MIR159e (SEQ ID NO:6481); MIR159f (SEQ ID NO:6482); MIR160a (SEQ ID NO:6483); MIR160b (SEQ ID NO:6484); MIR160c (SEQ ID NO:6485); MIR160d (SEQ ID NO:6486); MIR160e (SEQ ID NO:6487); MIR160f (SEQ ID NO:6488); MIR162a (SEQ ID NO:6489); MIR162b (SEQ ID NO:6490); MIR164a (SEQ ID NO:6491); MIR164b (SEQ ID NO:6492); MIR164c (SEQ ID NO:6493); MIR164d (SEQ ID NO:6494); MIR164e (SEQ ID NO:6495); MIR164f (SEQ ID NO:6496); MIR166a (SEQ ID NO:6497); MIR166b (SEQ ID NO:6498); MIR166c (SEQ ID NO:6499); MIR166d (SEQ ID NO:6500); MIR166e (SEQ ID NO:6501); MIR166f (SEQ ID NO:6502); MIR166g (SEQ ID NO:6503); MIR166h (SEQ ID NO:6504); MIR166i (SEQ ID NO:6505); MIR166j (SEQ ID NO:6506); MIR166k (SEQ ID NO:6507); MIR166l (SEQ ID NO:6508); MIR166m (SEQ ID NO:6509); MIR167a (SEQ ID NO:6510); MIR167b (SEQ ID NO:6511); MIR167c (SEQ ID NO:6512); MIR167d (SEQ ID NO:6513); MIR167e (SEQ ID NO:6514); MIR167f (SEQ ID NO:6515); MIR167g (SEQ ID NO:6516); MIR167h (SEQ ID NO:6517); MIR167i (SEQ ID NO:6518); MIR167j (SEQ ID NO:6519); MIR168a (SEQ ID NO:6520); MIR168b (SEQ ID NO:6521); MIR169a (SEQ ID NO:6522); MIR169b (SEQ ID NO:6523); MIR169c (SEQ ID NO:6524); MIR169d (SEQ ID NO:6525); MIR169e (SEQ ID NO:6526); MIR169f (SEQ ID NO:6527); MIR169g (SEQ ID NO:6528); MIR169h (SEQ ID NO:6529); MIR169i (SEQ ID NO:6530); MIR169j (SEQ ID NO:6531); MIR169k (SEQ ID NO:6532); MIR169l (SEQ ID NO:6533); MIR169m (SEQ ID NO:6534); MIR169n (SEQ ID NO:6535); MIR169o (SEQ ID NO:6536); MIR169p (SEQ ID NO:6537); MIR169q (SEQ ID NO:6538); MIR169r (SEQ ID NO:6539); MIR171a (SEQ ID NO:6540); MIR171b (SEQ ID NO:6541); MIR171c (SEQ ID NO:6542); MIR171d (SEQ ID NO:6543); MIR171e (SEQ ID NO:6544); MIR171f (SEQ ID NO:6545); MIR171g (SEQ ID NO:6546); MIR171h (SEQ ID NO:6547); MIR171i (SEQ ID NO:6548); MIR172a (SEQ ID NO:6549); MIR172b (SEQ ID NO:6550); MIR172c (SEQ ID NO:6551); MIR172d (SEQ ID NO:6552); MIR319a (SEQ ID NO:6553); MIR319b (SEQ ID NO:6554); MIR390 (SEQ ID NO:6555); MIR393a (SEQ ID NO:6556); MIR393b (SEQ ID NO:6557); MIR394 (SEQ ID NO:6558); MIR395a (SEQ ID NO:6559); MIR395b (SEQ ID NO:6560); MIR395c (SEQ ID NO:6561); MIR395d (SEQ ID NO:6562); MIR395e (SEQ ID NO:6563); MIR395f (SEQ ID NO:6564); MIR395g (SEQ ID NO:6565); MIR395h (SEQ ID NO:6566); MIR395i (SEQ ID NO:6567); MIR395j (SEQ ID NO:6568); MIR395k (SEQ ID NO:6569); MIR395l (SEQ ID NO:6570); MIR395m (SEQ ID NO:6571); MIR395n (SEQ ID NO:6572); MIR395o (SEQ ID NO:6573); MIR395p (SEQ ID NO:6574); MIR395q (SEQ ID NO:6575); MIR395r (SEQ ID NO:6576); MIR395s (SEQ ID NO:6577); MIR395t (SEQ ID NO:6578); MIR395u (SEQ ID NO:6579); MIR395v (SEQ ID NO:6580); MIR395w (SEQ ID NO:6581); MIR395x (SEQ ID NO:6582); MIR395y (SEQ ID NO:6583); MIR396a (SEQ ID NO:6584); MIR396b (SEQ ID NO:6585); MIR396c (SEQ ID NO:6586); MIR396d (SEQ ID NO:6587); MIR396e (SEQ ID NO:6588); MIR396f (SEQ ID NO:6589); MIR396g (SEQ ID NO:6590); MIR396h (SEQ ID NO:6591); MIR397a (SEQ ID NO:6592); MIR397b (SEQ ID NO:6593); MIR398a (SEQ ID NO:6594); MIR398b (SEQ ID NO:6595); MIR399a (SEQ ID NO:6596); MIR399b (SEQ ID NO:6597); MIR399c (SEQ ID NO:6598); MIR399d (SEQ ID NO:6599); MIR399e (SEQ ID NO:6600); MIR399f (SEQ ID NO:6601); MIR399g (SEQ ID NO:6602); MIR399h (SEQ ID NO:6603); MIR399i (SEQ ID NO:6604); MIR399j (SEQ ID NO:6605); MIR399k (SEQ ID NO:6606); MIR408 (SEQ ID NO:6607); MIR413 (SEQ ID NO:6608); MIR414 (SEQ ID NO:6609); MIR415 (SEQ ID NO:6610); MIR416 (SEQ ID NO:6611); MIR417 (SEQ ID NO:6612); MIR418 (SEQ ID NO:6613); MIR419 (SEQ ID NO:6614); MIR426 (SEQ ID NO:6615); MIR435 (SEQ ID NO:6616); MIR437 (SEQ ID NO:6617); MIR438 (SEQ ID NO:6618); MIR439a (SEQ ID NO:6619); MIR439b (SEQ ID NO:6620); MIR439c (SEQ ID NO:6621); MIR439d (SEQ ID NO:6622); MIR439e (SEQ ID NO:6623); MIR439f (SEQ ID NO:6624); MIR439g (SEQ ID NO:6625); MIR439h (SEQ ID NO:6626); MIR439i (SEQ ID NO:6627); MIR440 (SEQ ID NO:6628); MIR443 (SEQ ID NO:6629); MIR444a (SEQ ID NO:6630); MIR444b (SEQ ID NO:6631); MIR444c (SEQ ID NO:6632); MIR444d (SEQ ID NO:6633); MIR444e (SEQ ID NO:6634); MIR444f (SEQ ID NO:6635); MIR528 (SEQ ID NO:6636); MIR529a (SEQ ID NO:6637); MIR529b (SEQ ID NO:6638); MIR530 (SEQ ID NO:6639); MIR531a (SEQ ID NO:6640); MIR531b (SEQ ID NO:6641); MIR531c (SEQ ID NO:6642); MIR535 (SEQ ID NO:6643); MIR810a (SEQ ID NO:6644); MIR810b (SEQ ID NO:6645); MIR812a (SEQ ID NO:6646); MIR812b (SEQ ID NO:6647); MIR812c (SEQ ID NO:6648); MIR812d (SEQ ID NO:6649); MIR812e (SEQ ID NO:6650); MIR812f (SEQ ID NO:6651); MIR812g (SEQ ID NO:6652); MIR812h (SEQ ID NO:6653); MIR812i (SEQ ID NO:6654); MIR812j (SEQ ID NO:6655); MIR812k (SEQ ID NO:6656); MIR812l (SEQ ID NO:6657); MIR812m (SEQ ID NO:6658); MIR812n (SEQ ID NO:6659); MIR812o (SEQ ID NO:6660); MIR812p (SEQ ID NO:6661); MIR812q (SEQ ID NO:6662); MIR812r (SEQ ID NO:6663); MIR812s (SEQ ID NO:6664); MIR812t (SEQ ID NO:6665); MIR812u (SEQ ID NO:6666); MIR812v (SEQ ID NO:6667); MIR814a (SEQ ID NO:6668); MIR814b (SEQ ID NO:6669); MIR814c (SEQ ID NO:6670); MIR815a (SEQ ID NO:6671); MIR815b (SEQ ID NO:6672); MIR815c (SEQ ID NO:6673); MIR816 (SEQ ID NO:6674); MIR817 (SEQ ID NO:6675); MIR818a (SEQ ID NO:6676); MIR818b (SEQ ID NO:6677); MIR818c (SEQ ID NO:6678); MIR818d (SEQ ID NO:6679); MIR818e (SEQ ID NO:6680); MIR818f (SEQ ID NO:6681); MIR820a (SEQ ID NO:6682); MIR820b (SEQ ID NO:6683); MIR820c (SEQ ID NO:6684); MIR821a (SEQ ID NO:6685); MIR821b (SEQ ID NO:6686); MIR821c (SEQ ID NO:6687); MIR827 (SEQ ID NO:6688); MIR1319a (SEQ ID NO:6689); MIR1319b (SEQ ID NO:6690); MIR1320 (SEQ ID NO:6691); MIR1423 (SEQ ID NO:6692); MIR1424 (SEQ ID NO:6693); MIR1425 (SEQ ID NO:6694); MIR1426 (SEQ ID NO:6695); MIR1427 (SEQ ID NO:6696); MIR1428a (SEQ ID NO:6697); MIR1428b (SEQ ID NO:6698); MIR1428c (SEQ ID NO:6699); MIR1428d (SEQ ID NO:6700); MIR1428e (SEQ ID NO:6701); MIR1428f (SEQ ID NO:6702); MIR1428g (SEQ ID NO:6703); MIR1429 (SEQ ID NO:6704); MIR1430 (SEQ ID NO:6705); MIR1431 (SEQ ID NO:6706); MIR1432 (SEQ ID NO:6707); MIR1435 (SEQ ID NO:6708); MIR1436 (SEQ ID NO:6709); MIR1437 (SEQ ID NO:6710); MIR1437b (SEQ ID NO:6711); MIR1438 (SEQ ID NO:6712); MIR1439 (SEQ ID NO:6713); MIR1440a (SEQ ID NO:6714); MIR1440b (SEQ ID NO:6715); MIR1441 (SEQ ID NO:6716); MIR1442 (SEQ ID NO:6717); MIR1846a (SEQ ID NO:6718); MIR1846b (SEQ ID NO:6719); MIR1846c (SEQ ID NO:6720); MIR1846d (SEQ ID NO:6721); MIR1846e (SEQ ID NO:6722); MIR1847 (SEQ ID NO:6723); MIR1848 (SEQ ID NO:6724); MIR1849 (SEQ ID NO:6725); MIR1850 (SEQ ID NO:6726); MIR1851 (SEQ ID NO:6727); MIR1852 (SEQ ID NO:6728); MIR1853 (SEQ ID NO:6729); MIR1854 (SEQ ID NO:6730); MIR1855 (SEQ ID NO:6731); MIR1856 (SEQ ID NO:6732); MIR1857 (SEQ ID NO:6733); MIR1858a (SEQ ID NO:6734); MIR1858b (SEQ ID NO:6735); MIR1859 (SEQ ID NO:6736); MIR1860 (SEQ ID NO:6737); MIR1861a (SEQ ID NO:6738); MIR1861b (SEQ ID NO:6739); MIR1861c (SEQ ID NO:6740); MIR1861d (SEQ ID NO:6741); MIR1861e (SEQ ID NO:6742); MIR1861f (SEQ ID NO:6743); MIR1861g (SEQ ID NO:6744); MIR1861h (SEQ ID NO:6745); MIR1861i (SEQ ID NO:6746); MIR1861j (SEQ ID NO:6747); MIR1861k (SEQ ID NO:6748); MIR1861l (SEQ ID NO:6749); MIR1861m (SEQ ID NO:6750); MIR1861n (SEQ ID NO:6751); MIR1861o (SEQ ID NO:6752); MIR1862a (SEQ ID NO:6753); MIR1862b (SEQ ID NO:6754); MIR1862c (SEQ ID NO:6755); MIR1862d (SEQ ID NO:6756); MIR1862e (SEQ ID NO:6757); MIR1862f (SEQ ID NO:6758); MIR1862g (SEQ ID NO:6759); MIR1863a (SEQ ID NO:6760); MIR1863b (SEQ ID NO:6761); MIR1863c (SEQ ID NO:6762); MIR1864 (SEQ ID NO:6763); MIR1865 (SEQ ID NO:6764); MIR1866 (SEQ ID NO:6765); MIR1868 (SEQ ID NO:6766); MIR1869 (SEQ ID NO:6767); MIR1870 (SEQ ID NO:6768); MIR1871 (SEQ ID NO:6769); MIR1872 (SEQ ID NO:6770); MIR1873 (SEQ ID NO:6771); MIR1874 (SEQ ID NO:6772); MIR1875 (SEQ ID NO:6773); MIR1876 (SEQ ID NO:6774); MIR1877 (SEQ ID NO:6775); MIR1878 (SEQ ID NO:6776); MIR1879 (SEQ ID NO:6777); MIR1880 (SEQ ID NO:6778); MIR1881 (SEQ ID NO:6779); MIR1882a (SEQ ID NO:6780); MIR1882b (SEQ ID NO:6781); MIR1882c (SEQ ID NO:6782); MIR1882d (SEQ ID NO:6783); MIR1882e (SEQ ID NO:6784); MIR1882f (SEQ ID NO:6785); MIR1882g (SEQ ID NO:6786); MIR1882h (SEQ ID NO:6787); MIR1883a (SEQ ID NO:6788); MIR1883b (SEQ ID NO:6789); MIR2055 (SEQ ID NO:6790); MIR2090 (SEQ ID NO:6791); MIR2091 (SEQ ID NO:6792); MIR2092 (SEQ ID NO:6793); MIR2093 (SEQ ID NO:6794); MIR2094 (SEQ ID NO:6795); MIR2095 (SEQ ID NO:6796); MIR2096 (SEQ ID NO:6797); MIR2097 (SEQ ID NO:6798); MIR2098 (SEQ ID NO:6799); MIR2099 (SEQ ID NO:6800); MIR2100 (SEQ ID NO:6801); MIR2101 (SEQ ID NO:6802); MIR2102 (SEQ ID NO:6803); MIR2103 (SEQ ID NO:6804); MIR2104 (SEQ ID NO:6805); MIR2105 (SEQ ID NO:6806); MIR2106 (SEQ ID NO:6807); MIR2118a (SEQ ID NO:6808); MIR2118b (SEQ ID NO:6809); MIR2118c (SEQ ID NO:6810); MIR2118d (SEQ ID NO:6811); MIR2118e (SEQ ID NO:6812); MIR2118f (SEQ ID NO:6813); MIR2118g (SEQ ID NO:6814); MIR2118h (SEQ ID NO:6815); MIR2118i (SEQ ID NO:6816); MIR2118j (SEQ ID NO:6817); MIR2118k (SEQ ID NO:6818); MIR2118l (SEQ ID NO:6819); MIR2118m (SEQ ID NO:6820); MIR2118n (SEQ ID NO:6821); MIR2118o (SEQ ID NO:6822); MIR2118p (SEQ ID NO:6823); MIR2118q (SEQ ID NO:6824); MIR2118r (SEQ ID NO:6825); MIR2120 (SEQ ID NO:6826); MIR2121a (SEQ ID NO:6827); MIR2121b (SEQ ID NO:6828); MIR2122 (SEQ ID NO:6829); MIR2275a (SEQ ID NO:6830); MIR2275b (SEQ ID NO:6831); MIR2275c (SEQ ID NO:6832); MIR2275d (SEQ ID NO:6833); MIR2863a (SEQ ID NO:6834); MIR2863b (SEQ ID NO:6835); MIR2863c (SEQ ID NO:6836); MIR2864 (SEQ ID NO:6837); MIR2865 (SEQ ID NO:6838); MIR2866 (SEQ ID NO:6839); MIR2867 (SEQ ID NO:6840); MIR2868 (SEQ ID NO:6841); MIR2869 (SEQ ID NO:6842); MIR2870 (SEQ ID NO:6843); MIR2871a (SEQ ID NO:6844); MIR2871b (SEQ ID NO:6845); MIR2872 (SEQ ID NO:6846); MIR2873a (SEQ ID NO:6847); MIR2873b (SEQ ID NO:6848); MIR2873c (SEQ ID NO:6849); MIR2874 (SEQ ID NO:6850); MIR2875 (SEQ ID NO:6851); MIR2876 (SEQ ID NO:6852); MIR2877 (SEQ ID NO:6853); MIR2878 (SEQ ID NO:6854); MIR2879 (SEQ ID NO:6855); MIR2880 (SEQ ID NO:6856); MIR2905 (SEQ ID NO:6857); MIR2907a (SEQ ID NO:6858); MIR2907b (SEQ ID NO:6859); MIR2907c (SEQ ID NO:6860); MIR2907d (SEQ ID NO:6861); MIR2918 (SEQ ID NO:6862); MIR2919 (SEQ ID NO:6863); MIR2920 (SEQ ID NO:6864); MIR2921 (SEQ ID NO:6865); MIR2922 (SEQ ID NO:6866); MIR2923 (SEQ ID NO:6867); MIR2924 (SEQ ID NO:6868); MIR2925 (SEQ ID NO:6869); MIR2926 (SEQ ID NO:6870); MIR2927 (SEQ ID NO:6871); MIR2928 (SEQ ID NO:6872); MIR2929 (SEQ ID NO:6873); MIR2930 (SEQ ID NO:6874); MIR2931 (SEQ ID NO:6875); MIR2932 (SEQ ID NO:6876); MIR3979 (SEQ ID NO:6877); MIR3980a (SEQ ID NO:6878); MIR3980b (SEQ ID NO:6879); MIR3981 (SEQ ID NO:6880); MIR3982 (SEQ ID NO:6881); MIR5071 (SEQ ID NO:6882); MIR5072 (SEQ ID NO:6883); MIR5073 (SEQ ID NO:6884); MIR5074 (SEQ ID NO:6885); MIR5075 (SEQ ID NO:6886); MIR5076 (SEQ ID NO:6887); MIR5077 (SEQ ID NO:6888); MIR5078 (SEQ ID NO:6889); MIR5079a (SEQ ID NO:6890); MIR5079b (SEQ ID NO:6891); MIR5080 (SEQ ID NO:6892); MIR5081 (SEQ ID NO:6893); MIR5082 (SEQ ID NO:6894); MIR5083 (SEQ ID NO:6895); MIR5143a (SEQ ID NO:6896); MIR5143b (SEQ ID NO:6897); MIR5144 (SEQ ID NO:6898); MIR5145 (SEQ ID NO:6899); MIR5146 (SEQ ID NO:6900); MIR5147 (SEQ ID NO:6901); MIR5148a (SEQ ID NO:6902); MIR5148b (SEQ ID NO:6903); MIR5148c (SEQ ID NO:6904); MIR5149 (SEQ ID NO:6905); MIR5150 (SEQ ID NO:6906); MIR5151 (SEQ ID NO:6907); MIR5152 (SEQ ID NO:6908); MIR5153 (SEQ ID NO:6909); MIR5154 (SEQ ID NO:6910); MIR5155 (SEQ ID NO:6911); MIR5156 (SEQ ID NO:6912); MIR5157a (SEQ ID NO:6913); MIR5157b (SEQ ID NO:6914); MIR5158 (SEQ ID NO:6915); MIR5159 (SEQ ID NO:6916); MIR5160 (SEQ ID NO:6917); MIR5161 (SEQ ID NO:6918); MIR5162 (SEQ ID NO:6919); MIR5179 (SEQ ID NO:6920); MIR5337a (SEQ ID NO:6921); MIR5337b (SEQ ID NO:6922); MIR5338 (SEQ ID NO:6923); MIR5339 (SEQ ID NO:6924); MIR5340 (SEQ ID NO:6925); MIR5484 (SEQ ID NO:6926); MIR5485 (SEQ ID NO:6927); MIR5486 (SEQ ID NO:6928); MIR5487 (SEQ ID NO:6929); MIR5488 (SEQ ID NO:6930); MIR5489 (SEQ ID NO:6931); MIR5490 (SEQ ID NO:6932); MIR5491 (SEQ ID NO:6933); MIR5492 (SEQ ID NO:6934); MIR5493 (SEQ ID NO:6935); MIR5494 (SEQ ID NO:6936); MIR5495 (SEQ ID NO:6937); MIR5496 (SEQ ID NO:6938); MIR5497 (SEQ ID NO:6939); MIR5498 (SEQ ID NO:6940); MIR5499 (SEQ ID NO:6941); MIR5500 (SEQ ID NO:6942); MIR5501 (SEQ ID NO:6943); MIR5502 (SEQ ID NO:6944); MIR5503 (SEQ ID NO:6945); MIR5504 (SEQ ID NO:6946); MIR5505 (SEQ ID NO:6947); MIR5506 (SEQ ID NO:6948); MIR5507 (SEQ ID NO:6949); MIR5508 (SEQ ID NO:6950); MIR5509 (SEQ ID NO:6951); MIR5510 (SEQ ID NO:6952); MIR5511 (SEQ ID NO:6953); MIR5512a (SEQ ID NO:6954); MIR5512b (SEQ ID NO:6955); MIR5513 (SEQ ID NO:6956); MIR5514 (SEQ ID NO:6957); MIR5515 (SEQ ID NO:6958); MIR5516a (SEQ ID NO:6959); MIR5516b (SEQ ID NO:6960); MIR5517 (SEQ ID NO:6961); MIR5518 (SEQ ID NO:6962); MIR5519 (SEQ ID NO:6963); MIR5521 (SEQ ID NO:6964); MIR5522 (SEQ ID NO:6965); MIR5523 (SEQ ID NO:6966); MIR5524 (SEQ ID NO:6967); MIR5525 (SEQ ID NO:6968); MIR5526 (SEQ ID NO:6969); MIR5527 (SEQ ID NO:6970); MIR5528 (SEQ ID NO:6971); MIR5529 (SEQ ID NO:6972); MIR5530 (SEQ ID NO:6973); MIR5531 (SEQ ID NO:6974); MIR5532 (SEQ ID NO:6975); MIR5533 (SEQ ID NO:6976); MIR5534a (SEQ ID NO:6977); MIR5534b (SEQ ID NO:6978); MIR5535 (SEQ ID NO:6979); MIR5536 (SEQ ID NO:6980); MIR5537 (SEQ ID NO:6981); MIR5538 (SEQ ID NO:6982); MIR5539a (SEQ ID NO:6983); MIR5539b (SEQ ID NO:6984); MIR5540 (SEQ ID NO:6985); MIR5541 (SEQ ID NO:6986); MIR5542 (SEQ ID NO:6987); MIR5543 (SEQ ID NO:6988); MIR5544 (SEQ ID NO:6989); MIR5788 (SEQ ID NO:6990); MIR5789 (SEQ ID NO:6991); MIR5790 (SEQ ID NO:6992); MIR5791 (SEQ ID NO:6993); MIR5792 (SEQ ID NO:6994); MIR5793 (SEQ ID NO:6995); MIR5794 (SEQ ID NO:6996); MIR5795 (SEQ ID NO:6997); MIR5796 (SEQ ID NO:6998); MIR5797 (SEQ ID NO:6999); MIR5798 (SEQ ID NO:7000); MIR5799 (SEQ ID NO:7001); MIR5800 (SEQ ID NO:7002); MIR5801 (SEQ ID NO:7003); MIR5802 (SEQ ID NO:7004); MIR5803 (SEQ ID NO:7005); MIR5804 (SEQ ID NO:7006); MIR5805 (SEQ ID NO:7007); MIR5806 (SEQ ID NO:7008); MIR5807 (SEQ ID NO:7009); MIR5808 (SEQ ID NO:7010); MIR5809 (SEQ ID NO:7011); MIR5810 (SEQ ID NO:7012); MIR5811 (SEQ ID NO:7013); MIR5812 (SEQ ID NO:7014); MIR5813 (SEQ ID NO:7015); MIR5814 (SEQ ID NO:7016); MIR5815 (SEQ ID NO:7017); MIR5816 (SEQ ID NO:7018); MIR5817 (SEQ ID NO:7019); MIR5818 (SEQ ID NO:7020); MIR5819 (SEQ ID NO:7021); MIR5820 (SEQ ID NO:7022); MIR5821 (SEQ ID NO:7023); MIR5822 (SEQ ID NO:7024); MIR5823 (SEQ ID NO:7025); MIR5824 (SEQ ID NO:7026); MIR5825 (SEQ ID NO:7027); MIR5826 (SEQ ID NO:7028); MIR5827 (SEQ ID NO:7029); MIR5828 (SEQ ID NO:7030); MIR5829 (SEQ ID NO:7031); MIR5830 (SEQ ID NO:7032); MIR5831 (SEQ ID NO:7033); MIR5832 (SEQ ID NO:7034); MIR5833 (SEQ ID NO:7035); MIR5834 (SEQ ID NO:7036); MIR5835 (SEQ ID NO:7037); MIR5836 (SEQ ID NO:7038); MIR5837 (SEQ ID NO:7039); MIR6245 (SEQ ID NO:7040); MIR6246 (SEQ ID NO:7041); MIR6247 (SEQ ID NO:7042); MIR6248 (SEQ ID NO:7043); MIR6249a (SEQ ID NO:7044); MIR6249b (SEQ ID NO:7045); MIR6250 (SEQ ID NO:7046); MIR6251 (SEQ ID NO:7047); MIR6252 (SEQ ID NO:7048); MIR6253 (SEQ ID NO:7049); MIR6254 (SEQ ID NO:7050); MIR6255 (SEQ ID NO:7051); MIR6256 (SEQ ID NO:7052); MIR7692 (SEQ ID NO:7053); MIR7693 (SEQ ID NO:7054); MIR7694 (SEQ ID NO:7055); and MIR7695 (SEQ ID NO:7056).

When used, any generic description of an miRNA refers to any of its gene family members, unless otherwise indicated. A "gene family" refers to a group of genes that have the same miRNA coding sequence. Typically, members of a gene family are identified by a number or letter following the initial designation. For example, miR-16-1 and miR-16-2 are members of the miR-16 gene family and "mir-7" refers to miR-7-1, miR-7-2 and miR-7-3. Likewise, "let-7," for example, refers to let-7a-1, let7-a-2, let-7b, let-7c, let-7d, let-7e, let-7f-1, and let-7f-2.

The artificially-designed RNA disclosed herein can include RNA flanking sequences. "RNA flanking sequences" refer to nucleotide sequences including RNA processing elements that flank one or both sides of the Drosha cutting site.

"miRNA flanking sequence" refers to nucleotide sequences including miRNA processing elements. miRNA processing elements are the minimal nucleic acid sequences which contribute to the production of mature miRNA from precursor miRNA. Often these elements are located within a 40 nucleotide sequence that flanks a miRNA stem-loop structure. In some instances the miRNA processing elements are found within a stretch of nucleotide sequences of between 5 and 4,000 nucleotides in length that flank a miRNA stem-loop structure.

Thus, in some embodiments the flanking sequences are 5-4,000 nucleotides in length. As a result, the length of the precursor molecule may be, in some instances at least about 150 nucleotides or 270 nucleotides in length. The total length of the precursor molecule, however, may be greater or less than these values. In other embodiments the minimal length of the miRNA flanking sequence is 10, 20, 30, 40, 50, 60, 70, 80, 90, 100, 150, 200 and any integer there between. In other embodiments the maximal length of the miRNA flanking sequence is 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900 4,000 and any integer there between.

The miRNA flanking sequences may be native/endogenous miRNA flanking sequences or artificial miRNA flanking sequences. A native/endogenous miRNA flanking sequence is a nucleotide sequence that is ordinarily associated in naturally existing systems with miRNA sequences, i.e., these sequences are found within the genomic sequences surrounding the minimal miRNA hairpin in vivo. Artificial miRNA flanking sequences are nucleotide sequences that are not found to be flanking to miRNA sequences in naturally existing systems. The artificial miRNA flanking sequences may be flanking sequences found naturally in the context of other miRNA sequences. Alternatively they may be composed of minimal miRNA processing elements which are found within naturally occurring flanking sequences and inserted into other random nucleic acid sequences that do not naturally occur as flanking sequences or only partially occur as natural flanking sequences.

The miRNA flanking sequences within the precursor miRNA molecule may flank one or both sides of the stem-loop structure encompassing the miRNA sequence. Thus, one end (i.e., 5') of the stem-loop structure may be adjacent to a single flanking sequence and the other end (i.e., 3') of the stem-loop structure may not be adjacent to a flanking sequence. Particular structures have flanking sequences on both ends of the stem-loop structure. The flanking sequences may be directly adjacent to one or both ends of the stem-loop structure or may be connected to the stem-loop structure through a linker, additional nucleotides or other molecules.

In some instances the pri-miRNA molecule may include more than one stem-loop structure. The multiple stem-loop structures may be linked to one another through a linker, such as, for example, a nucleic acid linker or by a miRNA flanking sequence or other molecule or some combination thereof.

In particular embodiments, useful interfering RNAs can be designed with a number of software programs, e.g., the OligoEngine RNA design tool available at www.oligoengine.com. RNAs within this context can be about, e.g., 19-33 basepairs in length for the double-stranded portion. In some embodiments, the RNAs are hairpin RNAs having an about 19-33 bp stem and an about 4-34 nucleotide loop. Particular RNAs are highly specific for a region of a target gene and may comprise 19-33 bp fragments of a target gene mRNA that has at least one, at least two, or at least three, by mismatches with a nontargeted gene-related sequence. In some embodiments, the RNAs do not bind to RNAs having more than 3 mismatches with the target region.

The artificial RNAs disclosed herein are formed from a polymer of nucleotides (i.e. molecules comprising a sugar (e.g. ribose) linked to a phosphate group and to an exchangeable organic base, which is either a substituted pyrimidine (e.g. cytosine (C), or uracil (U)) or a substituted purine (e.g. adenine (A) or guanine (G)). As used herein, the term nucleotides also can include polynucleosides (i.e. a polynucleotide minus the phosphate) and any other organic base containing polymer.

The artificial miRNAs can also encompass nucleotides with substitutions or modifications, such as in the bases and/or sugars. Modified bases include any base that is chemically distinct from the naturally occurring bases typically found in RNA (C, G, A, and U), but which share basic chemical structures with these naturally occurring bases. The modified nucleotide base may be, for example, dihydrouracil, pseudouracil, 2-thiouracil, 4-thiouracil, 5-aminouracil, 5-($C_1$-$C_6$)-alkyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 2,4-diamino-purine, 8-azapurine, a substituted 7-deazapurine, 7-deaza-7-substituted and/or 7-deaza-8-substituted purine, 5-hydroxymethylcytosine, N4-alkylcytosine, N4-ethylcytosine, 5-hydroxydeoxycytidine, 5-hydroxymethyldeoxycytidine, N4-alkyldeoxycytidine, N4-ethyldeoxycytidine, 6-thiodeoxyguanosine, deoxyribonucleosides of nitropyrrole, C5-propynylpyrimidine, diaminopurine, 2,6-diaminopurine, inosine, 5-methylcytosine, 2-aminopurine, 2-amino-6-chloropurine, hypoxanthine or other modifications of a natural nucleoside bases.

The artificial RNAs can also encompass various chemical modifications and substitutions, in comparison to natural RNA involving phosphodiester internucleotide bridges and/or β-D-ribose units. Replacing a phosphodiester bridge located at the 3' and/or the 5' end of a nucleotide can make artificial RNAs disclosed herein more resistant to degradation (i.e., are stabilized). Exemplary modified internucleotide bridges include phosphorothioate, phosphorodithioate, $NR^{1R2}$-phosphoramidate, boranophosphate, α-hydroxybenzyl phosphonate, phosphate-($C_1$-$C_{21}$)—O-alkyl ester, phosphate-[($C_6$-$C_{12}$)aryl-($C_1$-$C_{21}$)—O-alkyl]ester, ($C_1$-$C_8$)alkylphosphonate and/or ($C_6$-$C_{12}$)arylphosphonate bridges, ($C_7$-$C_{12}$)-α-hydroxymethyl-aryl, wherein ($C_6$-$C_{12}$)aryl, ($C_6$-$C_{20}$) aryl and ($C_6$-$C_{14}$)aryl are optionally substituted by halogen, alkyl, alkoxy, nitro, cyano, and where $R^1$ and $R^2$ are, independently of each other, hydrogen, ($C_1$-$C_{18}$)-alkyl, ($C_6$-$C_{20}$)-aryl, ($C_6$-$C_{14}$)-aryl-($C_1$-$C_8$)-alkyl, hydrogen, ($C_1$-$C_8$)-alkyl, ($C_1$-$C_4$)-alkyl and/or methoxyethyl, or $R^1$ and $R^2$ form, together with the nitrogen atom carrying them, a 5-6-membered heterocyclic ring which can additionally contain a further heteroatom from the group O, S and N. Dephospho bridges can also be used. Dephospho bridges are described, for example, in Uhlmann and Peyman in "Methods in Molecular Biology", Vol. 20, "Protocols for Oligonucleotides and Analogs", Agrawal, Ed., Humana Press, Totowa 1993, Chapter 16, pp. 355 ff). Exemplary dephospho bridges include formacetal, 3'-thioformacetal, methylhydroxylamine, oxime, methylenedimethyl-hydrazo, dimethylenesulfone and/or silyl groups.

Beta-ribose units can be replaced by modified sugar units such as 3-D-ribose, β-D-2'-deoxyribose, L-2'-deoxyribose, 2'-F-2'-deoxyribose, 2'-F-arabinose, 2'-O—($C_1$-$C_6$)alkyl-ribose, 2'-O—($C_1$-$C_6$)alkyl-ribose, 2'-O-methylribose, 2'-O—($C_2$-$C_6$)alkenyl-ribose, 2'-[O—($C_1$-$C_6$)alkyl-O—($C_1$-$C_6$) alkyl]-ribose, 2'-$NH_2$-2'-deoxyribose, β-D-xylo-furanose, α-arabinofuranose, 2,4-dideoxy-β-D-erythro-hexo-pyranose or carbocyclic and/or open-chain sugar analogs and/or bicyclosugar analogs.

Sugar phosphate units from the sugar phosphate backbone can also be replaced by other units such as "morpholino-derivative" oligomers (see, for example, Stirchak et al. (1989) Nucleic Acids Res 17:6129-41); polyamide nucleic acids (PNA; see, for example, Nielsen et al. (1994) Bioconjug Chem 5:3-7) such as by 2-aminoethylglycine; peptide nucleic acids with phosphate groups (PHONA); locked nucleic acids (LNA); and/or nucleotides having backbone sections with alkyl linkers or amino linkers. Alkyl linkers can be branched or unbranched, substituted or unsubstituted, and chirally pure or a racemic mixture.

Artificial RNAs disclosed herein can also be conjugated to lipophilic or lipid moieties. Exemplary lipophilic or lipid moieties include cholesteryls, modified cholesteryls, cholesterol derivatives, reduced cholesterols, substituted cholesterols, cholestans, $C_{1-6}$ alkyl chains, cholic acid, taurocholic acid, deoxycholate, oleyl litocholic acid, oleoyl cholenic acid, glycolipids, phospholipids, sphingolipids, isoprenoids, saturated fatty acids, unsaturated fatty acids or fatty acid esters. The lipophilic or lipid moieties can be attached via any suitable direct or indirect linkage such as, without limitation, by an ester or an amide. Linkages can include spacer moieties, for example one or more nucleotide residues, oligoethyleneglycol, triethyleneglycol, hexaethylenegylcol or an alkanediol, such as butanediol.

Artificial RNAs disclosed herein can also be conjugated to Nuclear Localization Signals (NLS). "Nuclear localization signals" are sequences (in some embodiments amino acid sequences) that can direct artificial RNAs in the cytoplasm of a cell across the nuclear membrane and into the nucleus of the cell. A nuclear localization signal can also target the exterior surface of a cell. Thus, a single nuclear localization signal can direct the artificial RNA with which it is associated to the exterior of a cell and to the nucleus of a cell. Nuclear localization signals are generally basic, comprise a short sequence of 4-8 amino acids and are typically rich in lysine and arginine residues while also often comprising proline residues.

While particular RNA sequences are described, the current disclosure also encompasses RNA sequences that hybridize with the specifically disclosed RNA sequences. An RNA sequence "hybridizes" to another RNA sequences when a single stranded form of the RNA sequence anneals to the other RNA sequence under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Ed., Cold Spring Harbor Laboratory Press, Cold Spring Harbor (1989), particularly Chapter 11 and Table 11.1 therein (incorporated by reference herein for its teachings regarding the same). The conditions of temperature and ionic strength determine the "stringency" of the hybridization. Stringency conditions can be adjusted to screen for moderately similar RNA sequences to highly similar RNA sequences. Post-hybridization washes determine stringency conditions. One set of hybridization conditions to demonstrate that RNA sequences hybridize uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Stringent conditions use higher temperatures in which the washes are identical to those above except for the temperature of the final two 30 min washes in 0.2× SSC, 0.5% SDS is increased to 60° C. Highly stringent conditions use two final washes in 0.1 SSC, 0.1% SDS at 65° C. Those of ordinary skill in the art will recognize that these temperature and wash solution salt concentrations may be adjusted as necessary according to factors such as the length of the tested RNA sequences.

RNA sequences that share a % identity with the RNA sequences explicitly disclosed herein are also within the scope of the present disclosure. The % identity is at least 90%, at least 91%, at least 92%, at least 93%, at least 94%, at least 95%, at least 96%, at least 97%, at least 98% or at least 99%. As is known in the art, "% identity" refers to a relationship between two or more RNA sequences, as determined by comparing the sequences. In the art, "identity" also means the degree of sequence relatedness between RNA sequences as determined by the match between strings of such sequences. "Identity" (often referred to as "similarity") can be readily calculated by known methods, including (but not limited to) those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992), each incorporated by reference herein for its teachings regarding the same. Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp (1989) CABIOS. 5:151-153, incorporated by reference herein for its teaching regarding the same) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410, 1990, incorporated by reference herein for its teaching regarding the same); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. incorporated by reference herein for its teaching regarding the same). Within the context of this disclosure, and where not otherwise specified, it will be understood that where sequence analysis software is used for analysis, the results of the analysis are based on the "default values" of the program referenced. As used herein "default values" will mean any set of values or parameters which originally load with the software when first initialized.

IV. Production of Artificial RNAs and/or Drosha Protein

General texts which describe molecular biological techniques to form nucleotide sequences and proteins include Sambrook, Molecular Cloning: a Laboratory Manual (2nd ed.) Vols. 1-3, Cold Spring Harbor Laboratory, (1989); Current Protocols in Molecular Biology Ausubel, ed. John Wiley & Sons, Inc., New York (1997); Laboratory Techniques in Biochemistry and Molecular Biology: Hybridization with Nucleic Acid Probes, Part 1. Theory and Nucleic Acid Preparation, P. Tijssen, ed. Elsevier, N.Y. (1993); Berger and Kimmel, Guide to Molecule Cloning Techniques Methods in Enzymology volume 152 Academic Press, Inc., San Diego, Calif. These texts describe the synthesis of nucleic acids and proteins as well as mutagenesis, the use of vectors, promoters and many other relevant topics related to generation and expression of genes encoding RNA, miRNA and protein. Techniques for isolation, purification and manipulation of nucleic acids, RNA, miRNA, genes, and proteins such as subcloning into expression vectors, labeling probes, and nucleotide hybridization are also described in the texts above and are well known to one of ordinary skill in the art.

The RNAs (including, without limitation, artificial RNAs, miRNAs and artificial miRNAs) and proteins disclosed herein can be formed by any technique known to one of ordinary skill in the art, including by chemical synthesis, enzymatic production or recombinant methods.

Chemical synthesis can be achieved by the diester method, the triester method, the phosphorylase method and/or by solid-phase chemistry. For example, chemical synthesis of RNAs can be performed using phosphotriester, phosphite or phosphoramidite chemistry and solid phase techniques such as described in EP 266,032 or via deoxynucleoside H-phosphonate intermediates as described in U.S. Pat. No. 5,705,629, each incorporated herein by reference for their teachings regarding the same.

A non-limiting example of enzymatic production includes amplification reactions such as polymerase chain reactions (PCR; see for example, U.S. Pat. Nos. 4,683,202 and 4,682,195, each incorporated by reference for their teachings regarding the same), or enzymatic synthesis as described in U.S. Pat. No. 5,645,897, incorporated by reference herein for its teachings regarding the same.

Recombinant RNAs and recombinant proteins include those produced from cells transformed by an exogenous DNA construct encoding the desired RNA or protein. Recombinant production methods are also well known in the art. For example, RNA molecules or proteins can be encoded by a nucleic acid molecule within a vector. The term "vector" refers to a carrier nucleic acid molecule into which a nucleic acid sequence can be inserted for introduction into a cell where it can be replicated. Vectors include plasmids, cosmids, viruses (bacteriophage, animal viruses, and plant viruses), and artificial chromosomes (e.g., YACs). One of ordinary skill in the art is well equipped to construct appropriate vectors through standard recombinant techniques. In addition to encoding RNA or proteins as disclosed herein, vectors can also encode sequences such as tags or targeting molecules. Targeting molecules can direct expressed RNA or protein to a particular location in a cell, to an organ, tissue, distant cell, or other location in a subject's body.

There are a number of ways in which vectors can be introduced into cells. Exemplary methods include microinjection, electroporation, lipid transfection, liposome mediated transfection, calcium phosphate transfection, calcium phosphate precipitation, DEAE-dextran followed by polyethylene glycol, sonic loading, microprojectile bombardment; or agitation with silicon carbide fibers. Recombinant methods can also be performed in cell free systems so long as the reagents for generating the RNA molecule are present. Additional methods for artificial RNA synthesis can be found in, without limitation, U.S. Pat. Nos. 4,659,774; 4,704,362; 4,816,571; 4,959,463; 5,141,813; 5,221,619; 5,264,566; 5,428,148; and 5,554,744; 5,574,146; 5,583,013; and 5,602,244 each of which is incorporated by reference herein for their teachings regarding the same.

V. Methods of Use

RNA, including miRNA, have been implicated in a wide variety of diseases and disorders. miRNA, artificial miRNA and Drosha up- and down-regulation disclosed herein can be used in therapeutic applications directed to, without limitation, acne, ADHD, adult-onset diabetes, age spots, age-related hearing loss, age-related macular degeneration, age-related vision change, AIDS, alcohol withdrawal, alcoholism, allergic rhinitis, allergies, alopecia, altitude sickness, Alzheimer's disease, amyotrophic lateral sclerosis (ALS), anemia, aneurism, angina, anxiety disorder, aplastic anemia, areata, arthritis, asthma, atherosclerosis, athlete's foot, atopic dermatitis, atrial fibrillation, autoimmune disease, Behcet's syndrome, Bell's palsy, bipolar disorder, bone disease, bradycardia, cardiovascular disease, cataracts, celiac disease, cerebral palsy, chloasma, congestive heart failure, conjunctivitis, cornea keratitis, Crohn's disease, cystic fibrosis, dandruff, dementia, depressive disorders, dermatitis, diabetes, diabetes mellitus, type 1, diabetes mellitus, type 2, dry-eye syndrome, dry skin, dysthymia, eclampsia, eczema, endocarditis, endometriosis, enlarged prostate, epilepsy, erectile dysfunction, essential tremor, fibroids, fibromyalgia, glaucoma, Graves disease, Guillain-Barre syndrome, hemophilia, high blood pressure, high cholesterol, Huntington's disease, hyperthyroidism, hypoparathyroidism, hypothyroidism, immune thrombocytopenic purpura, inflammatory bowel disease, insomnia, irritable bowel syndrome, juvenile arthritis, keloids, lactose intolerance, liver spots, locomotor dysfunction, lupus, major depression, manic depression, melasma, memory loss, multiple sclerosis, muscular dystrophy, myasthenia gravis, myocardial infarction, myocarditis, myopia, narcolepsy, obesity, obsessive-compulsive disorder, optic nerve swelling, osteoarthritis, osteoporosis, Paget's disease, Parkinson's disease, pain, panic disorder, peripheral vascular disease, pernicious anemia, phobia, pigmentation disorders, post-partum depression, post-traumatic stress disorder, preeclampsia, pregnancy-induced hypertension, presbyopia, psoriasis, psoriatic arthritis, renal failure, restless legs syndrome, Reye's syndrome, rheumatoid arthritis, rosacea, scars, schizophrenia, sciatica, scleroderma, seizures, sexual dysfunction, sickle cell anemia, skin blemishes, spider veins, sterility, stroke, sun-damaged skin, systemic lupus, Tay-Sachs disease, tendonitis, tennis elbow, tension headache, thrombocytopenia, tinnitus, ulcer, urinary incontinenece, varicose veins, vitiligo, and wrinkles.

miRNA, artificial miRNA and Drosha up- and down-regulation disclosed herein can be used in therapeutic applications directed to treatment of various cancers including, without limitation, bladder cancer, blood cancer, bone cancer, bone marrow cancer, brain cancer, breast cancer, colon cancer, esophageal cancer, gastrointestinal cancer, gum cancer, head cancer, kidney cancer, liver cancer, lung cancer, nasopharynx cancer, neck cancer, ovarian cancer, prostate cancer, skin cancer, stomach cancer, testicular cancer, tongue cancer, uterine cancer, neoplastic cancer, malignant cancer; carcinomas; sarcomas; lymphomas; Hodgkin's lymphomas; non-Hodgkin's lymphomas; and leukemias.

miRNA, artificial miRNA and Drosha up- and down-regulation disclosed herein can be used in therapeutic applications directed to infectious diseases, i.e., those arising from the presence of a foreign microorganism in the body. A microbial antigen, as used herein, is an antigen of a microorganism. Microorganisms include but are not limited to, infectious viruses, infectious bacteria, and infectious fungi.

Examples of infectious viruses include: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Examples of infectious bacteria include: *Helicobacter pyloris, Borelia burgdorferi, Legionella pneumophilia, Mycobacteria* (M.) sps (e.g. *M. tuberculosis, M. avium, M. intracellulare, M. kansaii, M. gordonae*), *Staphylococcus aureus, Neisseria* (N.) *gonorrhoeae, N. meningitidis, Listeria monocytogenes, Streptococcus* (S.) *pyogenes* (Group A S.), *S. agalactiae* (Group B S.), *S.* (*viridans* group), *S. faecalis, S. bovis, S. pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Treponema palladium, Treponema pertenue, Leptospira, Rickettsia*, and *Actinomyces israelli*.

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium* such as *Plasmodium* (P.) *falciparum, P. malariae, P. ovale*, and *P. vivax* and *Toxoplasma gondii*.

Other exemplary infections include athlete's foot, chickenpox, common cold, diarrheal diseases, flu, genital herpes, malaria, meningitis, pneumonia, sinusitis, various skin diseases, strep throat, tuberculosis, urinary tract infections, vaginal infections, viral hepatitis, and prion diseases.

miRNAs that up-regulate cell growth include miR-31, miR-150, miR-187, miR-125a, miR-190, miR-191, miR-193, miR-204, and miR-218. Accordingly, in conditions with less than optimal cell growth, such as degenerative diseases, including neural degeneration, multiple sclerosis, or macular degeneration, it would be beneficial to up-regulate these miRNAs. Of these miRNAs, for example, miR-31 and miR-150 are semi-rigid and miR-193 is mis-matched. When an up-regulation of cell growth is intended, mis-matches at positions 5 and/or 9-12 from the Drosha cutting site of these miRNAs can be removed to render them less susceptible to fluctuating Drosha expression levels. When a down-regulation of cell growth is intended, additional mis-matches can be introduced at positions 5 and/or 9-12 from the Drosha cutting site to render the miRNA more susceptible to fluctuating Drosha expression levels.

miRNAs that down-regulate cell growth include miR-21 and miR-24. Of these miRNAs, miR-21 is semi-rigid and miR-24 is rigid. Accordingly, in conditions with excessive cell growth, such as breast cancer, cervical cancer, colon cancer, liver cancer, lung cancer, prostate cancer, skin cancer, stomach cancer, and testicular cancer, it would be beneficial to up-regulate these miRNAs. When a down-regulation of cell growth is intended, mis-matches at positions 5 and/or 9-12 from the Drosha cutting site of these miRNAs can be removed to render them less susceptible to fluctuating Drosha expression levels. When an up-regulation of cell growth is intended, additional mis-matches can be introduced at positions 5 and/or 9-12 from the Drosha cutting site to render the miRNA more susceptible to fluctuating Drosha expression levels.

miRNAs such as miR-7, miR-19a, miR-23, miR-24, miR-27a, miR-31, miR-32, miR-134, miR-140, miR-150, miR-192, and miR-193 reduce cell viability. Of these miRNAs, for example, miR-7 and miR-23 are semi-rigid, and miR-19a is rigid. In conditions related to increased cell viability, such as cancerous tumors, hyperthyroidism, overactive adrenal gland, and hyperlipidemia, it would be beneficial to up-regulate these miRNAs in order to reduce cell viability. When a down-regulation of cell viability is intended, mis-matches at positions 5 and/or 9-12 from the Drosha cutting site of these miRNAs can be removed to render them less susceptible to fluctuating Drosha expression levels. When an up-regulation of cell viability is intended, additional mis-matches can be introduced at positions 5 and/or 9-12 from the Drosha cutting site to render the miRNA more susceptible to fluctuating Drosha expression levels.

miRNAs such as miR-107, miR-133, miR-137, miR-152, miR-155, miR-181a, miR-191, miR-203, and miR-215 increase cell viability. Of these miRNAs, for example, miR-155, miR-191, miR-203, and miR-215 are semi-rigid. Accordingly, in conditions with decreased cell viability, such as cirrhosis of the liver, HIV, and cell degeneration, it would be beneficial to up-regulate these miRNAs in order to increase cell viability. When an up-regulation of cell viability is intended, mis-matches at positions 5 and/or 9-12 from the Drosha cutting site of these miRNAs can be removed to render them less susceptible to fluctuating Drosha expression levels. When a down-regulation of cell viability is intended, additional mis-matches can be introduced at positions 5 and/or 9-12 from the Drosha cutting site to render the miRNA more susceptible to fluctuating Drosha expression levels.

An increase in the percentage of apoptotic cells is caused by miR-338, miR-27a, miR-128, miR-23a, miR-324, miR-22, miR-181a, mmu-miR-293, mmu-miR-412, miR-196, miR-31, Let-7d, miR-23b, mu-miR-290, miR-217, miR-199, miR-24, miR-214, and miR-198. Of these miRNAs, miR-23a and miR-338 are semi-rigid and miR-27a is quasi-rigid, for example. Accordingly, in conditions related to insufficient apoptosis, such as carcinomas, bone cancers, tumors, glioma, thyroid cancer, and throat cancer, it would be beneficial to up-regulate these miRNAs. When an up-regulation of apoptosis is intended, mis-matches at positions 5 and/or 9-12 from the Drosha cutting site of these miRNAs can be removed to render them less susceptible to fluctuating Drosha expression levels. When a down-regulation of apoptosis is intended, additional mis-matches can be introduced at positions 5 and/or 9-12 from the Drosha cutting site to render the miRNA more susceptible to fluctuating Drosha expression levels.

miRNAs that decrease the percentage of apoptotic cells include miR-105, miR-34a, miR-96, mmu-miR-292, miR-126, miR-137, and miR-101. Of these miRNAs, miR-96 and miR-126 are semi-rigid. Accordingly, in conditions related to excessive apoptosis, such as HIV, neurodegenerative diseases, hematologic diseases, and tissue damage, it would be beneficial to up-regulate these miRNAs. When a down-regulation of apoptosis is intended, mis-matches at positions 5 and/or 9-12 from the Drosha cutting site of these miRNAs can be removed to render them less susceptible to fluctuating Drosha expression levels. When an up-regulation of apoptosis is intended, additional mis-matches can be introduced at positions 5 and/or 9-12 from the Drosha cutting site to render the miRNA more susceptible to fluctuating Drosha expression levels.

miRNAs including miR-31 and miR-214 reduce cell proliferation. Of these miRNAs, miR-31 is semi-rigid, and miR-214 is mis-matched. When a down-regulation of cell proliferation is intended, mis-matches at positions 5 and/or 9-12 from the Drosha cutting site of these miRNAs can be removed to render them less susceptible to fluctuating Drosha expression levels. When an up-regulation of cell proliferation is intended, additional mis-matches can be introduced at positions 5 and/or 9-12 from the Drosha cutting site to render the miRNA more susceptible to fluctuating Drosha expression levels.

An increase in cell proliferation is caused by miRNAs such as miR-7, miR-1-2, miR-148, miR-195, miR-196, miR-199a, miR-204, miR-210, miR-211, miR-212, miR-215, miR-216, miR-218, miR-296, and miR-321. Of these miRNAs, miR-7, miR-148, and miR-195 are semi-rigid, for example. When an up-regulation of cell proliferation is intended, mis-matches at positions 5 and/or 9-12 from the Drosha cutting site of these miRNAs can be removed to render them less susceptible to fluctuating Drosha expression levels. When a down-regulation of cell proliferation is intended, additional mis-matches can be introduced at positions 5 and/or 9-12 from the Drosha cutting site to render the miRNA more susceptible to fluctuating Drosha expression levels.

miRNAs such as miR-100, miR-130a, miR-211, miR-212, miR-213, miR-215, miR-224, miR-292, miR-320, miR-324, miR-325, miR-330, miR-338, miR-369, miR-370, and miR-99a increase the proliferation of Prostate 22Rv1 cells. Of these miRNAs, miR-211 and miR-212 are quasi-rigid. When an up-regulation of cell proliferation is intended, mis-matches at positions 5 and/or 9-12 from the Drosha cutting site of these miRNAs can be removed to render them less susceptible to fluctuating Drosha expression levels. When a down-regulation of cell proliferation is intended, additional mis-matches can be introduced at positions 5 and/or 9-12 from the Drosha cutting site to render the miRNA more susceptible to fluctuating Drosha expression levels.

miRNAs such as miR-10b and miR-152 decrease proliferation of Prostate 22Rv1 cells. Of these miRNAs, miR-10b is rigid, and miR-152 is semi-rigid. When a down-regulation of cell proliferation is intended, mis-matches at positions 5 and/or 9-12 from the Drosha cutting site of these miRNAs can be removed to render them less susceptible to fluctuating Drosha expression levels. When an up-regulation of cell proliferation is intended, additional mis-matches can be introduced at positions 5 and/or 9-12 from the Drosha cutting site to render the miRNA more susceptible to fluctuating Drosha expression levels.

miRNAs including miR-210 and miR-216 increase the proliferation of skin TE354T cells. Of these miRNAs, miR-210 and miR-216 are quasi-rigid. When an up-regulation of cell proliferation is intended, mis-matches at positions 5 and/or 9-12 from the Drosha cutting site of these miRNAs can be removed to render them less susceptible to fluctuating Drosha expression levels. When a down-regulation of cell proliferation is intended, additional mis-matches can be introduced at positions 5 and/or 9-12 from the Drosha cutting site to render the miRNA more susceptible to fluctuating Drosha expression levels.

miRNAs including Let-7a, Let-7b, Let-7g, miR-10a, miR-10b, miR-133b, miR-155, miR-15a, miR-16, miR-181a, miR-182, miR-193, miR-194, miR-196, mi-204, miR-23a, miR-24, miR-25, miR-92, and miR-95 decrease proliferation of skin TE354T cells. Of these miRNAs, let-7a is semi-rigid, and miR-181a is quasi-rigid. When a down-regulation of cell proliferation is intended, mis-matches at positions 5 and/or 9-12 from the Drosha cutting site of these miRNAs can be removed to render them less susceptible to fluctuating Drosha expression levels. When an up-regulation of cell proliferation is intended, additional mis-matches can be introduced at positions 5 and/or 9-12 from the Drosha cutting site to render the miRNA more susceptible to fluctuating Drosha expression levels.

miRNAs including miR-216, miR-217, and miR-294 increase the proliferation of breast MCF12a cells. Of these miRNAs, miR-216 is quasi-rigid, and miR-217 is semi-rigid. When an up-regulation of cell proliferation is intended, mis-matches at positions 5 and/or 9-12 from the Drosha cutting site of these miRNAs can be removed to render them less susceptible to fluctuating Drosha expression levels. When a down-regulation of cell proliferation is intended, additional mis-matches can be introduced at positions 5 and/or 9-12 from the Drosha cutting site to render the miRNA more susceptible to fluctuating Drosha expression levels.

miRNAs including Let-7a, Let-7b-1, Let-7c, Let-7d, miR-10a, miR-10b, miR-133a, miR-152, miR-153, miR-155, miR-16, miR-181a, miR-183, miR-184, miR-186, miR-191, miR-200b, miR-412, and miR-9 decrease proliferation of breast MCF12a cells. Of these miRNAs, let-7c is quasi-rigid, miR-152 is semi-rigid, and miR-10a is rigid. When a down-regulation of cell proliferation is intended, mis-matches at positions 5 and/or 9-12 from the Drosha cutting site of these miRNAs can be removed to render them less susceptible to fluctuating Drosha expression levels. When an up-regulation of cell proliferation is intended, additional mis-matches can be introduced at positions 5 and/or 9-12 from the Drosha cutting site to render the miRNA more susceptible to fluctuating Drosha expression levels.

miRNAs including miR-129, miR-326, miR-331, miR-338, miR-341, miR-370, and miR-92 increase the proliferation of lung A549 cells. Of these miRNAs, mir-129 is semi-rigid, and miR-370 is quasi-rigid. When an up-regulation of cell proliferation is intended, mis-matches at positions 5 and/or 9-12 from the Drosha cutting site of these miRNAs can be removed to render them less susceptible to fluctuating Drosha expression levels. When a down-regulation of cell proliferation is intended, additional mis-matches can be introduced at positions 5 and/or 9-12 from the Drosha cutting site to render the miRNA more susceptible to fluctuating Drosha expression levels.

miRNAs such as Let-7a-1, miR-133a-2, miR-142, miR-187, miR-199a-1, miR-206, miR-211, miR-222, miR-223, miR-23b, miR-298, miR-328, miR-342, and miR-371 decrease proliferation of lung A549 cells. Of these miRNAs, miR-187 is semi-rigid, and miR-211 is quasi-rigid. When a down-regulation of cell proliferation is intended, mis-matches at positions 5 and/or 9-12 from the Drosha cutting site of these miRNAs can be removed to render them less susceptible to fluctuating Drosha expression levels. When an up-regulation of cell proliferation is intended, additional mis-matches can be introduced at positions 5 and/or 9-12 from the Drosha cutting site to render the miRNA more susceptible to fluctuating Drosha expression levels.

Lupus-related miRNAs include miR-301, miR-199, miR-95, miR-105, mu-miR-290, miR-215, miR-188, miR-186, miR-211, miR-331, miR-137, miR-21, miR-223, and miR-342. miRNAs that may be related to prion diseases include miR-95, miR-135a, miR-7, miR-9, miR-27a, miR-130a, miR-16, miR-26a, and miR-24. miRNAs that are potentially associated with stroke include Let-7F-2, miR-16, miR-138, miR-139, miR30A, miR-31, miR-140, miR-298, miR-28, and miR-291-5P.

An additional aspect of the current disclosure is the design of drugs for use in the central nervous system (anti-depressants; anti-anxiety; anti-Alzheimer's; anti-Parkinson's; etc.) that have low activity in the liver. These drugs would be RNA-based with mis-matches introduced at one or more of positions 5 and/or 9-12 from the Drosha cutting site. In particular embodiments, 1, 2, 3, 4, or 5 mis-matches are introduced at positions 5 and/or 9-12 from the Drosha cutting site. In particular embodiments, 3, 4, or 5 mis-matches are introduced at positions 5 and/or 9-12 from the Drosha cutting site.

Orally-administered RNA-based therapeutics are processed through the liver before reaching other sites of action. Introduction of mis-matches at positions 5 and/or 9-12 from the Drosha cutting site can minimize the RNA's effect in the liver while maintaining an effect in other targets of interest with higher Drosha expression. Accordingly, these drugs would be RNA-based with mis-matches introduced at one or more of positions 5 and/or 9-12 from the Drosha cutting site. In particular embodiments, 1, 2, 3, 4, or 5 mis-matches are introduced at positions 5 and/or 9-12 from the Drosha cutting site. In particular embodiments, 3, 4, or 5 mis-matches are introduced at positions 5 and/or 9-12 from the Drosha cutting site.

Alternatively, RNA-based drugs that target the liver could have mis-matches removed to increase potency in the liver. Such RNA-based drugs could be used as therapies for, without limitation, obesity, alcohol metabolism, altering drug processing and/or glycogen storage. In particular embodiments, these drugs would be RNA-based with mis-matches removed at one or more of positions 5 and/or 9-12 from the Drosha cutting site. In particular embodiments, 1, 2, 3, 4, or 5 mis-matches are removed at positions 5 and/or 9-12 from the Drosha cutting site. In particular embodiments, 1, 2 or 3 mis-matches are removed at positions 5 and/or 9-12 from the Drosha cutting site.

For applications where a local effect of an RNA therapy is desired, the secondary structure can be altered to minimize the effect on surrounding tissues relative to the target tissue. For example the intestine has high Drosha expression levels compared to the liver and pancreas, so a mismatched, highly mis-matched or fully mis-matched RNA administered to the intestine would show relatively high levels in the intestine, whereas any RNA that is diffused or transported to the liver and/or pancreas would have a minimal effect in the those organs, thus reducing the risk of side effects. Applications include obesity medications that inhibit uptake of nutrients by the intestine, as well as other gastric conditions, intestinal parasites, cancer, irritable bowel syndrome, lactose intolerance, etc. These drugs would be RNA-based with mis-matches introduced at one or more of positions 5 and/or 9-12 from the Drosha cutting site. In particular embodiments, 1, 2, 3, 4, or 5 mis-matches are introduced at positions 5 and/or 9-12 from the Drosha cutting site. In particular embodiments, 3, 4, or 5 mis-matches are introduced at positions 5 and/or 9-12 from the Drosha cutting site.

As another example, the ovaries have relatively high drosha expression levels compared to the uterus. For RNA therapeutics specifically targeting the ovaries (such as potential fertility treatments) RNA can be designed with mis-matches incorporated to minimize the effect on the uterus as well as surrounding tissues, while still having an effect on the targeted ovaries. These drugs would be RNA-based with mis-matches introduced at one or more of positions 5 and/or 9-12 from the Drosha cutting site. In particular embodiments, 1, 2, 3, 4, or 5 mis-matches are introduced at positions 5 and/or 9-12 from the Drosha cutting site. In particular embodiments, 3, 4, or 5 mis-matches are introduced at positions 5 and/or 9-12 from the Drosha cutting site.

As another example, Drosha levels vary throughout T-cell development, where young T-cells have high Drosha expression levels, which decrease as the T-cells mature. RNA therapeutics can be designed with or without mismatches in the positions 5 and/or 9-12 nucleotides from the Drosha cutting site to target mature or young T-cells respectively. This could be of importance in any therapeutic involving the immune response, such as AIDS, allergies, cancer, parasites, viral and bacterial infections, autoimmune diseases, etc. (e.g., the majority of all diseases). Embodiments targeting young T-cells would have mis-matches introduced at one or more of positions 5 and/or 9-12 from the Drosha cutting site. In particular embodiments, 1, 2, 3, 4, or 5 mis-matches are introduced at positions 5 and/or 9-12 from the Drosha cutting site. In particular embodiments, 3, 4, or 5 mis-matches are introduced at positions 5 and/or 9-12 from the Drosha cutting site. In embodiments targeting mature T-cells, mis-matches would be removed at one or more of positions 5 and/or 9-12 from the Drosha cutting site. In particular embodiments, 1, 2, 3, 4, or 5 mis-matches are removed at positions 5 and/or 9-12 from the Drosha cutting site. In particular embodiments, 3, 4, or 5 mis-matches are removed at positions 5 and/or 9-12 from the Drosha cutting site.

In further examples, Drosha levels vary during many types of cellular differentiation (such as neuronal differentiation), with a maximum expression 6-12 days after differentiation begins. miRNAs for over expression can be designed (i) without mismatches in the 5, and 9-12 positions to maintain constant levels throughout the differentiation process, or (ii) alternatively with mismatches to maximize the effect specifically for the 6-12 day time point. In these embodiments, mis-matches would be removed at one or more of positions 5 and/or 9-12 from the Drosha cutting site to maintain constant levels. In particular embodiments, 1, 2, 3, 4, or 5 mis-matches are removed at positions 5 and/or 9-12 from the Drosha cutting site. In particular embodiments, 3, 4, or 5 mis-matches are removed at positions 5 and/or 9-12 from the Drosha cutting site. In further embodiments, mis-matches would be introduced at one or more of positions 5 and/or 9-12 from the Drosha cutting site to target the 6-12 day period. In these particular embodiments, 1, 2, 3, 4, or 5 mis-matches are introduced at positions 5 and/or 9-12 from the Drosha cutting site. In particular embodiments, 3, 4, or 5 mis-matches are introduced at positions 5 and/or 9-12 from the Drosha cutting site.

The current disclosure also applies to the tissue culture environment. In the tissue culture environment several cell types are grown simultaneously in the same environment, e.g. embryonic stem cells are commonly grown on a layer of irradiated mouse embryonic fibroblasts. Depending on the stage the embryonic cells are in, RNA that are overexpressed can be tailored to minimize the effect on other cell types that are present.

As noted, many cancer cells have high Drosha expression levels. Accordingly, miRNA therapeutics can be designed that are maximally effective in the cancerous cells while having fewer effects in healthy cells. In these embodiments, the miRNA would have mis-matches introduced at one or more of positions 5 and/or 9-12 from the Drosha cutting site to target the cancer cells. In these particular embodiments, 1, 2, 3, 4, or 5 mis-matches are introduced at positions 5 and/or 9-12 from the Drosha cutting site. In particular embodiments, 3, 4, or 5 mis-matches are introduced at positions 5 and/or 9-12 from the Drosha cutting site.

In therapeutic applications, an effective amount of miRNA, artificial miRNA, Drosha protein or Drosha inhibitor can be administered to a subject in the form of an administered therapeutic and/or as part of a genetic therapy. An "effective amount" is the amount of miRNA, artificial miRNA, Drosha protein or Drosha inhibitor necessary to result in a desired physiological change in the subject. The term "therapeutically effective amount" is the amount of miRNA, artificial miRNA, Drosha protein or Drosha inhibitor necessary to achieve a desired effect with respect to a disease or condition. The therapeutically effective amount can, but need not, cure the disease or condition. For example, the therapeutically effective amount can provide a partial benefit, such as alleviation or improvement of at least one symptom of the disease or condition.

In the context of cancers, therapeutically effective amounts can inhibit tumor growth, inhibit cancer cell proliferation, prevent metastasis, reduce the number of metastases, induce cancer cell death, induce apoptosis of cancer cells, inhibit angiogenesis near cancer cells, reduce cancer-associated pain, reduce relapse or re-occurrence, induce chemo- or radiosensitivity in cancer cells and/or prolong a subject's life.

For administration, effective amounts and therapeutically effective amounts (referred to herein as doses) can be initially be estimated based on results from in vitro assays and/or animal model studies. For example, a dose can be formulated in animal models to achieve a circulating concentration range that includes the $IC_{50}$ as determined in cell culture. Such information can be used to more accurately determine useful doses in humans, veterinary animals (for example, dogs, cats and horses), livestock (for example, cattle, buffalo, sheep, pigs, goats, chickens), research animals (for example, monkeys, rats, mice, fish, flies and worms), other domesticated animals (for example, animals in zoos, circuses and aquariums including elephants, tigers, lions, sharks, rays and dolphins) and plants (all subjects herein).

The actual dosage amount administered to a particular subject can be determined by a physician, veterinarian or researcher taking into account parameters such as physical and physiological factors including body weight, severity of condition, type of disease, previous or concurrent therapeutic interventions, idiopathy of the subject and route of administration.

Useful doses often range from 0.1 to 5 mg/kg/day or from 0.5 to 1 mg/kg/day or from 0.1 to 5 µg/kg/day or from 0.5 to 1 µg/kg/day. In other non-limiting examples, a dose can comprise from 1 µg/kg/day, 5 µg/kg/day, 10 µg/kg/day, 50 µg/kg/day, 100 µg/kg/day, 200 µg/kg/day, 350 µg/kg/day, 500 µg/kg/day, 1 mg/kg/day, 5 mg/kg/day, 10 mg/kg/day, 50 mg/kg/day, 100 mg/kg/day, 200 mg/kg/day, 350 mg/kg/day, 500 mg/kg/day or 1000 mg/kg/day. Effective amounts and therapeutically effective amounts can be achieved by administering single or multiple doses during the course of a treatment regimen (days, weeks, months, etc.).

In certain embodiments, miRNA, artificial miRNA, Drosha protein, Drosha inducer or Drosha inhibitor are provided as part of pharmaceutical compositions. The pharmaceutical compositions can comprise, for example, at least 0.1% miRNA, artificial miRNA, Drosha protein or Drosha inhibitor. In other embodiments, the pharmaceutical composition can comprise between 2% to 75% of the weight of the unit, or between 25% to 60% of the weight of the unit miRNA, artificial miRNA, Drosha protein or Drosha inhibitor.

Pharmaceutical compositions can be formulated in any conventional manner using one or more physiologically acceptable carriers, diluents, excipients or auxiliaries which facilitate processing of miRNA, artificial miRNA, Drosha protein, Drosha inhibitor miRNA vectors, artificial miRNA vectors, Drosha protein vectors or Drosha inhibitor vectors (in the context of formulations, all hereafter collectively referred to as "the therapeutics") into preparations which can be used pharmaceutically. Proper formulation is dependent upon the route of administration chosen.

The therapeutics can be included within formulations for administration as free bases, neutral or as pharmaceutically acceptable salts. Pharmaceutically acceptable salts are those that substantially retain the biologic activity of free bases. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in solvents than the corresponding free base forms.

The therapeutics can also be attached or conjugated to other chemical entities to increase cellular uptake. Exemplary chemical entities include acridine derivatives, 2-methoxy-6-chloro-9-aminoacridine, cross-linkers, psoralen derivatives, azidophenacyl, proflavin, azidoproflavin, metal complexes, EDTA-Fe(II), o-phenanthroline-Cu(I), porphyrin-Fe(II), alkylating moieties, endonucleases, artificial endonucleases, amino-1-hexanolstaphylococcal nuclease, alkaline phosphatase, terminal transferases, abzymes, cholesteryl moieties, lipophilic carriers, lipofectin, DOTMA, DOPE, DOTAP, peptide conjugates, long chain alcohols, phosphate esters, amino acids, mercapto groups, polylysine or other polyamines.

The therapeutics may particularly be administered in combination with a cationic amine such as poly (L-lysine) and/or may be conjugated to a chemical moiety, such as transferrin and/or cholesteryls. In particular embodiments, linking the therapeutics to a suitable array of mannose residues targets them to the liver.

In particular embodiments, the therapeutics can be introduced into cells by microinjection, electroporation, lipid transfection, liposome mediated transfection, calcium phosphate transfection, calcium phosphate precipitation, DEAE-dextran followed by polyethylene glycol, sonic loading, microprojectile bombardment, or agitation with silicon carbide fibers.

Certain aspects of the disclosure include contacting and introducing into a target cell a vector capable of expressing a pri-miRNA to regulate the expression of a target gene in the cell. The vector produces the pri-miRNA transcript, which is then processed into precursor microRNA in the cell, which is then processed to produce the mature functional miRNA which is capable of altering accumulation of a target protein in the target cell. Accumulation of the protein may be effected in a number of different ways. For instance the miRNA may directly or indirectly affect translation or may result in cleavage of the mRNA transcript or even effect stability of the protein being translated from the target mRNA. MiRNA may function through a number of different mechanisms. The methods and products of the disclosure are not limited to any one mechanism. The method may be performed in vitro, e.g., for studying gene function, ex vivo or in vivo, e.g. for therapeutic purposes.

The therapeutics can also be provided as pro-drugs. The term "prodrug" refers to a therapeutic that can undergo biotransformation (e.g., either spontaneous or enzymatic) within the subject to release, or to convert (e.g., enzymatically, mechanically, electromagnetically, etc.) an active or more active form of the therapeutic after administration. Prodrugs can be used to overcome issues associated with stability, toxicity, lack of specificity, or limited bioavailability and often offer advantages related to solubility, tissue compatibility, and/or delayed release (See e.g., Bundgard, Design of Prodrugs, pp. 7-9, 21-24, Elsevier, Amsterdam (1985); and Silverman, The Organic Chemistry of Drug Design and Drag Action, pp. 352-401, Academic Press, San Diego, Calif. (1992) both incorporated by reference for their teachings regarding the same).

For example, a subject can be provided an miRNA or artificial miRNA molecule corresponding to a particular miRNA by administering a nucleic acid molecule that functions as the corresponding miRNA once inside the cell. In these embodiments, the nucleic acid molecule is processed into the intended miRNA or artificial miRNA once it has access to the cell's miRNA processing machinery. In particular embodiments, the processing is post-translational modifications, such as, without limitation, adenosine to inosine editing.

Exemplary protein prodrugs can comprise an active protein and a chemical masking group (e.g., a group that reversibly suppresses the activity of the protein). Some preferred prodrugs are variations or derivatives of proteins that have sequences that are cleavable under metabolic conditions. Exemplary prodrugs become active or more active in vivo or in vitro when they undergo a biochemical transformation (e.g., phosphorylation, hydrogenation, dehydrogenation, glycosylation, etc.).

When the therapeutics are provided as part of a genetic therapy, "in vivo expression elements" are any regulatory nucleotide sequence, such as a promoter sequences or promoter-enhancer combinations, which facilitate the efficient expression of the therapeutic following administration to a subject. The in vivo expression element may, for example, be a mammalian or viral promoter, such as a constitutive or inducible promoter or a tissue specific promoter, examples of which are well known to one of ordinary skill in the art. Constitutive mammalian promoters include polymerase promoters as well as the promoters for the following genes: hypoxanthine phosphoribosyl transferase (HPTR), adenosine deaminase, pyruvate kinase, and beta-actin. Exemplary viral promoters which function constitutively in eukaryotic cells include promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. Inducible promoters are expressed in the presence of an inducing agent and include metal-inducible promoters and steroid-regulated promoters. For example, the metallothionein promoters is induced to promote transcription in the presence of certain metal ion. Other inducible promoters are known to those of ordinary skill in the art.

Examples of tissue-specific promoters include: for muscle and cardiac tissue, creatine kinase and alpha-actin promoter; for B cells, immunoglobulin heavy or light chain promoters; for liver, HMG-COA reductase promoter, sterol regulatory element 1, phosphoenol pyruvate carboxy kinase (PEPCK) promoter, human C-reactive protein (CRP) promoter, human glucokinase promoter, cholesterol 7-alpha hydroylase (CYP- 7) promoter, beta-galactosidase alpha-2,6 sialyltransferase promoter, insulin-like growth factor binding protein (IGFBP-1) promoter, aldolase B promoter, human transferrin promoter, and collagen type I promoter; for prostate, prostatic acid phosphatase (PAP) promoter, prostatic secretory protein of 94 (PSP 94) promoter, prostate specific antigen complex promoter, and human glandular kallikrein gene promoter (hgt-1); for gastric tissue, human H+/K+-ATPase alpha subunit promoter; for pancreas, pancreatitis associated protein promoter (PAP), elastase 1 transcriptional enhancer, pancreas specific amylase, elastase enhancer promoter, and pancreatic cholesterol esterase gene promoter; for endometrium, uteroglobin promoter; for adrenal cells, cholesterol side-chain cleavage (SCC) promoter; for nervous system, gamma-gamma enolase (neuron-specific enolase, NSE) promoter; for brain, neurofilament heavy chain (NF-H) promoter; for lymphocytes, human CGL-1/granzyme B promoter, terminal deoxy transferase (TdT), lambda 5, VpreB, Ick (lymphocyte specific tyrosine protein kinase p561ck) promoter, the human CD2 promoter and its 3' transcriptional enhancer, and the human NK and T cell specific activation (NKG5) promoter; for colon, pp60c-src tyrosine kinase promoter, organ-specific neoantigens (OSNs) promoter, and colon specific antigen-P promoter; for breast cells, human alpha-lactalbumin promoter; and for lung, cystic fibrosis transmembrane conductance regulator (CFTR) gene promoter. Other elements aiding specificity of expression in a tissue of interest can include secretion leader sequences, enhancers, nuclear localization signals, endosmolytic peptides, etc. In particular embodiments, these elements are derived from the tissue of interest to aid specificity.

VI. Formulations & Routes of Administration

Pharmaceutical compositions disclosed herein generally include pharmaceutically acceptable carriers which refer to compositions that do not produce significantly adverse, allergic or other untoward reactions that outweigh the therapeutic benefit of administration. Exemplary pharmaceutically acceptable carriers and formulations are disclosed in Remington's Pharmaceutical Sciences, 18th Ed. Mack Printing Company, 1990, which is incorporated by reference herein for its teachings regarding the same. Moreover, for human administration, all formulations will meet sterility, pyrogenicity, general safety and purity standards as required by U.S. FDA Office of Biological Standards and/or other relevant foreign regulatory agencies.

Generally used pharmaceutically acceptable carriers include any and all solvents, dispersion media, coatings, surfactants, antioxidants, preservatives (e.g., antioxidants, antibacterial agents, antifungal agents including parabens (e.g., methylparabens, propylparabens), chlorobutanol, phenol, sorbic acid, thimerosal or combinations thereof), isotonic agents, absorption delaying agents, salts, preservatives, stabilizers, gels, binders, disintegration agents, and lubricants. Except insofar as any conventional pharmaceutically acceptable carrier is incompatible with the particular therapeutic disclosed herein, its use in the pharmaceutical compositions is encompassed.

Formulations can be generated based on the chosen route of administration. Formulations can be administered by injection, inhalation, infusion, perfusion, lavage or ingestion. Routes of administration can include intravenous, intradermal, intraarterial, intraperitoneal, intralesional, intracranial, intraarticular, intraprostatic, intrapleural, intratracheal, intranasal, intravitreal, intravaginal, intrarectal, topically, intratumoral, intramuscular, intravesicular, intrapericardial, intraumbilical, intraocularal, subcutaneous, subconjunctival and/or mucosal.

For injection, formulations can be made as aqueous solutions, such as in buffers such as Hanks' solution, Ringer's solution, or physiological saline. The solutions can contain formulatory agents such as suspending, stabilizing and/or dispersing agents. Alternatively, the formulation can be in lyophilized and/or powder form for constitution with a suitable vehicle, e.g., sterile pyrogen-free water, before use.

For topical administration formulations can be made as solutions, gels, ointments, creams, suspensions, etc. as are well-known in the art.

For nasal administration, formulations can be made as aqueous solutions designed to be administered to the nasal passages in drops or sprays. Nasal solutions are prepared so that they are similar in many respects to nasal secretions, so that normal ciliary action is maintained. Thus, in preferred embodiments aqueous nasal solutions usually are isotonic or slightly buffered to maintain a pH of 5.5 to 6.5.

For transmucosal administration, formulations can be made with penetrants appropriate to the barrier to be permeated. Such penetrants are generally known in the art.

For oral administration, the formulations can be made as tablets, pills, dragees, capsules, liquids, gels, syrups, slurries, suspensions and the like. For oral solid formulations such as, for example, powders, capsules and tablets, suitable excipients include binders (gum tragacanth, acacia, cornstarch, gelatin), fillers such as sugars, e.g. lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

For administration by inhalation, formulations can be made as aerosol sprays from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the therapeutic and a suitable powder base such as lactose or starch.

Therapeutics can also be formulated as depot preparations. Such long acting formulations may be administered by implantation (for example subcutaneously or intramuscularly) or by intramuscular injection. Thus, for example, the therapeutic can be formulated with suitable polymeric or hydrophobic materials (for example as an emulsion in an acceptable oil) or ion exchange resins, or as sparingly soluble derivatives, for example, as a sparingly soluble salts.

Additionally, therapeutics can be delivered using sustained-release systems, such as semipermeable matrices of solid polymers containing the therapeutic. Various sustained-release materials have been established and are well known by those skilled in the art. Sustained-release capsules may, depending on their chemical nature, release the therapeutic for a few weeks up to over 100 days.

EXAMPLES

Materials and Methods

Counting Method. Position 1 was assigned to the first nucleotide pair after the Drosha cutting site. The nucleotides that would form the single stranded overhang after Drosha processing were assigned negative positions (−1, −2 etc.) and if the cutting site was known for only one strand the overhang was assumed to be 2 nt. Positions were then assigned for each nucleotide pair in ascending order moving towards the Dicer cleavage site. The average hairpin contains several mismatches, which occasionally contain more nucleotides in one strand than in the other. Whenever such a length discrepancy occurred, the shorter strand was used to assign the mismatch position, using the later position whenever an asymmetric mismatch was located between two positions. Each position where the nucleotides were bound to each other was assigned the score 0, while positions with at least one nucleotide mismatched were given the score 1.

Genomic location. Data from miRBase was used to determine whether each miRNA was intronic or intergenic. The fold change values in the two groups are visualized in FIG. 2. Significance was calculated using a t-test. Information regarding whether each miRNA was intronic or intergenic was retrieved from miRBase and fold change distribution was analyzed for each of the two groups and differences in distribution was calculated using a t-test.

miRNA machinery and structure in neuronal differentiation. H1 cells were differentiated into neurons using 90% confluent cells on Matrigel. The differentiation was performed using a modified version of the dual SMAD inhibition protocol (Chambers et al. 2009), using the TGF-β inhibitor SB432542, ALK inhibitor LDN193189, and cyclopamine in CDM Basal media, which was changed daily for 12 days. At time points 0, 6, and 12 days starting from the first addition of inhibitors, cells were harvested. mRNA and miRNA were purified using the RNeasy Plus Mini Kit, and the miRNeasy Mini Kit, respectively, according to manufacturer instructions (Qiagen). Expression levels were measured using RNAseq (Expression Analysis Inc) and single-color miRNA microarrays (LC Sciences) respectively. RNAseq expression data were then count- and length-normalized to transcripts per million (TPM) after exclusion of mitochondrial genes, and miRNA expression data were Lowess normalized for cross-chip comparisons.

H1 Cell Culture.

H1 human embryonic stem cell lines were cultured on a feeder layer (MEFs) in Dulbecco's modified Eagle's medium (DMEM)/Ham's F-12 medium containing GlutaMax supplemented with 20% serum replacer (SR), 1 mM sodium pyruvate, 0.1 mM non-essential amino acids, 50 U/ml penicillin, 50 ug/ml streptomycin, 0.1 mM β-mercapto-ethanol (Sigma-Aldrich, St. Louis), and 2 ng/ml basic fibroblast growth factor (Qi et al 2009). Knockdowns of Drosha and Dicer were generated by infection with lentiviral vectors containing shRNA constructs against Drosha and Dicer respectively. Control cells were infected with control viruses. After passaging the next day, infected cells were treated with blasticidin (0.5 ug/ul) for selection until discrete clusters of cells appeared. If cells showed less stability with respect to Drosha knockdown, cells were repeatedly selected with antibiotics (Qi et al. 2009).

Generation of HeLa line with Drosha knockdown. HeLa cells were transduced with a pL6-Tet lentiviral vector containing shRNA against Drosha (Qi et al. 2009) (Titer 1.79E+08, MOI of 1:10; 10 μg/ml blasticidin selection for 4 days). Generation of the control cells was done with a pLKO.1 control lentivirus, (MOI 1:10; 10 μg/ml puromycin selection for 4 days).

Drosha qPCR analysis. Drosha and DGCR8 levels were measured in Drosha KD and Control HeLa cells using the SYBR-GREEN Q-PCR kit. Drosha Ct values were normalized to GAPDH (ΔCt: Drosha-GAPDH). The ΔΔCt values were calculated by subtracting the Drosha ΔCt values in the Control cells from those values in the KD cells. Fold change was calculated using the $(2^{(-\Delta\Delta Ct)})$ method.

Total RNA extraction and quantitative RT-PCR analysis. Brain and liver tissues were dissected from WT mice (n=3). Tissues were homogenized using mortar and pestle in a liquid nitrogen bath. RNA was extracted from cells adherent on plates or from tissue homogenate using Trizol reagent (Invitrogen) and cDNA was synthesized with the Omniscript RT kit (Qiagen). Beta-actin or UBC was used as endogenous control for normalization. Quantitative PCR reactions were performed in triplicate using the SyberGreen (Applied Biosystems) with the 7300 real time PCR system (Applied Biosystems). Primers used in our study are listed in the following Table 4.

TABLE 4 qPCR Primer Sequences.

| Primer | Sequence |
|---|---|
| Drosha | SS-AGGAGTACGCCATAACCAACG |
|  | AS-CAATCGTGGAAAGAAGCAGACA |
| β-actin | F-TCCCTGGAGAAGAGCTACG |
|  | R-GTAGTTTCGTGGATGCCACA |
| Gapdh | SS-TGATGACATCAAGAAGCTGGTGAAG |
|  | AS-TCCTTGGAGGCCATGTGGGCCAT |
| Bleomycin | F-AGCTGTACGCCGAGTGGTC |
|  | R-CGTGTCAGTCCTGCTCCTC |
| Ubc | F-ATTTGGGTCGCGGTTCTTG |
|  | R-TGCCTTGACATTCTCGATGGT |

Normalized Drosha levels in the brain were compared to those in the liver and the fold change was calculated using the $2^{(-\Delta\Delta Ct)}$ methods.

qPCR of miRNAs was conducted using TaqMan® miRNA assays (Applied Biosystems). miRNA expression was measured in both DroshaKD and Control HeLa cells. Raw Ct values for miRNAs were first normalized to RNU66 (endogenous snoRNA, internal control). Bleomycin values were normalized to GAPDH. To normalize to transfection efficiency, the normalized miRNA values were re-normalized to the normalized Bleomycin values (normalized miRNA ΔCt−normalized Bleomycin ΔCt). This new normalized value from control cells was subtracted from the corresponding value in the knockdown cells to generate the ΔΔCt values. Fold change with respect to the control cells was calculated using the $2^{(-\Delta\Delta Ct)}$ method.

Protein extraction and Western blot. With the exception of mouse tissues, protein extraction and Western blot analysis followed procedures that were described previously (Zhou et al., 2011). Briefly, cells were washed with Dulbecco's PBS (Sigma Aldrich, St. Louis, Mo.) and directly lysed on culture dish using M-PER Mammalian Protein Extraction Reagent (Thermo Scientific, Rockford, Ill.; 0.5 ml per 35 mm plate) and protease inhibitor cocktail (Complete Mini, Roche Applied Science, Germany). 20 μg of protein extracts were loaded, separated by 4-20% SDS-PAGE using Mini-PRO- TEAN TGX Precast Gels (Bio-Rad, Hercules, Calif.), and transferred to polyvinylidene difluoride transfer membranes (Thermo Scientific). Membranes were blocked with 5% non-fat dry milk for at least 60 minutes at room temperature, and incubated overnight at 4° C. with primary antibody. Blots were incubated for one hour with horseradish peroxidase-conjugated Blotting Grade Affinity Purified secondary antibodies (Bio-Rad) and were visualized by enhanced chemiluminescence (Millipore Corp, Billerica, Mass.). Protein expression levels in the gel were quantified by densitometry implemented in Image-J (National Institutes of Health, Bethesda http://rsb.info.nih.gov/ij/, 1997-2013). Antibodies used in this study are: rabbit anti-Drosha antibody (Cell Signaling Technology, Beverly, Mass.) diluted at 1:1000, mouse anti-β-actin antibody (Santa Cruz Biotechnology, Santa Cruz, Calif.) diluted at 1:5000, goat anti-rabbit antibody (Bio-Rad Laboratories, Hercules, Calif.) diluted at 1:10000 and goat anti-mouse antibody (Bio-Rad Laboratories, Hercules, Calif.). For mouse tissues, the protocol above was followed for protein extraction, gel loading, and the quantification of Drosha expression. As a control, either Western using actin Ab or Coomassie Brilliant Blue R (Sigma Aldrich) staining was used. Entire-cell protein expression was quantified using Image-J.

Transfections. The mutations were performed on the passenger strand, leaving the mature strand unchanged in order to be able to detect both the mutated and non-mutated miRNAs using the same TaqMan® assay. The pri-miRNA inserts were amplified from genomic DNA by PCR, including the hairpin and ~200 nt flanks on each side. The inserts were ligated into a modified pcDNA3.1+ plasmid with the neomycin selection marker replaced with a bleomycin resistance gene. Mutated versions of the constructs, with altered mismatches in the 9-12 region, were ordered from Genscript. The miRNA constructs were transiently transfected into HeLa cells using Lipofectamine2000. RNA was extracted after 48 hours using Trizol.

Analysis of Drosha and miRNA expression in mouse tissues. For GDS3052 and GDS3142: These are two microarray analyses done in mouse using an Affymetrix Mouse Genome 430 2.0 chip. Drosha expression values were extracted from the datasets and were normalized to a gene that in both studies showed minimal variation between tissues; Eef2 (eukaryotic translation elongation factor 2). Drosha expression was represented as percent of Eef2 in the tissues.

For Takada et al. 2006: The miRNAs expressed in each tissue were first sorted according to number of clones (highest number of clones being highest expression and lowest number of clones being lowest expression). The miRNAs were then divided into groups based on the number of mismatches in the 5, 9-12 region (X-axis) and within each group the average expression level (Y-axis) was calculated by geometric mean.

In vitro processing of miRNAs. Plasmids for wild type (wt) and modified versions of mir-137 and mir-200b were linearized, gel purified and in vitro transcribed using the Riboprobe (Promega) protocol and labeled with $\alpha^{32}$P-CTP. Transcripts were purified using the RNAeasy mini kit (Qiagen) and then allowed to fold by addition of KAc, heating to 95° C. for 5 min and then kept on ice till the processing reaction. Processing was performed by mixing folded pri-microRNA transcripts with 8 μg 293T cell nuclear extract (Protein One) for 10, 30 and 90 minutes at 37° C. followed by trizol extraction and run on a 10% polyacrylamide-urea gel for 4 hours at 650V. Gel exposures were quantified using ImageJ64 software where intensities of bands corresponding to pre-miRNAs were normalized to regions containing pri-miRNA transcripts.

Statistical analysis. Throughout the experiments, P values for expression levels were calculated using Student's t-test. *, $P<0.05$; and **, $P<0.01$. Bars show Standard error of the mean (SEM) for at least 3 separate experiments. P-values for differences in mismatch trends were calculated in R using a chi-square test with Yate's continuity correction.

Results

Differences in change of miRNA expression due to Drosha knockdown in hESC (H1) correlate with differences in predicted pri-miRNA secondary structures. Previous research in the laboratory used H1 human embryonic stem cells with Drosha KD to study the response to a general decrease of miRNAs in stem cells (Bar et al. 2008; Qi et al. 2009; Stadler et al. 2010). qPCR of 220 microRNAs in Drosha KD hESCs showed a general decrease of miRNA expression. However, a group of miRNAs was still processed efficiently, despite the 3-fold reduction of Drosha expression (FIG. 1). It seems logical that mirtrons (which bypass Drosha processing) would be unaffected by Drosha KD, however, few mirtrons are known (Berezikov et al. 2007) and none of the known mirtrons are in the 220 miRNAs assayed by qPCR. Mirtrons are generally located within small introns, but no statistically significant correlation could be verified between genomic location and fold change of miRNA expression (p=0.27); the mean fold change was 2.8 for intergenic miRNAs, and 2.4 for the intronic miRNAs (FIG. 2).

Figure 3A:
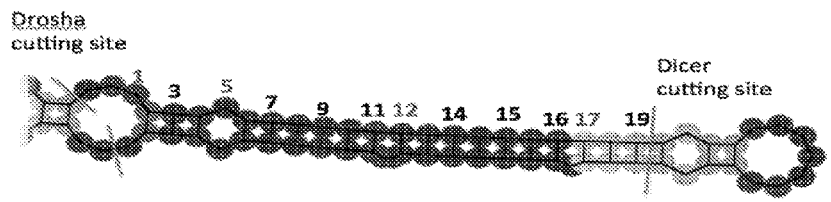
FIG. 3. Counting of mismatches in miRNAs in H1 cells with DroshaKD and control cells. Positions regarded as mismatched are marked by numerals in light grey (FIG. 3A). Mismatches summed for positions counted from the Drosha cutting site for a set of 202 miRNAs split in two equal groups based on fold change in the Drosha knockdown (FIG. 3B). P-values were calculated using Pearson's Chi-squared test with Yates' continuity correction, giving log p-values <−2 for positions 5, 10, 11 and 12 for the full data set split in half (dark grey) and for the quartiles at the extreme ends with sample size extrapolated to that of the full data set (FIG. 3C).

Given that bulges in the stem of RNA hairpins seem to prevent processing by the miRNA pathway in general, and that others have shown Drosha to differentially process miRNAs based on structural features (Han et al. 2006; Ritchie et al. 2007; Feng et al. 2011), it seems logical that differences in the number of mismatches in miRNA hairpins would alter their interaction with the Microprocessor, and could explain the variation of fold change in response to Drosha KD. In order to compare the three-dimensional shape of the pri-miRNAs in the described dataset, a novel method of assigning position within the miRNA hairpin was developed in order to give a better representation of the mismatch locations relative to each other and the Drosha cutting site in three dimensional space (FIG. 3A). Position assignment and mismatch counting was performed by defining the location of each mismatch in terms of distance from the Drosha cutting site using predicted secondary structure, counting asymmetric mismatches as the length of the shorter strand; this is different from previously described methods to calculate mismatch positions in pri-miRNAs, where asymmetry was not taken into account (Han et al. 2006).

Figure 3B:
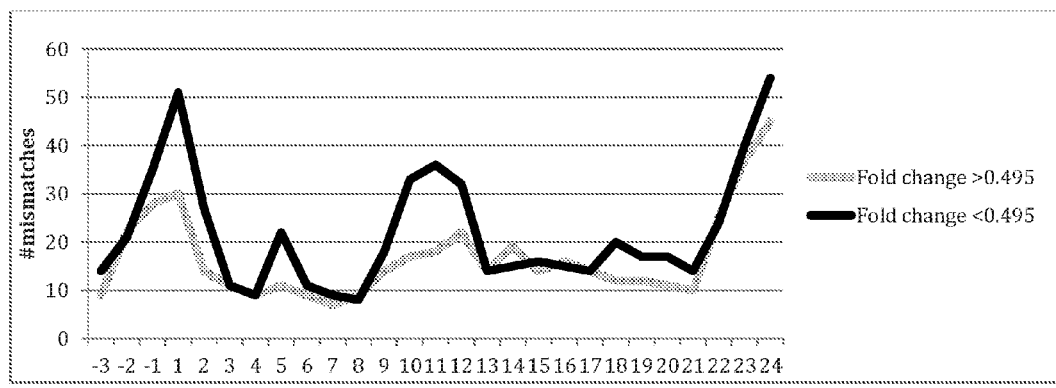
Figure 3C:
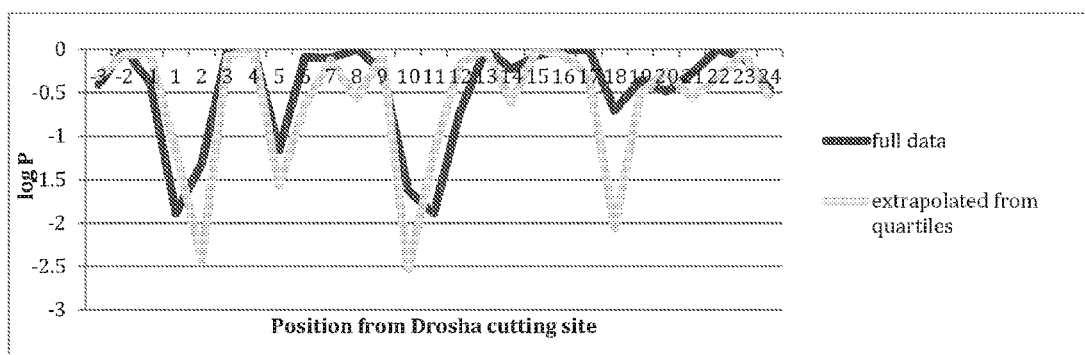
Figure 10:
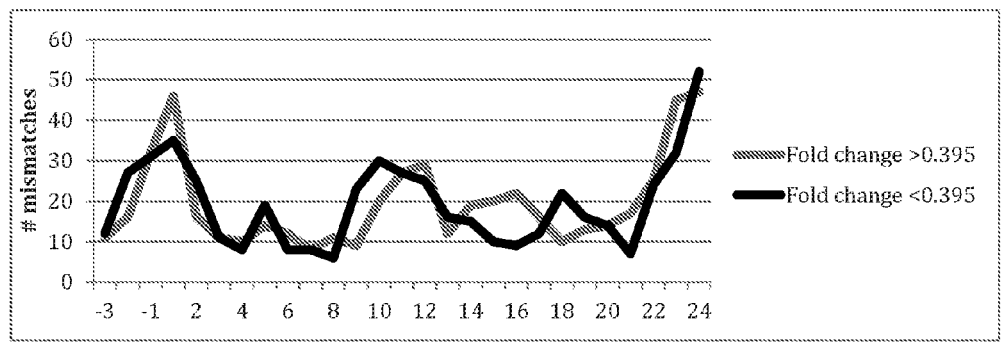
FIG. 10. Counting of mismatches in miRNAs in H1 cells with DicerKD and control cells. Mismatches summed for positions counted from the Drosha cutting site for a set of 202 miRNAs split in two equal groups based on fold change (median=0.395) in the Dicer knockdown.

The secondary structures for the 220 miRNAs from the H1 dataset were calculated using the ViennaRNA package (Hofacker et al. 1994), and exact locations of cutting sites were found through miRBase. The dataset contained 220 miRNAs, and 202 were selected by sorting out any miRNAs with ambiguous secondary structure predictions. The dataset was split in half based on fold change (FIG. 1, arrow), and the sums of mismatches at each nucleotide position were compared between the two groups. The summation revealed that miRNAs with a high fold change when Drosha levels were reduced had more mismatches in position(s) 5 and 10-12 than miRNAs with low fold change, and that these differences were statistically significant (FIG. 3B, C). A knockdown of Dicer did not result in the same trend (FIG. 10) In addition p-values were calculated for the quartiles at the extreme ends of the DroshaKD dataset, with a sample size extrapolated to that of the total data set (FIG. 3C). For subsequent experiments and analysis position 9 was also included because it follows the same trend as positions 10-12. This takes into account any lack of specificity in the method of assigning positions.

Correlation of Drosha expression and miRNA secondary structure profile in mature tissues. Having shown that pri-miRNA processing by Drosha is affected by the pri-miRNA secondary structure in cell culture whether this mechanism is used in vivo as a mechanism to selectively regulate groups of miRNAs based on secondary structure was also investigated. Because Drosha expression alters the expression of miRNAs with bulges in the central region more than miRNAs without (FIG. 3), and because of the crucial role of miRNAs for cellular biology, whether or not Drosha expression levels vary across cell type or according to developmental stage in mammals was examined. To find naturally occurring examples of Drosha variation, the Gene Expression Omnibus (GEO) was used to find microarray data of relevant gene expression in mature and differentiating mouse tissues.

Figure 4:
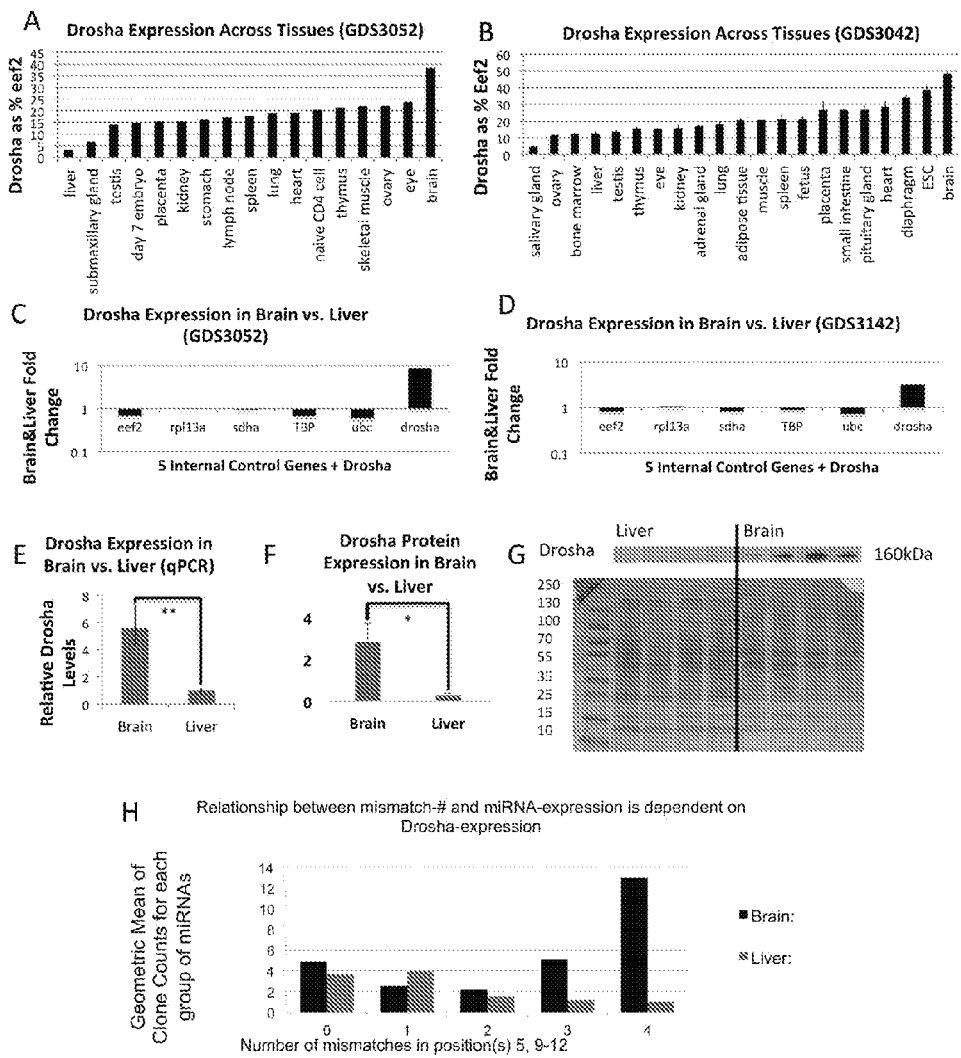
FIG. 4. Differential expression of Drosha in mouse tissues. Expression levels in Drosha in mouse tissues, normalized to EEF2; GEO(GDS3052) (A), GEO(GDS3142) (B). Fold change of Drosha expression in liver, compared to the average expression of EEF2, RPL13A, SDHA, TBO and UBC; GDS3052 (C), GDS3142 (D). qPCR analysis of Drosha mRNA levels in mouse brain and liver (E), Quantification of Drosha protein levels show 9.6 fold increase in brain compared to liver tissue (p<0.05) (F), Western blot of Drosha protein in mouse brain and liver normalized to total protein (Coomassie Blue) (G), Geometric mean of clone counts of miRNAs with 1, 2, 3, 4 and 5 mismatches in the positions 5, 9-12 nucleotides from the Drosha cutting site in mouse liver and brain (Takada et al. 2006) (H).

From the GEO expression datasets GDS3052 and -3142, expression data for Drosha and common housekeeping genes in multiple mouse tissues was extracted and analyzed. In both datasets the expression of Drosha is dramatically lower in liver and submaxillary/salivary gland (4-10 fold) than in brain tissues when normalized to EEF2 (FIG. 4A-B). To test whether the difference in Drosha expression was dependent on the housekeeping gene used for normalization, the fold change of expression between liver and brain tissues for five housekeeping genes; EEF2, RPL13A, SDHA, TBP, and UBC was analyzed. The data revealed that the expression change for Drosha is greater than variation among known housekeeping genes (FIG. 4C-D), showing that Drosha is differentially expressed regardless of the housekeeping gene used for normalization.

Figure 11:
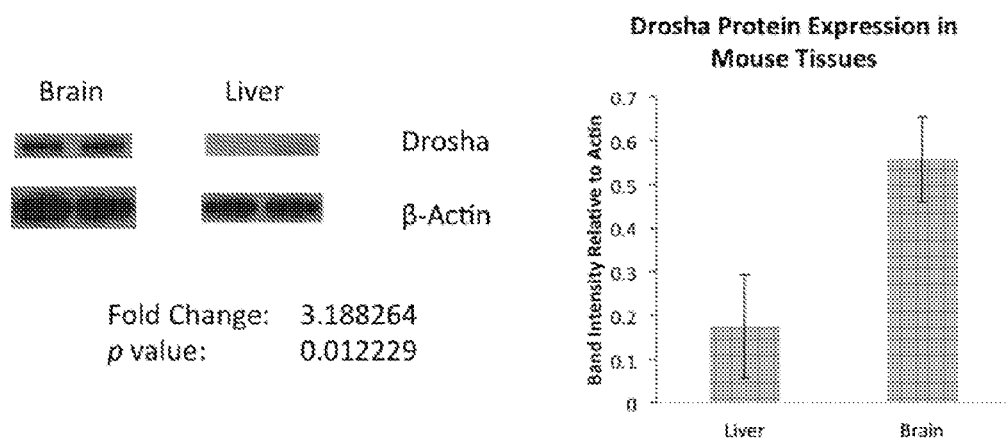
FIG. 11. Drosha protein expression levels in mouse brain and liver. Protein levels of Drosha and β-actin measured by western blots (A). Quantification of Protein levels using triplicates extrapolated from different gels. Fold change=3.2, p<0.05 (B).

The differential expression of Drosha in mouse brain and liver by qPCR was validated, and normalized to UBC, verifying that Drosha expression was 5.6 fold higher in the brain than in the liver (FIG. 4E; n=3, p<0.01). Furthermore, Western blotting revealed 9.6 or 3.2 fold higher Drosha protein expression in brain than in liver when normalized to total protein or to β-actin expression, respectively (Coomassie Blue staining or to β-actin Western; FIG. 4F,G; FIG. 11).

Figure 12:
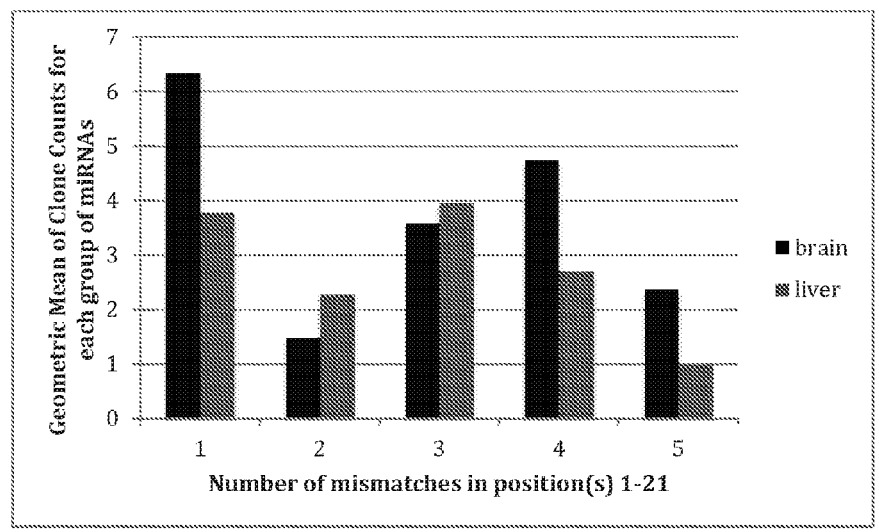
FIG. 12. Control mismatch counts for mouse brain and liver. Average expression of miRNAs with different numbers of mismatches in the 1-21 region in mouse liver and brain (Takada et al. 2006).

Having validated that Drosha levels are higher in brain than in liver, whether miRNA expression varies according to the number of mismatches in the 9-12 nt region of the miRNAs in the two tissues was examined. miRNA expression data from mouse brain and liver (Takada et al. 2006) was analyzed. It was found that miRNAs with mismatches in positions 5 and 9-12 are enriched in brain but not in liver and that the difference was larger the more mismatches present (FIG. 4H), supporting the hypothesis that miRNAs with central mismatches are not processed efficiently when Drosha is limiting. This trend for miRNA expression did not correlate with mismatches in the other positions (FIG. 12).

Figure 5:
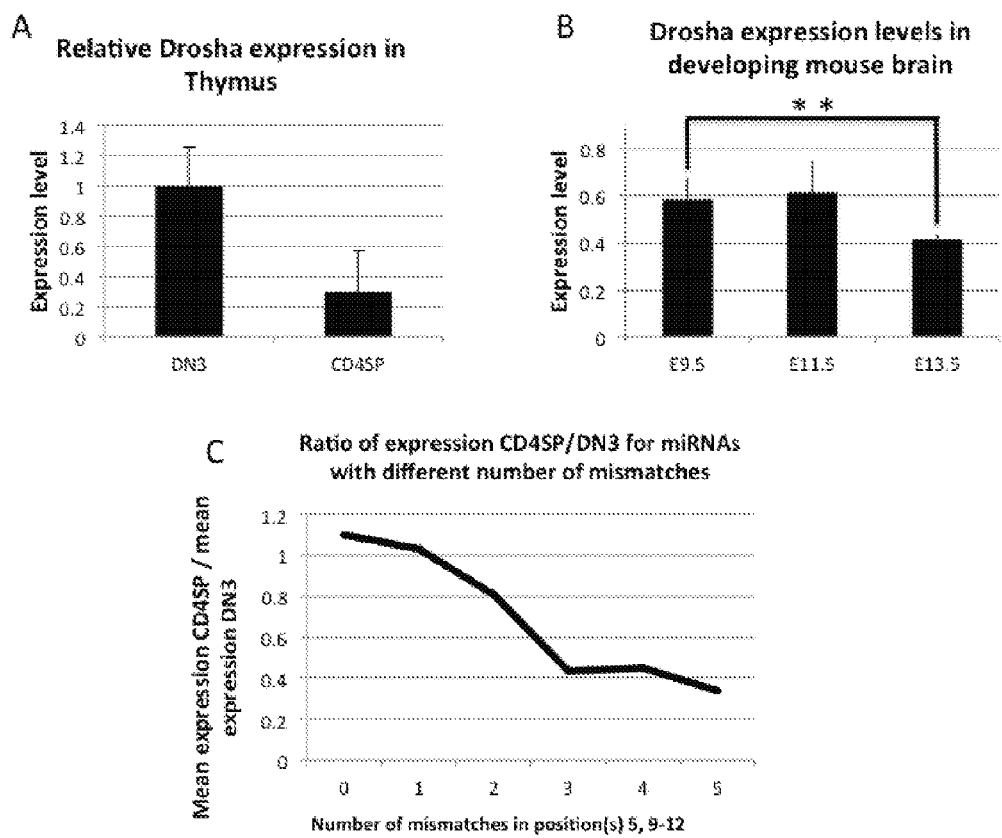
FIG. 5. Drosha levels and miRNA profiles during T-cell differentiation. Drosha levels in T-cells measured by qPCR, normalized to β-actin (Chong et al. 2010) (A). Drosha levels in developing mouse brain (GDS3442), normalized to EEF2 (B). Ratio (CD4SP/DN3) of average expression for each miRNA group based on number of mismatches in the 5, 9-12 region (C).

Coordination of Drosha and miRNA expression by microRNA secondary structure during T-cell development and neuronal differentiation. Because Drosha levels vary between mature tissue types and expression levels of miR-NAs with mismatches in the central region are high relative to rigid miRNAs when Drosha levels are high, whether this mechanism is used to dynamically alter the miRNA expression profiles during cell development was tested. In order to establish this relationship, Drosha expression levels during T-cell differentiation was determined and a 3-fold decrease in Drosha expression from double-negative T-cells (DN3) to CD4+ cells (Chong et al. 2010) (FIG. 5A) was found. In neuronal lineage, Drosha and Eef2 expression were compared during the proliferation of mouse neural progenitors (GDS3442). A significant decrease (p<0.01) in Drosha expression as the cells proliferate and mature in embryonic mouse brains was observed (FIG. 5B).

Figure 13:
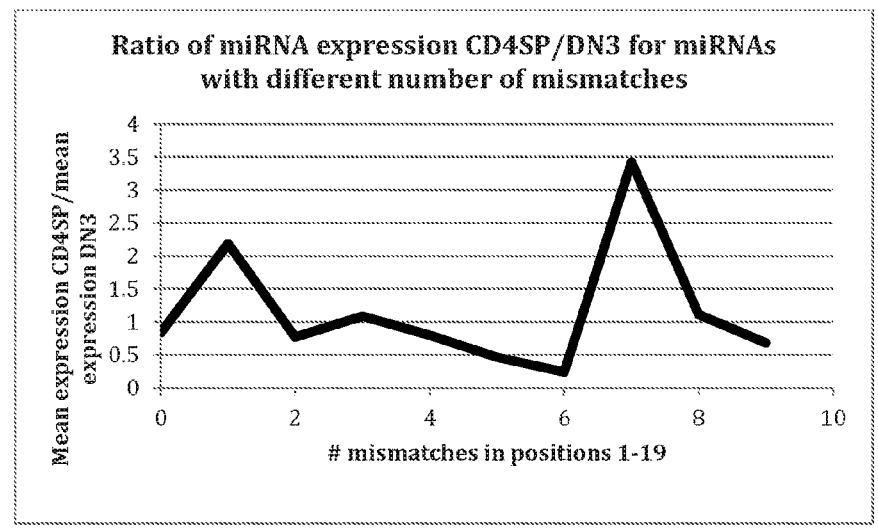
FIG. 13. Control mismatch ratios in T-cells. Ratio (CD4SP/DN3) of average expression for each miRNA group based on number of mismatches in the 5, 9-12 region.

Whether the miRNA groups correlate with the Drosha levels was tested. It was found that the lower Drosha expression in CD4+ compared to DN3 cells correlates with lower expression of miRNAs with 5 mismatches in the region 5, 9-12 nt from the Drosha cutting site and the ratio of expression between DN3 and CD4+ for miRNAs grouped by the number of mismatches in positions 5 and 9-12 shows that the difference in Drosha expression between DN3 and CD4+ cells correlates with a decrease in miRNA expression based on number of mismatches (FIG. 5C). In DN3 cells Drosha levels are relatively high, and mismatched miRNAs are highly expressed; in CD4+ cells Drosha levels are low, and predominantly rigid miRNAs are produced. This agrees with previous results that when Drosha levels are low the levels of mature miRNAs generated from mismatched hairpins go down disproportionately compared to rigid miRNAs (FIG. 3B-C, 4C-D). Mismatch counting of the complete hairpin, to control for the difference being local to the 5, 9-12 region, did not result in a similar trend (FIG. 13).

Figure 6:
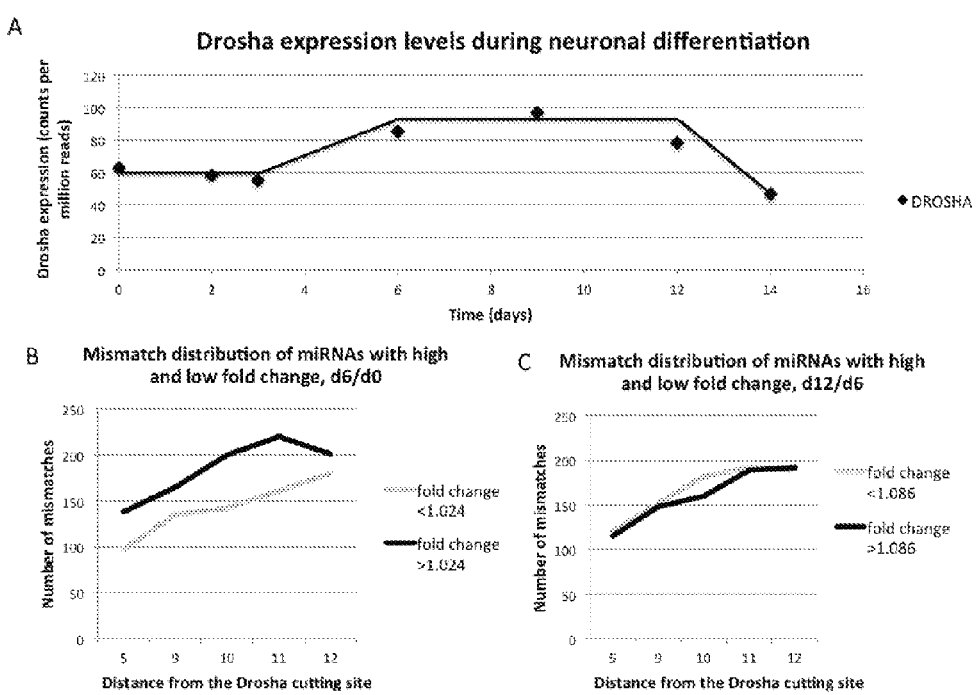
FIG. 6. Changes in gene expression levels during neuronal differentiation. Drosha expression in neuronal differentiation of H1 hESC into Pax6+ neural cells (RNAseq) (A). Number of mismatches in miRNAs with high and low fold change through days 0-6 (multiArray) (B). Number of mismatches in miRNAs with high and low fold change through days 6-12 (multiArray) (FIG. 3C).
Figure 14:
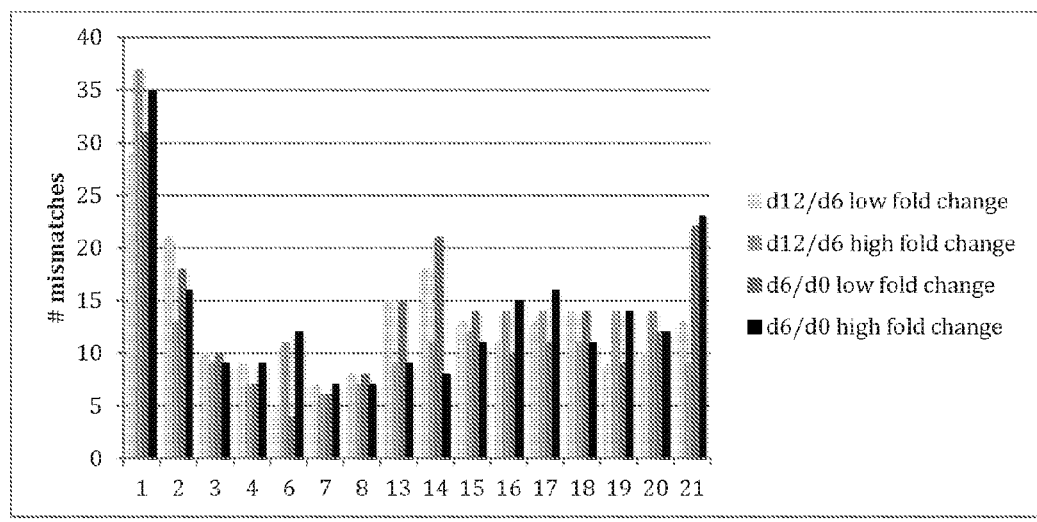
FIG. 14. Control mismatch counts during neuronal differentiation. Number of mismatches outside the 5, 9-12 region in miRNAs with high and low fold change (multiArray) in neuronal differentiation through days 0-6 and 6-12.

Drosha levels in hESC derived neuronal differentiation process were also determined. RNAseq data from early neuronal differentiation of H1 hESC shows an increase in Drosha, with a greater change occurring over day 0 to day 6 than day 6 to day 12 (FIG. 6A). Canonical and non-canonical components of the miRNA biogenesis pathway have a significantly greater change in expression between days 0 and 6 than between days 6 and 12 of the neural differentiation protocol. miRNA microarray data from the same period, day 0 to day 6, when Drosha levels increase, shows that the miRNAs with positive fold-change have significantly more mismatches in the region(s) 5, 9-12 than miRNAs with negative fold change (FIG. 6B). Between days 6 and 12, when changes in Drosha expression are significantly lower, no significant difference in number of mismatches can be found between miRNAs grouped by fold-change (FIG. 6C). This shows that when Drosha levels increase in early neuronal differentiation the expression of miRNAs generated from hairpins with mismatches in the 5, 9-12 region go up relative to more rigid hairpins, and when Drosha levels stabilize mismatched miRNAs no longer behave differently from rigid ones (FIG. 6B-C) Whether increasing or decreasing during cell development, changes in Drosha levels affect groups of miRNAs based on their secondary structure. To control for the difference being local to the 5, 9-12 region, mismatches were counted in the remaining positions for a subset of 166 miRNAs, where no similar trend was observed (FIG. 14).

Figure 7A:
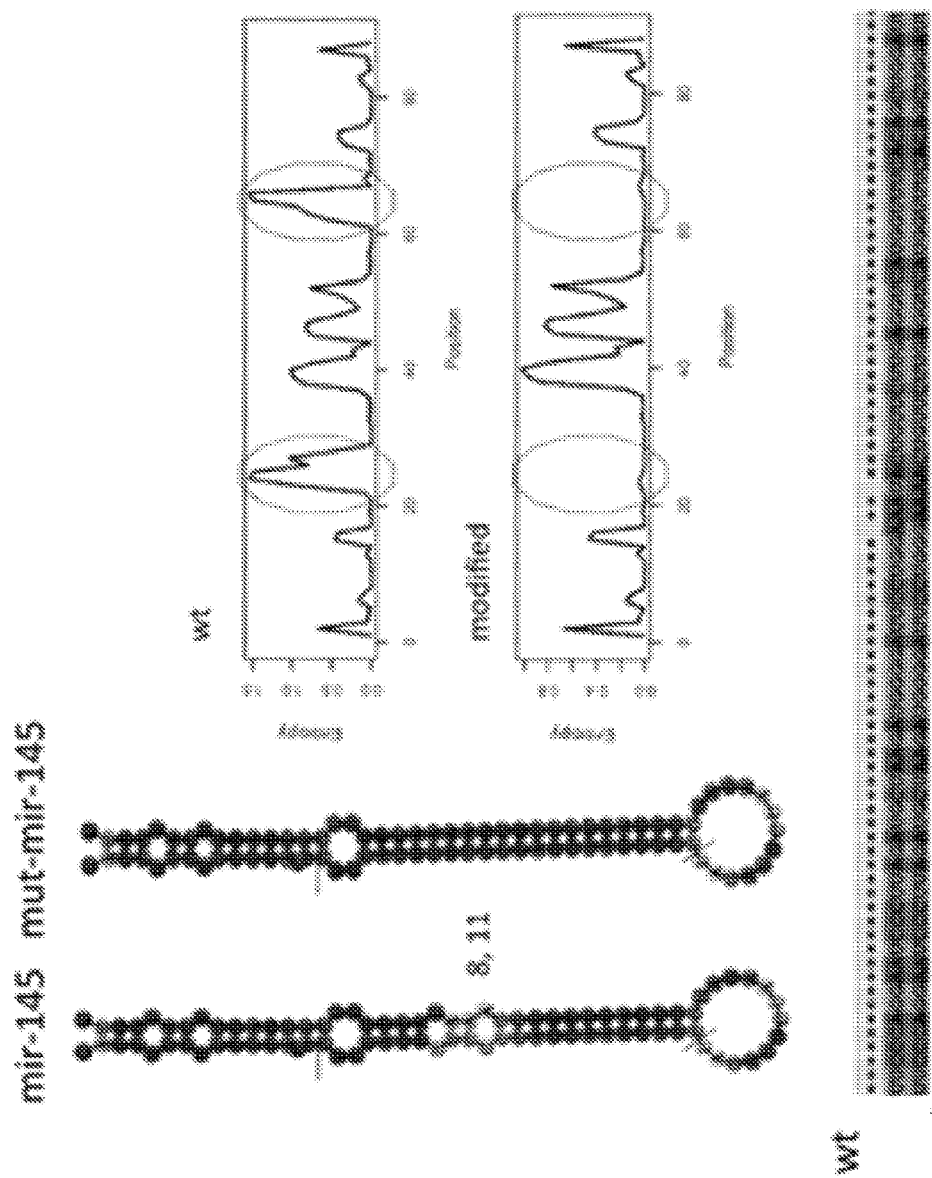
FIG. 7. Predicted structures of wild-type and modified hairpins of hsa-mir-145, (FIG. 7A), -137 (FIG. 7B), -9-1 (FIG. 7D) and 200b (FIG. 7C), demonstrating canonical "mismatched" and "rigid" miRNA hairpins. Entropy curves of the nucleotide sequence, starting at the 5' end, indicate stability changes being local to the changed regions.
Figure 7B:
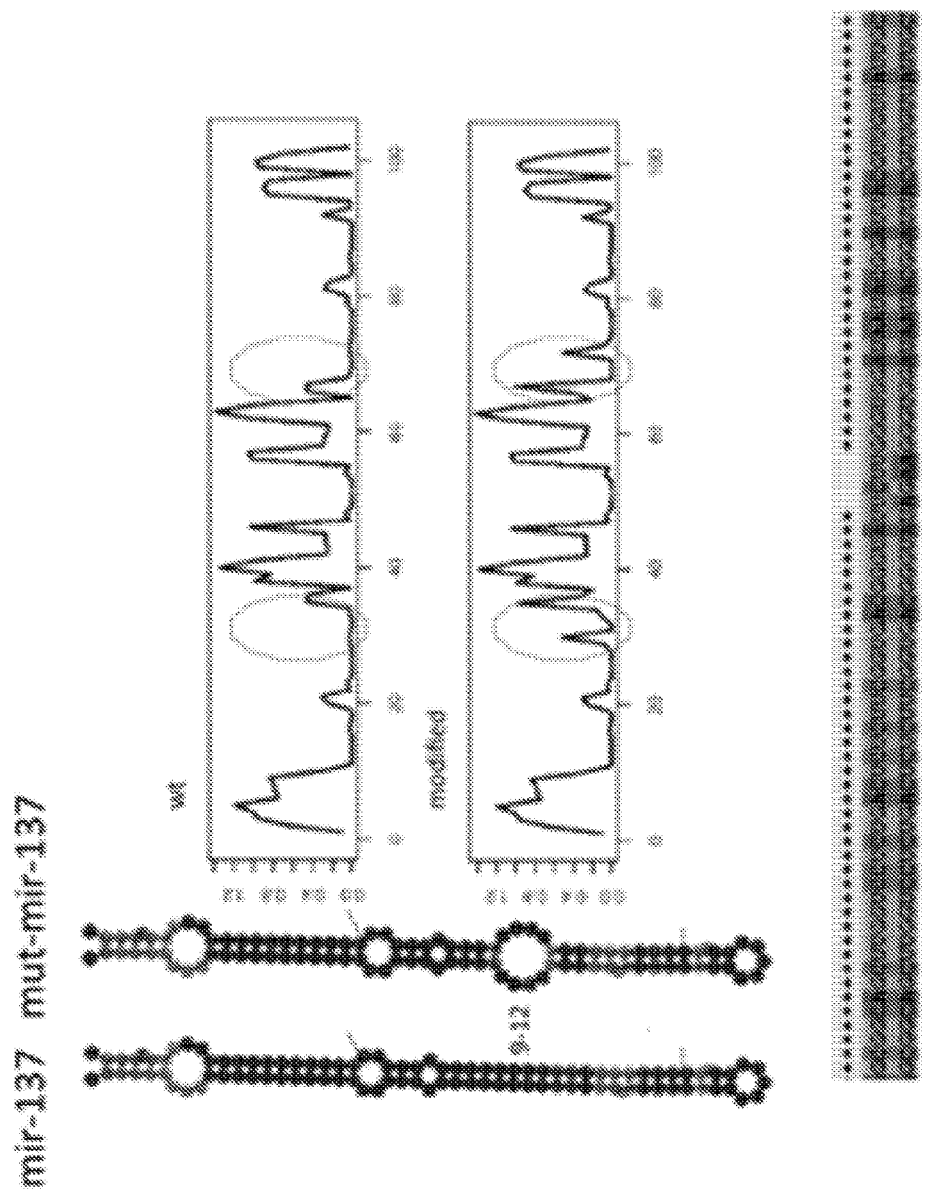
Figure 7C:
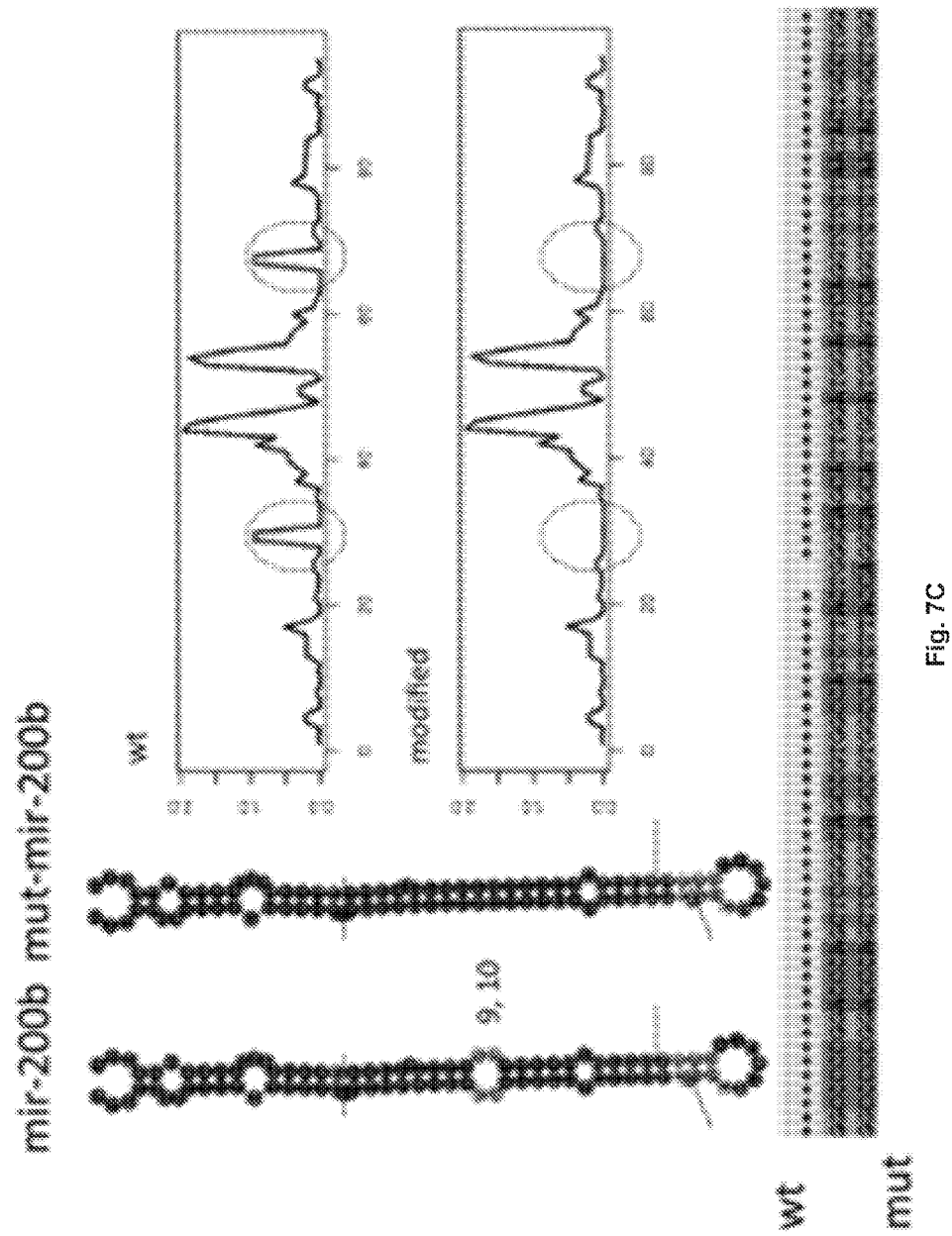
Figure 7D:
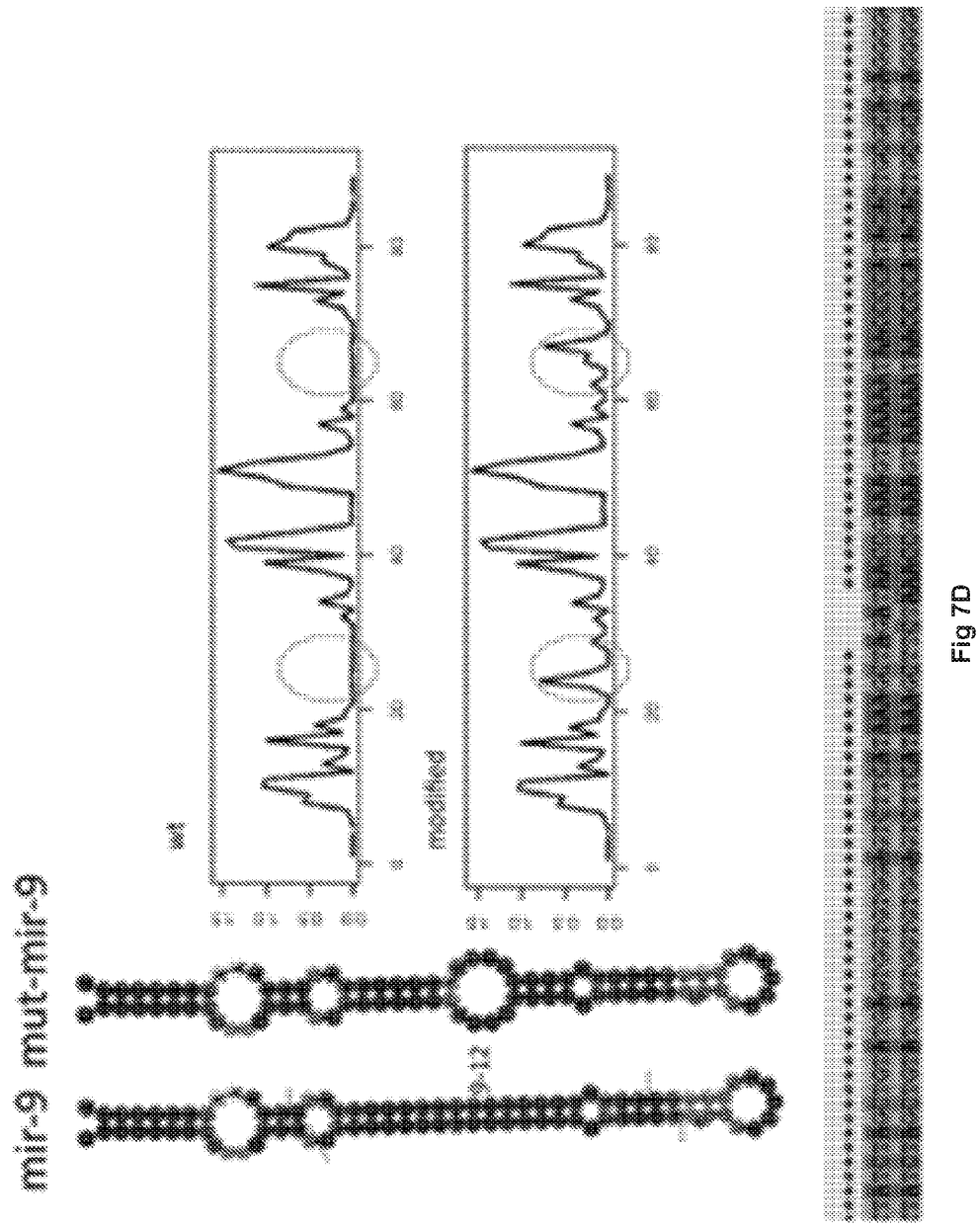
Figure 15:
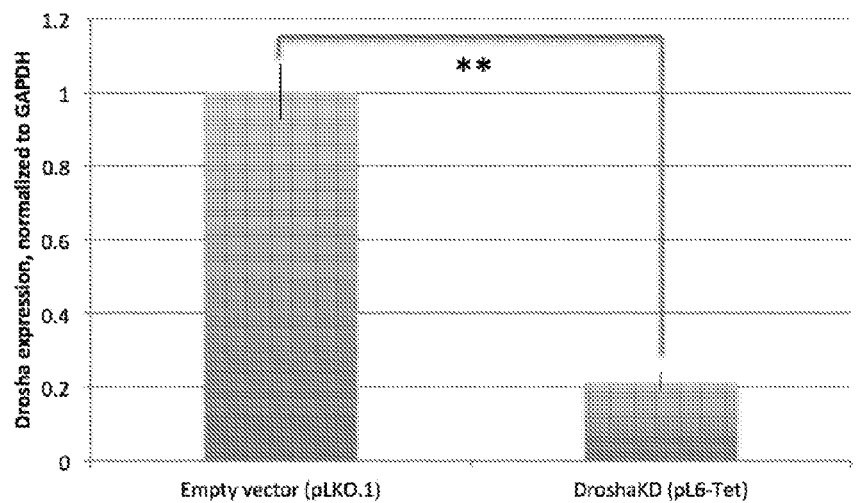
FIG. 15. DroshaKD in HeLa cells, verification of expression levels. Drosha levels measured by qPCR and normalized to GAPDH. 7 biological replicates showed an average 9-fold knock down (log p<−5) (A). Drosha protein expression levels measured by western blotting, normalized to β-actin. 3 biological replicates showed an average 5-fold knockdown (p<0.05) (B)
Figure 15:
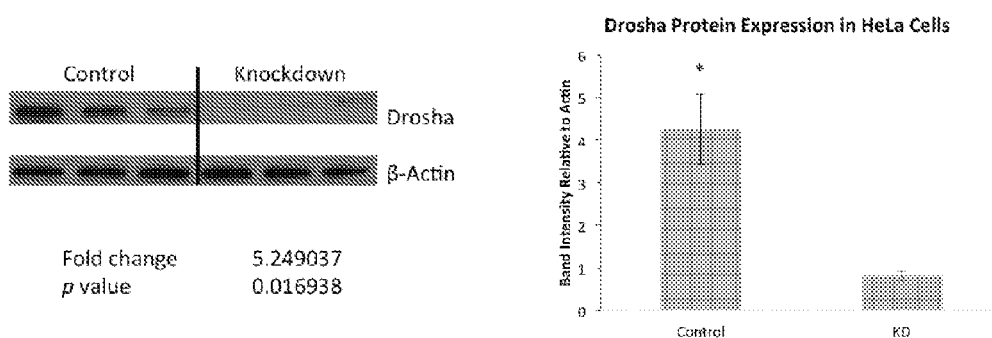
Figure 16:
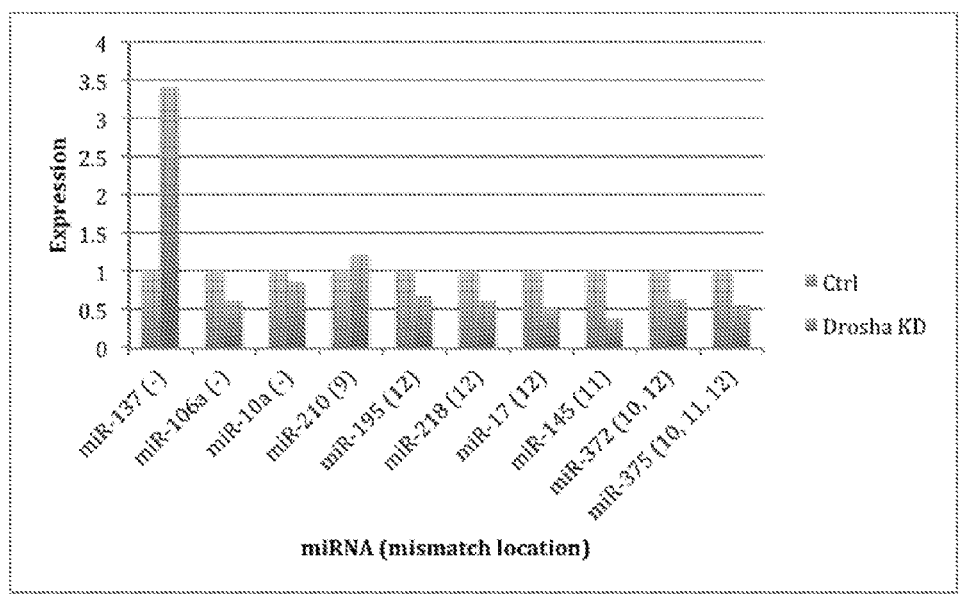
FIG. 16. Endogenous miRNA levels in DroshaKD and control cells. Endogenous levels for a random selection of miRNAs were measured by TaqMan qPCR, normalized to RNU66. The miRNAs are sorted right to left by increasing number of mismatches in region 9-12 nucleotides from the Drosha cutting site.

Biochemical validation of the relationship between pri-miRNA secondary structure, miRNA expression, and Drosha expression in viva Given the spatial and developmental heterogeneity of Drosha expression and its' correlation with miRNA expression based on secondary structure (FIG. 3-6), it was hypothesized that mismatches in a miRNA hairpin approximately 9-12 nt from the Drosha cutting site would confer increased sensitivity to low levels of Drosha. Conversely, the absence of mismatches would confer decreased sensitivity to Drosha expression. In order to test this hypothesis, the relative over expression of four miRNAs in two HeLa cell lines were compared; one with a stable Drosha knockdown, the other transduced with a control virus (Control). Drosha protein levels were significantly reduced in the KD line (5-fold reduction; FIG. 12) resulting in downregulation of endogenous miRNAs (FIG. 15). miR-145 and miR-200b were selected for over-expression in these cells due to the clear presence of mismatches 9-12 nt from the Drosha cutting site (FIG. 7A-B), making them ideal candidates to represent miRNAs at one end of the spectrum with regards to secondary structure. For the same reason, miR-137 and miR-9-1 were selected due to the clear absence of mismatches 9-12 nt from the Drosha cutting site (FIG. 7C-D). Modifications of the 9-12 nt region were designed to either insert or remove mismatches without disrupting the rest of the hairpin, while preserving the primary sequence of the mature miRNA, changing each miRNA from one extreme structure to the other while allowing for detection by traditional methods (FIG. 7A-D). Because alteration of the secondary structure close to the Drosha cutting site has previously been shown to completely disrupt processing and may affect strand selection during RISC loading, this region was not modified. (Zeng and Cullen 2003; Noland et al. 2011) Fold change of miRNA over expression (KD/ctrl; referred to as "relative over expression") was measured by qPCR to determine whether or not mismatches in the central region determine sensitivity to Drosha in vivo.

Figure 8:
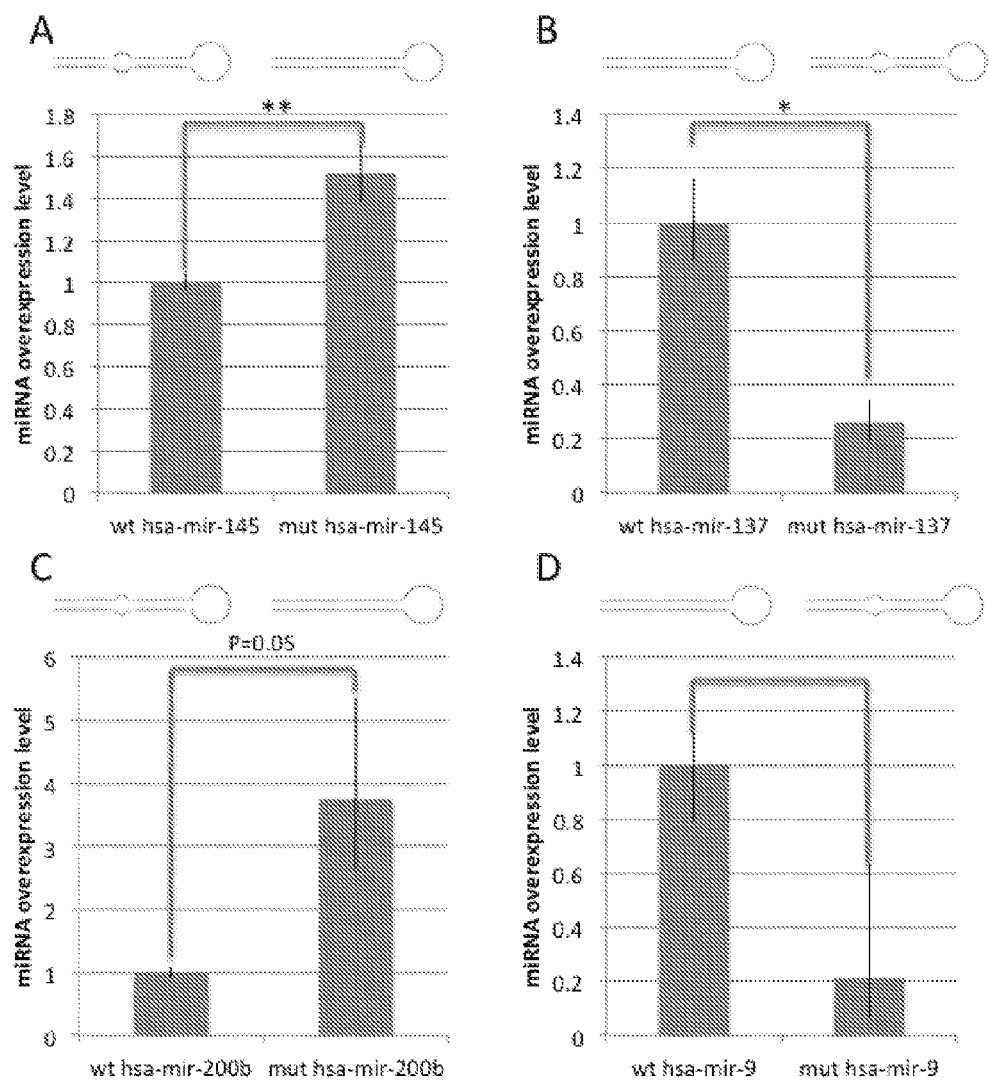
FIG. 8. Fold change of over expression levels of wild type and mutated versions of miR-145 (A), -137 (B), -200b (C) and -9 (D) between Drosha knockdown and control HeLa cells, assayed by TaqMan® probes and normalized to RNU66. (n=3). Transfection efficiency was accounted for by SYBRgreen® qPCR of the bleomycin resistance gene in the vector, normalized to GAPDH and subtracted from the ΔCt values from the TaqMan® assays. Final normalization was made to the fold change of over expression for each wt construct. Statistical significance was calculated using a student's t-test, resulting in p-values of <0.01 (mir-145), <0.05 (mir-137), =0.05 (mir-200b).

For miR-145, mutation from a semi-rigid to a rigid stem increased relative over expression by 1.52-fold, p<0.01 (FIG. 8A). For miR-137, mutation from a rigid stem to a less rigid stem decreased relative over expression by 3.84-fold, p<0.05 (FIG. 8B). For miR-200b, mutation from a quasi-rigid to a more rigid stem increased relative over-expression by 3.76-fold, p=0.05 (FIG. 8C). For miR-9-1, mutation to create mismatches in the 9-12 nt region decreased relative over-expression by 4.66-fold (FIG. 8D). These data show that the addition or removal of mismatches did affect the level of miRNA overexpression in DroshaKD/Control, with more mismatches generating a lower ratio than the corresponding miRNA without mismatches 9-12 nt from the Drosha cutting site.

Figure 9:
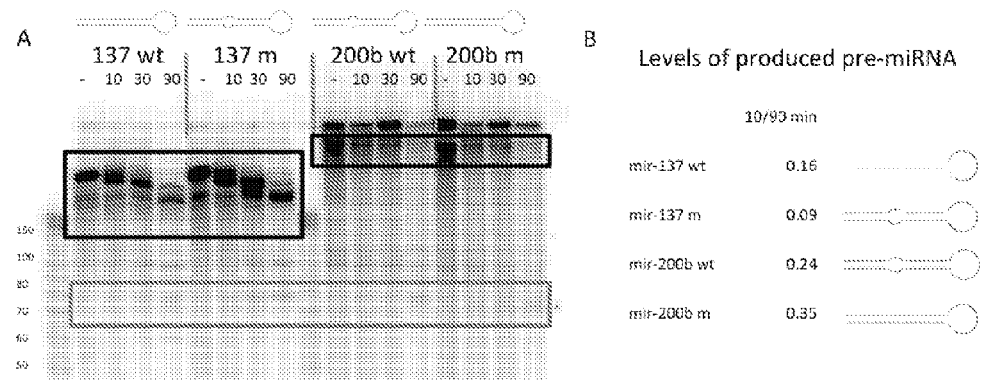
FIG. 9. in vitro processing of miRNAs using nuclear extract. A. in vitro transcribed miRNAs, processed by 293T cell nuclear extract and visualized on a 10% urea-polyacrylamide gel. Bands corresponding to processed pre-miRNAs are marked in grey, and areas containing pri-miRNAs used for normalization are labeled in black. B. 10/90 minute ratios of quantified pre-miRNA levels normalized to each respective pri-miRNA levels.

In vitro processing of modified miRNAs. Having shown the differential processing of rigid and mismatched miRNAs in vivo, this relationship was tested in vitro. Linearized plasmids containing wild type (wt) and modified versions of mir-137 (203 nt) and mir-200b (430 nt) were in vitro transcribed and radiolabeled, followed by Drosha processing for 10, 30 and 90 minutes using nuclear extract from 293T cells. The resulting RNA was purified and visualized on a 10% urea-polyacrylamide gel (FIG. 9A). Intensities of the bands corresponding to the pre-miRNA were quantified and normalized to the intensities of the regions containing pri-miRNA. Negative controls using only protein buffer and no lysate showed no detection in the bands used to quantify pre-miRNAs. Calculation of expression ratios of normalized 10 min and 90 min samples showed a consistently higher ratio for more rigid miRNAs than for their more mismatched counterparts (FIG. 9B). While the fold changes are smaller in in vitro assay compared to in vivo experiments (compare FIG. 8B-C to FIG. 9), the trend is the same, consistently showing that mismatched miRNAs have a higher sensitivity to reduced Drosha activity.

Discussion

It has been shown that when Drosha levels change, the change in expression levels of miRNAs with mismatches in the hairpin, 9-12 nt from the Drosha cutting site is greater than the change in expression levels of miRNAs that lack mismatches in the same region. This correlation was found in mature mouse tissues and during development. The sensitivity to changes in Drosha expression for miRNAs was also achieved by changing their secondary structure. These data suggest that secondary structure of miRNA affects miRNA's processing efficiency when Drosha is limiting and that differentiating cells may use this as a means of miRNA regulation.

Previous work on standardizing the miRNA secondary structure and cataloguing mismatch locations has used the approach of assigning mismatch positions for each strand of the hairpin separately (Han et al. 2006). In order to improve the representation of mismatch locations in three dimensional space, a mismatch mapping technique was developed that takes both strands into consideration simultaneously in the analysis. This counting method resulted in a very consistent measurement of 21 nt between the Drosha and Dicer cutting sites, which is consistent with previous reports indicating that Dicer processing of pre-miRNAs with asymmetric mismatches seems to explain the heterogeneity of length observed amongst mature miRNAs, and is also consistent with the idea that Dicer processing utilizes 'molecular rulers' which are size invariant (Starega-Roslan et al. 2010), which indicates that the developed counting method provides a good representation of the shape of the miRNA.

A relationship between secondary structure and pri-miRNA processing is well established, but no previous studies have focused specifically on the 9-12 nt region within the pre-miRNA portion of the pri-miRNA and processing. pri-miRNAs are generally shorter, have fewer bulges and internal loops, and overall less mismatched bases within the stem region than non-miRNA-generating RNA transcripts, implying that secondary structure prediction is a reliable predictor of Drosha and Dicer processing (Ritchie et al. 2007). Furthermore, the secondary structure of pri-miRNAs controls the specificity and efficiency of Drosha processing, in vitro and in vivo, suggesting that Drosha substrate specificity may act as a mechanism for global regulation of miRNA expression profiles (Feng et al. 2011). On the other hand, it has also been shown that polymorphisms in pri-miRNA secondary structure do not affect processing (Diederichs and Haber 2006), but only one of the examined single nucleotide polymorphisms (SNPs) was within the pre-miRNA portion of the pri-miRNA structure. In a wider search of human miRNA genes, it was determined that SNPs did affect the processing and function of miRNAs and most of these SNPs were found between the Dicer and Drosha cutting sites (Sun et al. 2009). The results presented herein could explain the significance of SNPs outside the seed region, but within the pre-miRNA structure, of some cancer and disease related miRNAs, such as the mutation in the stem of hsa-mir-125a (Duan et al. 2007), or in miR-181b-2, miR-208, miR-520e (Wu et al. 2008).

The miRNA biogenesis is regulated on multiple levels. The transcription of primary miRNAs (pri-miRNA) is regulated by common transcription factors, e.g. c-Myc (Abdelmohsen et al. 2012), and some miRNAs are also found to be subject to methylation (Brueckner et al. 2007). miRNAs are transcribed in the nucleus by RNA polymerase II or III (Borchert et al. 2006; Kim and Nam 2006) as part of the pri-miRNA, whose length is highly variable, ranging from ~200 up to several thousand nucleotides (Du and Zamore 2005; Cullen 2006). Drosha and DGCR8 bind the pri-miRNA, and Drosha cleaves pri-miRNAs at the base of the stem-loop and liberates a structure known as the precursor microRNA (pre-miRNA), which is ~60-70 nucleotides in length and forms a frequently mismatched hairpin structure with a 2 nucleotide 3' overhang (Basyuk et al. 2003; Lee et al. 2003; Ritchie et al. 2007). The DGCR8 mRNA has stem loop structures that can be cleaved by the Microprocessor, accordingly giving the Microprocessor a self regulating mechanism (Han et al. 2009). The pre-miRNA is transported from the nucleus to the cytoplasm by Exportin-5 and is subsequently cleaved by the enzyme Dicer with its cofactor trans-activator RNA (tar)-binding protein (TRBP) (Chendrimada et al. 2005), with a notable exception in mir-451, which bypasses Dicer cleavage and is processed by Ago instead (Cheloufi et al. 2010). Dicer cleavage is further regulated by Lin28, which binds to pre-miRNAs from the let-7 family (Nam et al. 2011). Dicer acts by binding the 3'-overhang and cleaves the pri-miRNA ~22 nt from the Drosha-cutting site to remove the terminal loop, resulting in an imperfect ~22 nt called miRNA:miRNA* (Hutvagner et al. 2001; Bernstein and Allis 2005; Feng et al. 2012). The miRNA enters the RNA-induced silencing complex (RISC), and the miRNA* is degraded, in a process where strand selection is variable (Bartel 2004; Du and Zamore 2005; Cullen 2006; Kim and Nam 2006). Although several mechanisms have been identified by which expression levels of select miRNAs are affected, and though Drosha is known to regulate overall Drosha expression, it has never previously been shown that the cell selectively can change miRNA expression profiles by altering levels of Drosha expression.

The current disclosure shows that Drosha levels vary between tissues and throughout cellular development, and that miRNAs without mismatches in the 9-12 nt region are overrepresented in cells with low levels of Drosha, while highly mismatched miRNAs are highly expressed in cells with high levels of Drosha, and that this behavior can be altered by changing the miRNA secondary structure. This supports the hypothesis that the cell selectively regulates more rigid and more mismatched miRNAs by altering Drosha expression. This mechanism contributes to the phenotypic relevance of specific levels of Drosha expression in development and terminal differentiation. In addition to other examples of post-transcriptional regulation, this can explain why some polycistronic miRNAs that are driven by the same promoter have very different expression levels, and the impact of SNPs, as stated above. This mechanism may be utilized while designing artificial miRNAs to increase stability, control expression levels throughout differentiation, or fine-tune miRNA expression in different tissue types.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would result in an RNA that remains relatively unaffected by Drosha regulation when compared to an RNA with a different number of mismatches in positions 5 and 9-12 from the Drosha cutting site.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

REFERENCES

Abdelmohsen K, Srikantan S, Kang M J, Gorospe M. 2012. Regulation of senescence by microRNA biogenesis factors. *Ageing Res Rev* 11(4): 491-500.

Anokye-Danso F, Trivedi C M, Juhr D, Gupta M, Cui Z, Tian Y, Zhang Y, Yang W, Gruber P J, Epstein J A et al. 2011. Highly efficient miRNA-mediated reprogramming of mouse and human somatic cells to pluripotency. *Cell Stem Cell* 8(4): 376-388.

Bar M, Wyman S K, Fritz B R, Qi J, Garg K S, Parkin R K, Kroh E M, Bendoraite A, Mitchell P S, Nelson A M et al. 2008. MicroRNA discovery and profiling in human embryonic stem cells by deep sequencing of small RNA libraries. *Stem Cells* 26(10): 2496-2505.

Bartel D P. 2004. MicroRNAs: genomics, biogenesis, mechanism, and function. *Cell* 116(2): 281-297.

Basyuk E, Suavet F, Doglio A, Bordonne R, Bertrand E. 2003. Human let-7 stem-loop precursors harbor features of RNase III cleavage products. *Nucleic Acids Res* 31(22): 6593-6597.

Berezikov E, Chung W J, Willis J, Cuppen E, Lai E C. 2007. Mammalian mirtron genes. *Mol Cell* 28(2): 328-336.

Bernstein E, Allis C D. 2005. RNA meets chromatin. *Genes Dev* 19(14): 1635-1655.

Borchert G M, Lanier W, Davidson B L. 2006. RNA polymerase III transcribes human microRNAs. *Nat Struct Mol Biol* 13(12): 1097-1101.

Brueckner B, Stresemann C, Kuner R, Mund C, Musch T, Meister M, Sultmann H, Lyko F. 2007. The human let-7a-3 locus contains an epigenetically regulated microRNA gene with oncogenic function. *Cancer Res* 67(4): 1419-1423.

Chambers S M, Fasano C A, Papapetrou E P, Tomishima M, Sadelain M, Studer L. 2009. Highly efficient neural conversion of human ES and iPS cells by dual inhibition of SMAD signaling. *Nat Biotechnol* 27(3): 275-280.

Cheloufi S, Dos Santos C O, Chong M M, Hannon G J. 2010. A dicer-independent miRNA biogenesis pathway that requires Ago catalysis. *Nature* 465(7298): 584-589.

Chendrimada T P, Gregory R I, Kumaraswamy E, Norman J, Cooch N, Nishikura K, Shiekhattar R. 2005. TRBP recruits the Dicer complex to Ago2 for microRNA processing and gene silencing. *Nature* 436(7051): 740-744.

Chong M M, Zhang G, Cheloufi S, Neubert T A, Hannon G J, Littman D R. 2010. Canonical and alternate functions of the microRNA biogenesis machinery. *Genes Dev* 24(17): 1951-1960.

Cullen B R. 2006. Viruses and microRNAs. *Nat Genet* 38 Suppl: S25-30.

Davis B N, Hata A. 2009. Regulation of MicroRNA Biogenesis: A miRiad of mechanisms. *Cell Commun Signal* 7: 18.

Davis B N, Hilyard A C, Lagna G, Hata A. 2008. SMAD proteins control DROSHA-mediated microRNA maturation. *Nature* 454(7200): 56-61.

Diederichs S, Haber D A. 2006. Sequence variations of microRNAs in human cancer: alterations in predicted secondary structure do not affect processing. *Cancer Res* 66(12): 6097-6104.

Du T, Zamore P D. 2005. microPrimer: the biogenesis and function of microRNA. *Development* 132(21): 4645-4652.

Duan R, Pak C, Jin P. 2007. Single nucleotide polymorphism associated with mature miR-125a alters the processing of pri-miRNA. *Hum Mol Genet* 16(9): 1124-1131.

Feng Y, Zhang X, Graves P, Zeng Y. 2012. A comprehensive analysis of precursor microRNA cleavage by human Dicer. *RNA* 18(11): 2083-2092.

Feng Y, Zhang X, Song Q, Li T, Zeng Y. 2011. Drosha processing controls the specificity and efficiency of global microRNA expression. *Biochim Biophys Acta* 1809 (11-12): 700-707.

Fukuda T, Yamagata K, Fujiyama S, Matsumoto T, Koshida I, Yoshimura K, Mihara M, Naitou M, Endoh H, Nakamura T et al. 2007. DEAD-box RNA helicase subunits of the Drosha complex are required for processing of rRNA and a subset of microRNAs. *Nat Cell Biol* 9(5): 604-611.

Gregory R I, Yan K P, Amuthan G, Chendrimada T, Doratotaj B, Cooch N, Shiekhattar R. 2004. The Microprocessor complex mediates the genesis of microRNAs. *Nature* 432 (7014): 235-240.

Griffiths-Jones S, Grocock R J, van Dongen S, Bateman A, Enright A J. 2006. miRBase: microRNA sequences, targets and gene nomenclature. *Nucleic Acids Res* 34 (Database issue): D140-144.

Han J, Lee Y, Yeom K H, Nam J W, Heo I, Rhee J K, Sohn S Y, Cho Y, Zhang B T, Kim V N. 2006. Molecular basis for the recognition of primary microRNAs by the Drosha-DGCR8 complex. *Cell* 125(5): 887-901.

Han J, Pedersen J S, Kwon S C, Belair C D, Kim Y K, Yeom K H, Yang W Y, Haussler D, Blelloch R, Kim V N. 2009. Posttranscriptional crossregulation between Drosha and DGCR8. *Cell* 136(1): 75-84.

Hatfield S D, Shcherbata H R, Fischer K A, Nakahara K, Carthew R W, Ruohola-Baker H. 2005. Stem cell division is regulated by the microRNA pathway. *Nature* 435(7044): 974-978.

Hofacker I L, Fontana W, Stadler P F, Bonhoeffer L S, Tacker M, Schuster P. 1994. Fast folding and comparison of RNA secondary structures. *Monatsh Chem* 125: 167-188.

Hutvagner G, McLachlan J, Pasquinelli A E, Balint E, Tuschl T, Zamore P D. 2001. A cellular function for the RNA-interference enzyme Dicer in the maturation of the let-7 small temporal RNA. *Science* 293(5531): 834-838.

Kim V N, Nam J W. 2006. Genomics of microRNA. *Trends Genet* 22(3): 165-173.

Kuehbacher A, Urbich C, Zeiher A M, Dimmeler S. 2007. Role of Dicer and Drosha for endothelial microRNA expression and angiogenesis. *Circ Res* 101(1): 59-68.

Kuppusamy K T, Sperber H, Ruohola-Baker H. 2013. MicroRNA Regulation and role in stem cell maintenance, cardiac differentiation and hypertrophy. *Curr Mol Med* Submitted.

Lagos-Quintana M, Rauhut R, Lendeckel W, Tuschl T. 2001. Identification of novel genes coding for small expressed RNAs. *Science* 294(5543): 853-858.

Lee Y, Ahn C, Han J, Choi H, Kim J, Yim J, Lee J, Provost P, Radmark O, Kim S et al. 2003. The nuclear RNase III Drosha initiates microRNA processing. *Nature* 425(6956): 415-419.

Mattick J S, Makunin I V. 2006. Non-coding RNA. *Hum Mol Genet* 15 Spec No 1: R17-29.

Nam Y, Chen C, Gregory R I, Chou J J, Sliz P. 2011. Molecular basis for interaction of let-7 microRNAs with Lin28. *Cell* 147(5): 1080-1091.

Noland C L, Ma E, Doudna J A. 2011. siRNA repositioning for guide strand selection by human Dicer complexes. *Mol Cell* 43(1): 110-121.

O'Donnell K A, Wentzel E A, Zeller K I, Dang C V, Mendell J T. 2005. c-Myc-regulated microRNAs modulate E2F1 expression. *Nature* 435(7043): 839-843.

Qi J, Yu J Y, Shcherbata H R, Mathieu J, Wang A J, Seal S, Zhou W, Stadler B M, Bourgin D, Wang L et al. 2009. microRNAs regulate human embryonic stem cell division. *Cell Cycle* 8(22): 3729-3741.

Ritchie W, Legendre M, Gautheret D. 2007. RNA stem-loops: to be or not to be cleaved by RNAse III. *RNA* 13(4): 457-462.

Ruby J G, Jan C H, Bartel D P. 2007. Intronic microRNA precursors that bypass Drosha processing. *Nature* 448(7149): 83-86.

Shcherbata H R, Hatfield S, Ward E J, Reynolds S, Fischer K A, Ruohola-Baker H. 2006. The MicroRNA pathway plays a regulatory role in stem cell division. *Cell Cycle* 5(2): 172-175.

Stadler B, Ivanovska I, Mehta K, Song S, Nelson A, Tan Y, Mathieu J, Darby C, Blau C A, Ware C et al. 2010. Characterization of microRNAs involved in embryonic stem cell states. *Stem Cells Dev* 19(7): 935-950.

Stadler B M, Ruohola-Baker H. 2008. Small RNAs: keeping stem cells in line. *Cell* 132(4): 563-566.

Starega-Roslan J, Krol J, Koscianska E, Kozlowski P, Szlachcic W J, Sobczak K, Krzyzosiak W J. 2010. Structural basis of microRNA length variety. *Nucleic Acids Res* 39(1): 257-268.

Stark A, Brennecke J, Bushati N, Russell R B, Cohen S M. 2005. Animal MicroRNAs confer robustness to gene expression and have a significant impact on 3'UTR evolution. *Cell* 123(6): 1133-1146.

Sun G, Yan J, Noltner K, Feng J, Li H, Sarkis D A, Sommer S S, Rossi J J. 2009. SNPs in human miRNA genes affect biogenesis and function. *RNA* 15(9): 1640-1651.

Takada S, Berezikov E, Yamashita Y, Lagos-Quintana M, Kloosterman W P, Enomoto M, Hatanaka H, Fujiwara S, Watanabe H, Soda M et al. 2006. Mouse microRNA profiles determined with a new and sensitive cloning method. *Nucleic Acids Res* 34 (17): e115.

Wu M, Jolicoeur N, Li Z, Zhang L, Fortin Y, L'Abbe D, Yu Z, Shen S H. 2008. Genetic variations of microRNAs in human cancer and their effects on the expression of miR-NAs. *Carcinogenesis* 29(9): 1710-1716.

Zeng Y, Cullen B R. 2003. Sequence requirements for micro RNA processing and function in human cells. *RNA* 9(1): 112-123.

Zeng Y, Yi R, Cullen B R. 2005. Recognition and cleavage of primary microRNA precursors by the nuclear processing enzyme Drosha. *EMBO J* 24(1): 138-148.

Zisoulis D G, Kai Z S, Chang R K, Pasquinelli A E. 2012. Autoregulation of microRNA biogenesis by let-7 and Argonaute. *Nature* 486(7404): 541-544.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09416369B2). An electronic copy of the "Sequence Listing" will also be available from the USPTO upon request and payment of the fee set forth in 37 CFR 1.19(b)(3).

What is claimed is:

1. An expression vector encoding an endogenous RNA nucleic acid molecule altered to remove at least one naturally-encoded mis-match at nucleotide position 5, 9, 10, 11 or 12 from the RNA's Drosha cutting site.

2. An expression vector of claim 1 altered to remove two naturally-encoded mis-matches at nucleotide positions selected from 5, 9, 10, 11 or 12 from the RNA's Drosha cutting site.

3. An expression vector of claim 1 altered to remove three naturally-encoded mis-matches at nucleotide positions selected from 5, 9, 10, 11 or 12 from the RNA's Drosha cutting site.

4. An expression vector of claim 1 altered to remove four naturally-encoded four mis-matches at nucleotide positions selected from 5, 9, 10, 11 or 12 from the RNA's Drosha cutting site.

5. An expression vector of claim 1 wherein the encoded RNA is miRNA.

6. An expression vector of claim 1 wherein the expression vector is provided as part of a therapeutic composition.

7. An RNA-based molecule comprising an endogenous RNA sequence altered to remove at least one naturally occurring mis-match at position 5, 9, 10, 11 or 12 from the RNA's Drosha cutting site.

8. An RNA-based molecule of claim 7 altered to remove at least two naturally occurring mis-matches at position 5, 9, 10, 11 or 12 from the RNA's Drosha cutting site.

9. An RNA-based molecule of claim 7 altered to remove at least three naturally occurring mis-matches at position 5, 9, 10, 11 or 12 from the RNA's Drosha cutting site.

10. An RNA-based molecule of claim 7 altered to remove at least four naturally occurring mis-matches at position 5, 9, 10, 11 or 12 from the RNA's Drosha cutting site.

11. An RNA-based molecule of claim 7 altered to remove five naturally occurring mis-matches at position 5, 9, 10, 11 and 12 from the RNA's Drosha cutting site.

12. An RNA-based molecule of claim 7 wherein the RNA-based molecule is provided as part of a therapeutic composition.

13. A method of reducing the effects of a naturally occurring RNA-based molecule in the liver when compared to a different tissue having higher Drosha expression levels than in the liver comprising administering an expression vector of claim 7 to a subject.

* * * * *